(12) United States Patent
Jewett et al.

(10) Patent No.: US 11,898,187 B2
(45) Date of Patent: Feb. 13, 2024

(54) PROTEIN GLYCOSYLATION SITES BY RAPID EXPRESSION AND CHARACTERIZATION OF N-GLYCOSYLTRANSFERASES

(71) Applicant: Northwestern University, Evanston, IL (US)

(72) Inventors: Michael Christopher Jewett, Evanston, IL (US); Weston K. Kightlinger, Evanston, IL (US); Liang Lin, Evanston, IL (US); Milan Mrksich, Hinsdale, IL (US)

(73) Assignee: Northwestern University, Evanston, IL (US)

( * ) Notice: Subject to any disclaimer, the term of this patent is extended or adjusted under 35 U.S.C. 154(b) by 528 days.

(21) Appl. No.: 16/639,500

(22) PCT Filed: Aug. 15, 2018

(86) PCT No.: PCT/US2018/000185
§ 371 (c)(1),
(2) Date: Feb. 14, 2020

(87) PCT Pub. No.: WO2019/035916
PCT Pub. Date: Feb. 21, 2019

(65) Prior Publication Data
US 2022/0235389 A1    Jul. 28, 2022

Related U.S. Application Data

(60) Provisional application No. 62/545,760, filed on Aug. 15, 2017.

(51) Int. Cl.
| | | |
|---|---|---|
| *C12P 21/00* | (2006.01) | |
| *C12N 9/10* | (2006.01) | |
| *C12N 15/10* | (2006.01) | |
| *C12Q 1/48* | (2006.01) | |
| *G01N 33/68* | (2006.01) | |

(52) U.S. Cl.
CPC .......... *C12P 21/005* (2013.01); *C12N 9/1051* (2013.01); *C12N 15/1044* (2013.01); *C12Q 1/48* (2013.01); *G01N 33/6851* (2013.01)

(58) Field of Classification Search
CPC . C12P 21/005; C12N 9/1051; C12N 15/1044; C12N 9/1048; C12Q 1/48; G01N 33/6851
See application file for complete search history.

(56) References Cited

U.S. PATENT DOCUMENTS

| | | |
|---|---|---|
| 4,458,066 A | 7/1984 | Caruthers |
| 4,683,195 A | 7/1987 | Mullis |
| 4,683,202 A | 7/1987 | Mullis |
| 5,478,730 A | 12/1995 | Alakhov |
| 5,494,810 A | 2/1996 | Barany |
| 5,556,769 A | 9/1996 | Wu |
| 5,665,563 A | 9/1997 | Beckler |
| 6,168,931 B1 | 1/2001 | Swartz |
| 6,548,276 B2 | 4/2003 | Swartz |
| 6,869,774 B2 | 3/2005 | Endo |
| 6,994,986 B2 | 2/2006 | Swartz |
| 7,118,883 B2 | 10/2006 | Inoue |
| 7,189,525 B2 | 3/2007 | Deleersnijder |
| 7,189,528 B2 | 3/2007 | Higashide |
| 7,235,382 B2 | 6/2007 | Endo |
| 7,338,789 B2 | 3/2008 | Swartz |
| 7,387,884 B2 | 6/2008 | Suzuki |
| 7,396,664 B2 | 7/2008 | Daly |
| 7,399,610 B2 | 7/2008 | Shikata |
| 7,776,535 B2 | 8/2010 | Mehl |
| 7,817,794 B2 | 10/2010 | Galvin |
| 8,298,759 B2 | 10/2012 | Voloshin |
| 8,703,471 B2 | 4/2014 | Aebi |
| 8,715,958 B2 | 5/2014 | Goerke |
| 8,734,856 B2 | 5/2014 | Endo |
| 8,999,668 B2 | 4/2015 | Delisa |
| 9,005,920 B2 | 4/2015 | Kusumegi |
| 2004/0209321 A1 | 10/2004 | Swartz |
| 2005/0054044 A1 | 3/2005 | Swartz |
| 2005/0170452 A1 | 8/2005 | Wildt |
| 2006/0211085 A1 | 9/2006 | Bobrowicz |
| 2006/0234345 A1 | 10/2006 | Schwartz et al. |
| 2006/0252672 A1 | 11/2006 | Betenbaugh |

(Continued)

FOREIGN PATENT DOCUMENTS

| | | |
|---|---|---|
| CN | 105505959 | 4/2016 |
| WO | 2003056914 | 7/2003 |

(Continued)

OTHER PUBLICATIONS

Laurent N et al. Enzymatic Glycosylation of Peptide Arrays on Gold Surfaces. 2008. Chemibiochem. 9(6): 883-887. (Year: 2008).*
Abouelfetouh, A. et al. The *E. coli* sirtuin CobB shows no preference for enzymatic and nonenzymatic lysine acetylation substrate sites. Microbiologyopen 4, 66-83 (2015).
Baker, J.L., et al. Expanding the glycoengineering toolbox: the rise of bacterial N-linked protein glycosylation. Trends in biotechnology 31, 313-323 (2013).
Ban et al., "On-Chip Synthesis and Label-Free Assays of Oligosaccharide Arrays," Chem. Int. Ed., 2008, 47(18), 3396-3399.

(Continued)

*Primary Examiner* — Paul J Holland
(74) *Attorney, Agent, or Firm* — Quarles & Brady LLP

(57) ABSTRACT

Disclosed are components, systems, and methods for glycoprotein or recombinant glycoprotein protein synthesis in vitro and in vivo. In particular, the present invention relates to components, systems, and methods for identifying amino acid glycosylation tag motifs for N-glycosyltransferases and the use of the identified amino acid glycosylation tag motifs in methods for preparing glycoproteins and recombinant glycoproteins in vitro and in vivo.

21 Claims, 68 Drawing Sheets

Specification includes a Sequence Listing.

(56) References Cited

U.S. PATENT DOCUMENTS

| | | | |
|---|---|---|---|
| 2006/0257399 A1 | 11/2006 | Gerngross et al. | |
| 2006/0286637 A1 | 12/2006 | Hamilton | |
| 2007/0026485 A1 | 2/2007 | Defrees | |
| 2007/0154983 A1 | 7/2007 | Calhoun | |
| 2007/0178551 A1 | 8/2007 | Gerngross | |
| 2008/0138857 A1 | 6/2008 | Swartz | |
| 2009/0325262 A1* | 12/2009 | Hodneland | C07K 1/1077 530/402 |
| 2012/0142547 A1 | 6/2012 | Mrksich | |
| 2012/0171720 A1 | 7/2012 | Church | |
| 2012/0252730 A1 | 10/2012 | Mrksich | |
| 2014/0045267 A1 | 2/2014 | Lajoie | |
| 2014/0134642 A1 | 5/2014 | Mrksich | |
| 2014/0194345 A1 | 7/2014 | Peoples | |
| 2014/0206570 A1 | 7/2014 | Mrksich | |
| 2014/0255987 A1 | 9/2014 | Delisa | |
| 2014/0256561 A1 | 9/2014 | Schwartz | |
| 2014/0295492 A1 | 10/2014 | Jewett | |
| 2014/0349353 A1 | 11/2014 | Nomura | |
| 2015/0259757 A1 | 9/2015 | Jewett | |
| 2015/0369816 A1 | 12/2015 | Mrksich | |
| 2016/0060301 A1 | 3/2016 | Jewett | |
| 2016/0252501 A1 | 9/2016 | Mrksich | |
| 2017/0349928 A1 | 12/2017 | Jewett | |
| 2018/0016612 A1 | 1/2018 | Jewett | |
| 2018/0016614 A1 | 1/2018 | Jewett | |
| 2018/0080058 A1 | 3/2018 | Mrksich | |
| 2018/0125990 A1 | 5/2018 | Zhu | |
| 2018/0231564 A1 | 8/2018 | Mrksich | |
| 2018/0298416 A1 | 10/2018 | Jewett | |
| 2019/0112591 A1 | 4/2019 | Farha | |
| 2019/0161556 A1 | 5/2019 | Mrksich | |
| 2019/0284600 A1 | 9/2019 | Jewett | |

FOREIGN PATENT DOCUMENTS

| | | | |
|---|---|---|---|
| WO | 2004013151 | 2/2004 | |
| WO | 2004035605 | 4/2004 | |
| WO | 2006102652 | 9/2006 | |
| WO | 2006119987 | 11/2006 | |
| WO | 2007120932 | 10/2007 | |
| WO | WO-2017093291 A1 * | 6/2017 | A61K 39/00 |

OTHER PUBLICATIONS

Ban, L. et al. Discovery of glycosyltransferases using carbohydrate arrays and mass spectrometry. Nat. Chem. Biol. 8, 769-773 (2012).
Brooks, S.A. Appropriate glycosylation of recombinant proteins for human use. Molecular Biotechnology 28, 241-255 (2004).
Bundy, B.C. et al. Site-Specific Incorporation of p-Propargyloxyphenylalanine in a Cell-Free Environment for Direct Protein-Protein Click Conjugation. Bioconjugate Chem. 21, 255-263 (2010).
Cappuccio, J.A. et al. Cell-free Co-expression of Functional Membrane Proteins and Apolipoprotein, Forming Soluble Nanolipoprotein Particles. Molecular & Cellular Proteomics 7, 2246-2253 (2008).
Caramelo, J.J. et al. A sweet code for glycoprotein folding. FEBS Lett. 589, 3379-3387 (2015).
Carlson, E.D., et al. Cell-free protein synthesis: applications come of age. Biotechnol. Adv. 30, 1185-1194 (2012).
Caschera, F. et al. Synthesis of 2.3 mg/ml of protein with an all *Escherichia coli* cell-free transcription-translation system. Biochimie 99, 162-168 (2014).
Chalkley, R.J., et al. Identification of protein O-GlcNAcylation sites using electron transfer dissociation mass spectrometry on native peptides. Proc. Natl. Acad. Sci. U.S.A. 106, 8894-8899 (2009).
Chen, M.M., et al. From Peptide to Protein:? Comparative Analysis of the Substrate Specificity of N-Linked Glycosylation in C. jejuni. Biochemistry 46, 5579-5585 (2007).
Choi, K.J., et al. The Actinobacillus pleuropneumoniae HMW1C-like glycosyltransferase mediates N-linked glycosylation of the Haemophilus influenzae HMW1 adhesin. PLOS ONE 5, e15888 (2010).

Cuccui, J. et al. Hijacking bacterial glycosylation for the production of glycoconjugates, from vaccines to humanised glycoproteins. J. Pharm. Pharmacol. 67, 338-350 (2015).
Cuccui, J. et al. Exploitation of bacterial N-linked glycosylation to develop a novel recombinant glycoconjugate vaccine against Francisella tularensis. Open Biol. 3, 130002 (2013).
Cuccui, J. et al. The N-linking glycosylation system from Actinobacillus pleuropneumoniae is required for adhesion and has potential use in glycoengineering. Open Biol. 7 (2017).
Espah Borujeni, A., et al. Translation rate is controlled by coupled trade-offs between site accessibility, selective RNA unfolding and sliding at upstream standby sites. Nucleic Acids Res. 42, 2646-2659 (2014).
Fernández-Tejada, A. et al. Total Synthesis of Glycosylated Proteins. Topics in current chemistry 362, 1-26 (2015).
Fisher, A.C. et al. Production of secretory and extracellular N-linked glycoproteins in *Escherichia coli*. Appl. Environ. Microbiol. 77, 871-881 (2011).
Garcia-Quintanilla, F., et al. Production of a recombinant vaccine candidate against Burkholderia pseudomallei exploiting the bacterial N-glycosylation machinery. Frontiers in microbiology 5, 381 (2014).
Gerken, T.A., et al. Identification of Common and Unique Peptide Substrate Preferences for the UDP-GalNAc: Polypeptide a-N-acetylgalactosaminyltransferases T1 and T2 Derived from Oriented Random Peptide Substrates. J. Biol. Chem. 281, 32403-32416 (2006).
Goerke, A.R. et al. High-level cell-free synthesis yields of proteins containing site-specific non-natural amino acids. Biotechnology and bioengineering 102, 400-416 (2009).
Goodchild, J. "Conjugates of oligonucleotides and modified oligonucleotides: a review of their synthesis and properties." Bioconjugate Chemistry 1.3 (1990): 165-187.
Grass, S. et al. The Haemophilus influenzae HMW1 adhesin is glycosylated in a process that requires HMW1C and phosphoglucomutase, an enzyme involved in lipooligosaccharide biosynthesis. Molecular Microbiology 48, 737-751 (2003).
Grass, S. et al. The Haemophilus influenzae HMW1C Protein is a Glycosyltransferase That Transfers Hexose Residues to Asparagine Sites in the HMW1 Adhesin. PLoS Pathog 6, e1000919 (2010).
Gross, J. et al. The Haemophilus influenzae HMW1 Adhesin is a Glycoprotein with an Unusual N-Linked Carbohydrate Modification. J. Biol. Chem. 283, 26010-26015 (2008).
Guarino, C., et al. (2012). A prokaryote-based cell-free translation system that efficiently synthesizes glycoproteins. Glycobiology, 22(5), 596-601.
Han, C. et al. A highly effective and adjustable dual plasmid system for O-GlcNAcylated recombinant protein production in *E. coli*. Journal of Biochemistry 157, 477-484 (2015).
Hang, I. et al. Analysis of site-specific N-glycan remodeling in the endoplasmic reticulum and the Golgi. Glycobiology 25, 1335-1349 (2015).
Hong, S.H. et al. Cell-free Protein Synthesis from a Release Factor 1 Deficient *Escherichia coli* Activates Efficient and Multiple Site-specific Nonstandard Amino Acid Incorporation. ACS Synth. Biol. 3, 398-409 (2014).
Hussain, M.R., et al. N-acetylgalactosaminyltransferases in cancer. Oncotarget 7, 54067-54081 (2016).
Ihssen, J. et al. Production of glycoprotein vaccines in *Escherichia coli*. Microbial cell factories 9, 61 (2010).
International Searching Authority, International Search Report and Written Opinion for application PCT/US2018/000185, dated Dec. 20, 2018.
Iwashkiw, J.A. et al. Exploiting the Campylobacter jejuni protein glycosylation system for glycoengineering vaccines and diagnostic tools directed against brucellosis. Microbial cell factories 11, 13 (2012).
Jaffé, S.R.P., et al. *Escherichia coli* as a glycoprotein production host: recent developments and challenges. Current Opinion in Biotechnology 30, 205-210 (2014).
Jewett, M.C. et al. Mimicking the *Escherichia coli* cytoplasmic environment activates long-lived and efficient cell-free protein synthesis. Biotechnol. Bioeng. 86, 19-26 (2004).

(56) References Cited

OTHER PUBLICATIONS

Jewett, M.C. et al. Rapid Expression and Purification of 100 nmol Quantities of Active Protein Using Cell-Free Protein Synthesis. Biotechnol. Prog. 20, 102-109 (2004).
Jewett, M.C., et al. An integrated cell-free metabolic platform for protein production and synthetic biology. Molecular systems biology 4, 220 (2008).
Kampf, M.M. et al. In vivo production of a novel glycoconjugate vaccine against Shigella flexneri 2a in recombinant *Escherichia coli*: identification of stimulating factors for in vivo glycosylation. Microbial cell factories 14, 12 (2015).
Kawai, F. et al. Structural insights into the glycosyltransferase activity of the Actinobacillus pleuropneumoniae HMW1C-like protein. J. Biol. Chem. 286, 38546-38557 (2011).
Kay, J.E. et al. Lysate of engineered *Escherichia coli* supports high-level conversion of glucose to 2,3-butanediol. Metab. Eng. 32, 133-142 (2015).
Keys, T.G. et al. Engineering protein glycosylation in prokaryotes. Curr. Opin. Syst. Biol. 5, 23-31 (2017).
Keys, T.G. et al. A biosynthetic route for polysialylating proteins in *Escherichia coli*. Metab. Eng. 44, 293-301 (2017).
Kightlinger, W. et al. Design of glycosylation sites by rapid synthesis and analysis of glycosyltransferases. Nature Chemical Biology 14, 627-635 (2018).
Kightlinger, W. et al. Design of protein glycosylation sites by cell-free protein synthesis and mass spectrometry of self-assembled monolayers. Conference: 2017 Synthetic Biology: Engineering, Evolution & Designt. Jun. 20, 2017.
Kim, E.J. et al. Versatile O-GlcNAc Transferase Assay for High-Throughput Identification of Enzyme Variants, Substrates, and Inhibitors. Bioconjugate Chem. 25, 1025-1030 (2014).
Kim, J. et al. Profiling the selectivity of DNA ligases in an array format with mass spectrometry. Nucleic Acids Res. 38, e2 (2010).
Knapp, K.G., et al. Cell-free synthesis of proteins that require disulfide bonds using glucose as an energy source. Biotechnol. Bioeng. 97, 901-908 (2007).
Kong, Y. et al. Probing polypeptide GalNAc-transferase isoform substrate specificities by in vitro analysis. Glycobiology 25, 55-65 (2015).
Kornacki, J.R., et al. Acetyltransferase p300/CBP Associated Factor (PCAF) Regulates Crosstalk-Dependent Acetylation of Histone H3 by Distal Site Recognition. ACS Chem. Biol. 10, 157-164 (2015).
Kuo, H.Y., et al. Profiling deacetylase activities in cell lysates with peptide arrays and SAMDI mass spectrometry. Anal. Chem. 85, 10635-10642 (2013).
Kwon, Y.-C et al. High-throughput preparation methods of crude extract for robust cell-free protein synthesis. Sci. Rep. 5, 8663 (2015).
Lajoie, M.. et al. Genomically Recoded Organisms Expand Biological Functions. Science 342, 357-360 (2013).
Lau, K. et al. Highly Efficient Chemoenzymatic Synthesis of ß1-4-Linked Galactosides with Promiscuous Bacterial ß1-4-Galactosyltransferases. Chemical communications (Cambridge, England) 46, 6066-6068 (2010).
Lauber, J., et al. Expression of the functional recombinant human glycosyltransferase GalNAcT2 in *Escherichia coli*. Microbial cell factories 14, 3 (2015).
Lazarus, M.B., et al. Structure of human O-GlcNAc transferase and its complex with a peptide substrate. Nature 469, 564-567 (2011).
Leavy, T.M. et al. A high-throughput assay for O-GlcNAc transferase detects primary sequence preferences in peptide substrates. Bioorg. Med. Chem. Lett. 17, 3851-3854 (2007).
Li, T. et al. Modulating IgG effector function by Fc glycan engineering. Proceedings of the National Academy of Sciences 114, 3485-3490 (2017).
Li, Y. et al. Donor substrate promiscuity of bacterial beta1-3-N-acetylglucosaminyltransferases and acceptor substrate flexibility of beta1-4-galactosyltransferases. Bioorg Med Chem 24, 1696-1705 (2016).

Lin, C.-W. et al. A common glycan structure on immunoglobulin G for enhancement of effector functions. Proc. Natl. Acad. Sci. U.S.A. 112, 10611-10616 (2015).
Liu, X. et al. A peptide panel investigation reveals the acceptor specificity of O-GlcNAc transferase. FASEB J. 28, 3362-3372 (2014).
Lombard, V., et al. The carbohydrate-active enzymes database (CAZy) in 2013. Nucleic Acids Res 42, D490-495 (2014).
Lomino, J.V. et al. A two-step enzymatic glycosylation of polypeptides with complex N-glycans. Biorg. Med. Chem. 21, 2262-2270 (2013).
Losfeld, M.-E. et al. Influence of protein/glycan interaction on site-specific glycan heterogeneity. The FASEB Journal 31, 4623-4635 (2017).
Lowary, T.L. Context and complexity: The next big thing in synthetic glycobiology. Current Opinion in Chemical Biology 17, 990-996 (2013).
Lowenthal, M. S., et al. "Identification of novel N-glycosylation sites at noncanonical protein consensus motifs." Journal of proteome research 15.7 (2016): 2087-2101.
Lu, Q., et al. Sweet Talk: Protein Glycosylation in Bacterial Interaction With the Host. Trends Microbiol 23, 630-641 (2015).
Mansell, T.J., et al. Engineered genetic selection links in vivo protein folding and stability with asparagine-linked glycosylation. Biotechnol. J. 8, 1445-1451 (2013).
Maverakis, E. et al. Glycans in the immune system and the Altered Glycan Theory of Autoimmunity: A critical review. J. Autoimmun. 57c, 1-13 (2015).
McCann, J.R. et al. The HMW1C-Like Glycosyltransferases—An Enzyme Family with a Sweet Tooth for Simple Sugars. PLoS Pathogens 10, e1003977 (2014).
Merritt, J.H., et al. Glycans-by-design: engineering bacteria for the biosynthesis of complex glycans and glycoconjugates. Biotechnology and bioengineering 110, 1550-1564 (2013).
Mitra, N., et al. N-linked oligosaccharides as outfitters for glycoprotein folding, form and function. Trends Biochem. Sci. 31, 156-163 (2006).
Moremen, K.W., et al. Vertebrate protein glycosylation: diversity, synthesis and function. Nature reviews Molecular cell biology 13, 448-462 (2012).
Murakami, M. et al. Chemical synthesis of erythropoietin glycoforms for insights into the relationship between glycosylation pattern and bioactivity. Science Advances 2, e1500678 (2016).
Naegeli, A. et al. Molecular analysis of an alternative N-glycosylation machinery by functional transfer from Actinobacillus pleuropneumoniae to *Escherichia coli*. J. Biol. Chem. 289, 2170-2179 (2014).
Naegeli, A. et al. Substrate Specificity of Cytoplasmic N-Glycosyltransferase. Journal of Biological Chemistry 289, 24521-24532 (2014).
Ollis, A.A., et al. Engineered oligosaccharyltransferases with greatly relaxed acceptor-site specificity. Nat. Chem. Biol. 10, 816-822 (2014).
Ortiz-Meoz, R.F., et al. Microarray discovery of new OGT substrates: the medulloblastoma oncogene OTX2 is O-GlcNAcylated. J. Am. Chem. Soc. 136, 4845-4848 (2014).
Pathak, S. et al. The active site of O-GlcNAc transferase imposes constraints on substrate sequence. Nat Struct Mol Biol 22, 744-750 (2015).
Phanse, Y. et al. A systems approach to designing next generation vaccines: combining alpha-galactose modified antigens with nanoparticle platforms. Scientific reports 4, 3775 (2014).
Quast, I., et al. Regulation of antibody effector functions through IgG Fc N-glycosylation. Cell. Mol. Life Sci. 74, 837-847 (2016).
Ravenscroft, N. et al. Purification and characterization of a Shigella conjugate vaccine, produced by glycoengineering *Escherichia coli*. Glycobiology 26, 51-62 (2016).
Rempe, K.A. et al. Unconventional N-Linked Glycosylation Promotes Trimeric Autotransporter Function in Kingella kingae and Aggregatibacter aphrophilus. mBio 6, e01206-01215 (2015).
Robinson, P.V., et al. Glyco-seek: Ultrasensitive Detection of Protein-Specific Glycosylation by Proximity Ligation Polymerase Chain Reaction. J. Am. Chem. Soc. 138, 10722-10725 (2016).

(56) References Cited

OTHER PUBLICATIONS

Schaffer, C. et al. Emerging facets of prokaryotic glycosylation. FEMS Microbiol Rev (2016).
Schoborg, J.A. et al. A cell-free platform for rapid synthesis and testing of active oligosaccharyltransferases. Biotechnol. Bioeng. (2017).
Schwarz, F. et al. A combined method for producing homogeneous glycoproteins with eukaryotic N-glycosylation. Nat. Chem. Biol. 6, 264-266 (2010).
Schwarz, F. et al. Cytoplasmic N-glycosyltransferase of Actinobacillus pleuropneumoniae is an inverting enzyme and recognizes the NX(S/T) consensus sequence. J. Biol. Chem. 286, 35267-35274 (2011).
Schwarz, F. et al. Mechanisms and principles of N-linked protein glycosylation. Current Opinion in Structural Biology 21, 576-582 (2011).
Shi, J., et al. Activity Based High-Throughput Screening for Novel O-GlcNAc Transferase Substrates Using a Dynamic Peptide Microarray. PLos ONE 11, e0151085 (2016).
Song, Q. et al. Production of homogeneous glycoprotein with multi-site modifications by an engineered N-glycosyltransferase mutant. J. Biol. Chem. (2017).
Srichaisupakit, A., et al. Production of initial-stage eukaryotic N-glycan and its protein glycosylation in *Escherichia coli*. Journal of Bioscience and Bioengineering 119, 399 405 (2015).
Steentoft, C. et al. Precision mapping of the human O-GalNAc glycoproteome through SimpleCell technology. EMBO J. 32, 1478-1488 (2013).
Szymanski, C.M., et al. Evidence for a system of general protein glycosylation in Campylobacter jejuni. Mol Microbiol 32, 1022-1030 (1999).
Tatusova T.A. et al. (1999), "Blast 2 sequences—a new tool for comparing protein and nucleotide sequences", FEMS Microbiol Lett. 174:247-250.
Tytgat, H.L.P. et al. The Sweet Tooth of Bacteria: Common Themes in Bacterial Glycoconjugates. Microbiology and Molecular Biology Reviews 78, 372-417 (2014).
Valderrama-Rincon, JD. An Engineered eukaryotic protein glycosylation pathway in *Escherichia coli*, J Nat Chem Biol, vol. 6, May 2012, pp. 434-436.
Van Kasteren, S.I et al. Expanding the diversity of chemical protein modification allows post-translational mimicry. Nature 446, 1105 (2007).
Van Kasteren, S.I. et al. Site-selective glycosylation of proteins: creating synthetic glycoproteins. Nature protocols 2, 3185 (2007).
Wacker, M. et al. N-linked glycosylation in Campylobacter jejuni and its functional transfer into *E. coli*. Science (New York, N.Y.) 298, 1790-1793 (2002).
Wacker, M. et al. Prevention of *Staphylococcus aureus* infections by glycoprotein vaccines synthesized in *Escherichia coli*. J Infect Dis 209, 1551-1561 (2014).
Wang, A.C., et al. Loss of O-GlcNAc glycosylation in forebrain excitatory neurons induces neurodegeneration. Proc. Natl. Acad. Sci. U.S.A. 113, 15120-15125 (2016).
Wang, L.-X et al. Chemical and Chemoenzymatic Synthesis of Glycoproteins for Deciphering Functions. Chemistry & biology 21, 51-66 (2014).
Wang, L.-X et al. Realizing the promise of chemical glycobiology. Chem. Sci. 4, 3381-3394 (2013).
Wang, L.-X et al. Emerging Technologies for Making Glycan-Defined Glycoproteins. ACS Chemical Biology 7, 110-122 (2012).
Wolfert, M.A. et al. Adaptive immune activation: glycosylation does matter. Nat. Chem. Biol. 9, 776-784 (2013).
Wright, T.H. et al. Posttranslational mutagenesis: A chemical strategy for exploring protein side chain diversity. Science (New York, N.Y.) 354 (2016).
Wu, Z. et al. Site-Directed Glycosylation of Peptide/Protein with Homogeneous O-Linked Eukaryotic N-Glycans. Bioconjugate chemistry 27, 1972-1975 (2016).
Wuu, J.J. et al. High yield cell-free production of integral membrane proteins without refolding or detergents. Biochim. Biophys. Acta 1778, 1237-1250 (2008).
Xu, Y. et al. A novel enzymatic method for synthesis of glycopeptides carrying natural eukaryotic N-glycans. Chem. Commun. 53, 9075-9077 (2017).
Yang, A. et al. A chemical biology route to site-specific authentic protein modifications. Science (New York, N.Y.) 354, 623-626 (2016).
Yang, Q. et al. Glycan Remodeling of Human Erythropoietin (EPO) Through Combined Mammalian Cell Engineering and Chemoenzymatic Transglycosylation. ACS Chemical Biology 12, 1665-1673 (2017).
Yang, Z. et al. Engineered CHO cells for production of diverse, homogeneous glycoproteins. Nat Biotech 33, 842-844 (2015).
Zegzouti, H. et al. Detection of glycosyltransferase activities with homogeneous bioluminescent UDP detection assay. Glycobiology 23, 1340-1341 (2013).
Zhang, Q., et al. Synthesis of granulocyte macrophage colony-stimulating factor as homogeneous glycoforms and early comparisons with yeast cell-derived material. Proceedings of the National Academy of Sciences of the United States of America 111, 2885-2890 (2014).
Zimmerman, E.S. et al. Production of site-specific antibody-drug conjugates using optimized non-natural amino acids in a cell-free expression system. Bioconjugate chemistry 25, 351-361 (2014).

* cited by examiner

PROTEIN GLYCOSYLATION SITES BY RAPID EXPRESSION AND CHARACTERIZATION OF N-GLYCOSYLTRANSFERASES

CROSS-REFERENCE TO RELATED PATENT APPLICATIONS

The present application is the U.S. national stage entry of international application PCT/US2018/000185, filed Aug. 15, 2018, which international application claims the benefit of priority under 35 U.S.C. § 119(e) to U.S. Provisional Application No. 62/545,760, filed on Aug. 15, 2017, the contents of which are incorporated herein by reference in their entireties.

STATEMENT REGARDING FEDERALLY SPONSORED RESEARCH OR DEVELOPMENT

This invention was made with government support under HDTRA1-15-1-0052/P00001 awarded by the Defense Threat Reduction Agency. The government has certain rights in the invention.

REFERENCE TO A SEQUENCE LISTING SUBMITTED VIA EFS-WEB

The content of the ASCII text file of the sequence listing named "2023-04-04_702581.01710_Sub ST25.txt" which is 98,298 bytes in size and was created on Apr. 4, 2023, is electronically submitted via EFS-Web herewith. The sequence listing is incorporated herein by reference in its entirety.

BACKGROUND

The present invention generally relates to components, systems, and methods for glycoprotein protein synthesis. In particular, the present invention relates to identification of amino acid glycosylation tag motifs ("GlycTags") for N-glycosyltransferases and their use in synthesizing glycoproteins and recombinant glycoproteins in cells, using purified enzymes, or in cell-free protein synthesis (CFPS).

Glycosylation modulates the pharmacokinetics and potency of protein therapeutics and vaccines. However, current methods cannot sufficiently explore the vast experimental landscapes required to accurately predict and design glycosylation sites for specific glycosyltransferases (GTs). Here, we used a systematic platform for Glycosylation Sequence Characterization and Optimization by Rapid Expression and Screening (GlycoSCORES) using Cell-Free Protein Synthesis (CFPS) and Self-Assembled Monolayers for Desorption Ionization Mass Spectrometry (SAMDI-MS) to produce five cytoplasmic N-linked glycosyltransferases (NGTs) in vitro and determine their peptide acceptor and sugar donor specificities at unprecedented depth and throughput with ~3,000 unique peptides and ~10,000 unique reaction conditions. We found that peptide selectivity data closely matched glycosylation trends on small sequon motifs (GlycTags) within heterologous proteins, including an Fc human antibody fragment, in vitro and in the cytoplasm of living cells. The data collected in this work allows for design of polypeptide sequences for efficient, site-specific modification with NGTs and the GlycoSCORES workflow provides a systematic tool to characterize other polypeptide glycosyltransferases, and site-specifically control glycosylation structures.

SUMMARY

Disclosed are components, systems, and methods for glycoprotein protein synthesis in vitro and in vivo. In particular, the present invention relates to components, systems, and methods for identifying amino acid glycosylation tag motifs ("GlycTags") for N-glycosyltransferases. The amino acid sequence of a protein may be modified to include a GlycTag that has been identified by the disclosed components, systems, and methods. The modified amino acid sequence of the protein then may be expressed in vitro, for example in a cell-free protein synthesis (CFPS) system, or in vivo, for example in a recombinant prokaryotic cell, in the presence of the corresponding N-glycosyltransferase and a sugar donor for the N-glycosyltransferase, where the N-glycosyltransferase transfers the sugar to the corresponding GlycTag in the amino acid sequence of the expressed protein to prepare a glycosylated variant of the protein.

As such, the disclosed methods may include methods for synthesizing a glycoprotein and/or a recombinant glycoprotein, for example a recombinant glycoprotein variant of a target protein. The disclosed methods may comprise (a) expressing in vivo, for example in a prokaryotic cell or a eukaryotic cell, or in vitro, for example in a prokaryotic-based or a eukaryotic based cell-free protein synthesis (CFPS) reaction, a polypeptide comprising the amino acid sequence of a target protein which includes an amino acid motif or that has been modified to include a heterologous amino acid motif (i.e., a "GlycTag") that is glycosylated by an N-glycosyltransferase. In some embodiment, the amino acid motif or heterologous amino acid motif comprises an amino acid sequence selected from SEQ ID NOs:1-1-549, for example where the amino acid sequence of the target protein has been modified to include an amino acid sequence selected from SEQ ID NOs:1-549. For example, the amino acid sequence of one of SEQ ID NOs: 1-549 may be present or inserted into the amino acid sequence of the target protein. Alternatively, the amino acid sequence of the target protein may be modified by replacing one or more amino acids such that an amino acid sequence selected from SEQ ID NOs: 1-549 is present in the modified amino acid sequence of the target protein. The disclosed methods for synthesizing a glycoprotein optionally also may comprise (b) expressing in vivo, for example in a prokaryotic cell or eukaryotic cell, or in vitro, for example in a prokaryotic-based or eukaryotic CFPS reaction, the N-glycosyltransferase which glycosylates the amino acid motif or heterologous amino acid motif, and optionally also may comprise (c) reacting the polypeptide and the N-glycosyltransferase in the presence of a sugar donor, wherein the N-glycosyltransferase glycosylates the amino acid motif or heterologous amino acid motif of the polypeptide with the sugar to synthesize the glycoprotein or recombinant glycoprotein.

In the disclosed methods for synthesizing a glycoprotein or recombinant glycoprotein, the amino acid motif or heterologous amino acid motif (i.e., a "GlycTag") may comprise an amino acid sequence of one of SEQ ID NOs:1-549. In some embodiments, the amino acid motif or heterologous amino acid motif comprises a sequence $X_{-2}$-$X_{-1}$-N-$X_{+1}$-S/T-$X_{+3}$, wherein $X_{-2}$ is selected from Gly, Asn, and Tyr; and/or $X_{-1}$ is selected from Gly and Ala; and/or $X_{+1}$ is selected from Trp, Val, His, Ala, and Ile; and/or $X_{+3}$ is selected from Thr, Met, and Phe.

In some embodiments of the disclosed methods for synthesizing a recombinant glycoprotein, a target protein whose amino acid sequence is modified to prepare a recombinant glycoprotein variant may be a eukaryotic protein. In other embodiments of the disclosed methods for synthesizing a recombinant glycoprotein, a target protein whose amino acid sequence is modified to prepare a recombinant glycoprotein variant may be a prokaryotic protein.

In the disclosed methods for synthesizing a glycoprotein or recombinant glycoprotein, the steps of the method may be performed in vivo, for example in a prokaryotic cell or a eukaryotic cell, or in vitro, for example in a prokaryotic-based or a eukaryotic-based CFPS reaction. In some embodiments, one or more steps of the methods for synthesizing a a glycoprotein or recombinant glycoprotein may be performed in vitro, for example in a prokaryotic-based or a eukaryotic-based CFPS reaction, and one or more other steps of the methods for synthesizing a a glycoprotein or recombinant glycoprotein may be performed in vivo, for example in a prokaryotic cell or a eukaryotic cell. In other embodiments, all steps of the methods for synthesizing a a glycoprotein or recombinant glycoprotein are performed in vitro, for example in a prokaryotic-based or a eukaryotic-based CFPS reaction, or all steps of the methods for synthesizing a a glycoprotein or recombinant glycoprotein are performed in vitro, for example in a prokaryotic-based or a eukaryotic-based CFPS reaction. Suitable prokaryotic-based CFPS reactions for the disclosed methods may include, but are not limited to, an *Escherichia coli*-based CFPS reaction (i.e., where a lysate from recombinant *E. coli* is used in the CFPS reaction). Suitable eukaryotic-based CFPS reactions for the disclosed methods include, but are not limited to a *Saccharomyces-cerevisiae*-based CFPS reaction (i.e., where a lysate from recombinant *Saccharomyces-cerevisiae* is used in the CFPS reaction).

In the disclosed methods for synthesizing a glycoprotein or recombinant glycoprotein, an N-glycosyltransferase typically is expressed and utilized to glycosylate a modified amino acid sequence of a target protein. In some embodiments, the N-glycosyltransferase is a prokaryotic N-glycosyltransferase. Suitable N-glycosyltransferases may include but are not limited to an N-glycosyltransferase from one of *Actinobacillus* spp., *Escherichia* spp., *Haemophilus* spp., or *Mannheimia* spp.. In particular, suitable N-glycosyltransferases may include but are not limited to an N-glycosyltransferase from one of *Actinobacillus pleuropneumoniae*, *Escherichia coli*, *Haemophilus influenza*, *Mannheimia haemolytica*, or *Haemophilus dureyi*. In other embodiments, the N-glycosyltransferase is a eukaryotic N-glycosyltransferase.

Also disclosed are methods for synthesizing a glycoprotein or recombinant glycoprotein, the methods comprising: (a) expressing in a cell or in a cell-free protein synthesis (CFPS) reaction a polypeptide comprising the amino acid sequence of a target protein which includes naturally two or more different amino acid motifs that includes an asparagine that is glycosylated by two or more different N-glycosyltransferases or that has been modified to include two or more different heterologous amino acid motifs that includes an asparagine that is glycosylated by two or more different N-glycosyltransferases, the amino acid motifs or heterologous amino acid motifs optionally comprising an amino acid sequence selected from SEQ ID NOs:1-549; (b) expressing in one or more cells or in one or more CFPS reactions the two or more different N-glycosyltransferases, where the two or more different N-glycosyltransferases are expressed simultaneously in the same cell or CFPS reaction or sequentially in two or more different cells or two or more different CFPS reactions; and (c) reacting the polypeptide and the two or more different N-glycosyltransferases in the presence of two or more sugar donors which are the same or different, where the polypeptide is reacted with the two or more different N-glycosyltransferases simultaneously for example in the same cell or CFPS reaction, or sequentially for example in two or more different cells or two or more different CFPS reactions, and where the two or more different N-glycosyltransferases glycosylate the two or more different amino acid motifs or heterologous amino acid motifs of the polypeptide with the sugar of the two or more sugar donors to synthesize the recombinant glycoprotein.

Also disclosed herein are methods for selecting an amino acid motif that is glycosylated by an N-glycosyltransferase. The disclosed methods may include (a) reacting a library of peptides comprising different amino acid motifs with a recombinant N-glycosyltransferase in the presence of a sugar donor, where the N-glycosyltransferase glycosylates one or more of the amino acid motifs of the peptides; and; (b) detecting glycosylation of the peptides to select the amino acid motif that is glycosylated by the N-glycosyltransferase.

In particular, the disclosed methods for selecting an amino acid motif that is glycosylated by an N-glycosyltransferase may include: (a) reacting a library of peptides comprising different amino acid motifs with an N-glycosyltransferase in the presence of a sugar donor, wherein the N-glycosyltransferase glycosylates one or more of the different amino acid motifs of the peptides; (b) detecting glycosylation of the reacted peptides by immobilizing the reacted peptides on a substrate comprising self-assembled monolayers, and performing matrix-assisted laser desorption/ionization mass spectrometry of the immobilized reacted peptides to select the amino acid motif that is glycosylated by the N-glycosyltransferase. In some embodiments of the disclosed selection methods, the library of peptides comprise a C-terminal Cys, the self-assembled monolayers comprise free maleimides, and the C-terminal Cys of the peptides reacts with the free maleimides to form a bond (e.g., a C—S bond) and covalently immobilize the peptide. In other embodiments of the disclosed selection methods, the library of peptides comprise a C-terminal alkyne, the self-assembled monolayers comprise free azides, and the C-terminal alkyne of the peptides reacts with the free azides to form a bond (e.g., a triazole and in particular a 1,2,3-triazole) and covalently immobilize the peptide. In alternative embodiments of the disclosed selection methods, the library of peptides comprise a C-terminal azide, the self-assembled monolayers comprise free alkynes, and the C-terminal azide of the peptides reacts with the free alkynes to form a bond (e.g., a triazole and in particular a 1,2,3-triazole) and covalently immobilize the peptide.

In some embodiments of the disclosed methods for selecting an amino acid motif that is glycosylated by an N-glycosyltransferase, the library of peptides comprises at least about 100, 500, 1000, 2000, 5000 or more peptides having a randomized sequence, where each peptide of the library has a different sequence. In some embodiments of the disclosed methods, the peptides comprise at least 6, 7, 8, or more amino acids and comprise at least a sequence $X_2$-$X_{-1}$-N-$X_{+1}$-S/T-R-C wherein X is any amino acid.

In the disclosed methods for selecting an amino acid motif that is glycosylated by an N-glycosyltransferase, self-assembled monolayers for matrix-assisted laser desorption/ionization mass spectrometry (SAMDI-MS) is utilized to detect peptides that are glycosylated by the N-glycosyltransferase. Typically, the peptides are covalently immobilized on the self-assembled monolayers via a reaction between free maleimides present on the self-assembled monolayers and the C-terminal Cys of the peptides where the free maleimides and the C-terminal Cys react to form a covalent C-S bond.

BRIEF DESCRIPTION OF THE FIGURES

FIG. 16. NGT only efficiently modifies peptides with Asn at the $X_0$ position. A 19-peptide library with naturally occurring amino acids substituted into YANATTRC (SEQ ID NO:511) at the $X_0$ position was synthesized and evaluated for NGT activity at three reaction conditions spanning the range of conditions relevant to GlycoSCORES analysis. Only Asn at $X_0$ position showed detectable modification. All reactions were conducted with 50 µM peptide and 2.5 mM UDP-Glc, reacted with 0.025 µM NGT synthesized in CFPS incubated at 30° C. for 1 h (1), 0.1 µM NGT synthesized in CFPS incubated at 30° C. for 1 h (1), or 0.5 µM NGT synthesized in CFPS incubated at 30° C. for 21 h (3). Heat maps show the average of n=2 SAMDI-MS spectra acquired from separate peptide immobilizations.

Figure 1A:
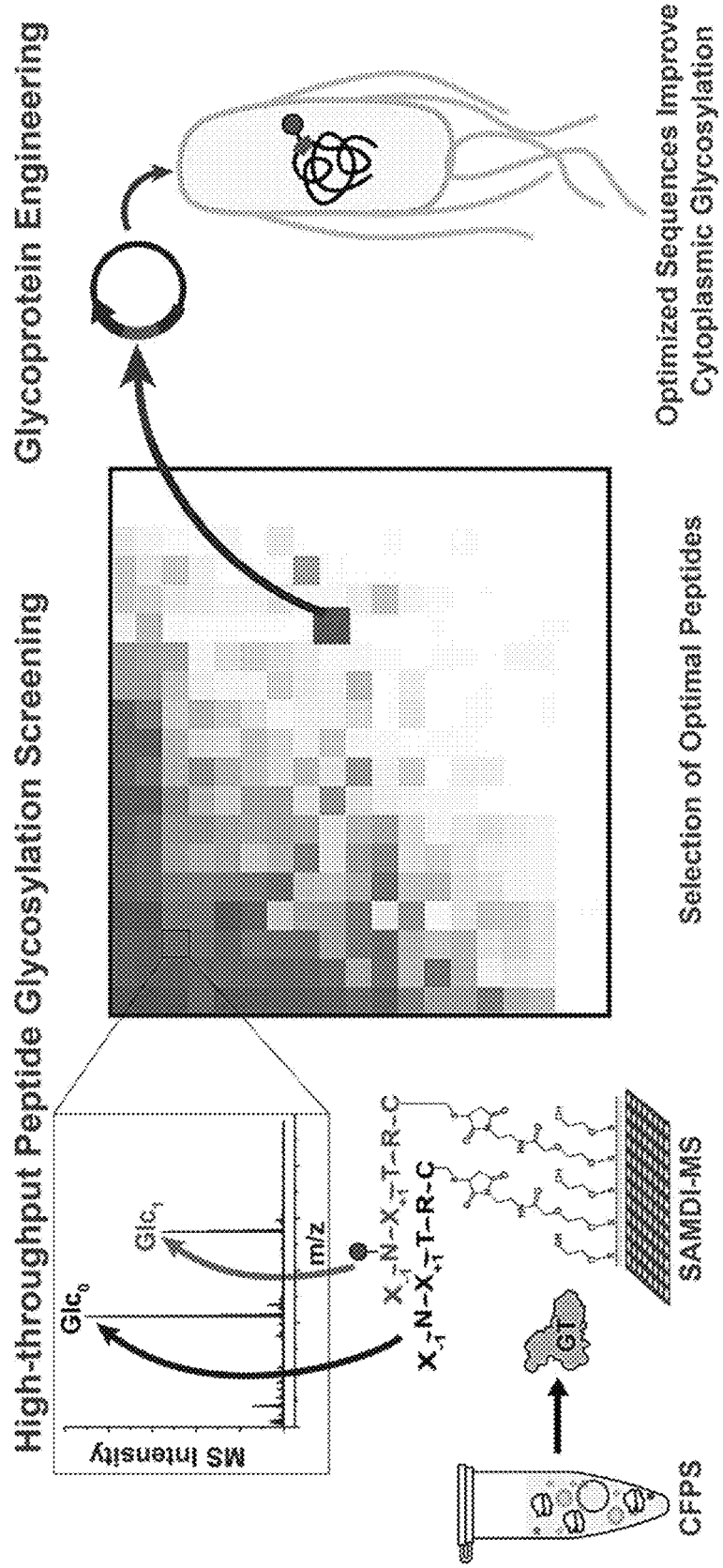
FIG. 1. Strategy for characterizing and designing glycosylation sites. Peptide acceptor and sugar donor preferences of N-glycosyltransferases from *A. pleuropneumoniae* (NGT), *Mannheimia haemolytica* and *Haemophilus ducreyi*, along with two human polypeptide-N-acetylgalactosyltransferases, and the human O-GlcNAc transferase were characterized with 3,480 unique peptides and 13,903 unique reactions using SAMDI and enzyme produced by CFPS. Optimized sequences from NGT were used to design glycosylation sites on three heterologous proteins. Proteins were synthesized and glycosylated in vitro and in the cytoplasm of living *E. coli*.

FIG. 21. In vitro synthesis and glycosylation of Fc. Sequence variants of the Fc target protein were expressed in CFPS for 20 h and glycosylated in vitro using NGT expressed in CFPS. Results show that Fc engineered with optimized GlycoSCORES GlycTag can be efficiently glycosylated in vitro. Unless otherwise noted, each IVG reaction contained 5 µM Fc variant, 4 µM NGT, and 2.5 mM UDP-Glc and was incubated for 2.5 h at 30° C. then purified by Ni-NTA magnetic beads and injected into Q-TOF. Fc and NGT concentration in IVG quantified by $^{14}$C-leucine incorporation. (A) Deconvoluted spectra of Fc-0 variant (QYNSTY (SEQ ID NO: 513)) bearing the naturally occurring glycosylation sequence showed no detectable glycosylation. (B) Deconvoluted spectra of Fc-6 variant (GGNWTT (SEQ ID NO: 514)) bearing optimized GlycTag showing efficient glycosylation. (C) Deconvoluted spectra of Fc-6 variant (GGNWTT (SEQ ID NO: 514)) bearing optimized GlycTag from 12 h IVG reaction showing nearly homogeneous glycosylation. (D) Deconvoluted spectra of Fc-6 variant (GGNWTT (SEQ ID NO: 514)) bearing optimized GlycTag in IVG reaction condition without NGT showing that modification is due to NGT. (E) Deconvoluted spectra of Fc-N/Q variant (QYQSTY (SEQ ID NO: 558)) showing no glycosylation at alternative sites. All spectra representative of n=2 IVGs. Spectra were processed by Bruker Compass Max Entropy Deconvolution of 700-3000 m/z range into mass range of 20,000-30,000 u.

FIG. 22. Deconvoluted mass spectra from LC-MS analysis of HMW1ct variants synthesized and glycosylated in the cytoplasm of living *E. coli*. The HMW1ct glycosylation site at Asn1366 was redesigned to the biological consensus sequence (GANATA)[18] (SEQ ID NO:515) or the GlycoSCORES optimized GlycTag (GGNWTT (SEQ ID NO:514)). All other Asn residues within N-X-S/T motifs were mutated to Gln, generating a variant with only one site available for efficient glycosylation by NGT. Variants of the HMW1ct target protein were induced for 1 h followed by a 2 h induction of NGT in BL21(DE3) *E. coli* then purified by Ni-NTA and injected into LC-TOF. (A) Representative deconvoluted spectra of n=3 expression cultures HMW1ct containing the indicated naturally occurring (0; NINATS (SEQ ID NO: 512)), biological consensus[18] (3; GANATA (SEQ ID NO: 515)), and optimized GlycTag (6; GGNWTT (SEQ ID NO: 514)) sequences are shown. Protein modification trends match those predicted by GlycoSCORES of peptides and show that the protein containing the optimized GlycTag sequence is the most efficiently modified. (B) Deconvoluted spectra of HMW1ct-0 variant (NIQATS (SEQ ID NO: 559)) with N/Q substitution to remove glycosylation site showed no detectable glycosylation, indicating that only the redesigned site was efficiently modified. (C) Deconvoluted spectrum of HMW1ct (GGNWTT (SEQ ID NO: 514)) in BL21(DE3) strain with no NGT plasmid present shows no detectable glycosylation. Sequence variants of the HMW1ct target protein were induced for 1 h followed by a 2 h induction of NGT. (A-C) spectra representative of analysis of n=3 cell cultures. (B-C) spectra are representative of n=2 expression cultures. All spectra processed by Agilent Mass Hunter Max Entropy Deconvolution of 700-2000 m/z range into mass range of 32,500-37,500 u. (D) Relative peak areas of $Glc_1/(Glc_0+Glc_1)$ for HMW1ct containing naturally occurring (0), biological consensus[18] (3), and GlycoSCORES optimized sequence (6) at Asn1366 position. Relative peak areas calculated from extracted ion chromatograms of the 10 most abundant peaks based on theoretical average masses (see Methods). Average and S.D. of triplicate (n=3) cell cultures are shown.  and * indicate significances by 2-tailed t-tests of p-values 0.0035 and 0.00037, respectively.

Figure 23:
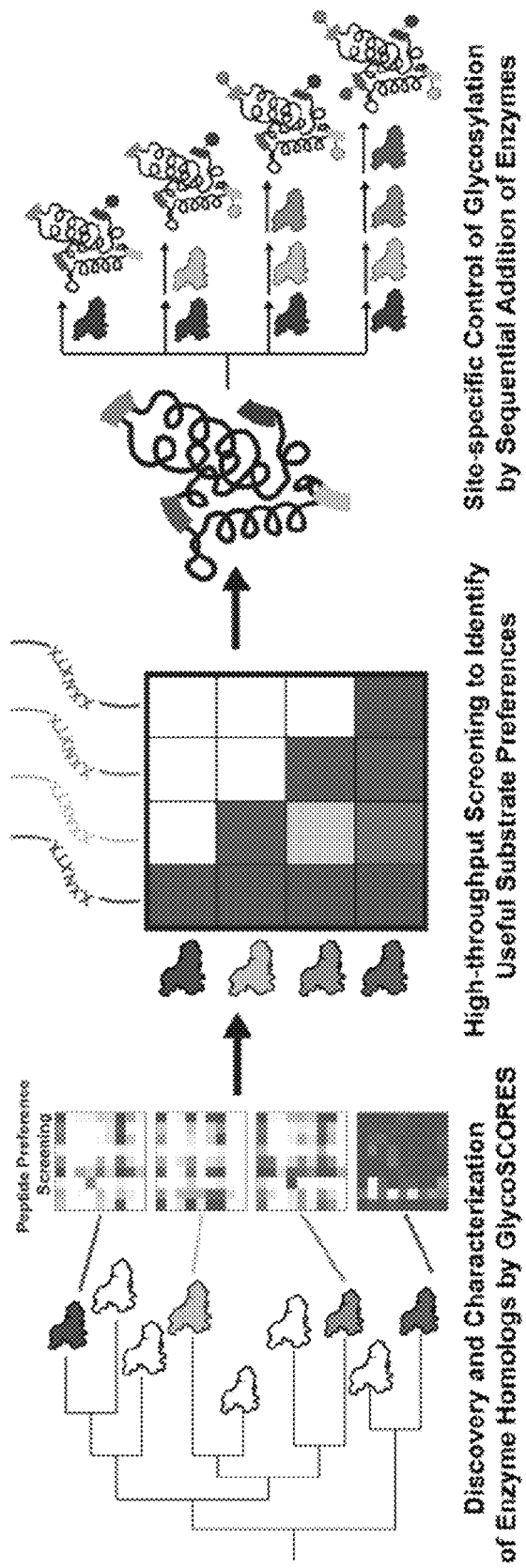

FIG. 23. Site-specific control of glycosylation by rapid enzyme characterization and sequential addition of enzymes. Four NGT homologs were selected from a phylogenetic screen of putative NGT enzymes and characterized using GlycoSCORES to find differences in peptide specificity. Peptide sequences showing conditional orthogonality which would enable site-specific glycosylation when applied in the correct order, were discovered by further GlycoSCORES optimization. Optimized GlycTags were incorporated into a single glycoprotein and NGTs were added sequentially to site-specifically control glycosylation at up to four glycosylation sites within one protein.

Figure 24:
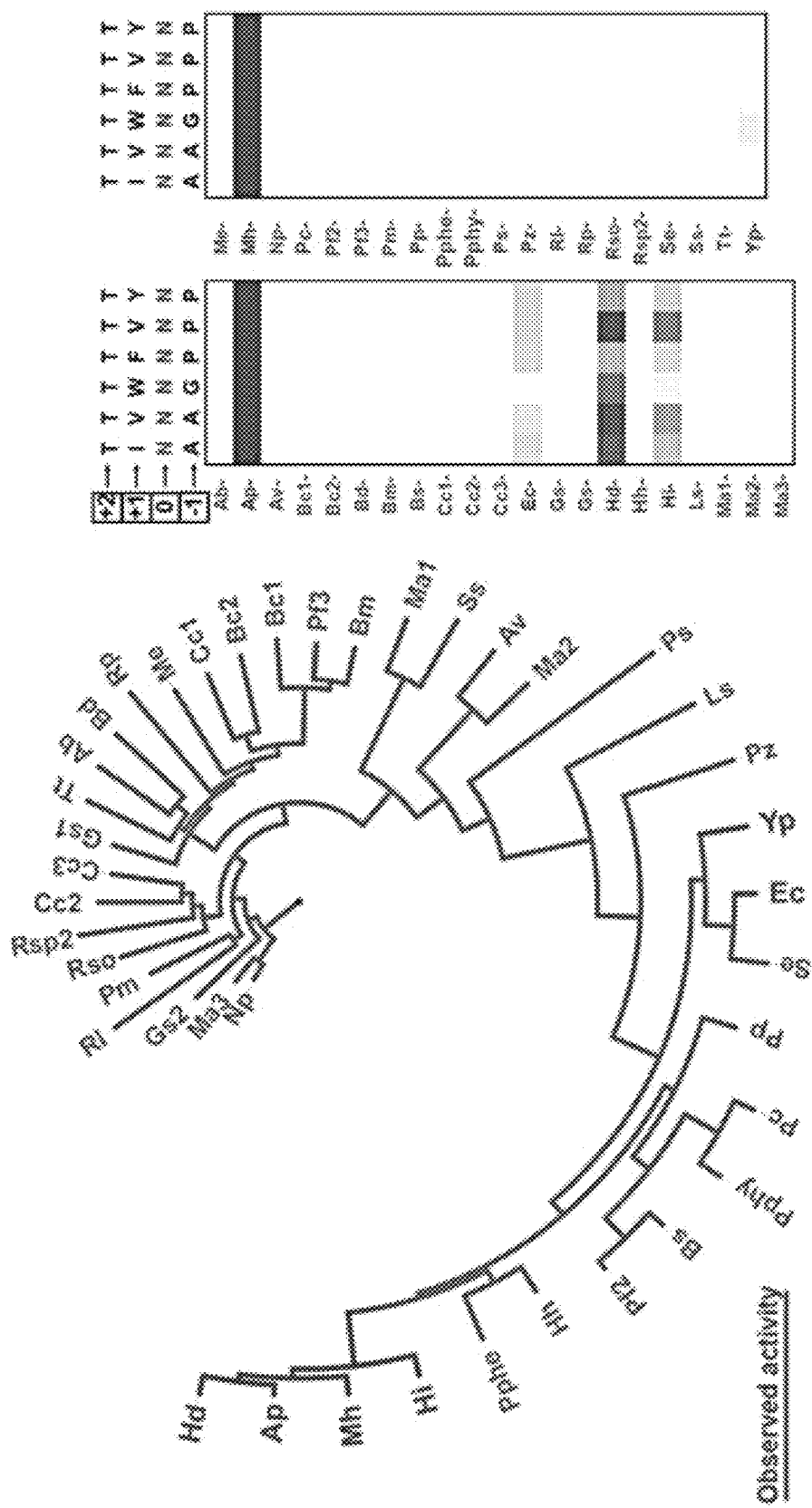
Figure 25A:
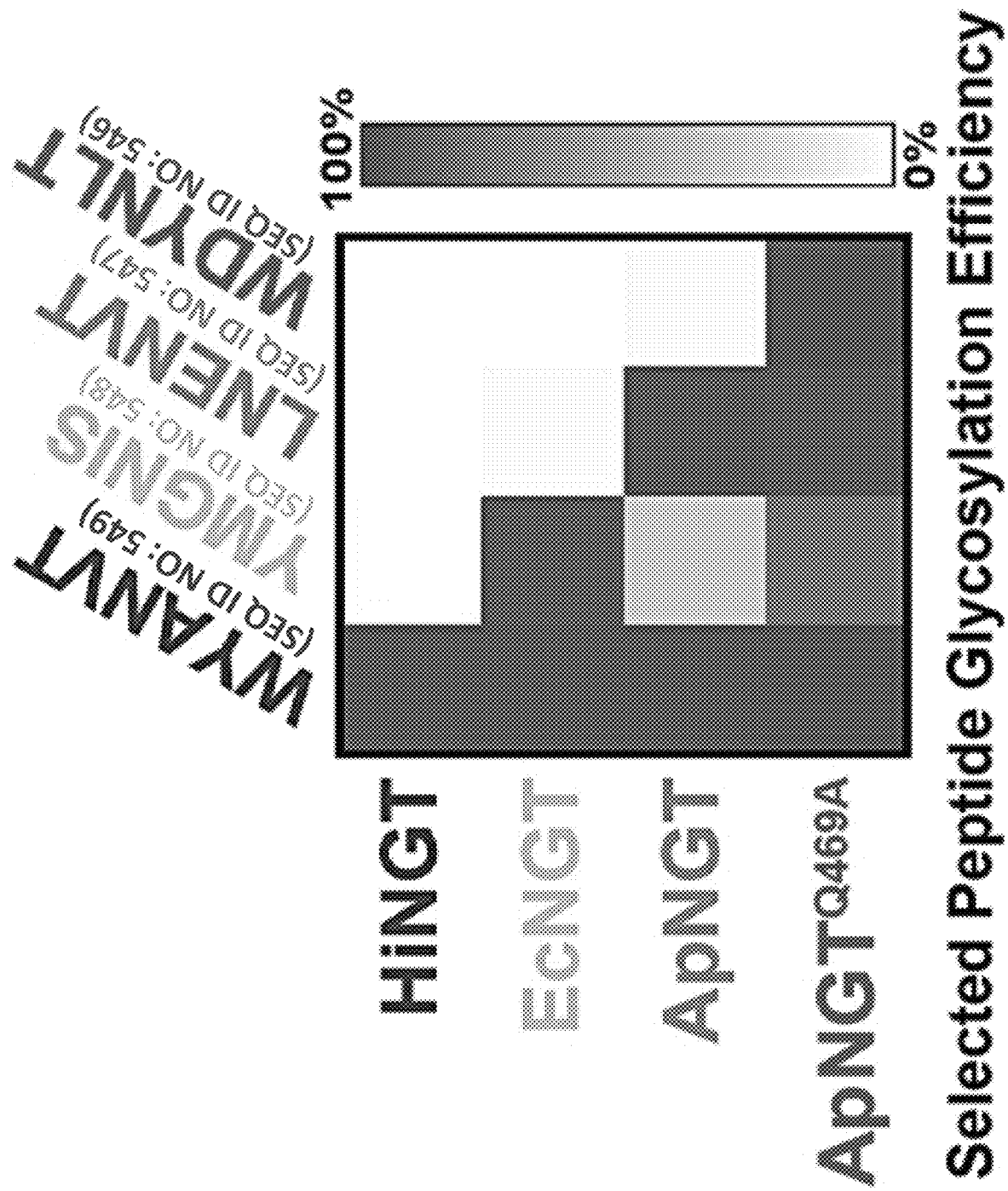
Figure 25B:
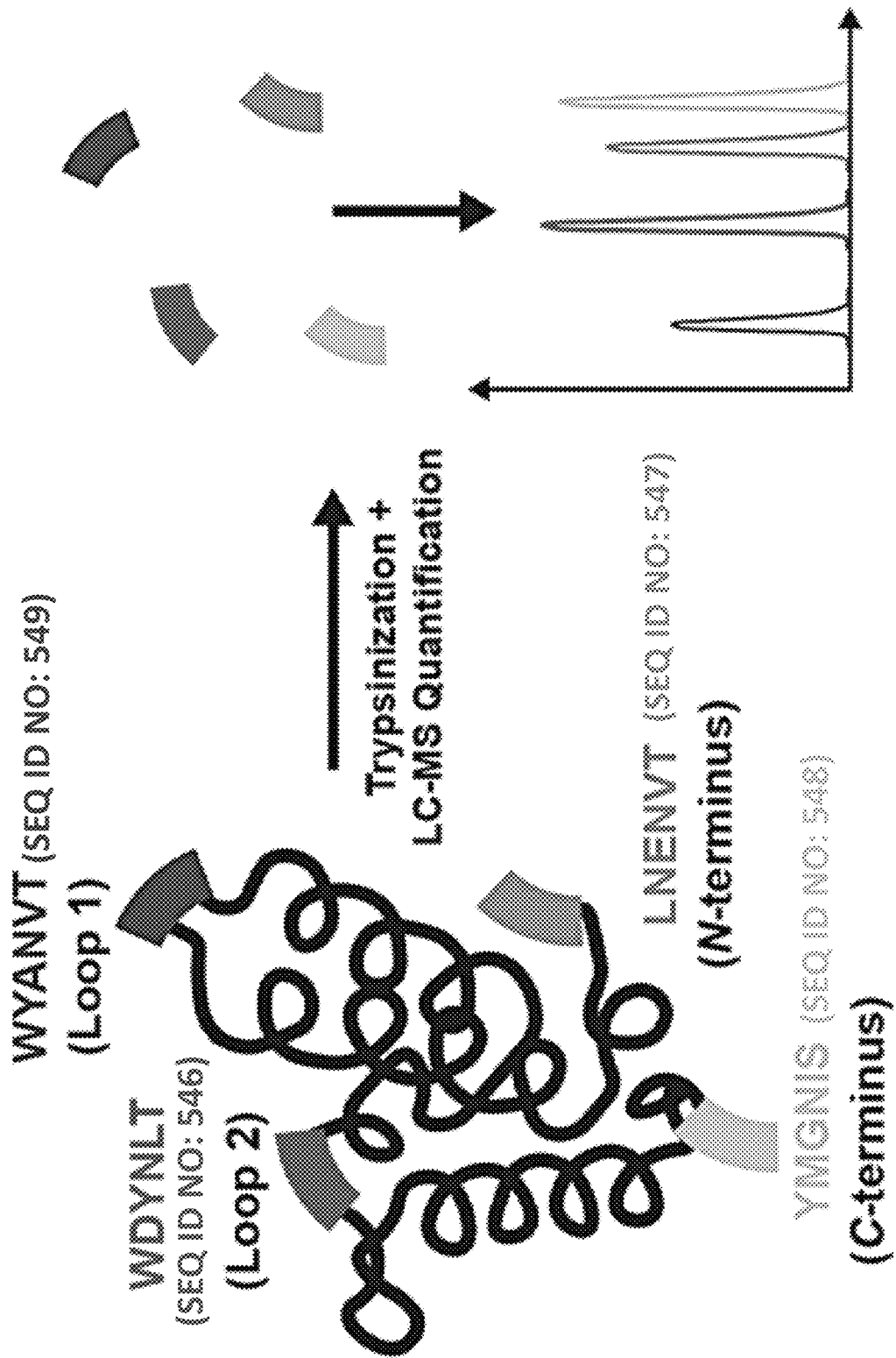
Figure 25C:
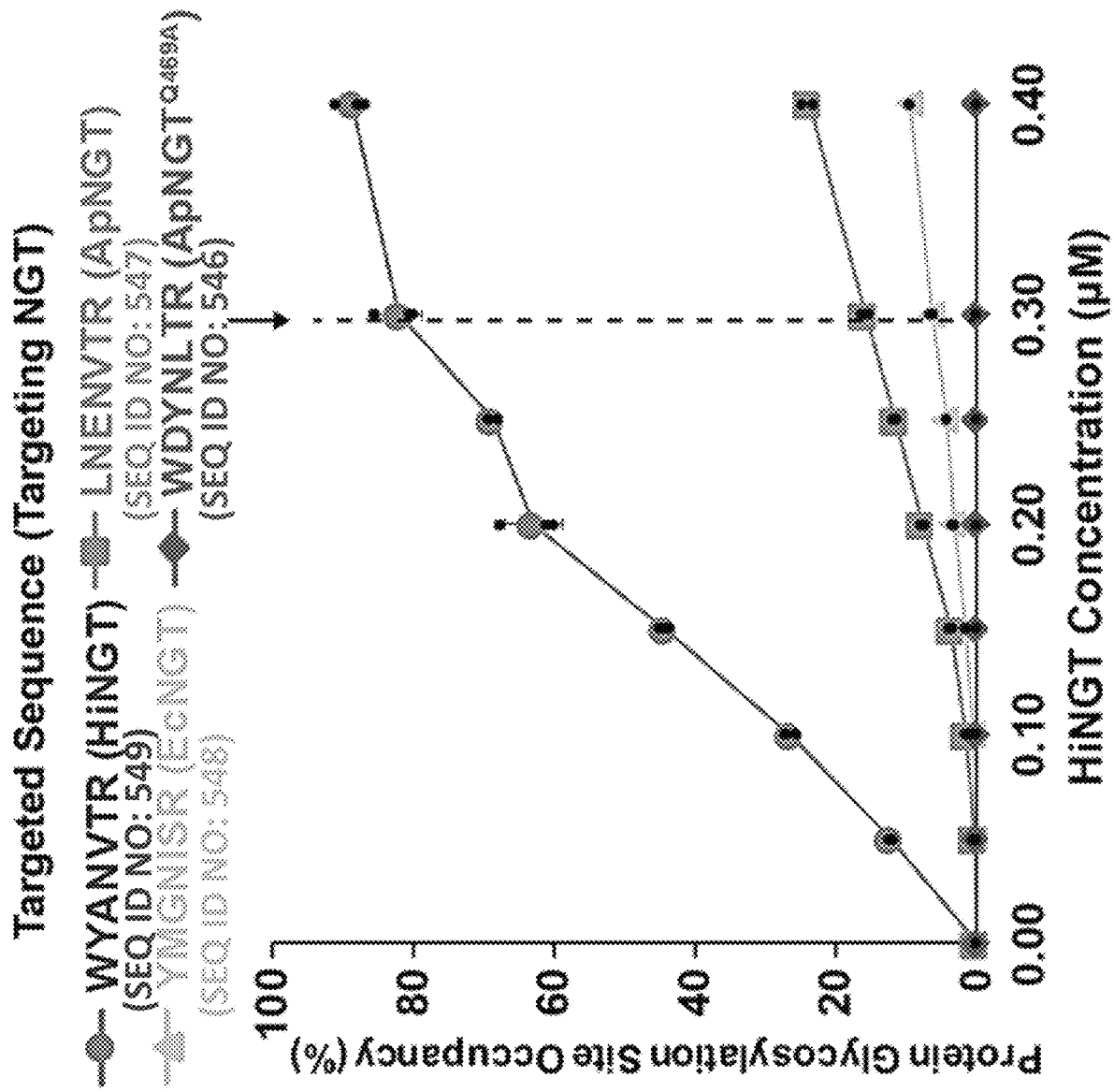
Figure 25D:
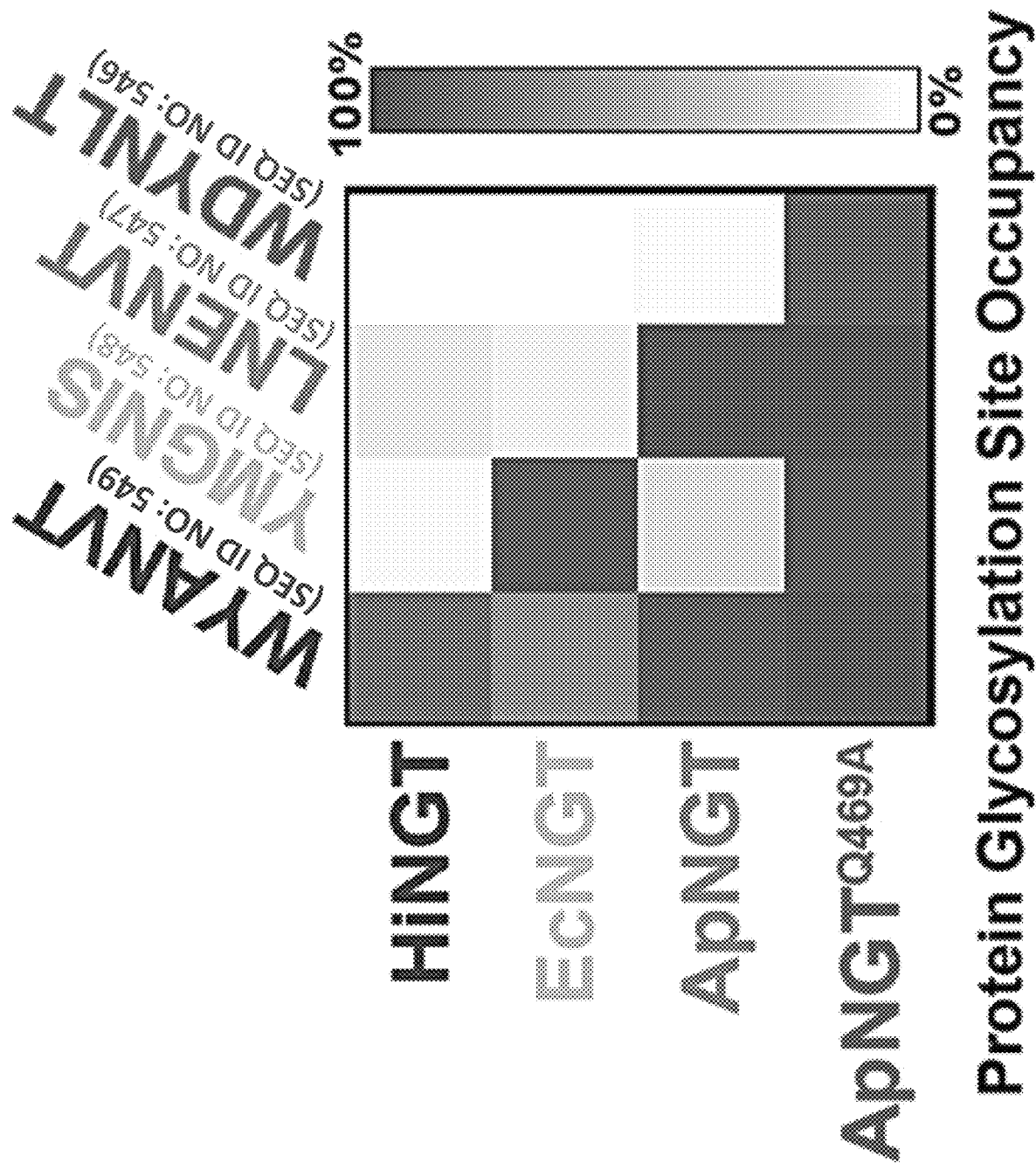

FIG. 24. Phylogenetic tree of 41 putative NGTs from CAZY database which were screened for N-glycosyltransferase activity by expression and CFPS and analysis by SAMDI-MS.

FIG. 25. Optimized GlycTag sequences show conditional orthogonality at peptide level and enable differential targeting of glycosylation sites within protein. (a) Conditional orthogonality of optimized 6-mer GlycTags. Selected GlycTags (WYANVT (SEQ ID NO: 549), YMGNIS (SEQ ID NO: 548), LNENVT (SEQ ID NO: 547), and WDYNLT (SEQ ID NO: 546)) were screened for HiNGT, EcNGT, ApNGT and ApNGT$^{Q469A}$ modification by SAMDI in triplicate experiments. Heat map shows conditional orthogonality. Experimental conditions: 0.2 µM purified HiNGT or 0.67 µM purified EcNGT, 30° C. for 21 h; 0.45 µM purified ApNGT or 0.1 µM purified ApNGT$^{Q469A}$ 30° C. for 3 h. (b) Optimized 6-mer GlycTags were inserted into the N-terminus (LNENVT (SEQ ID NO: 547)), C-terminus (YMGNIS (SEQ ID NO: 548)), and two exposed loops (WYANVT (SEQ ID NO: 549) and WDYNLT (SEQ ID NO: 546)) of the glycosylation model protein Im7, with flanking sequences of RATT (SEQ ID NO:516)-GlycTag-AGGR (SEQ ID NO:517) to facilitate trypsinization and quantitative LC-MS analysis. (c) Differential targeting of four optimized Glyc-Tags (WYANVT (SEQ ID NO: 549), YMGNIS (SEQ ID NO: 548), LNENVT (SEQ ID NO: 547), and WDYNLT (SEQ ID NO: 546)) within a single Im7 target protein. Im7 bearing the four optimized GlycTags was reacted with 2.5 mM UDP-Glucose and various concentrations of each purified NGT for 4 h. After the modification, Im7 was purified using Ni-NTA functionalized magnetic beads, treated with trypsin and analyzed by LC-qTOF. (d) Heatmap showing conditional orthogonality of each NGT for 6-mer GlycTags (WYANVT (SEQ ID NO: 549), YMGNIS (SEQ ID NO: 548), LNENVT (SEQ ID NO: 547), and WDYNLT (SEQ ID NO: 546)) within Im7 under optimized conditions. Experimental conditions: 0.3 µM purified HiNGT, 0.3 µM purified EcNGT, 0.04 µM purified ApNGT or 0.04 µM purified ApNGT$^{Q469A}$ 30° C. for 4 h. All are experimental triplicate. Similar differential modification patterns by different NGTs were observed for peptide sequences and GlycTags within an engineered Im7 acceptor protein.

Figure 26A:
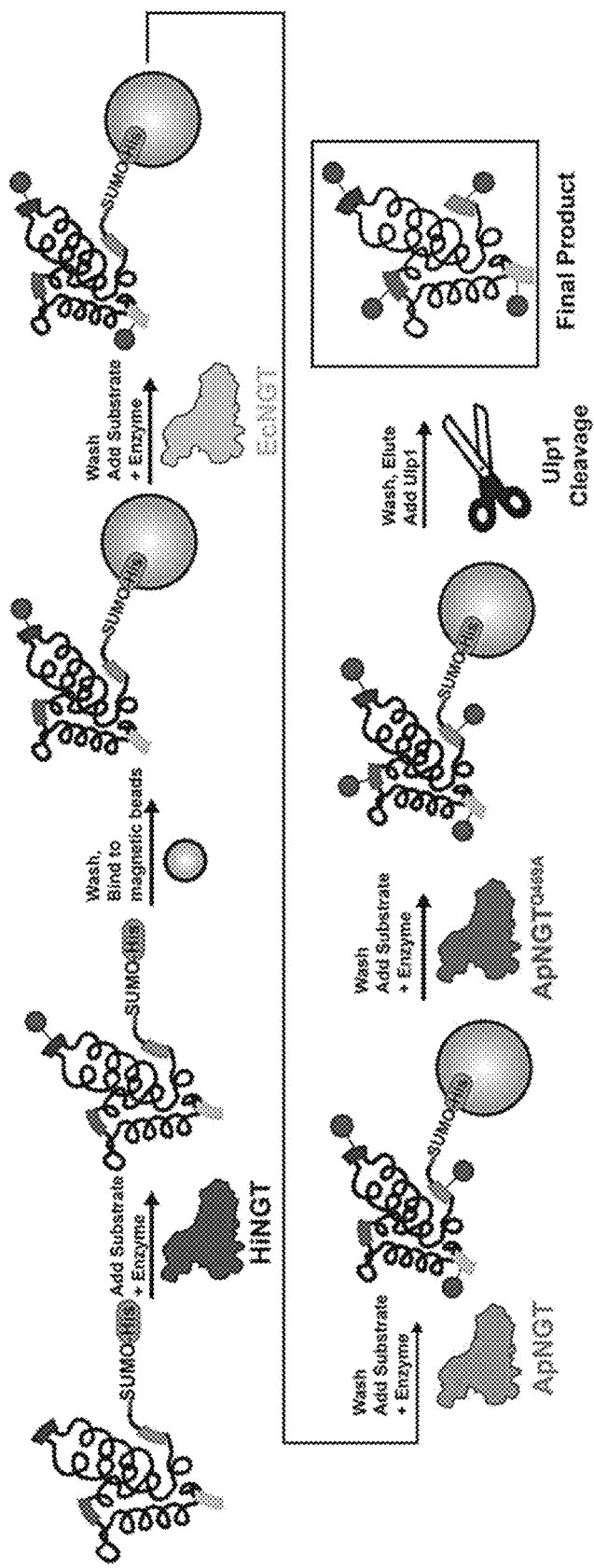
Figure 26B:
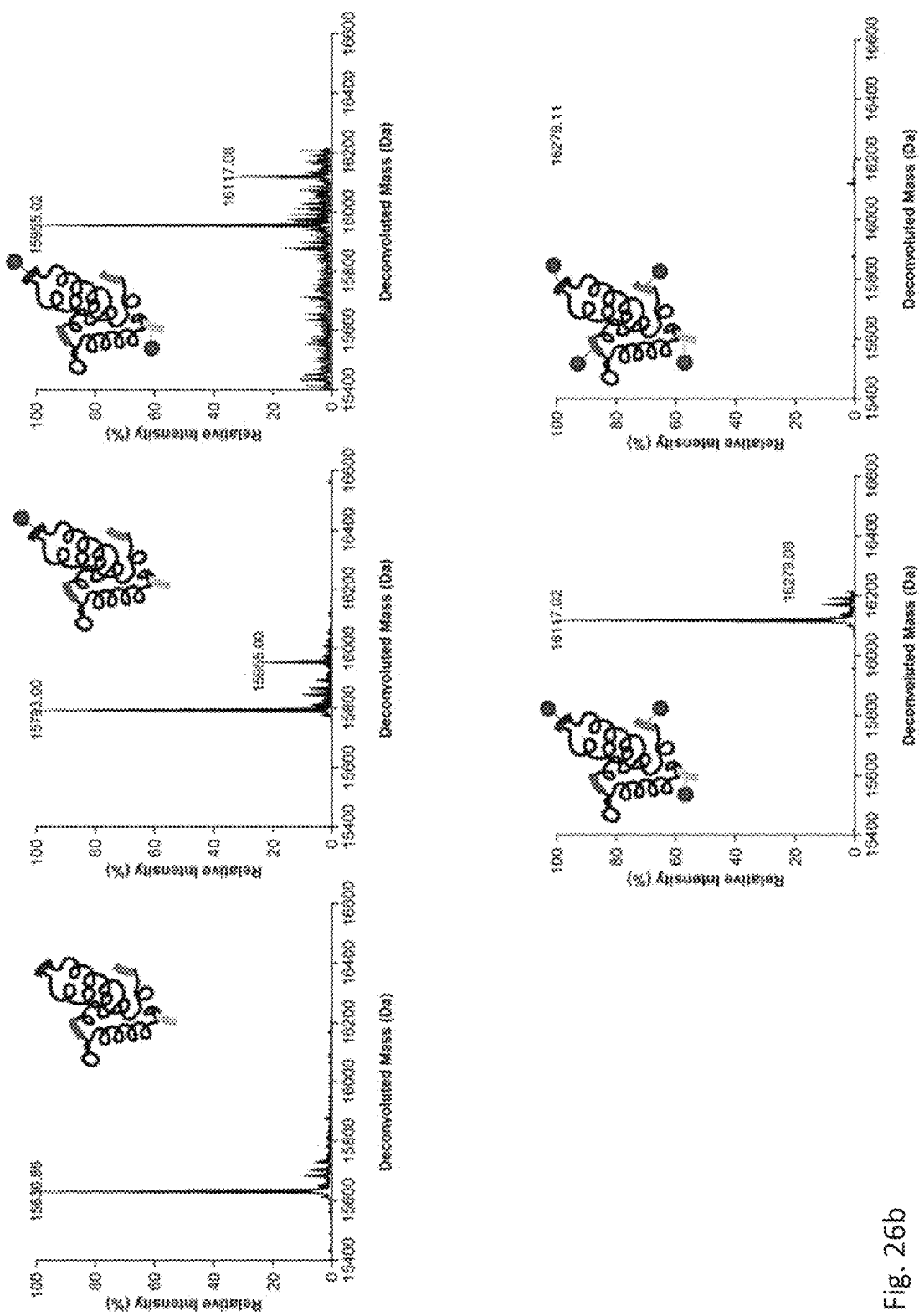
Figure 26C:
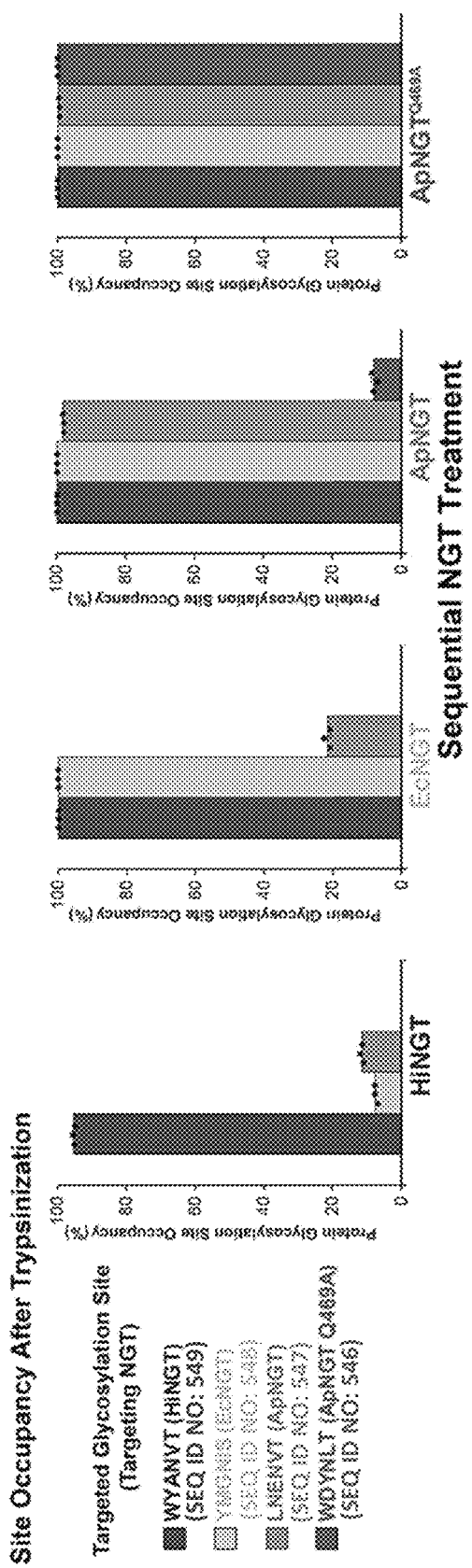

FIG. 26. Site-specific control of glycosylation at four distinct GlycTag sequences within one target protein. (a) A workflow for differential control of glycosylation at four sites within Im7 by sequential addition of NGT enzymes. (b) The intact Im7 MS spectra and bar graph percentage of nGlc-1m7 after each step; triplicate. (c) A bar graph of modification of each of the four GlycTags (WYANVT (SEQ ID NO: 549), YMGNIS (SEQ ID NO: 548), LNENVT (SEQ ID NO: 547), and WDYNLT (SEQ ID NO: 546)) after each step and trypsinization of the target protein bearing four distinct GlycTags; triplicate.

DETAILED DESCRIPTION

Definitions and Terminology

The disclosed components, systems, and methods for glycoprotein and recombinant glycoprotein protein synthesis may be further described using definitions and terminology as follows. The definitions and terminology used herein are for the purpose of describing particular embodiments only, and are not intended to be limiting.

As used in this specification and the claims, the singular forms "a," "an," and "the" include plural forms unless the context clearly dictates otherwise. For example, the term "a oligosaccharide" or "an N-glycosyltransferase" should be interpreted to mean "one or more oligosaccharides" and "one or more N-glycosyltransferase," respectively, unless the context clearly dictates otherwise. As used herein, the term "plurality" means "two or more."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

The phrase "such as" should be interpreted as "for example, including." Moreover the use of any and all exemplary language, including but not limited to "such as", is intended merely to better illuminate the invention and does not pose a limitation on the scope of the invention unless otherwise claimed.

Furthermore, in those instances where a convention analogous to "at least one of A, B and C, etc." is used, in general such a construction is intended in the sense of one having ordinary skill in the art would understand the convention (e.g., "a system having at least one of A, B and C" would include but not be limited to systems that have A alone, B alone, C alone, A and B together, A and C together, B and C together, and/or A, B, and C together.). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase "A or B" will be understood to include the possibilities of "A" or 'B or "A and B."

All language such as "up to," "at least," "greater than," "less than," and the like, include the number recited and refer to ranges which can subsequently be broken down into ranges and subranges. A range includes each individual member. Thus, for example, a group having 1-3 members refers to groups having 1, 2, or 3 members. Similarly, a group having 6 members refers to groups having 1, 2, 3, 4, or 6 members, and so forth.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use and aspect of a described embodiment or feature contained in the same, or a definitive decision to use a specific skill regarding a described embodiment or feature contained in the same. In this latter context, the modal verb "may" has the same meaning and connotation as the auxiliary verb "can."

As used herein, the terms "bind," "binding," "interact," "interacting," "occupy" and "occupying" refer to covalent interactions, noncovalent interactions and steric interactions. A covalent interaction is a chemical linkage between two atoms or radicals formed by the sharing of a pair of electrons (a single bond), two pairs of electrons (a double bond) or three pairs of electrons (a triple bond). Covalent interactions are also known in the art as electron pair interactions or electron pair bonds. Noncovalent interactions include, but are not limited to, van der Waals interactions, hydrogen bonds, weak chemical bonds (via short-range noncovalent forces), hydrophobic interactions, ionic bonds and the like. A review of noncovalent interactions can be found in Alberts et al., in Molecular Biology of the Cell, 3d edition, Garland Publishing, 1994. Steric interactions are generally understood to include those where the structure of the compound is such that it is capable of occupying a site by virtue of its three dimensional structure, as opposed to any attractive forces between the compound and the site.

Polynucleotides and Synthesis Methods

The terms "nucleic acid" and "oligonucleotide," as used herein, refer to polydeoxyribonucleotides (containing 2-deoxy-D-ribose), polyribonucleotides (containing D-ribose), and to any other type of polynucleotide that is an N glycoside of a purine or pyrimidine base. There is no intended distinction in length between the terms "nucleic acid", "oligonucleotide" and "polynucleotide", and these terms will be used interchangeably. These terms refer only to the primary structure of the molecule. Thus, these terms include double- and single-stranded DNA, as well as double- and single-stranded RNA. For use in the present methods, an oligonucleotide also can comprise nucleotide analogs in which the base, sugar, or phosphate backbone is modified as well as non-purine or non-pyrimidine nucleotide analogs.

Oligonucleotides can be prepared by any suitable method, including direct chemical synthesis by a method such as the phosphotriester method of Narang et al., 1979, *Meth. Enzymol.* 68:90-99; the phosphodiester method of Brown et al., 1979, *Meth. Enzymol.* 68:109-151; the diethylphosphoramidite method of Beaucage et al., 1981, *Tetrahedron Letters* 22:1859-1862; and the solid support method of U.S. Pat. No. 4,458,066, each incorporated herein by reference. A review of synthesis methods of conjugates of oligonucleotides and modified nucleotides is provided in Goodchild, 1990, *Bioconjugate Chemistry* 1(3): 165-187, incorporated herein by reference.

The term "amplification reaction" refers to any chemical reaction, including an enzymatic reaction, which results in increased copies of a template nucleic acid sequence or results in transcription of a template nucleic acid. Amplification reactions include reverse transcription, the polymerase chain reaction (PCR), including Real Time PCR (see U.S. Pat. Nos. 4,683,195 and 4,683,202; PCR Protocols: A Guide to Methods and Applications (Innis et al., eds, 1990)), and the ligase chain reaction (LCR) (see Barany et al., U.S. Pat. No. 5,494,810). Exemplary "amplification reactions conditions" or "amplification conditions" typically comprise either two or three step cycles. Two-step cycles have a high temperature denaturation step followed by a hybridization/elongation (or ligation) step. Three step cycles comprise a denaturation step followed by a hybridization step followed by a separate elongation step.

The terms "target," "target sequence", "target region", and "target nucleic acid," as used herein, are synonymous and refer to a region or sequence of a nucleic acid which is to be amplified, sequenced, or detected.

The term "hybridization," as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which hybridization of fully complementary nucleic acid strands is strongly preferred are referred to as "stringent hybridization conditions" or "sequence-specific hybridization conditions". Stable duplexes of substantially complementary sequences can be achieved under less stringent hybridization conditions; the degree of mismatch tolerated can be controlled by suitable adjustment of the hybridization conditions. Those skilled in the art of nucleic acid technology can determine duplex stability empirically considering a number of variables including, for example, the length and base pair composition of the oligonucleotides, ionic strength, and incidence of mismatched base pairs, following the guidance provided by the art (see, e.g., Sambrook et al., 1989, Molecular Cloning-A Laboratory Manual, Cold Spring Harbor Laboratory, Cold Spring Harbor, New York; Wetmur, 1991, Critical Review in Biochem. and Mol. Biol. 26(3/4):227-259; and Owczarzy et al., 2008, Biochemistry, 47: 5336-5353, which are incorporated herein by reference).

The term "primer," as used herein, refers to an oligonucleotide capable of acting as a point of initiation of DNA synthesis under suitable conditions. Such conditions include those in which synthesis of a primer extension product complementary to a nucleic acid strand is induced in the presence of four different nucleoside triphosphates and an agent for extension (for example, a DNA polymerase or reverse transcriptase) in an appropriate buffer and at a suitable temperature.

A primer is preferably a single-stranded DNA. The appropriate length of a primer depends on the intended use of the primer but typically ranges from about 6 to about 225 nucleotides, including intermediate ranges, such as from 15 to 35 nucleotides, from 18 to 75 nucleotides and from 25 to 150 nucleotides. Short primer molecules generally require cooler temperatures to form sufficiently stable hybrid complexes with the template. A primer need not reflect the exact sequence of the template nucleic acid, but must be sufficiently complementary to hybridize with the template. The design of suitable primers for the amplification of a given target sequence is well known in the art and described in the literature cited herein.

Primers can incorporate additional features which allow for the detection or immobilization of the primer but do not alter the basic property of the primer, that of acting as a point of initiation of DNA synthesis. For example, primers may contain an additional nucleic acid sequence at the 5' end which does not hybridize to the target nucleic acid, but which facilitates cloning or detection of the amplified product, or which enables transcription of RNA (for example, by inclusion of a promoter) or translation of protein (for example, by inclusion of a 5'-UTR, such as an Internal Ribosome Entry Site (IRES) or a 3'-UTR element, such as a poly(A)n sequence, where n is in the range from about 20 to about 200). The region of the primer that is sufficiently complementary to the template to hybridize is referred to herein as the hybridizing region.

As used herein, a primer is "specific," for a target sequence if, when used in an amplification reaction under sufficiently stringent conditions, the primer hybridizes primarily to the target nucleic acid. Typically, a primer is specific for a target sequence if the primer-target duplex stability is greater than the stability of a duplex formed between the primer and any other sequence found in the sample. One of skill in the art will recognize that various factors, such as salt conditions as well as base composition of the primer and the location of the mismatches, will affect the specificity of the primer, and that routine experimental confirmation of the primer specificity will be needed in many cases. Hybridization conditions can be chosen under which the primer can form stable duplexes only with a target sequence. Thus, the use of target-specific primers under suitably stringent amplification conditions enables the selective amplification of those target sequences that contain the target primer binding sites.

As used herein, a "polymerase" refers to an enzyme that catalyzes the polymerization of nucleotides. "DNA polymerase" catalyzes the polymerization of deoxyribonucleotides. Known DNA polymerases include, for example,

*Pyrococcus furiosus* (Pfu) DNA polymerase, *E. coli* DNA polymerase I, T7 DNA polymerase and *Thermus aquaticus* (Taq) DNA polymerase, among others. "RNA polymerase" catalyzes the polymerization of ribonucleotides. The foregoing examples of DNA polymerases are also known as DNA-dependent DNA polymerases. RNA-dependent DNA polymerases also fall within the scope of DNA polymerases. Reverse transcriptase, which includes viral polymerases encoded by retroviruses, is an example of an RNA-dependent DNA polymerase. Known examples of RNA polymerase ("RNAP") include, for example, T3 RNA polymerase, T7 RNA polymerase, SP6 RNA polymerase and *E. coli* RNA polymerase, among others. The foregoing examples of RNA polymerases are also known as DNA-dependent RNA polymerase. The polymerase activity of any of the above enzymes can be determined by means well known in the art.

The term "promoter" refers to a cis-acting DNA sequence that directs RNA polymerase and other trans-acting transcription factors to initiate RNA transcription from the DNA template that includes the cis-acting DNA sequence.

As used herein, the term "sequence defined biopolymer" refers to a biopolymer having a specific primary sequence. A sequence defined biopolymer can be equivalent to a genetically-encoded defined biopolymer in cases where a gene encodes the biopolymer having a specific primary sequence.

The polynucleotide sequences contemplated herein may be present in expression vectors. For example, the vectors may comprise: (a) a polynucleotide encoding an ORF of a protein; (b) a polynucleotide that expresses an RNA that directs RNA-mediated binding, nicking, and/or cleaving of a target DNA sequence; and both (a) and (b). The polynucleotide present in the vector may be operably linked to a prokaryotic or eukaryotic promoter. "Operably linked" refers to the situation in which a first nucleic acid sequence is placed in a functional relationship with a second nucleic acid sequence. For instance, a promoter is operably linked to a coding sequence if the promoter affects the transcription or expression of the coding sequence. Operably linked DNA sequences may be in close proximity or contiguous and, where necessary to join two protein coding regions, in the same reading frame. Vectors contemplated herein may comprise a heterologous promoter (e.g., a eukaryotic or prokaryotic promoter) operably linked to a polynucleotide that encodes a protein. A "heterologous promoter" refers to a promoter that is not the native or endogenous promoter for the protein or RNA that is being expressed. Vectors as disclosed herein may include plasmid vectors.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

As used herein, "expression template" refers to a nucleic acid that serves as substrate for transcribing at least one RNA that can be translated into a sequence defined biopolymer (e.g., a polypeptide or protein). Expression templates include nucleic acids composed of DNA or RNA. Suitable sources of DNA for use a nucleic acid for an expression template include genomic DNA, cDNA and RNA that can be converted into cDNA. Genomic DNA, cDNA and RNA can be from any biological source, such as a tissue sample, a biopsy, a swab, sputum, a blood sample, a fecal sample, a urine sample, a scraping, among others. The genomic DNA, cDNA and RNA can be from host cell or virus origins and from any species, including extant and extinct organisms. As used herein, "expression template" and "transcription template" have the same meaning and are used interchangeably.

In certain exemplary embodiments, vectors such as, for example, expression vectors, containing a nucleic acid encoding one or more rRNAs or reporter polypeptides and/or proteins described herein are provided. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Such vectors are referred to herein as "expression vectors." In general, expression vectors of utility in recombinant DNA techniques are often in the form of plasmids. In the present specification, "plasmid" and "vector" can be used interchangeably. However, the disclosed methods and compositions are intended to include such other forms of expression vectors, such as viral vectors (e.g., replication defective retroviruses, adenoviruses and adeno-associated viruses), which serve equivalent functions.

In certain exemplary embodiments, the recombinant expression vectors comprise a nucleic acid sequence (e.g., a nucleic acid sequence encoding one or more rRNAs or reporter polypeptides and/or proteins described herein) in a form suitable for expression of the nucleic acid sequence in one or more of the methods described herein, which means that the recombinant expression vectors include one or more regulatory sequences which is operatively linked to the nucleic acid sequence to be expressed. Within a recombinant expression vector, "operably linked" is intended to mean that the nucleotide sequence encoding one or more rRNAs or reporter polypeptides and/or proteins described herein is linked to the regulatory sequence(s) in a manner which allows for expression of the nucleotide sequence (e.g., in an in vitro transcription and/or translation system). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990).

Oligonucleotides and polynucleotides may optionally include one or more non-standard nucleotide(s), nucleotide analog(s) and/or modified nucleotides. Examples of modified nucleotides include, but are not limited to diaminopurine, $S^2T$, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine and the like. Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone.

The terms "polynucleotide," "polynucleotide sequence," "nucleic acid" and "nucleic acid sequence" refer to a nucleotide, oligonucleotide, polynucleotide (which terms may be used interchangeably), or any fragment thereof. These phrases also refer to DNA or RNA of genomic, natural, or synthetic origin (which may be single-stranded or double-stranded and may represent the sense or the antisense strand).

Regarding polynucleotide sequences, the terms "percent identity" and "% identity" refer to the percentage of residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences. Percent identity for a nucleic acid sequence may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including "blastn," that is used to align a known polynucleotide sequence with other polynucleotide sequences from a variety of databases. Also available is a tool called "BLAST 2 Sequences" that is used for direct pairwise comparison of two nucleotide sequences. "BLAST 2 Sequences" can be accessed and used interactively at the NCBI website. The "BLAST 2 Sequences" tool can be used for both blastn and blastp (discussed above).

Regarding polynucleotide sequences, percent identity may be measured over the length of an entire defined polynucleotide sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, figures, or Sequence Listing, may be used to describe a length over which percentage identity may be measured.

Regarding polynucleotide sequences, "variant," "mutant," or "derivative" may be defined as a nucleic acid sequence having at least 50% sequence identity to the particular nucleic acid sequence over a certain length of one of the nucleic acid sequences using blastn with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). Such a pair of nucleic acids may show, for example, at least 60%, at least 70%, at least 80%, at least 85%, at least 90%, at least 91%, at least 92%, at least 93%, at least 94%, at least 95%, at least 96%, at least 97%, at least 98%, or at least 99% or greater sequence identity over a certain defined length.

Nucleic acid sequences that do not show a high degree of identity may nevertheless encode similar amino acid sequences due to the degeneracy of the genetic code where multiple codons may encode for a single amino acid. It is understood that changes in a nucleic acid sequence can be made using this degeneracy to produce multiple nucleic acid sequences that all encode substantially the same protein. For example, polynucleotide sequences as contemplated herein may encode a protein and may be codon-optimized for expression in a particular host. In the art, codon usage frequency tables have been prepared for a number of host organisms including humans, mouse, rat, pig, E. coli, plants, and other host cells.

A "recombinant nucleic acid" is a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques known in the art. The term recombinant includes nucleic acids that have been altered solely by addition, substitution, or deletion of a portion of the nucleic acid. Frequently, a recombinant nucleic acid may include a nucleic acid sequence operably linked to a promoter sequence. Such a recombinant nucleic acid may be part of a vector that is used, for example, to transform a cell.

The nucleic acids disclosed herein may be "substantially isolated or purified." The term "substantially isolated or purified" refers to a nucleic acid that is removed from its natural environment, and is at least 60% free, preferably at least 75% free, and more preferably at least 90% free, even more preferably at least 95% free from other components with which it is naturally associated.

Peptides, Polypeptides, Proteins, and Synthesis Methods

As used herein, the terms "peptide," "polypeptide," and "protein," refer to molecules comprising a chain a polymer of amino acid residues joined by amide linkages. The term "amino acid residue," includes but is not limited to amino acid residues contained in the group consisting of alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W), and tyrosine (Tyr or Y) residues. The term "amino acid residue" also may include nonstandard or unnatural amino acids. The term "amino acid residue" may include alpha-, beta-, gamma-, and delta-amino acids.

In some embodiments, the term "amino acid residue" may include nonstandard or unnatural amino acid residues contained in the group consisting of homocysteine, 2-Aminoadipic acid, N-Ethylasparagine, 3-Aminoadipic acid, Hydroxylysine, β-alanine, β-Amino-propionic acid, allo-Hydroxylysine acid, 2-Aminobutyric acid, 3-Hydroxyproline, 4-Aminobutyric acid, 4-Hydroxyproline, piperidinic acid, 6-Aminocaproic acid, Isodesmosine, 2-Aminoheptanoic acid, allo-Isoleucine, 2-Aminoisobutyric acid, N-Methylglycine, sarcosine, 3-Aminoisobutyric acid, N-Methylisoleucine, 2-Aminopimelic acid, 6-N-Methyllysine, 2,4-Diaminobutyric acid, N-Methylvaline, Desmosine, Norvaline, 2,2'-Diaminopimelic acid, Norleucine, 2,3-Diaminopropionic acid, Ornithine, and N-Ethylglycine. The term "amino acid residue" may include L isomers or D isomers of any of the aforementioned amino acids.

Other examples of nonstandard or unnatural amino acids include, but are not limited, to a p-acetyl-L-phenylalanine, a p-iodo-L-phenylalanine, an O-methyl-L-tyrosine, a p-propargyloxyphenylalanine, a p-propargyl-phenylalanine, an L-3-(2-naphthyl)alanine, a 3-methyl-phenylalanine, an O-4-allyl-L-tyrosine, a 4-propyl-L-tyrosine, a tri-O-acetyl-GlcNAcpβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-bromophenylalanine, a p-amino-L-phenylalanine, an isopropyl-L-phenylalanine, an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an unnatural analogue of a methionine amino acid; an unnatural analogue of a leucine amino acid; an unnatural analogue of a isoleucine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, 32ufa32hor, phosphono, phosphine, heterocyclic, enone, imine, aldehyde, hydroxylamine, keto, or amino substituted amino acid, or a combination thereof; an amino acid with a photoactivatable cross-linker; a spin-labeled amino acid; a fluorescent amino acid; a metal binding amino acid; a metal-containing amino acid; a radioactive amino acid; a photocaged and/or photoisomerizable amino acid; a biotin or biotin-analogue containing amino acid; a keto containing amino acid; an amino acid comprising polyethylene glycol or polyether; a heavy atom substituted amino acid; a chemically cleavable or photocleavable amino acid; an amino acid with an elongated side chain; an amino acid containing a toxic group; a sugar substituted amino acid; a carbon-linked sugar-containing amino acid; a redox-active amino acid; an α-hydroxy containing acid; an amino thio acid; an α,α disubstituted amino acid; a β-amino acid; a γ-amino acid, a cyclic amino acid other than proline or histidine, and an aromatic amino acid other than phenylalanine, tyrosine or tryptophan.

As used herein, a "peptide" is defined as a short polymer of amino acids, of a length typically of 20 or less amino acids, and more typically of a length of 12 or less amino acids (Garrett & Grisham, Biochemistry, $2^{nd}$ edition, 1999, Brooks/Cole, 110). In some embodiments, a peptide as contemplated herein may include no more than about 2, 3, 4, 5, 6, 7, 8, 9, 10, 11, 12, 13, 14, 15, 16, 17, 18, 19, or 20 amino acids. A polypeptide, also referred to as a protein, is typically of length >100 amino acids (Garrett & Grisham, Biochemistry, $2^{nd}$ edition, 1999, Brooks/Cole, 110). A polypeptide, as contemplated herein, may comprise, but is not limited to, 100, 101, 102, 103, 104, 105, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or more amino acid residues.

A peptide as contemplated herein may be further modified to include non-amino acid moieties. Modifications may include but are not limited to acylation (e.g., O-acylation (esters), N-acylation (amides), S-acylation (thioesters)), acetylation (e.g., the addition of an acetyl group, either at the N-terminus of the protein or at lysine residues), formylation lipoylation (e.g., attachment of a lipoate, a C8 functional group), myristoylation (e.g., attachment of myristate, a C14 saturated acid), palmitoylation (e.g., attachment of palmitate, a C16 saturated acid), alkylation (e.g., the addition of an alkyl group, such as an methyl at a lysine or arginine residue), isoprenylation or prenylation (e.g., the addition of an isoprenoid group such as farnesol or geranylgeraniol), amidation at C-terminus, glycosylation (e.g., the addition of a glycosyl group to either asparagine, hydroxylysine, serine, or threonine, resulting in a glycoprotein). Distinct from glycation, which is regarded as a nonenzymatic attachment of sugars, polysialylation (e.g., the addition of polysialic acid), glypiation (e.g., glycosylphosphatidylinositol (GPI) anchor formation, hydroxylation, iodination (e.g., of thyroid hormones), and phosphorylation (e.g., the addition of a phosphate group, usually to serine, tyrosine, threonine or histidine).

The modified amino acid sequences that are disclosed herein may include a deletion in one or more amino acids. As utilized herein, a "deletion" means the removal of one or more amino acids relative to the native amino acid sequence. The modified amino acid sequences that are disclosed herein may include an insertion of one or more amino acids. As utilized herein, an "insertion" means the addition of one or more amino acids to a native amino acid sequence. The modified amino acid sequences that are disclosed herein may include a substitution of one or more amino acids. As utilized herein, a "substitution" means replacement of an amino acid of a native amino acid sequence with an amino acid that is not native to the amino acid sequence. For example, the modified amino sequences disclosed herein may include one or more deletions, insertions, and/or substitutions in order modified the native amino acid sequence of a target protein to include one or more heterologous amino acid motifs that are glycosylated by an N-glycosyltransferase.

Regarding proteins, a "deletion" refers to a change in the amino acid sequence that results in the absence of one or more amino acid residues. A deletion may remove at least 1, 2, 3, 4, 5, 10, 20, 50, 100, 200, or more amino acids residues. A deletion may include an internal deletion and/or a terminal deletion (e.g., an N-terminal truncation, a C-terminal truncation or both of a reference polypeptide). A "variant," "mutant," or "derivative" of a reference polypeptide sequence may include a deletion relative to the reference polypeptide sequence.

Regarding proteins, "fragment" is a portion of an amino acid sequence which is identical in sequence to but shorter in length than a reference sequence. A fragment may comprise up to the entire length of the reference sequence, minus at least one amino acid residue. For example, a fragment may comprise from 5 to 1000 contiguous amino acid residues of a reference polypeptide, respectively. In some embodiments, a fragment may comprise at least 5, 10, 15, 20, 25, 30, 40, 50, 60, 70, 80, 90, 100, 150, 250, or 500 contiguous amino acid residues of a reference polypeptide. Fragments may be preferentially selected from certain regions of a molecule. The term "at least a fragment" encompasses the full-length polypeptide. A fragment may include an N-terminal truncation, a C-terminal truncation, or both truncations relative to the full-length protein. A "variant," "mutant," or "derivative" of a reference polypeptide sequence may include a fragment of the reference polypeptide sequence.

Regarding proteins, the words "insertion" and "addition" refer to changes in an amino acid sequence resulting in the addition of one or more amino acid residues. An insertion or addition may refer to 1, 2, 3, 4, 5, 10, 20, 30, 40, 50, 60, 70, 80, 90, 100, 150, 200, or more amino acid residues. A "variant," "mutant," or "derivative" of a reference polypeptide sequence may include an insertion or addition relative to the reference polypeptide sequence. A variant of a protein may have N-terminal insertions, C-terminal insertions, internal insertions, or any combination of N-terminal insertions, C-terminal insertions, and internal insertions.

Regarding proteins, the phrases "percent identity" and "% identity," refer to the percentage of residue matches between at least two amino acid sequences aligned using a standardized algorithm. Methods of amino acid sequence alignment are well-known. Some alignment methods take into account conservative amino acid substitutions. Such conservative substitutions, explained in more detail below, generally preserve the charge and hydrophobicity at the site of substitution, thus preserving the structure (and therefore function) of the polypeptide. Percent identity for amino acid sequences may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including "blastp," that is used to align a known amino acid sequence with other amino acids sequences from a variety of databases.

Regarding proteins, percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

Regarding proteins, the amino acid sequences of variants, mutants, or derivatives as contemplated herein may include conservative amino acid substitutions relative to a reference amino acid sequence. For example, a variant, mutant, or derivative protein may include conservative amino acid substitutions relative to a reference molecule. "Conservative amino acid substitutions" are those substitutions that are a substitution of an amino acid for a different amino acid where the substitution is predicted to interfere least with the properties of the reference polypeptide. In other words, conservative amino acid substitutions substantially conserve the structure and the function of the reference polypeptide. The following table provides a list of exemplary conservative amino acid substitutions which are contemplated herein:

| Original Residue | Conservative Substitution |
| --- | --- |
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Lett, Trp, Tyr |
| Ser | Cys, Thr |
| Thr | Ser, Val |
| Trp | Phe, Tyr |
| Tyr | His, Phe, Trp |
| Val | Ile, Leu, Thr |

Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain. Non-conservative amino acids typically disrupt (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

The disclosed proteins, mutants, variants, or described herein may have one or more functional or biological activities exhibited by a reference polypeptide (e.g., one or more functional or biological activities exhibited by wild-type protein).

The disclosed proteins may be substantially isolated or purified. The term "substantially isolated or purified" refers to proteins that are removed from their natural environment, and are at least 60% free, preferably at least 75% free, and more preferably at least 90% free, even more preferably at least 95% free from other components with which they are naturally associated.

Cell-Free Protein Synthesis (CFPS)

The components, systems, and methods disclosed herein may be applied to cell-free protein synthesis methods as known in the art. See, for example, U.S. Pat. Nos. 5,478,730; 5,556,769; 5,665,563; 6,168,931; 6,548,276; 6,869,774; 6,994,986; 7,118,883; 7,186,525; 7,189,528; 7,235,382; 7,338,789; 7,387,884; 7,399,610; 7,776,535; 7,817,794; 8,703,471; 8,298,759; 8,715,958; 8,734,856; 8,999,668; and 9,005,920. See also U.S. Published Application Nos. 2018/0016614, 2018/0016612, 2016/0060301, 2015-0259757, 2014/0349353, 2014-0295492, 2014-0255987,2014-0045267,2012-0171720,2008-0138857, 2007-0154983, 2005-0054044, and 2004-0209321. See also U.S. Published Application Nos. 2005-0170452; 2006-0211085; 2006-0234345; 2006-0252672; 2006-0257399; 2006-0286637; 2007-0026485; 2007-0178551. See also Published PCT International Application Nos. 2003/056914; 2004/013151; 2004/035605; 2006/102652; 2006/119987; and 2007/120932. See also Jewett, M. C., Hong, S. H., Kwon, Y. C., Martin, R. W., and Des Soye, B. J. 2014, "Methods for improved in vitro protein synthesis with proteins containing non standard amino acids," U.S. Patent Application Ser. No. 62/044,221; Jewett, M. C., Hodgman, C. E., and Gan, R. 2013, "Methods for yeast cell-free protein synthesis," U.S. Patent Application Ser. No. 61/792,290; Jewett, M. C., J. A. Schoborg, and C. E. Hodgman. 2014, "Substrate Replenishment and Byproduct Removal Improve Yeast Cell-Free Protein Synthesis," U.S. Patent Application Ser. No. 61/953,275; and Jewett, M. C., Anderson, M. J., Stark, J. C., Hodgman, C. E. 2015, "Methods for activating natural energy metabolism for improved yeast cell-free protein synthesis," U.S. Patent Application Ser. No. 62/098,578. See also Guarino, C., & DeLisa, M. P. (2012). A prokaryote-based cell-free translation system that efficiently synthesizes glycoproteins. Glycobiology, 22(5), 596-601. The contents of all of these references are incorporated in the present application by reference in their entireties.

In some embodiments, a "CFPS reaction mixture" typically may contain a crude or partially-purified cell extract, an RNA translation template, and a suitable reaction buffer for promoting cell-free protein synthesis from the RNA translation template. In some aspects, the CFPS reaction mixture can include exogenous RNA translation template. In other aspects, the CFPS reaction mixture can include a DNA expression template encoding an open reading frame operably linked to a promoter element for a DNA-dependent RNA polymerase. In these other aspects, the CFPS reaction mixture can also include a DNA-dependent RNA polymerase to direct transcription of an RNA translation template encoding the open reading frame. In these other aspects, additional NTP's and divalent cation cofactor can be included in the CFPS reaction mixture. A reaction mixture is referred to as complete if it contains all reagents necessary to enable the reaction, and incomplete if it contains only a subset of the necessary reagents. It will be understood by one of ordinary skill in the art that reaction components are routinely stored as separate solutions, each containing a subset of the total components, for reasons of convenience, storage stability, or to allow for application-dependent adjustment of the component concentrations, and that reaction components are combined prior to the reaction to create a complete reaction mixture. Furthermore, it will be understood by one of ordinary skill in the art that reaction components are packaged separately for commercialization and that useful commercial kits may contain any subset of the reaction components of the invention.

The disclosed cell-free protein synthesis systems may utilize components that are crude and/or that are at least partially isolated and/or purified. As used herein, the term "crude" may mean components obtained by disrupting and lysing cells and, at best, minimally purifying the crude components from the disrupted and lysed cells, for example by centrifuging the disrupted and lysed cells and collecting the crude components from the supernatant and/or pellet after centrifugation. The term "isolated or purified" refers to components that are removed from their natural environment, and are at least 60% free, preferably at least 75% free, and more preferably at least 90% free, even more preferably at least 95% free from other components with which they are naturally associated.

As used herein, "translation template" for a polypeptide refers to an RNA product of transcription from an expression template that can be used by ribosomes to synthesize polypeptides or proteins.

The term "reaction mixture," as used herein, refers to a solution containing reagents necessary to carry out a given reaction. A reaction mixture is referred to as complete if it contains all reagents necessary to perform the reaction. Components for a reaction mixture may be stored separately in separate container, each containing one or more of the total components. Components may be packaged separately for commercialization and useful commercial kits may contain one or more of the reaction components for a reaction mixture.

A reaction mixture may include an expression template, a translation template, or both an expression template and a translation template. The expression template serves as a substrate for transcribing at least one RNA that can be translated into a sequence defined biopolymer (e.g., a polypeptide or protein). The translation template is an RNA product that can be used by ribosomes to synthesize the sequence defined biopolymer. In certain embodiments the platform comprises both the expression template and the translation template. In certain specific embodiments, the reaction mixture may comprise a coupled transcription/translation ("Tx/Tl") system where synthesis of translation template and a sequence defined biopolymer from the same cellular extract.

The reaction mixture may comprise one or more polymerases capable of generating a translation template from an expression template. The polymerase may be supplied exogenously or may be supplied from the organism used to prepare the extract. In certain specific embodiments, the polymerase is expressed from a plasmid present in the organism used to prepare the extract and/or an integration site in the genome of the organism used to prepare the extract.

Altering the physicochemical environment of the CFPS reaction to better mimic the cytoplasm can improve protein synthesis activity. The following parameters can be considered alone or in combination with one or more other components to improve robust CFPS reaction platforms based upon crude cellular extracts (for examples, S12, S30 and S60 extracts).

The temperature may be any temperature suitable for CFPS. Temperature may be in the general range from about 10° C. to about 40° C., including intermediate specific ranges within this general range, include from about 15° C. to about 35° C., from about 15° C. to about 30° C., from about 15° C. to about 25° C. In certain aspects, the reaction temperature can be about 15° C., about 16° C., about 17° C., about 18° C., about 19° C., about 20° C., about 21° C., about 22° C., about 23° C., about 24° C., about 25° C.

The reaction mixture may include any organic anion suitable for CFPS. In certain aspects, the organic anions can be glutamate, acetate, among others. In certain aspects, the concentration for the organic anions is independently in the general range from about 0 mM to about 200 mM, including intermediate specific values within this general range, such as about 0 mM, about 10 mM, about 20 mM, about 30 mM, about 40 mM, about 50 mM, about 60 mM, about 70 mM, about 80 mM, about 90 mM, about 100 mM, about 110 mM, about 120 mM, about 130 mM, about 140 mM, about 150 mM, about 160 mM, about 170 mM, about 180 mM, about 190 mM and about 200 mM, among others.

The reaction mixture may include any halide anion suitable for CFPS. In certain aspects the halide anion can be chloride, bromide, iodide, among others. A preferred halide anion is chloride. Generally, the concentration of halide anions, if present in the reaction, is within the general range from about 0 mM to about 200 mM, including intermediate specific values within this general range, such as those disclosed for organic anions generally herein.

The reaction mixture may include any organic cation suitable for CFPS. In certain aspects, the organic cation can be a polyamine, such as spermidine or putrescine, among others. Preferably polyamines are present in the CFPS reaction. In certain aspects, the concentration of organic cations in the reaction can be in the general about 0 mM to about 3 mM, about 0.5 mM to about 2.5 mM, about 1 mM to about 2 mM. In certain aspects, more than one organic cation can be present.

The reaction mixture may include any inorganic cation suitable for CFPS. For example, suitable inorganic cations can include monovalent cations, such as sodium, potassium, lithium, among others; and divalent cations, such as magnesium, calcium, manganese, among others. In certain aspects, the inorganic cation is magnesium. In such aspects, the magnesium concentration can be within the general range from about 1 mM to about 50 mM, including intermediate specific values within this general range, such as about 1 mM, about 2 mM, about 3 mM, about 5 mM, about 6 mM, about 7 mM, about 8 mM, about 9 mM, about 10 mM, among others. In preferred aspects, the concentration of inorganic cations can be within the specific range from about 4 mM to about 9 mM and more preferably, within the range from about 5 mM to about 7 mM.

The reaction mixture may include endogenous NTPs (i.e., NTPs that are present in the cell extract) and or exogenous NTPs (i.e., NTPs that are added to the reaction mixture). In certain aspects, the reaction use ATP, GTP, CTP, and UTP. In certain aspects, the concentration of individual NTPs is within the range from about 0.1 mM to about 2 mM.

The reaction mixture may include any alcohol suitable for CFPS. In certain aspects, the alcohol may be a polyol, and more specifically glycerol. In certain aspects the alcohol is between the general range from about 0% (v/v) to about 25% (v/v), including specific intermediate values of about 5% (v/v), about 10% (v/v) and about 15% (v/v), and about 20% (v/v), among others.

The components, systems, and methods disclosed herein may be applied to recombinant cell systems and cell-free protein synthesis methods in order to prepare glycosylated proteins. Glycosylated proteins that may be prepared using the disclosed components, systems, and methods may include proteins having N-linked glycosylation (i.e., glycans attached to nitrogen of asparagine). The glycosylated proteins disclosed herein may include unbranched and/or branched sugar chains composed of monomers as known in the art such as glucose (e.g., β-D-glucose), galactose (e.g., β-D-galactose), mannose (e.g., j-D-mannose), fucose (e.g., α-L-fucose), N-acetyl-glucosamine (GlcNAc), N-acetyl-galactosamine (GalNAc), neuraminic acid, N-acetyl-neuraminic acid (i.e., sialic acid), and xylose, which may be attached to the glycosylated proteins, growing glycan chain, or donor molecule (e.g., a sugar donor nucleotide) via respective glycosyltransferases (e.g., N-glycosyltransferases). The glycosylated proteins disclosed herein may include glycans as known in the art including but not limited to $Man_3GlcNAc_2$ glycan, $Man_5GlcNAc_3$ glycan, and the fully sialylated human glycan $Man_3GlcNAc_4Gal_2Neu_5Ac_2$.

In certain exemplary embodiments, one or more of the methods described herein are performed in a vessel, e.g., a single, vessel. The term "vessel," as used herein, refers to any container suitable for holding on or more of the reactants (e.g., for use in one or more transcription, translation, and/or glycosylation steps) described herein. Examples of vessels include, but are not limited to, a microtitre plate, a test tube, a microfuge tube, a beaker, a flask, a multi-well plate, a cuvette, a flow system, a microfiber, a microscope slide and the like.

Glycosylation in Prokaryotes

Glycosylation in prokaryotes is known in the art. (See e.g., U.S. Pat. Nos. 8,703,471; and 8,999,668; and U.S. Published Application Nos. 2005/0170452; 2006/0211085; 2006/0234345; 2006/0252672; 2006/0257399; 2006/0286637; 2007/0026485; 2007/0178551; and International Published Applications WO2003/056914A1; WO2004/035605A2; WO2006/102652A2; WO2006/119987A2; and WO2007/120932A2; the contents of which are incorporated herein by reference in their entireties).

Self-Assembled Monolayers for Matrix-Assisted Laser Desorption/Ionization Mass Spectrometry (SAMDI-MS)

The disclosed methods may utilize self-assembled monolayers for matrix-assisted laser desorption/ionization mass spectrometry (SAMDI-MS), for example, as a method for detecting glycosylation of peptides and proteins in the disclosed methods and systems. SAMDI-MS is known in the art and has been utilized to study peptides, proteins, and carbohydrates and their reaction products. (See Ban et al., "Discovery of Glycosyltransferases Using Carbohydrate Arrays and Mass Spectrometry," Nat. Chem. Biol., 2012, 8, 769-773; Ban et al., "On-Chip Synthesis and Label-Free Assays of Oligosaccharide Arrays," Chem. Int. Ed., 2008, 47(18), 3396-3399; Houseman et al., "Maleimide-Functionalized Self-Assembled Monolayers for the Preparation of Peptide and Carbohydrate Biochips," Langmuir, 2003, 19(5), 1522-1531; Su et al., "Using Mass Spectrometry to Characterize Self-Assembled Monolayers Presenting Peptides, Proteins and Carbohydrates," Angew. Chem. Int. Ed., 2002, 41, 4715-4718; Houseman et al., "Toward Quantitative Assays with Peptide Chips: A Surface Engineering Approach," Trends Biotech., 2002, 20 (7), 279-281; Houseman et al., "Carbohydrate Arrays for the Evaluation of Protein Binding and Enzyme Activity," Chem. Biol., 2002, 9, 443-454); and Laurent, N., et al. (2008). "Enzymatic Glycosylation of Peptide Arrays on Gold Surfaces." Chembiochem 9(6): 883-887); the contents of which are incorporated herein by reference in their entireties).

Miscellaneous

The steps of the methods described herein can be performed in any suitable order unless otherwise indicated herein or otherwise clearly contradicted by context. The steps may be repeated or reiterated any number of times to achieve a desired goal unless otherwise indicated herein or otherwise clearly contradicted by context.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

ILLUSTRATIVE EMBODIMENTS

The following embodiments are illustrative and are not intended to limit the scope of the claimed subject matter.

Embodiment 1. A method for synthesizing a glycoprotein or a recombinant glycoprotein, the method comprising: (a) expressing in a cell or in a cell-free protein synthesis (CFPS) reaction a polypeptide comprising the amino acid sequence of a target protein which naturally includes an amino acid motif optionally comprising at least about four (4) amino acids including an asparagine that is glycosylated by an N-glycosyltransferase or that has been modified to include a heterologous amino acid motif optionally comprising at least about four (4) amino acids including an asparagine that is glycosylated by an N-glycosyltransferase, the amino acid motif or heterologous amino acid motif optionally comprising an amino acid sequence selected from SEQ ID NOs:1-549; (b) expressing in a cell or in a CFPS reaction the N-glycosyltransferase; and (c) reacting the polypeptide and the N-glycosyltransferase in the presence of a sugar donor, wherein the N-glycosyltransferase glycosylates the amino acid motif or the heterologous amino acid motif of the polypeptide with the sugar to synthesize the glycoprotein or recombinant glycoprotein (optionally wherein step (a) comprises expressing in a cell or in a cell-free protein synthesis (CFPS) reaction a polypeptide comprising the amino acid sequence of a target protein which has been modified to include two or more different heterologous amino acid motifs that includes an asparagine that is glycosylated by two or more different N-glycosyltransferases, the heterologous amino acid motifs optionally comprising an amino acid sequence selected from SEQ ID NOs:1-549; and optionally wherein step (b) comprises expressing in one or more cells or in one or more CFPS reactions the two or more different N-glycosyltransferases, wherein the two or more different N-glycosyltransferases are expressed simultaneously in the same cell or CFPS reaction or sequentially in two or more different cells or two or more different CFPS reactions; and optionally wherein step (c) comprises reacting the polypeptide and the two or more different N-glycosyltransferases in the presence of two or more sugar donors which are the same or different, wherein the polypeptide is reacted with the two or more different N-glycosyltransferases simultaneously for example in the same cell or CFPS reaction, or sequentially for example in two or more different cells or two or more different CFPS reactions, and wherein the two or more different N-glycosyltransferases glycosylate the two or more different heterologous amino acid motifs of the polypeptide with the sugar of the two or more sugar donors to synthesize the glycoprotein or recombinant glycoprotein).

Embodiment 2. The method of embodiment 1, wherein the amino acid motif or heterologous amino acid motif comprises a sequence $X_{-2}$-$X_{-1}$-N-$X_{+1}$-S/T-$X_{+3}$, wherein $X_{-2}$ is selected from Gly, Asn, and Tyr; $X_{-1}$ is selected from Gly and Ala; $X_{+1}$ is selected from Trp, Val, His, Ala, and Ile; and $X_{+3}$ is selected from Thr, Met, and Phe.

Embodiment 3. The method of embodiment 1, wherein the target protein is a eukaryotic protein.

Embodiment 4. The method of embodiment 1, wherein the target protein is a prokaryotic protein.

Embodiment 5. The method of any of embodiments 1-4, wherein step (a) is performed in a prokaryotic cell.

Embodiment 6. The method of any of embodiments 1-4, wherein step (b) is performed in a prokaryotic cell.

Embodiment 7. The method of any of embodiments 1-4, wherein step (a) and step (b) are performed in the same prokaryotic cell.

Embodiment 8. The method of any of embodiments 1-4, wherein step (a) is performed in a eukaryotic cell.

Embodiment 9. The method of any of embodiments 1-4, wherein step (b) is performed in a eukaryotic cell.

Embodiment 10. The method of any of embodiments 1-4, wherein step (a) and step (b) are performed in the same eukaryotic cell.

Embodiment 11. The method of any of embodiments 1-4, wherein step (a) is performed in a prokaryotic-based CFPS reaction.

Embodiment 12. The method of any of embodiments 1-4, wherein step (b) is performed in a prokaryotic-based CFPS reaction.

Embodiment 13. The method of any of embodiments 1-4, wherein step (a) and step (b) are performed in the same prokaryotic-based CFPS reaction.

Embodiment 14. The method of any of embodiments 11-13, wherein step (c) is performed in the same prokaryotic-based CFPS reaction as step (a) and/or step (b).

Embodiment 15. The method of any of the foregoing embodiments, wherein the N-glycosyltransferase is a prokaryotic N-glycosyltransferase.

Embodiment 16. The method of embodiment 15, wherein the prokaryotic N-glycosyltransferase is a prokaryotic N-glycosyltransferase from one of *Actinobacillus* spp., *Escherichia* spp., *Haemophilus* spp., or *Mannheimia* spp.

Embodiment 17. The method of embodiment 15, wherein the prokaryotic N-glycosyltransferase is a prokaryotic N-glycosyltransferase from one of *Actinobacillus pleuropneumoniae, Escherichia coli, Haemophilus influenza, Mannheimia haemolytica,* or *Haemophilus dureyi.*

Embodiment 18. The method of any of embodiments 1-17, wherein multiple distinct and/or non-naturally occurring glycans are introduced to a protein by specifically choosing unique sequence:enzyme pairs that allow for orthogonal, and/or parallel and/or independent glycosylation.

Embodiment 19. The method of any of embodiments 1-18 further comprising immobilizing the polypeptide (e.g., covalently immobilizing the polypeptide) on a solid support (e.g., magnetic beads) prior to performing one or more of step (a), step (b), and/or step (c), wherein the polypeptide may be immobilized directly to the solid support or indirectly to the solid support via a linking moiety (e.g., a covalently linking protein or peptide).

Embodiment 20. A method for synthesizing a glycoprotein or recombinant glycoprotein, the method comprising: (a) expressing in a cell or in a cell-free protein synthesis (CFPS) reaction a polypeptide comprising the amino acid sequence of a target protein which includes naturally two or more different amino acid motifs that includes an asparagine that is glycosylated by two or more different N-glycosyltransferases or that has been modified to include two or more different heterologous amino acid motifs that includes an asparagine that is glycosylated by two or more different N-glycosyltransferases, the amino acid motifs or heterologous amino acid motifs optionally comprising an amino acid sequence selected from SEQ ID NOs:1-549; (b) expressing in one or more cells or in one or more CFPS reactions the two or more different N-glycosyltransferases, wherein the two or more different N-glycosyltransferases are expressed simultaneously in the same cell or CFPS reaction or sequentially in two or more different cells or two or more different CFPS reactions; and (c) reacting the polypeptide and the two or more different N-glycosyltransferases in the presence of two or more sugar donors which are the same or different, wherein the polypeptide is reacted with the two or more different N-glycosyltransferases simultaneously for example in the same cell or CFPS reaction, or sequentially for example in two or more different cells or two or more different CFPS reactions, and wherein the two or more different N-glycosyltransferases glycosylate the two or more different amino acid motifs or heterologous amino acid motifs of the polypeptide with the sugar of the two or more sugar donors to synthesize the glycoprotein or recombinant glycoprotein; optionally wherein the method comprises sequentially conjugating monosaccharides to the polypeptide by reacting the two or more different N-glycosyltransferases with the polypeptide wherein the two or more different N-glycosyltranferases transfer single or multiple saccharides to the polypeptide at different positions and produce different glycosylation structures at the different positions.

Embodiment 21. The method of embodiment 20, further comprising immobilizing the polypeptide (e.g., covalently immobilizing the polypeptide) on a solid support (e.g., magnetic beads) prior to performing one or more of step (a), step (b), and/or step (c); and optionally washing the polypeptide after performing one or more of step (a), step (b), and/or step (c) (for example after a glycosylation step); and optionally releasing the polypeptide from the solid support (for example, via treatment with a protease) after performing one or more of step (a), step (b), and/or step (c), wherein the polypeptide may be immobilized directly to the solid support or indirectly to the solid support via a linking moiety (e.g., covalently linking protein or peptide).

Embodiment 22. A method for selecting an amino acid motif that is glycosylated by an N-glycosyltransferase, the method comprising: (a) reacting a library of peptides with an N-glycosyltransferase in the presence of a sugar donor, wherein the N-glycosyltransferase glycosylates one or more of the peptides; (b) detecting glycosylation of the reacted peptides by immobilizing the reacted peptides on a substrate comprising self-assembled monolayers, and performing matrix-assisted laser desorption/ionization mass spectrometry of the immobilized reacted peptides to select the amino acid motif that is glycosylated by the N-glycosyltransferase.

Embodiment 23. The method of embodiment 22, wherein the library comprises at least about 10, 50, 100, 500, or 1000 peptides.

Embodiment 24. The method of embodiment 22 or 23, wherein the peptides comprise at least 6 amino acids and have a sequence $X_{-2}$-$X_{-1}$-N-$X_{+1}$-S/T-R-C wherein X is any amino acid.

Embodiment 25. The method of any of embodiments 22-24, wherein the peptides are covalently immobilized on the substrate comprising the self-assembled monolayers.

Embodiment 26. The method of embodiment 25, wherein the library of peptides comprise a C-terminal Cys, the self-assembled monolayers comprise free maleimides, and the C-terminal Cys of the peptides reacts with the free maleimides to form a bond (e.g., a C—S bond) and covalently immobilize the peptide.

Embodiment 27. The method of embodiment 26, wherein the self-assembled monolayers comprise alkylthiolates which provide the free maleimides.

Embodiment 28. The method of embodiment 25, wherein: (i) the library of peptides comprise a C-terminal alkyne, the self-assembled monolayers comprise free azides, and the C-terminal alkyne of the peptides reacts with the free azides to form a bond (e.g., a triazole and in particular a 1,2,3-triazole) and covalently immobilize the peptide; or (ii) the library of peptides comprise a C-terminal azide, the self-assembled monolayers comprise free alkynes, and the C-terminal azide of the peptides reacts with the free alkynes to form a bond (e.g., a triazole and in particular a 1,2,3-triazole) and covalently immobilize the peptide.

EXAMPLES

The following Examples are illustrative and are not intended to limit the scope of the claimed subject matter.

Example 1—Design of Protein Sequence for Cytoplasmic Glycosylation

Abstract

Glycosylation modulates the pharmacokinetics and potency of protein therapeutics and vaccines. However, current methods cannot sufficiently explore the vast experimental landscapes required to accurately predict and design glycosylation sites for specific glycosyltransferases (GTs). We used a systematic platform for Rapid Expression and Characterization to Direct Efficient Glycosylation (RECoDE-G) using Cell-Free Protein Synthesis (CFPS) and Self-Assembled Monolayers for Desorption Ionization Mass Spectrometry (SAMDI-MS) to produced >500 µg/mL of five cytoplasmic N-linked glycosyltransferases (NGTs) in vitro and determine their peptide acceptor and sugar donor specificities at unprecedented depth and throughput with ~3,000 unique peptides and ~10,000 unique reaction conditions. We found that peptide selectivity data closely matched glycosylation trends on small sequon motifs (GlycTags) within heterologous proteins, including an Fc human antibody fragment, in vitro and in the cytoplasm of living cells. The data collected in this work allows for design of polypeptide sequences for efficient modification with NGTs and the RECoDE-G workflow provides a systematic tool to characterize other polypeptide glycosyltransferases.

Applications

The applications of the disclosed technology may include, but are not limited to: (i) design of therapeutic polypeptide amino acid sequences for improved glycosylation by an N-linked glycosyltransferase in vitro or in a cell; (ii) high-throughput characterization of glycosyltransferases peptide specificities or engineering of glycosyltransferases for alternative peptide or sugar specificities; and (iii) production of high titers of proteins in industrial bacterial host organisms which are glycosylated site-specifically in the bacterial cytoplasm.

Advantages

The advantages of the disclosed technology may include, but are not limited to: (i) NGT glycosylation systems allow for efficient modification of polypeptides without a eukaryotic host or lipid-bound substrates and enzymes, where previously this system was only functional on autotransporter protein substrates or long, repeated glycosylation sequences, and our findings allow for informed design of glycosylation sites within polypeptides for efficient modification in vitro or in living cells; (ii) demonstrated first glycosylation of human IgG Fc fragment in E. coli cytoplasm using redesigned sequences which direct efficient glycosylation by NGT; (iii) the ability to design glycosylation sites for modification with NGT allows for the production of glycoproteins in the bacterial cytoplasm, obviating the need for transport to the bacterial periplasm (as is required to use existing oligosaccharyltransferase glycosylation methods); (iv) this innovation will increase the diversity of glycoproteins which can be produced in bacteria, a preferred industrial host strain; and (v) the use of the SAMDI method allows for the rapid study of 1000's of peptides across multiple enzymes and 10,000's of reaction conditions, where in contrast, current studies of glycosyltransferase specificity require expression and purification of the enzyme from cells by affinity purification, screening by incorporation of radioactively or chemically labeled sugars or liquid chromatography (LC) methods, and validation by mass spectrometry (typically LC-MS), and these current methods limit investigations to 10-100 peptides.

Description of Technology

Most methods for glycoprotein synthesis use eukaryotic organisms. Bacterial glycosylation offers the opportunity to more closely control glycosylation patterns and more rapidly develop more diverse glycosylation systems. Most existing methods use a membrane bound oligosaccharyltransferase (OST) to transfer lipid-linked sugar donors en bloc onto proteins.

NGTs are soluble enzymes which transfer sugars from activated donors directly onto proteins without the use of membrane bound components. However, their use for the modification of heterologous proteins has been limited, likely due to an incomplete understanding of peptide specificity and therefore an inability to design efficiently modified glycosylation sites.

Two studies by Naegali et al. in 2014 attempted to characterize the sequence specificity of NGT by directly measuring modification of ~10 peptides by HPLC analysis and by LC-MS/MS of *E. coli* cells in which ApNGT was expressed. (See Naegeli, A. et al., "Substrate Specificity of Cytoplasmic N-Glycosyltransferase," *Journal of Biological Chemistry* 289, 24521-24532 (2014); and Naegeli, A. et al., "Molecular analysis of an alternative N-glycosylation machinery by functional transfer from *Actinobacillus pleuropneumoniae* to *Escherichia coli*," *The Journal of biological chemistry* 289, 2170-2179 (2014)). These studies showed that NGT can efficiently modify some N-X-S/T motifs with glucose, galactose, xylose, or mannose and showed trends of modification in living cells. This study also showed that ApNGT can modify wildtype human erythropoietin in the *E. coli* cytoplasm (although protein solubility and glycosylation efficiency was not determined). Other work by the Aebi lab disclosed in a patent showed modification of wildtype bacterial autotransporter proteins (native substrates for NGTs) in cells and their potential use as a vaccine. (See Schwarz, et al, "Cytoplasmic N-Glycosyltransferase of *Actinobacillus pleuropneumoniae* Is an Inverting Enzyme and Recognizes the NX(S/T) Consensus Sequence," *Journal of Biological Chemistry* 286, 35267-35274 (2011)).

In 2017, Cuccui et al. achieved glycosylation in cells with NGT by fusing 12 repeating glycosylation sites to the C-terminus of a bacterial protein (no data was provided on glycosylation efficiency or if this glycosylation was due to native sites within the protein rather than the added sites). (See Cuccui, J. et al., "The N-linking glycosylation system from *Actinobacillus pleuropneumoniae* is required for adhesion and has potential use in glycoengineering," *Open biology* 7 (2017)). Another 2017 study by Song et al. developed an ApNGT variant with improved activity and wider peptide specificity. (See Song et al., "Production of homogeneous glycoprotein with multi-site modifications by an engineered N-glycosyltransferase mutant," *Journal of Biological Chemistry* (2017)). In this study, peptide specificity of wildtype ApNGT and the engineered variant was characterized using ~40 peptides and the sequence of the bacterial autotransporter protein HMW1 was altered to improve its glycosylation in vitro. The scope of our SAMDI study of peptide specificity characterization exceeds this work by an order of magnitude. Efficiency of glycosylation of HMW1 was not reported site-by-site but rather in aggregate, leading to uncertainties in the direct effect of modifying each site. Furthermore, the breadth of our specificity data enabled us to redesign glycosylation sites into diverse proteins not usually modified by NGT including a therapeutically relevant human IgG protein in cells and a protein which previously did not contain glycosylation sites (*E. coli* protein Im7).

Our findings allow for site-specific and efficient enzymatic N-linked glycosylation of diverse proteins in vitro and in the bacterial cytoplasm by design of primary amino acid sequences. This technique could enable quicken development and reduce production costs for glycoprotein therapeutics. The method we developed using SAMDI-MS and CFPS can rapidly recapitulate these results for other enzymes homologs or enzyme variants of interest.

This technology also allows for the production of site-specifically glycosylated proteins, including protein therapeutics and vaccines. The lipid-independent nature of this system makes it attractive for in vitro modification of protein therapeutics and glycosylation in the bacterial cytoplasm. These high-titer, rapid expression systems could allow glycoprotein therapeutics to be developed and produced more quickly and at lower cost.

Example 2—Design of Glycosylation Sites by Rapid Expression and High-Throughput Characterization of N-Glycosyltransferases Reference is made to the manuscript entitled "Design of glycosylation sites by rapid expression and high-throughput characterization of N-glycosyltransferase," by Weston Kightlinger, Liang Lin, Madisen Rosztoczy, Matthew P. DeLisa, Milan Mrksich, and Michael C. Jewett, Nat. Chem. Biol., 2018 May 7, doi: 10.1038/s41589-018-0051-2, which content is incorporated herein by reference in its entirety.

Abstract

Glycosylation is an abundant post-translational modification that is important in disease and biotechnology. Current methods to understand and engineer glycosylation cannot sufficiently explore the vast experimental landscapes required to accurately predict and design glycosylation sites modified by glycosyltransferases. Here we describe a systematic platform for glycosylation sequence characterization and optimization by rapid expression and screening (GlycoSCORES), which combines cell-free protein synthesis and mass spectrometry of self-assembled monolayers. We produced six N- and O-linked polypeptide-modifying glycosyltransferases from bacteria and humans in vitro and rigorously determined their substrate specificities using 3,480 unique peptides and 13,903 unique reaction conditions. We then used GlycoSCORES to optimize and design small glycosylation sequence motifs that directed efficient, N-linked glycosylation in vitro and in the *Escherichia coli* cytoplasm for three heterologous proteins, including human immunoglobulin Fc domain. We find that GlycoSCORES is a broadly applicable method to facilitate fundamental understanding of glycosyltransferases and engineer synthetic glycoproteins.

Introduction

Protein glycosylation is the post-translational attachment of complex oligosaccharides (glycans), most commonly at asparagine (N-linked) or serine and threonine (O-linked) amino acid side chains[1,2]. Glycosylation is found in all domains of life and plays critical roles in cellular function[2]. Glycosylation is also present in 70% of approved or preclinical protein therapeutics[3] and has profound effects on protein stability[4], immunogenicity[5], and potency[6], motivating close study and intentional engineering of glycosylation sites and structures[7]. Production of glycoproteins within native hosts often results in structural heterogeneity, limits titers and genetic tractability, and constrains the diversity of glycans that can be produced[8-10]. These difficulties have motivated the development of highly-engineered glycosylation systems within mammalian cells[11], yeast[12], bacteria[8,9], and in vitro[6,13] to produce more homogeneous human-like glycans for therapeutics[12], bacterial glycans for vaccines[9], and synthetic glycans for fundamental biology studies[6,10].

Despite these advances, major glycoengineering challenges and gaps in understanding of natural glycosylation systems still remain due, in large part, to a lack of high-throughput methods for synthesis and detailed biochemical characterization of glycosyltransferases (GTs), the enzymes that attach and elaborate glycans on proteins. GTs are the catalytic nodes of natural systems and the parts from which synthetic glycosylation systems are constructed; and yet, less than 1% of putative GTs have been biochemically characterized[14] with far fewer at sufficient depth to be useful in biocatalysis[15]. Typically, studies of GT specificity require expression and purification of the enzyme from cells; screening by incorporation of radioactively or chemically labeled sugars[16, 17] antibody detection[17, 18], or liquid chromatography (LC) separation[19]; and validation by mass spectrometry (usually LC-MS/MS)[20]. Existing methods are particularly problematic for characterizing GTs that attach glycans to polypeptides. These polypeptide GTs (ppGTs) include the O-linked polypeptide N-acetylgalactosaminyltransferase (ppGalNAcT), O-linked N-acetylglucosamine transferase (OGT), and oligosaccharyltransferase (OST) enzyme families. Such enzymes are of particular interest because they determine which sites on a protein are glycosylated and constrain the possible glycoforms that can be installed. A recently discovered ppGT called N-glycosyltransferase from the bacterial pathogen *Actinobacillus pleuropneumoniae* (NGT), has elicited a great deal of interest for biocatalysis[9, 21, 22] because it is a soluble, cytoplasmic enzyme which can efficiently install an N-linked glucose on N-X-S/T amino acid sequence motifs resembling those in eukaryotic proteins using uracil-diphosphate-glucose (UDP-Glc) as a sugar donor[23]. While pioneering efforts by several groups reported several protein and peptide substrates that can be modified by NGT[19, 20, 24-27], current methods for GT analysis limits investigations of NGT and also other ppGTs to only dozens of unique peptide substrates. These methods undersample the vast amino acid sequence space available for modification, providing incomplete information of amino acid preferences at each position surrounding the glycosylation site and the interdependency of amino acids at these positions, which are required for a full understanding of GTs in natural systems and for the rational design of efficient protein glycosylation sites.

Here we report a generalizable and systematic strategy for glycosylation sequence characterization and optimization by rapid expression and screening (GlycoSCORES). GlycoSCORES couples expression by *Escherichia coli*-based cell-free protein synthesis (CFPS) to functional characterization of GTs with self-assembled monolayers for matrix-assisted desorption/ionization (SAMDI) mass spectrometry. This workflow enables high-throughput, label-free, quantitative analysis of peptide glycosylation without time-consuming cell lysis and protein purification. We apply the GlycoSCORES workflow to the study of NGT, two previously uncharacterized NGT homologs, namely human ppGalNAcT1 and ppGalNAcT2, and human OGT (hOGT) using 3,480 unique acceptor peptides and 13,903 unique reaction conditions. We demonstrate the utility of GlycoSCORES for glycoprotein engineering by rigorously optimizing NGT acceptor sequences to inform the design of improved glycosylation sites. We identify several small glycosylation tag sequence motifs termed "GlycTags" (originally described by Imperiali[28], DeLisa[29], and others) and used them to direct efficient glycosylation of several target proteins including the *E. coli* immunity protein Im7, the *H. influenzae* autotransporter protein (HMW1ct) and the constant region (Fc) of a human immunoglobulin (IgG1) antibody. We find that glycosylation efficiencies of GlycTag sequences within proteins closely mirrored trends observed from GlycoSCORES analysis of peptides. Upon synthesis and glycosylation by NGT in the cytoplasm of living *E. coli*, proteins glycosylation sites that were redesigned according to a GlycoSCORES-derived GlycTag sequence were modified more efficiently than naturally occurring glycosylation sequences and a previously identified NGT glycosylation consensus sequence[20].

Results

Figure 1B:
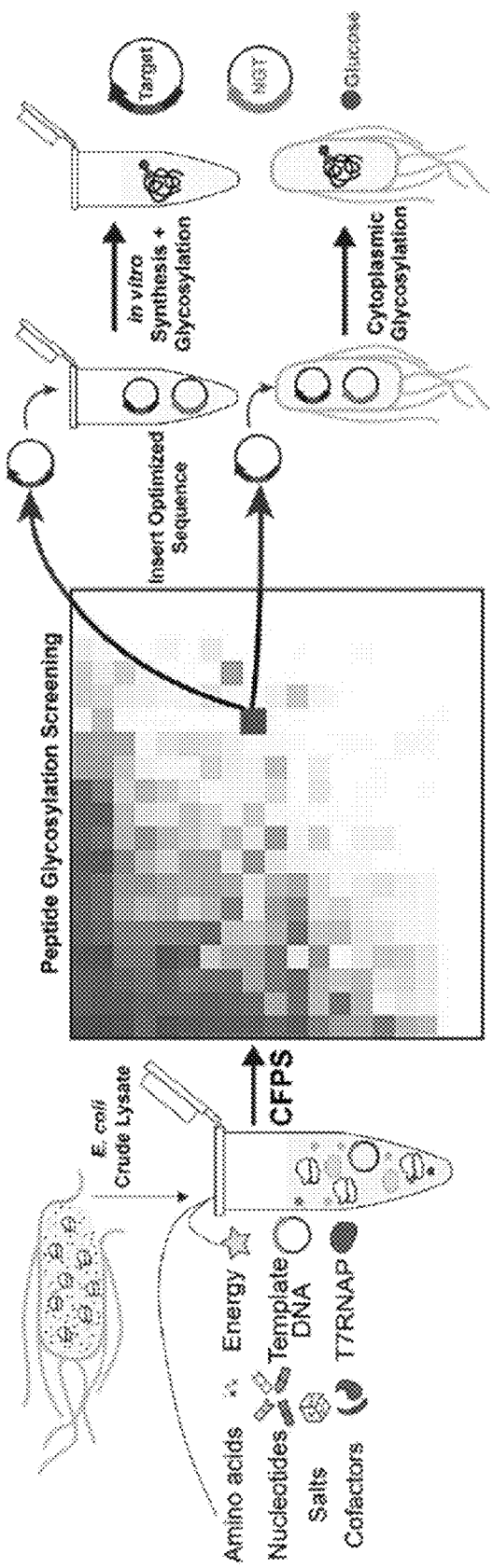
Figure 7:
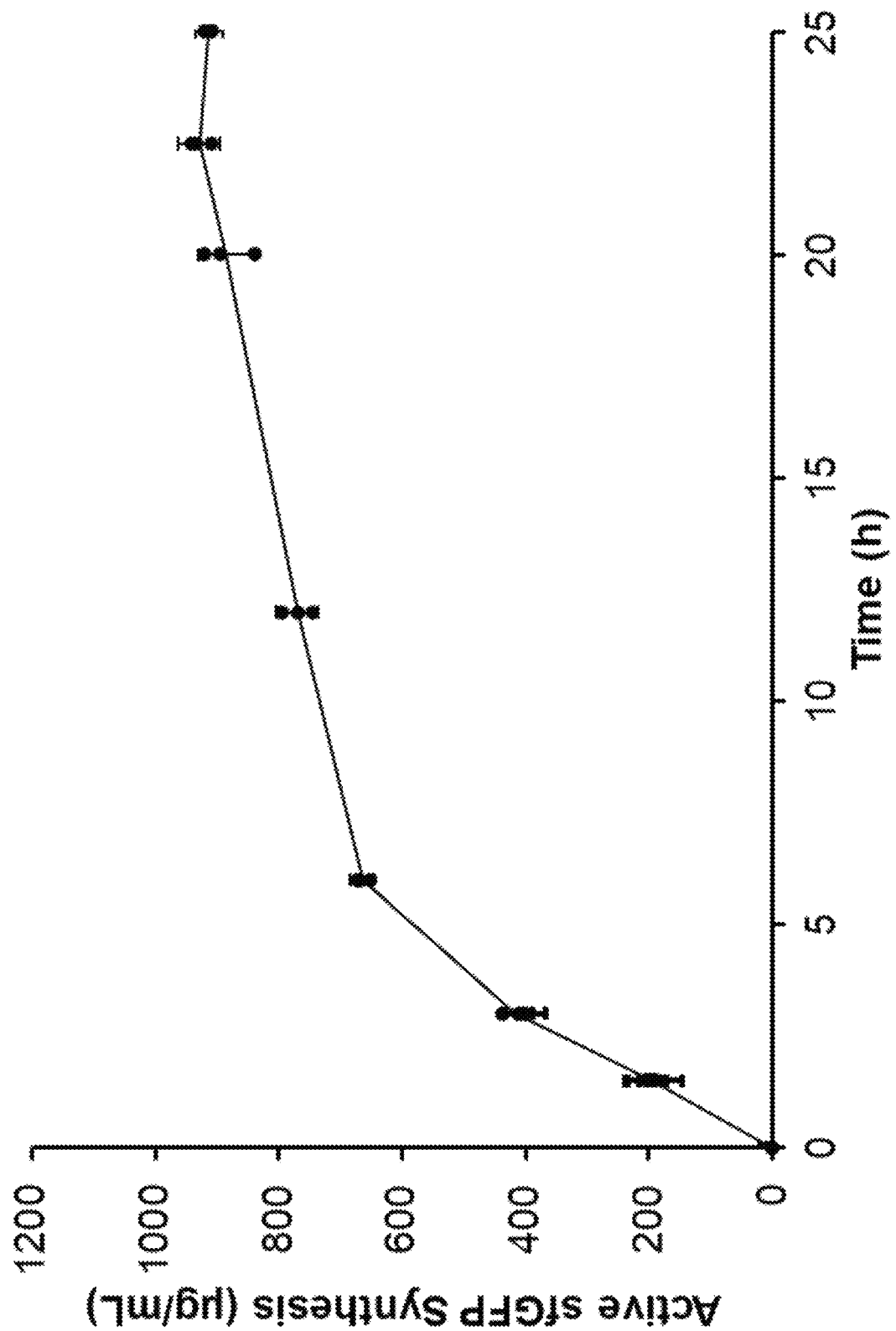
FIG. 7. Cell-free protein synthesis at 20° C. is >95% complete after 20 h. Superfolder green fluorescent protein (sfGFP) expression over time at 20° C. Fluorescence of 15 µL CFPS reactions synthesizing sfGFP were incubated at 20° C., flash frozen on liquid nitrogen and measured on a 96-well plate fluorimeter. Average and S.D. of n=3 CFPS reactions are shown at each time-point.
Figure 8:
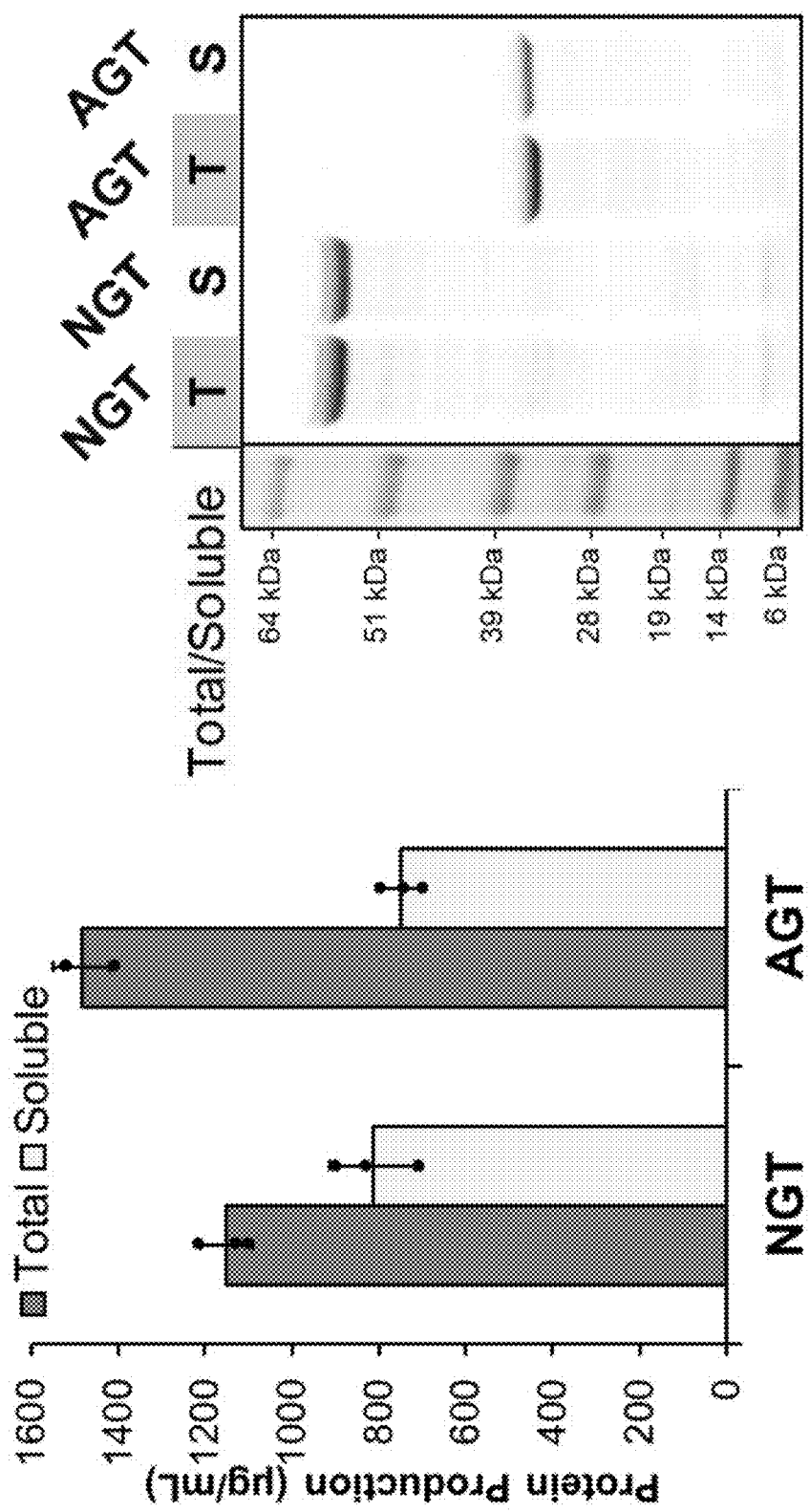
FIG. 8. CFPS provides high soluble expression titers of NGT and AGT. (A) Total and soluble yields of NGT and the α-1,6 glucose polymerase from *A. pleuropneumoniae* (AGT) from CFPS reactions were determined using $^{14}$C-leucine incorporation. Results indicate high and consistent yields of both enzymes. Average and S.D. of n=3 CFPS reactions are shown. (B) An autoradiogram representative of n=2 experiments with similar results confirmed that the CFPS reactions primarily produced full-length product without large truncations. The autoradiogram was generated by a 48-h exposure of a 4-12% SDS-PAGE gel run in MOPS with NGT and AGT produced in CFPS with $^{14}$C-leucine. Soluble samples were taken after centrifugation at 12,000×g for 15 min at 4° C. The same gel was Coomassie stained and aligned with autoradiogram image for molecular weight standard reference.

Development of GlycoSCORES for characterization of NGT. We selected NGT as the primary GT model to demonstrate the GlycoSCORES framework (FIG. 1) because of its potential for biocatalysis and our hypothesis that a deeper analysis of the NGT acceptor substrate sequence space would enable the rational redesign of protein glycosylation sites for improved modification by NGT. Because difficulties in protein expression and purification are key challenges for GT characterization, we chose to use *E. coli*-based crude lysate CFPS for GT expression in the GlycoSCORES workflow. CFPS can rapidly produce g/L quantities of many complex proteins, is compatible with liquid handling robotics for direct coupling to our SAMDI analysis pipeline, and allows for enzyme quantification and functional analysis without cell lysis, affinity tags, or purification[30]. *E. coli* lysates also lack native protein glycosylation activity, providing a blank canvas for bottom-up engineering and characterization. CFPS reactions were used to express soluble NGT at 20° C. for 20 h, at which point protein synthesis was >95% complete (FIG. 7 and data not shown). Soluble NGT was quantified as 814±97 µg/mL by $^{14}$C-leucine incorporation and visualized by SDS-PAGE autoradiogram (FIG. 8).

Figure 2A:
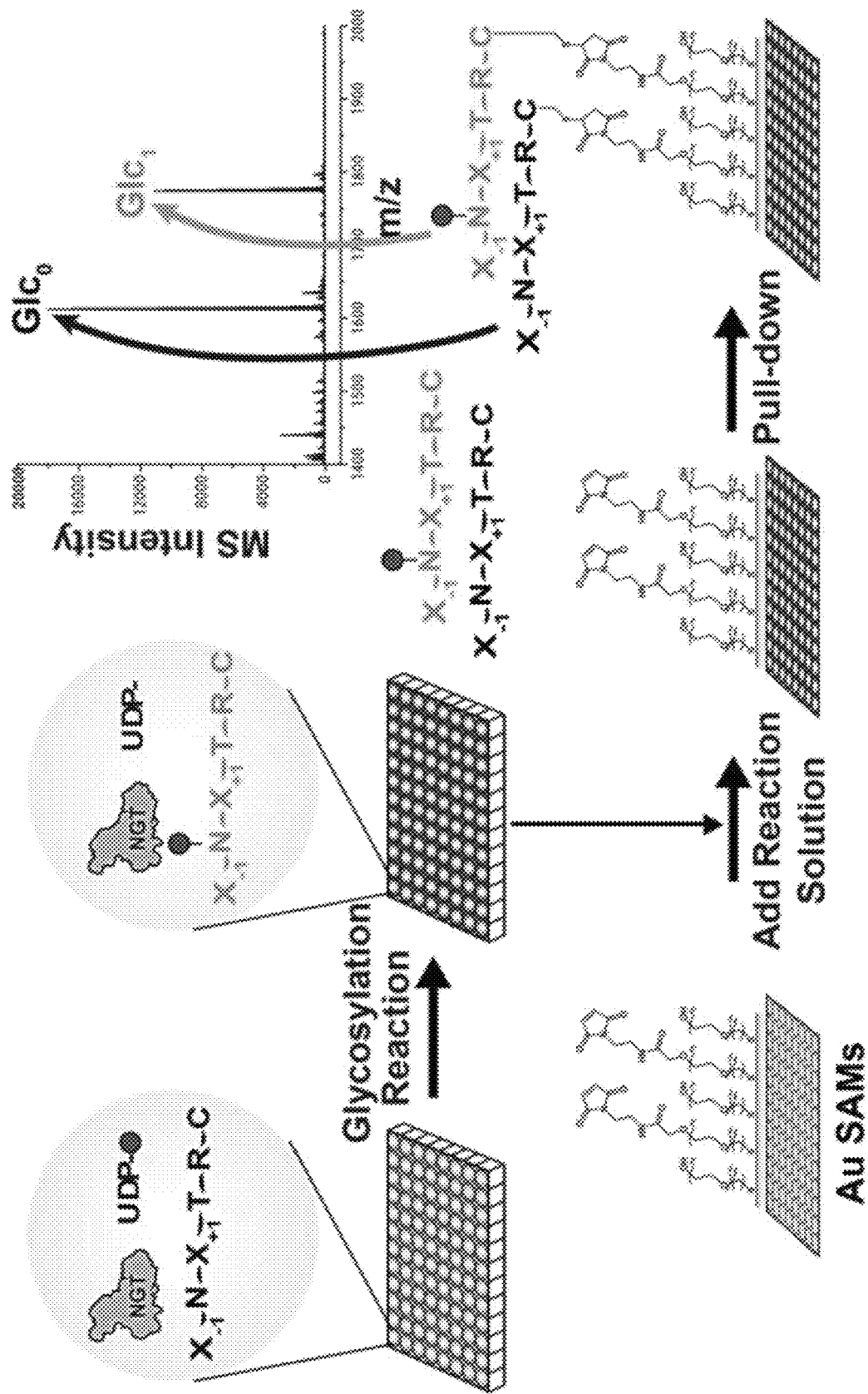
FIG. 2: GlycoSCORES workflow and application to $X_{-1}$ and $X_{+1}$ position screening of NGT substrates. (a) Scheme of GlycoSCORES. NGT produced in CFPS was reacted with peptide acceptor and sugar donor in 384 well plates. Reaction products were applied directly to self-assembled maleimide functionalized alkanethiolate monolayers on gold islands. Peptides were captured to the monolayer by a terminal Cys residue via Michael Addition. MALDI-MS spectrum of this monolayer shows the addition of a single glucose residue (+162 Da) on a representative peptide. (b) NGT peptide acceptor preferences were determined at the $X_{-1}$ and $X_{+1}$ position relative to the modified Asn residue using the scheme in a. All NGT heat maps are arranged by mean glycosylation efficiency of each amino acid and the combination of amino acids at the other positions in descending order from left to right and top to bottom. NGT sequences showing high modification (blue boxes, >66%) and low modification (grey boxes, <3%) were chosen for subsequent screens towards an optimized GlycTag. Glycosylation reactions were performed with 50 µM peptide, 2.5 mM UDP-Glucose, and 0.2 µM CFPS NGT incubated at 30° C. for 3 h. Conversion efficiencies were determined by integration of mass spectra peaks at substrate and products masses and adjusted by measured relative ionization factor (RIFs) (data not shown). Numerical values of modification efficiencies from SAMDI-MS spectra were acquired from n=2 peptide immobilizations (data not shown). Control peptide maps also were generated using CFPS without NGT (data not shown).
Figure 9:
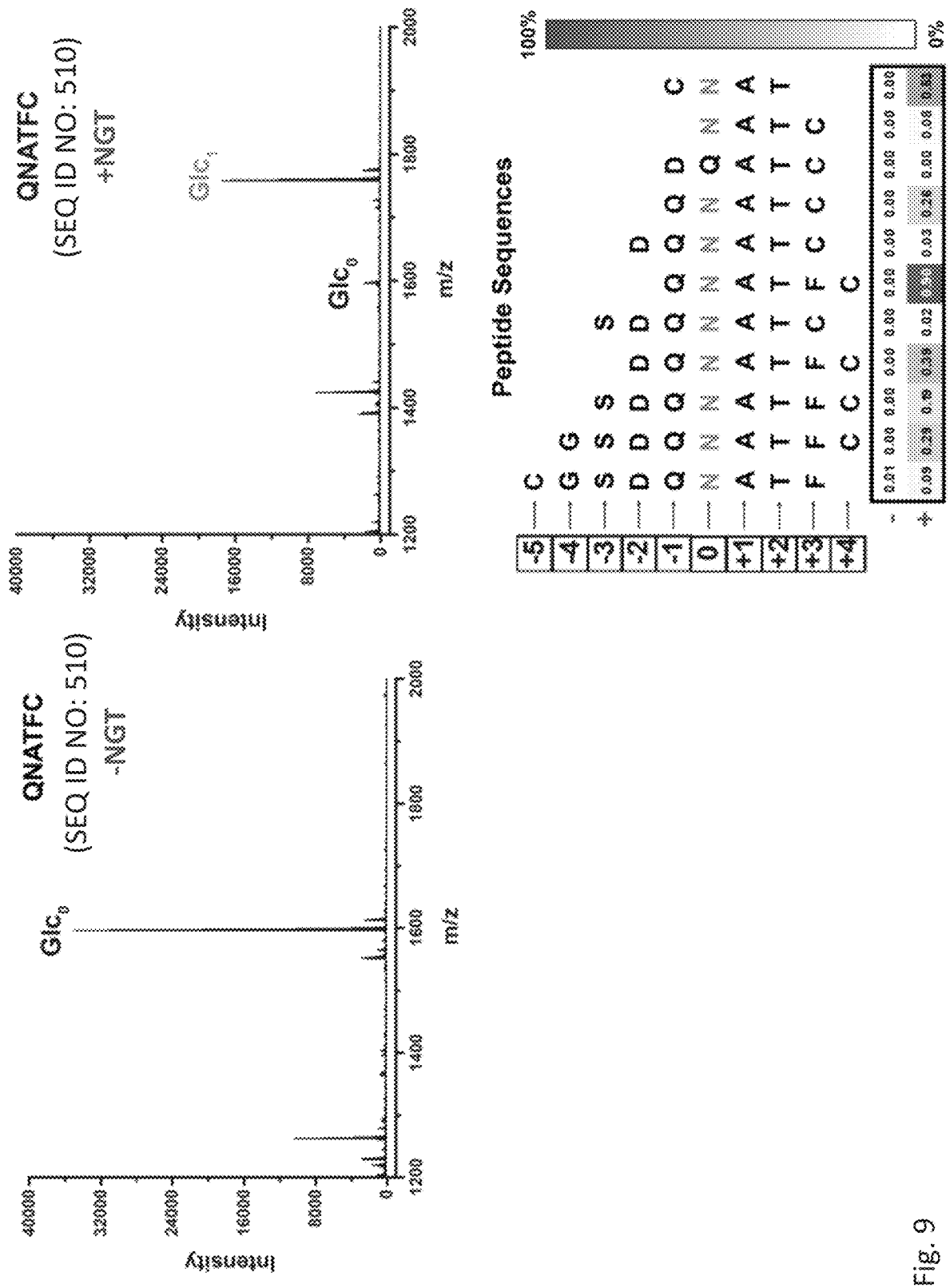
FIG. 9. Purified NGT installs glucose onto short peptide sequences at asparagine residues. SAMDI mass spectra of peptide QNATFC (SEQ ID NO:510) before (A) and after (B) NGT treatment. A shift of +162 m/z was observed after NGT treatment. (C) Truncated versions of the previously studied GSDQNATF[9] peptide (SEQ ID NO:507) were modified with Cys at the N-terminal or C-terminal for SAMDI pull-down. The relative intensities of peptide substrates and glycosylated products, $Glc_1/(Glc_1+Glc_0)$, observed in mass spectra with and without purified NGT are shown in the heat map. Peptides as small as CNAT (SEQ ID NO:508) and NATC (SEQ ID NO:509) could be modified by NGT and QNATFC (SEQ ID NO:510) showed the most efficient glucose modification. Reaction condition: 50 µM peptide, 2.5 mM UDP-Glc, and 0.5 µM purified NGT incubated at 30° C. for 3 h. Heat map shows the relative intensities calculated from SAMDI-MS spectra acquired from n=1 immobilization of each peptide.

We next developed a SAMDI method for high-throughput analysis of NGT peptide specificity. The SAMDI method uses alkanethiolate self-assembled monolayers (SAMs) to capture enzyme reaction substrates and products, which are purified on-chip, detected, and quantified by matrix-assisted laser desorption/ionization mass spectrometry (MALDI-MS). We previously demonstrated that the SAMDI assay could be used to profile the substrate specificities of several enzyme classes including deacetylases[31], acetyltransferases[32], and DNA ligases[33]. We also reported SAMDI screening of GT activities using monolayers presenting 24 immobilized sugars[15]. Previous works[34,35] by the Sabine group have also reported the activity of the polypeptide N-acetyl-galactosylamine transferase 2 (ppGalNAcT2) on immobilized peptides, though with limited substrate numbers. Here, we synthesized peptide sequence libraries for testing NGT activity by solid-phase peptide synthesis (SPPS) with a C-terminal Cys residue for specific immobilization via a Michael-Addition reaction onto SAMs that present maleimide groups against a background of tri(ethylene glycol) groups (FIG. 2a). We then performed in vitro glycosylation (IVG) reactions by adding NGT and UDP-Glc sugar donor to peptide libraries. Completed IVG reactions were transferred onto SAMDI plates for immobilization onto 384 maleimide SAM spots followed by rinsing and MALDI-MS of the SAMs, which provided distinct mass peaks for alkyldisulfides terminated in unmodified and glycosylated peptides. Integration of these peaks (with adjustments for ionization suppression due to glycosylation, see Methods, and data not shown) provided the glycosylation efficiency of each reaction (FIG. 2a). We validated this approach using NGT purified from BL21 (DE3) *E. coli* (data not shown) and truncated versions of the previously used NGT peptide substrate GSDQNATF[19]. We observed the appearance of a new MS signal at +162 m/z (the mass of a glucose moiety) in peptides as short as CNAT and NATC (FIG. 9).

Figure 2B:
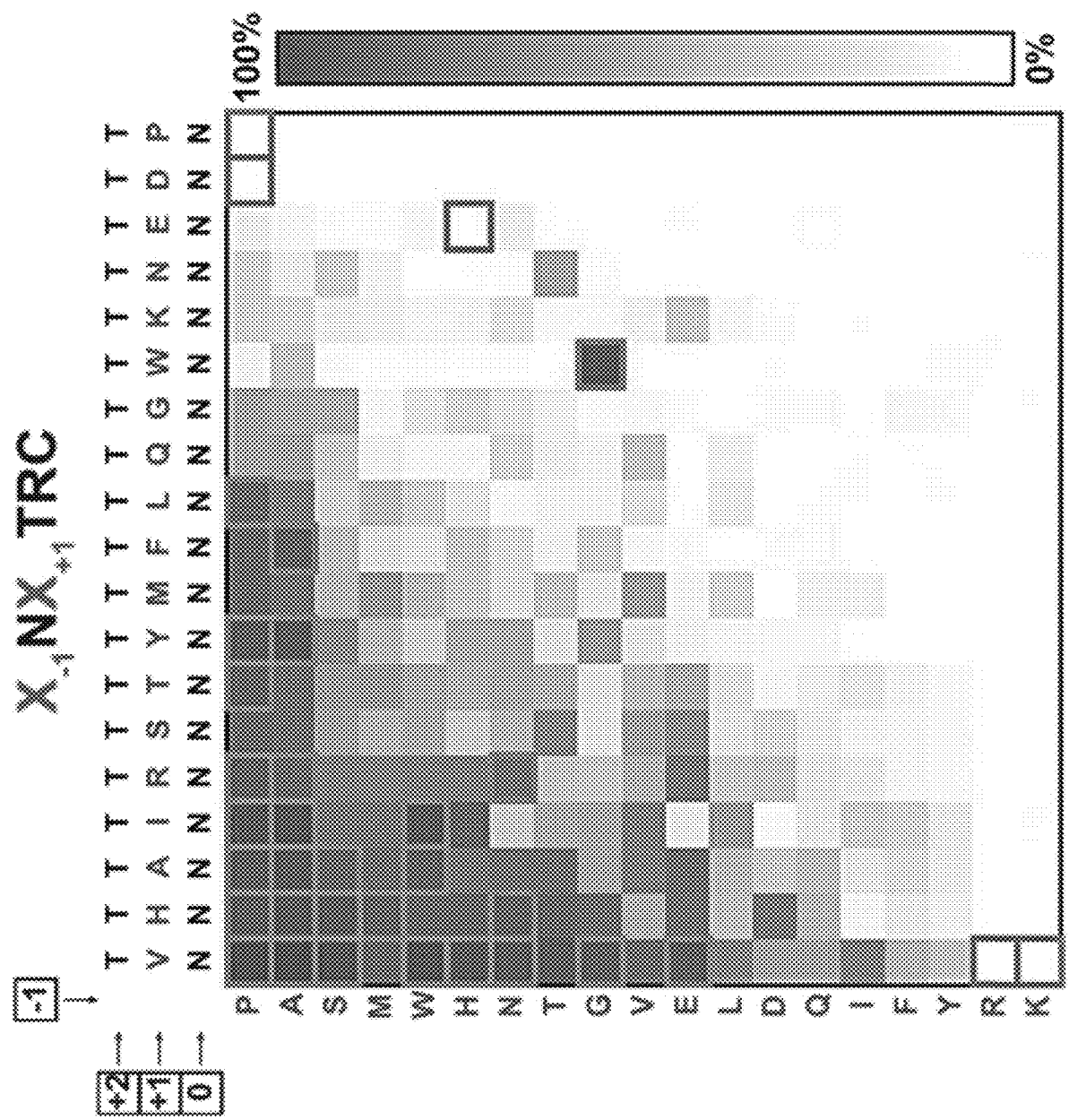

Using the methods above, we then created the complete GlycoSCORES platform using NGT synthesized in crude lysate CFPS reactions to glycosylate peptides in solution, which are then captured on-chip and directly analyzed by SAMDI (FIG. 2a). We evaluated the activity of NGT produced in CFPS against a peptide library having the sequence $X_{-1}NX_{+1}TRC$ where $X_{+1}$ and $X_{-1}$ are one of 19 amino acids (Cys is excluded) (FIG. 2b and data not shown). The glycosylation efficiency of these peptide sequences varied from no observed activity to nearly 100% conversion. NGT preferred Pro and Ala at the $X_{-1}$ position and Val, His, Ala, and Ile at the $X_{-1}$ position. Low modification was observed for Lys and Arg (basic residues) at the $X_{-1}$ position, Pro (a conformationally constrained residue) at the $X_{+1}$ position, and Asp and Glu (acidic residues) at the $X_{+1}$ position (FIG. 2b). Our results extend recent findings that charged amino acids adjacent to the NGT modification site are generally disfavored[24] by showing that positively charged residues are most disfavored in the $X_{+1}$ position while negatively charged residues are most disfavored in the $X_{-1}$ position.

Figure 10A:
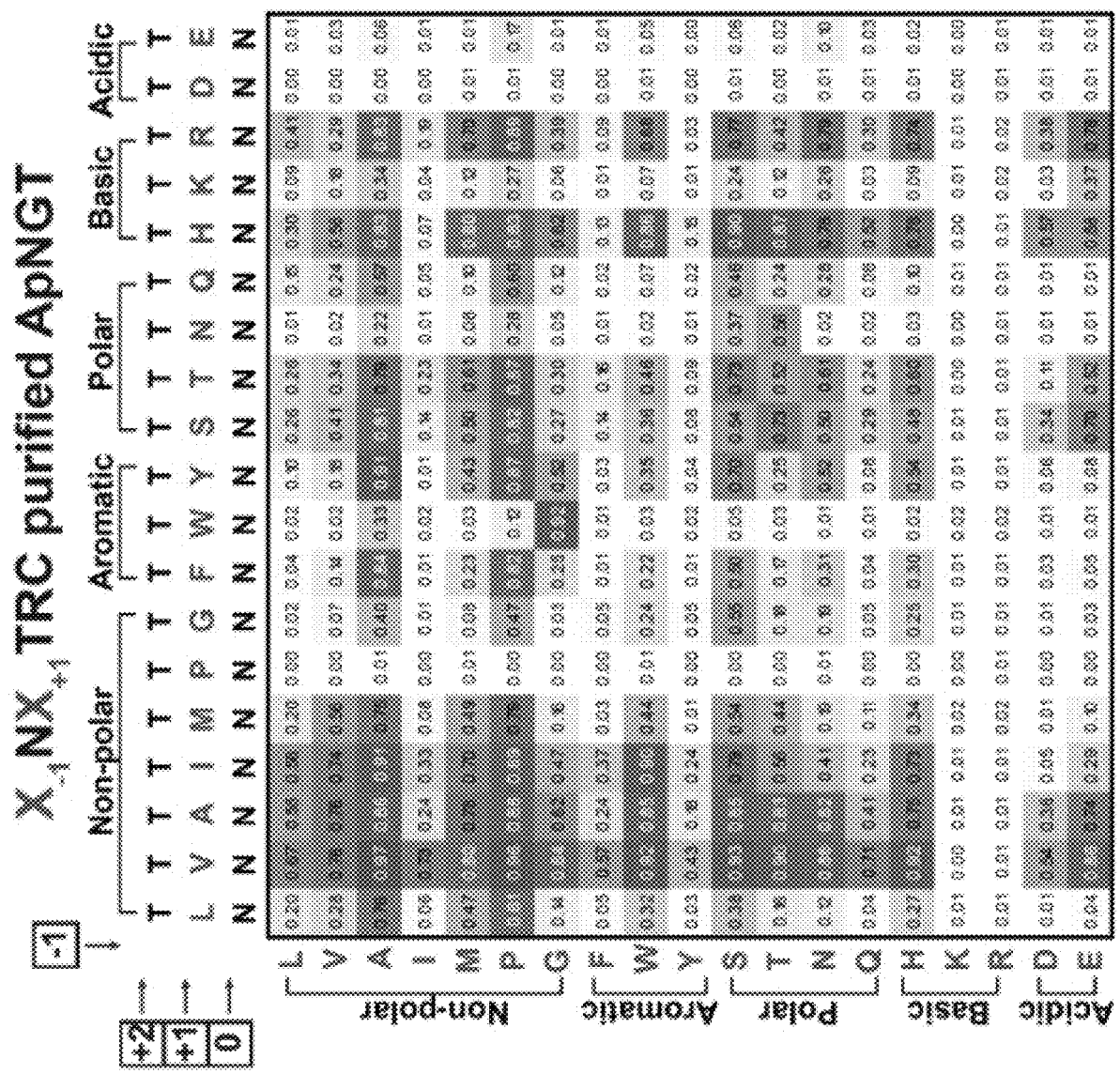
FIG. 10. NGT purified from living *E. coli* and synthesized by CFPS have similar peptide selectivity and specific activity. Percentage glucose modifications of $X_{-1}NX_{+1}TRC$ peptide library was determined using NGT purified from living *E. coli* (A) and NGT produced by CFPS (B, the same data as FIG. 2b). The slight differences in conversion is near to expected variation (less than 0.10) between experiments with identical reaction conditions. Reaction conditions: 50 µM peptide, 2.5 mM UDP-Glc, and 0.2 µM NGT incubated for 3 h at 30° C. Heat maps show the average of n=2 SAMDI-MS spectra acquired from separate peptide immobilizations.
Figure 10B:
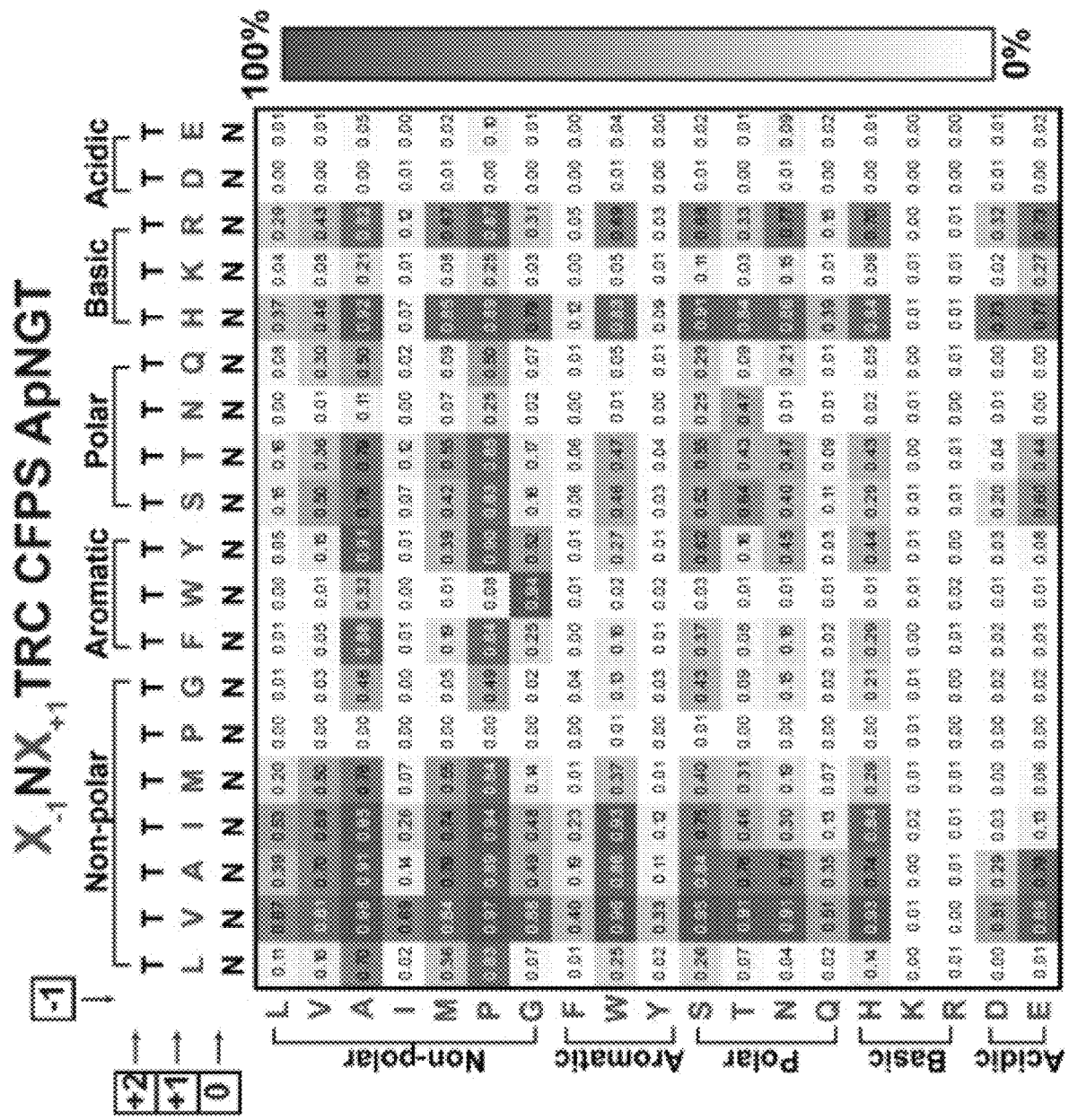

Interestingly, the preference of NGT for a given amino acid at a given sequence position is dependent on nearby amino acids. For example, Trp in the $X_{+1}$ position is generally not well tolerated, however, the motif GNWTRC was among the most efficiently glycosylated sequences (FIG. 2b). These unexpected dependencies necessitate the sampling of large, combinatorial libraries, which requires a high-throughput assay such as GlycoSCORES. Importantly, NGT produced in CFPS showed similar peptide selectivity and specific activity to purified NGT across the $X_{-1}NX_{+1}TRC$ library (FIG. 10). Control IVG reactions performed with CFPS reactions synthesizing superfolder green fluorescent protein (sfGFP) rather than NGT showed no peptide modification (data not shown).

Figure 11A:
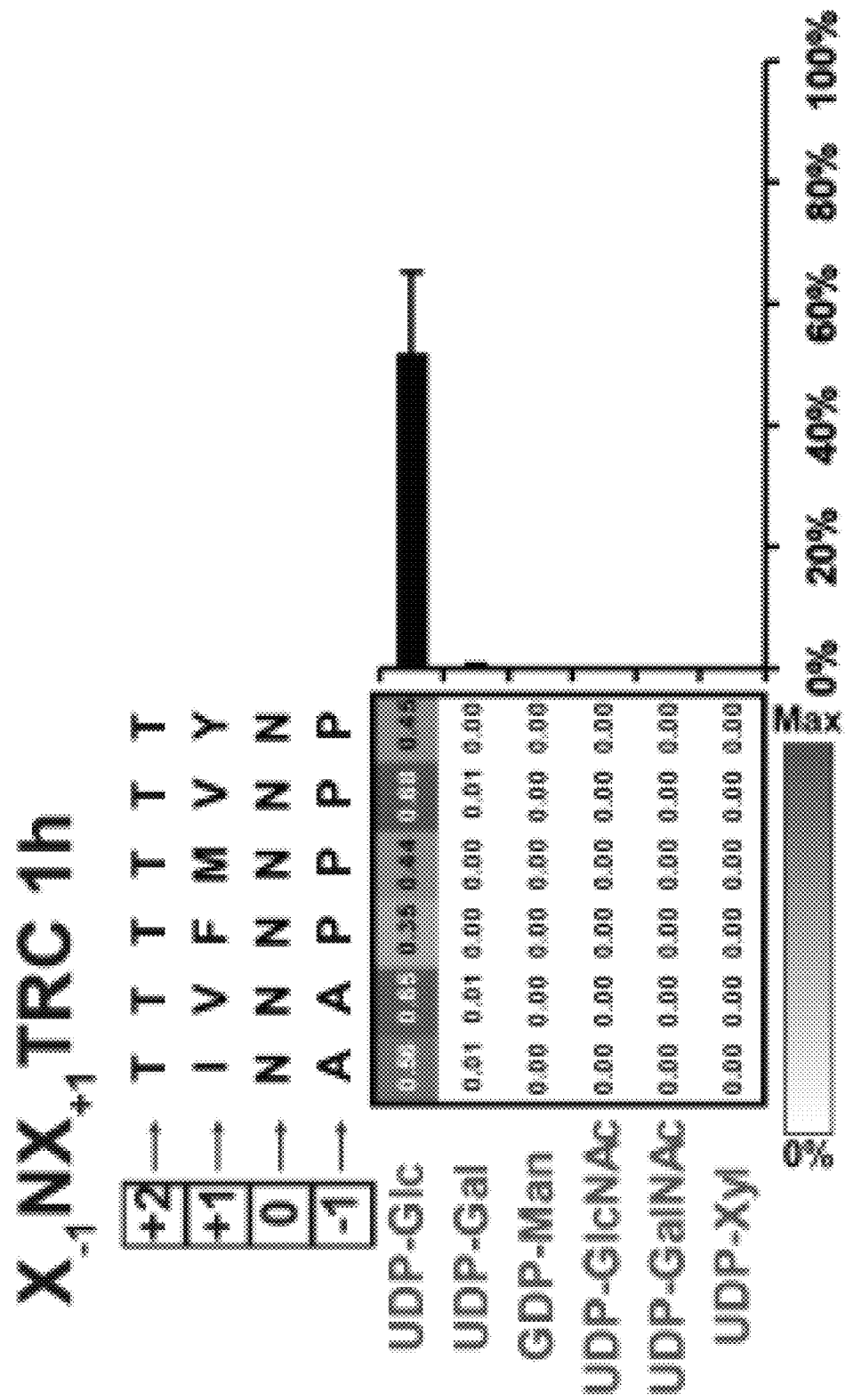
FIG. 11. Sugar donor preferences of NGT. (A-C) Relative intensities of peptide substrates and glycosylated products observed in mass spectra of 6 peptides from $X_{-1}NX_{+1}T$ library reacted with NGT and different sugar donors UDP-Glc, UDP-Gal, GDP-Man, UDP-GlcNAc, UDP-GalNAc and UDP-Xyl. The mean and S.D. of relative intensities of the 6 peptide modification values from heat maps are shown on the right. Only UDP-Glc, UDP-Gal and UDP-Xyl could be modified under these conditions, with UDP-Glc strongly preferred. All reactions were conducted with 50 µM peptide and 1 mM sugar donor, reacted with 0.1 µM purified NGT incubated at 30° C. for 1 h (A), 0.1 µM purified NGT incubated at 30° C. for 4 h (B), or 0.2 µM purified NGT incubated at 30° C. for 21 h (C). (D-F) Relative intensities of peptide substrates and glycosylated products observed in mass spectra for the $X_{-1}NX_{+1}TRC$ peptide library reacted with UDP-Glc (D), UDP-Gal (E) and UDP-Xyl (F). Peptide preferences are weakly dependent on sugar donors UDP-Glc, UDP-Gal, and UDP-Xyl. For example, NGT is less tolerant of Trp at the $X_{-1}$ position when transferring xylose compared to glucose or galactose. All reactions were conducted with 50 µM peptide and 1 mM sugar donor and reacted with 0.1 µM purified NGT incubated at 30° C. for 4 h (D), 10 µM purified NGT incubated at 30° C. for 21 h (E), or 4 µM purified NGT incubated at 30° C. for 21 h (F). To ensure that endogenous activated sugar donors or metabolic processes in CFPS did not provide false positives of galactose transfer, sugar donor experiments were completed with purified NGT. Relative intensities were calculated using I(P) (I(S)+I(P)) where I(P) is the MS intensity of the glycosylated product and I(S) is the MS intensity of the aglycosylated substrate. Heat maps show the average of n=2 SAMDI-MS spectra acquired from separate peptide immobilizations.
Figure 11B:
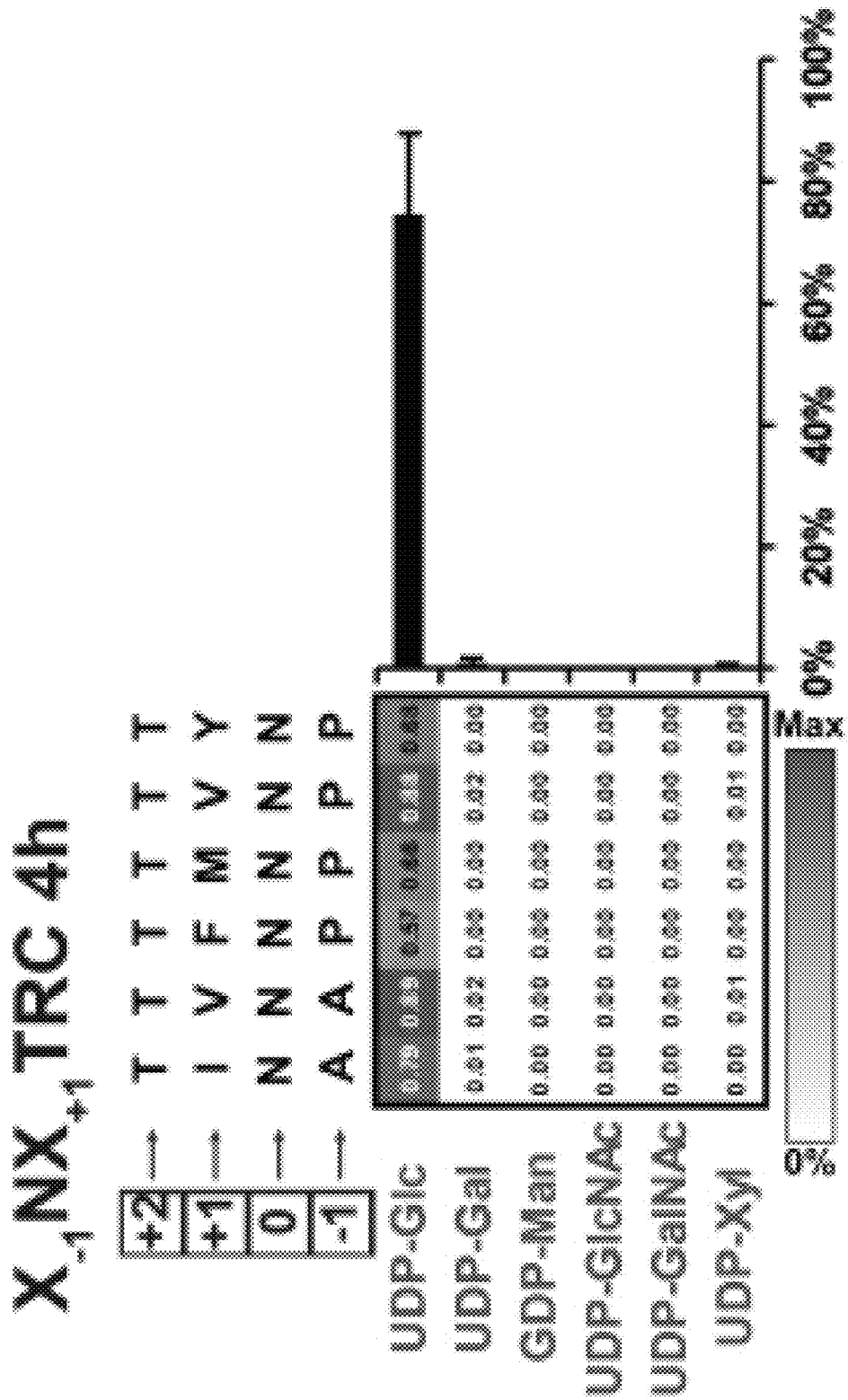
Figure 11C:
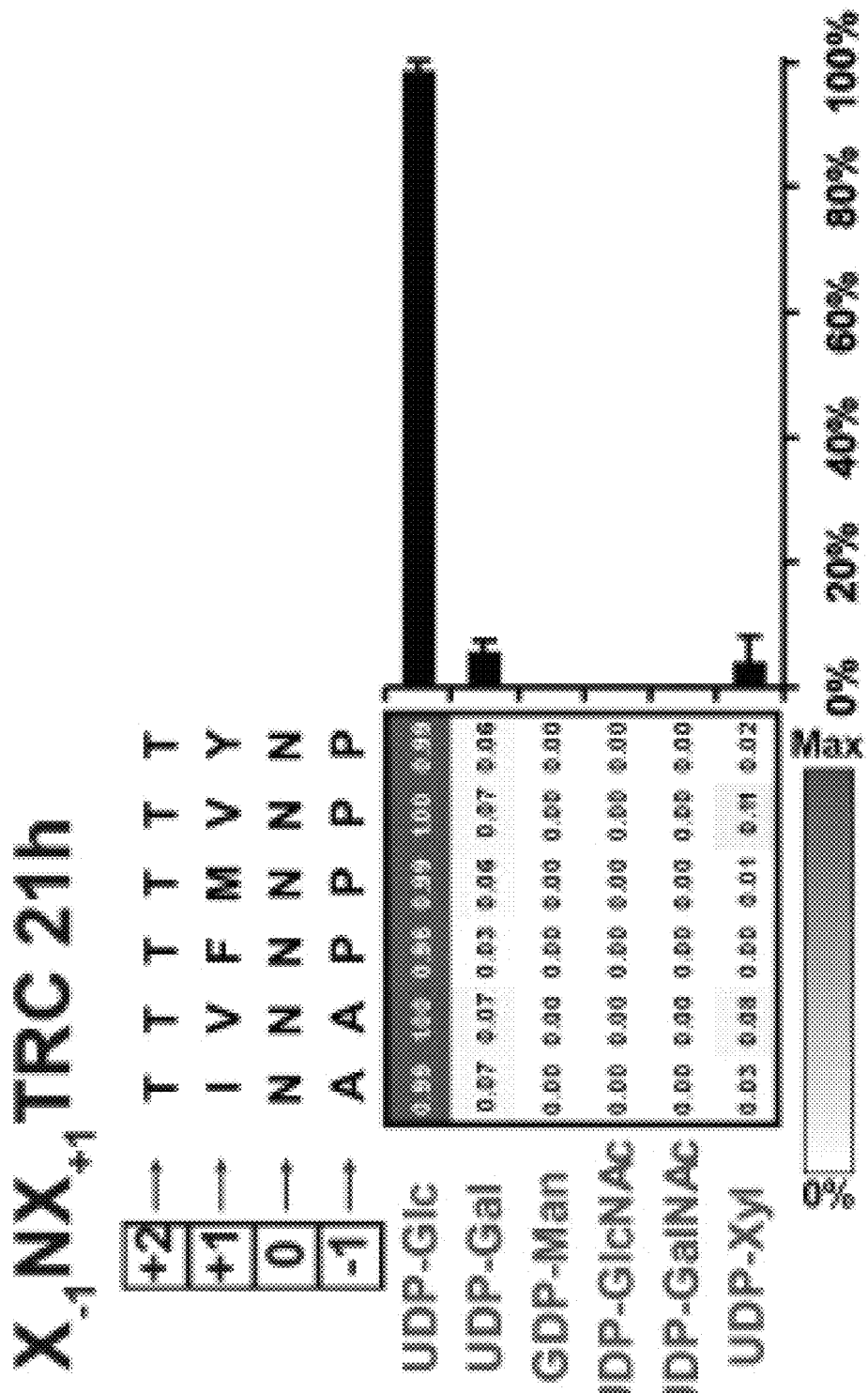

While we focused on peptide specificity, we also showed the breadth of the platform by screening NGT activity with 6 different nucleotide-activated sugar donors: UDP-Glc, UDP-galactose (UDP-Gal), UDP-N-acetylglucosamine (UDP-GlcNAc), UDP-N-acetylgalactosamine (UDP-GalNAc), guanosine-diphosphate mannose (GDP-Man), and UDP-xylose (UDP-Xyl). Consistent with previous results[19], we found that NGT transferred UDP-Glc with the highest efficiency and UDP-Gal and UDP-Xyl with much lower efficiencies (FIG. 11). We also tested the interdependency of sugar donor on the $X_{-1}NX_{+1}T$ peptide library selectivity. While the peptide selectivity remained similar with each of the UDP-Glc, UDP-Gal, and UDP-Xyl donors, sugar donor identity did influence relative $X_{-1}$ and $X_{+1}$ residue preferences in some cases. For example, NGT is less tolerant of Trp at the $X_{-1}$ position when transferring xylose compared to glucose or galactose.

Figure 12A:
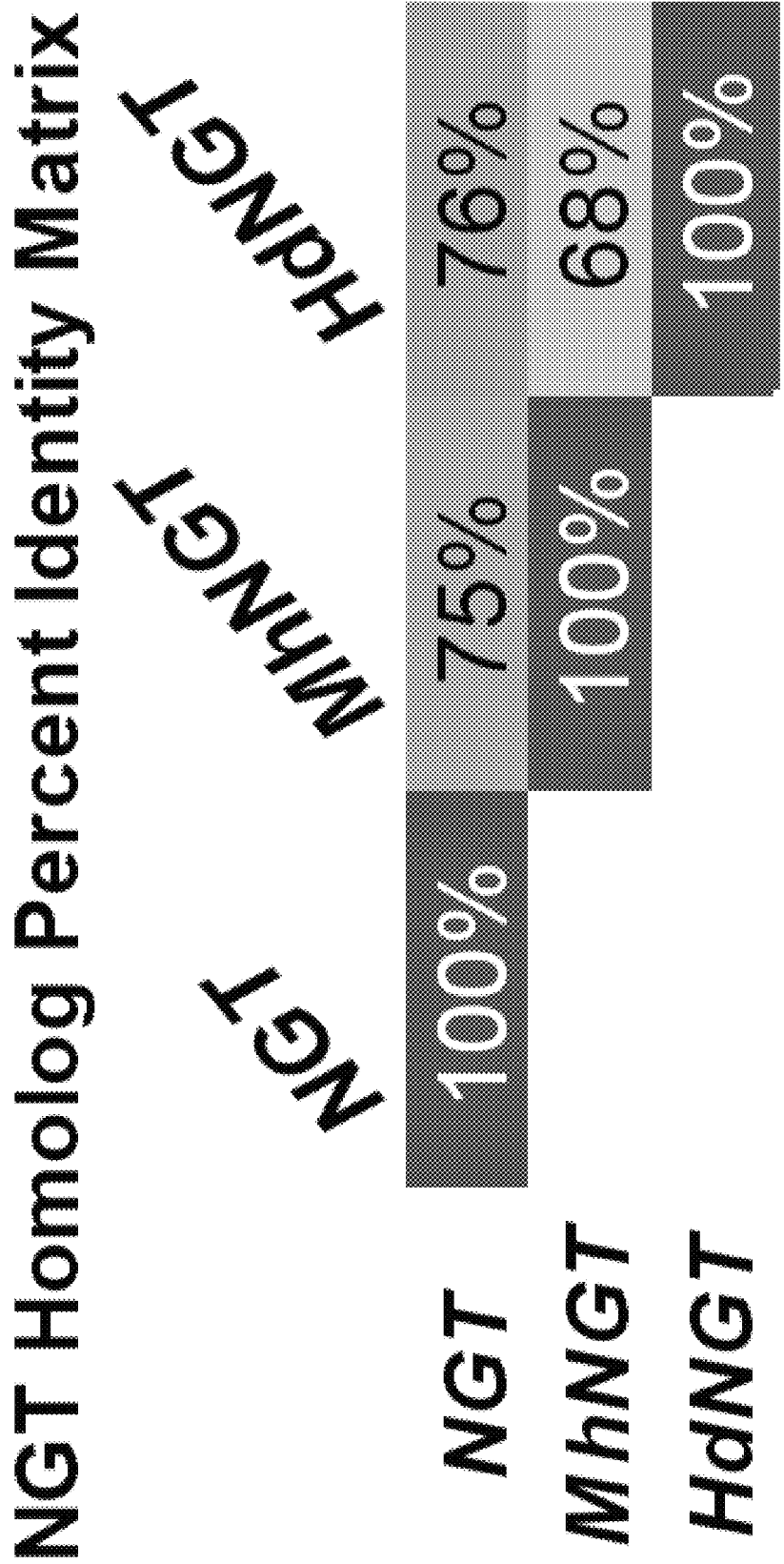
FIG. 12. Percent identity matrix and alignment of NGT homologs used in this study. (A) Percent identity matrix of NGT homologs characterized in this study, NGT (Uniprot: NGT_ACTP2), MhNGT (Uniprot: A0A0B5BRN9_MANHA), and HdNGT (Uniprot: Q7VKK3_HAEDU). (B) CLUSTAL OMEGA alignment of NGT homologs showing levels of conservation across enzymes.
Figure 12B:
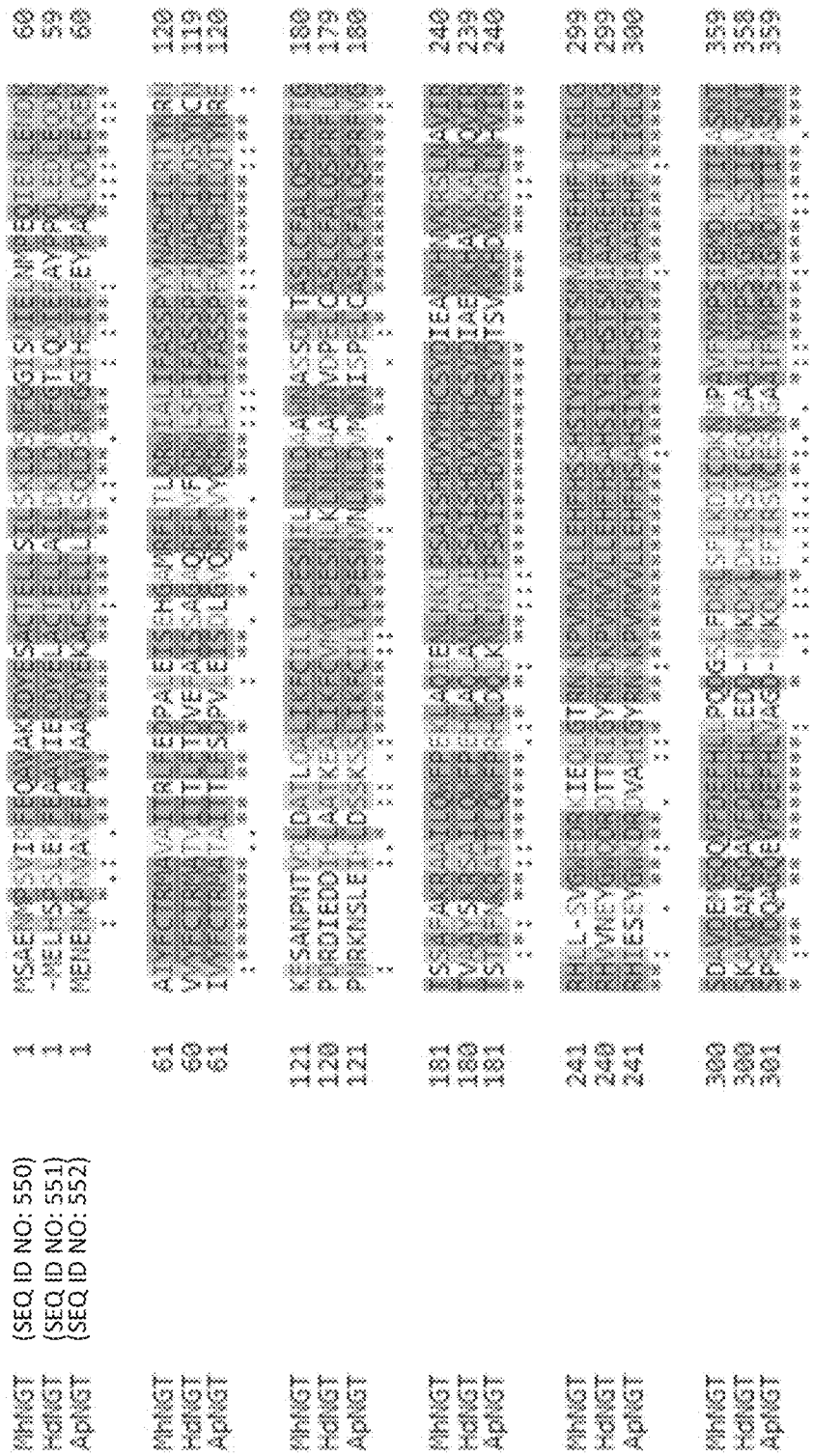

Study of NGT homolog and human O-linked GT peptide specificities. To demonstrate the utility of GlycoSCORES for analysis of uncharacterized glycosyltransferases, we synthesized NGT homologs from the bacterial pathogens *Mannheimia haemolytica* and *Haemophilus ducreyi* (MhNGT and HdNGT), found that they are in fact NGTs, and determined their specificity on all possible acceptor sequences within the canonical NGT target sequence of $X_{-1}$-N-$X_{+1}$-S/T (FIG. 12 and data not shown). Given sequence identities of 68-76% (FIG. 12), these enzymes show striking similarities to NGT acceptor sequence preferences. This may indicate two-fold evolutionary pressure for these enzymes to modify designated target proteins, but not modify and interfere with essential cytoplasmic proteins. The discovery of NGTs with conserved specificities in these organisms motivates further studies to understand the roles these enzymes in their pathogenesis.

Figure 3A:
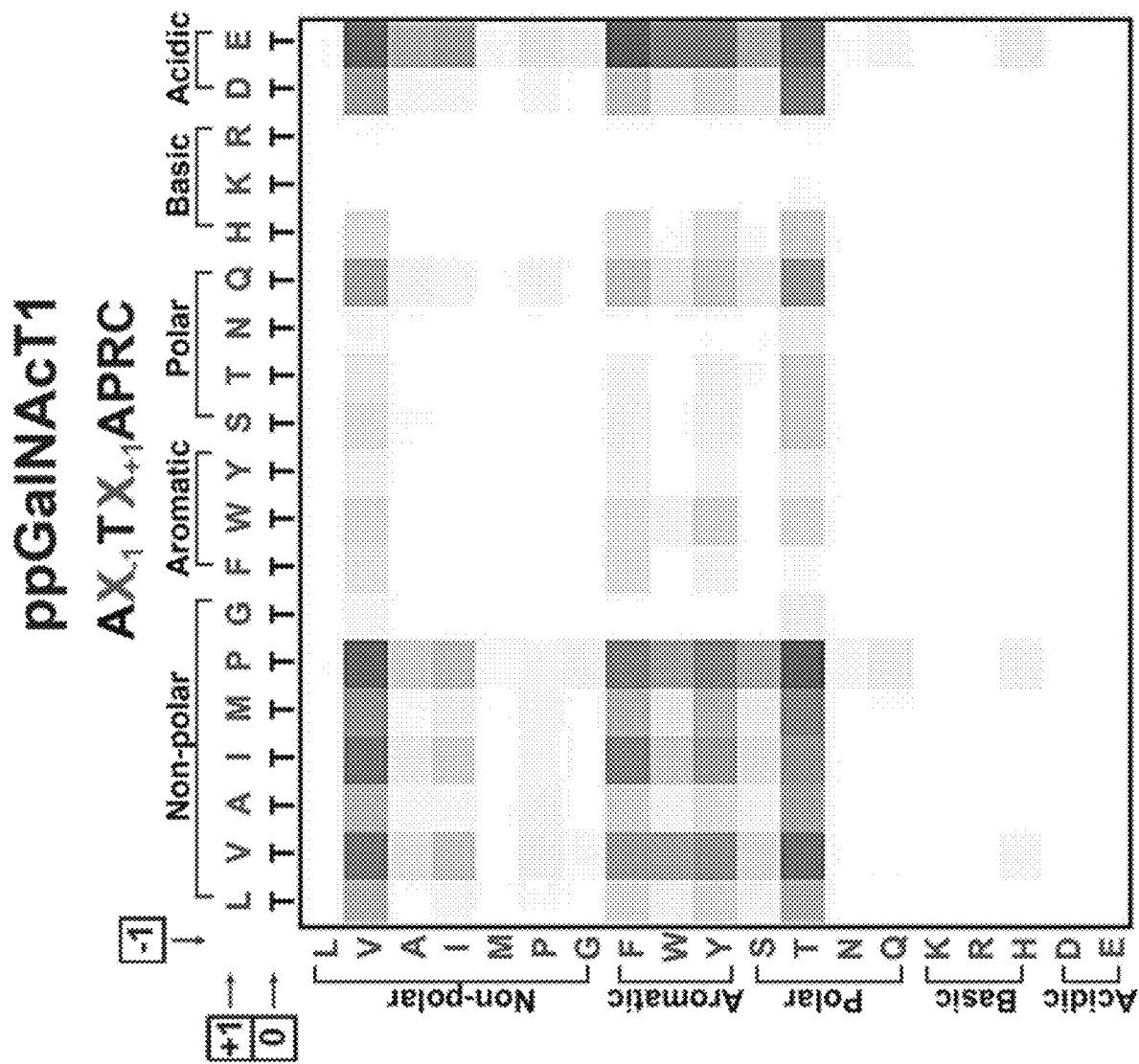
FIG. 3: Using GlycoSCORES to determine peptide selectivity of human ppGalNAcTs. (a) Specificity of ppGalNAcT1 produced in CFPS on peptide array of $AX_{-1}TX_{+1}$ APRC designed from peptide AATPAP[38]. (b) The same peptide array with ppGalNAcT2 produced in CFPS. Reaction conditions: 100 µM peptide, 1 mM UDP-GalNAc, and 0.024 µM CFPS ppGalNAcT1 (a) or 0.04 µM CFPS ppGalNAcT2 (b) incubated at 37° C. for 1 h. Isoforms ppGalNAcT1 and ppGalNAcT2 share 40% sequence identity (Uniprot Clustal Omega Alignment[50]) and showed major difference in peptide preferences. Peptide maps annotated with numerical values of the relative intensities of peptide substrates and glycosylated products and a negative control library generated using CFPS without ppGalNAcTs averaged from n=2 SAMDI-MS spectra from separate peptide immobilizations are shown in FIG. 13.
Figure 3B:
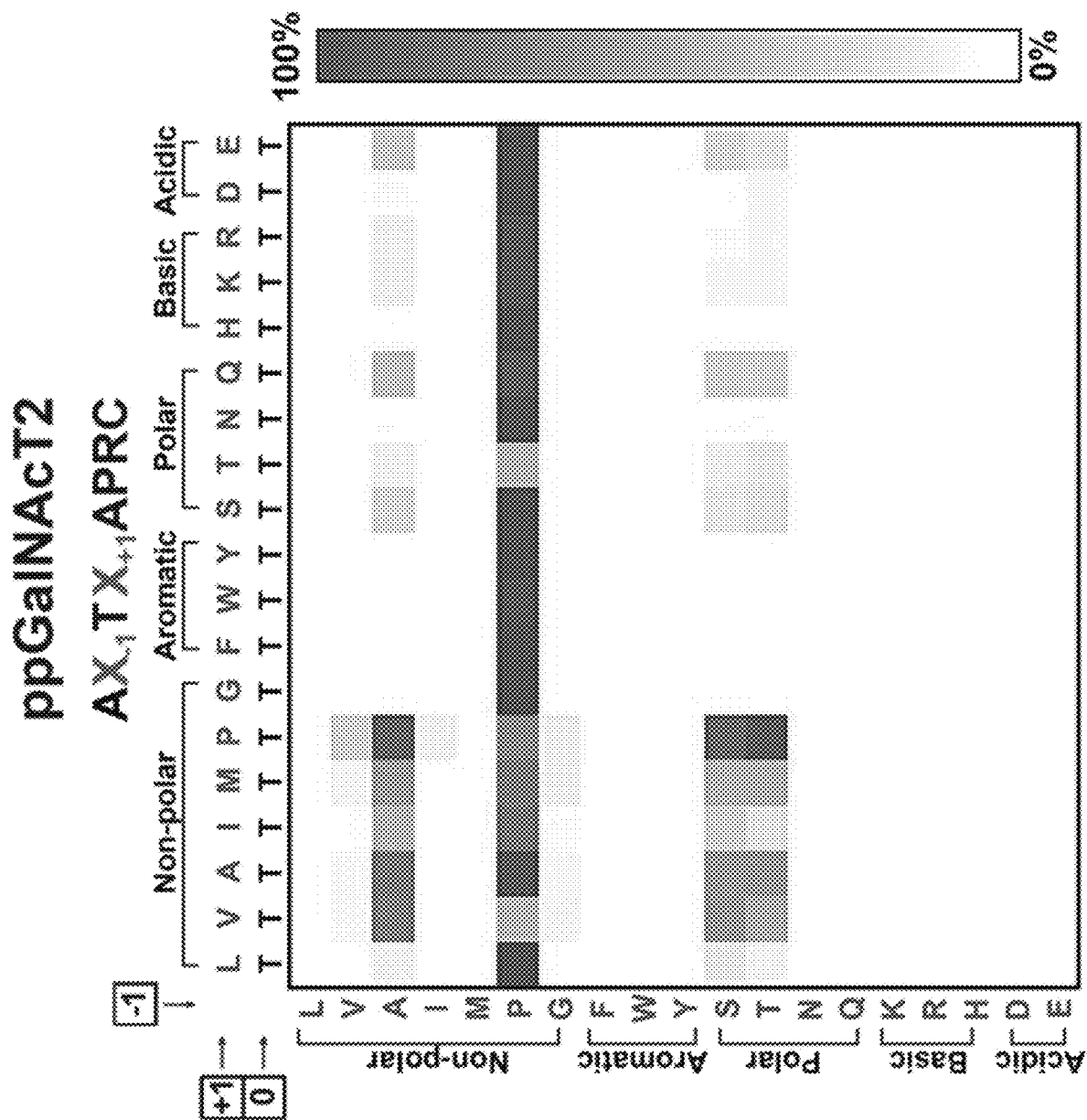
Figure 13A:
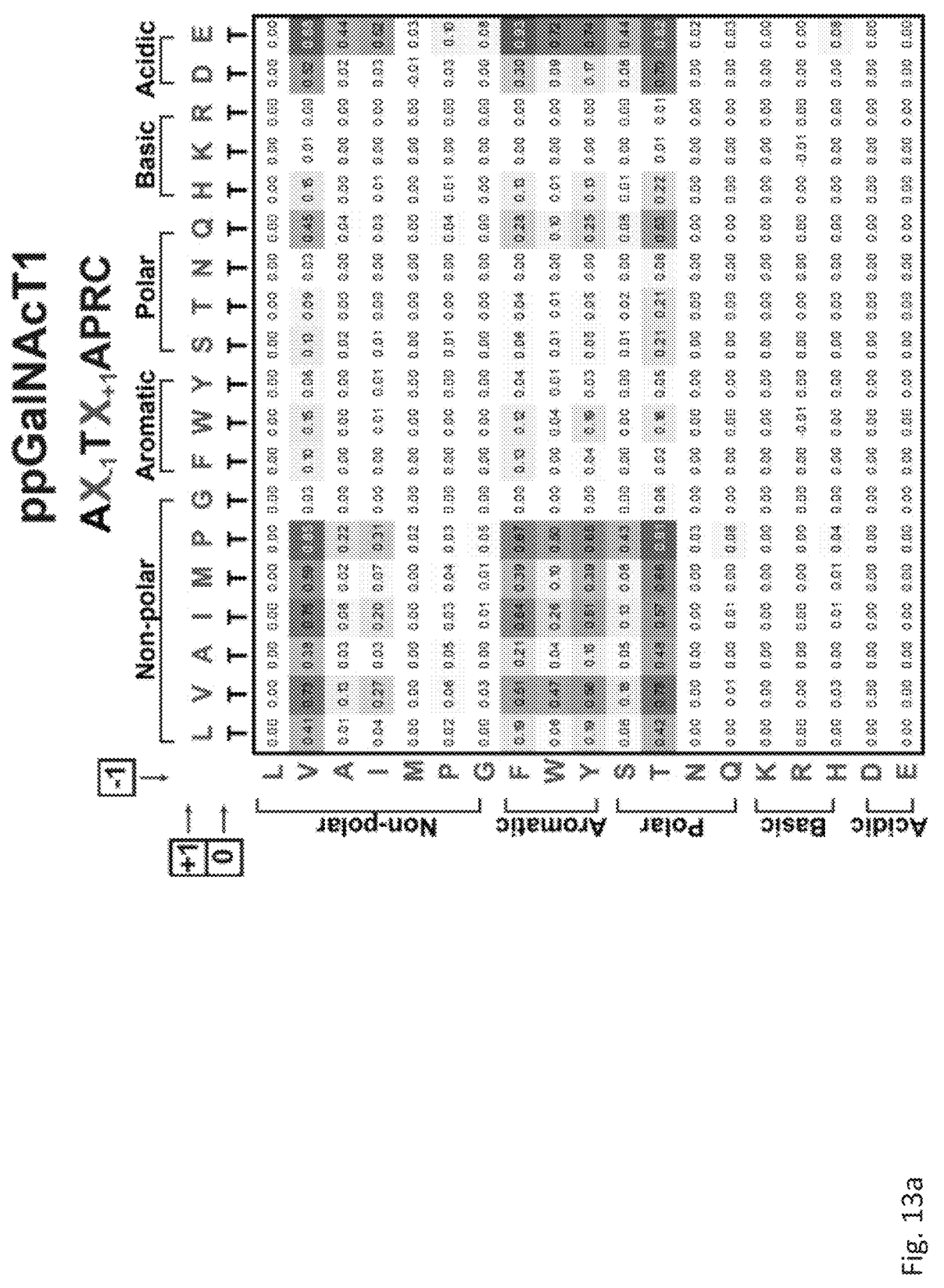
Figure 13B:
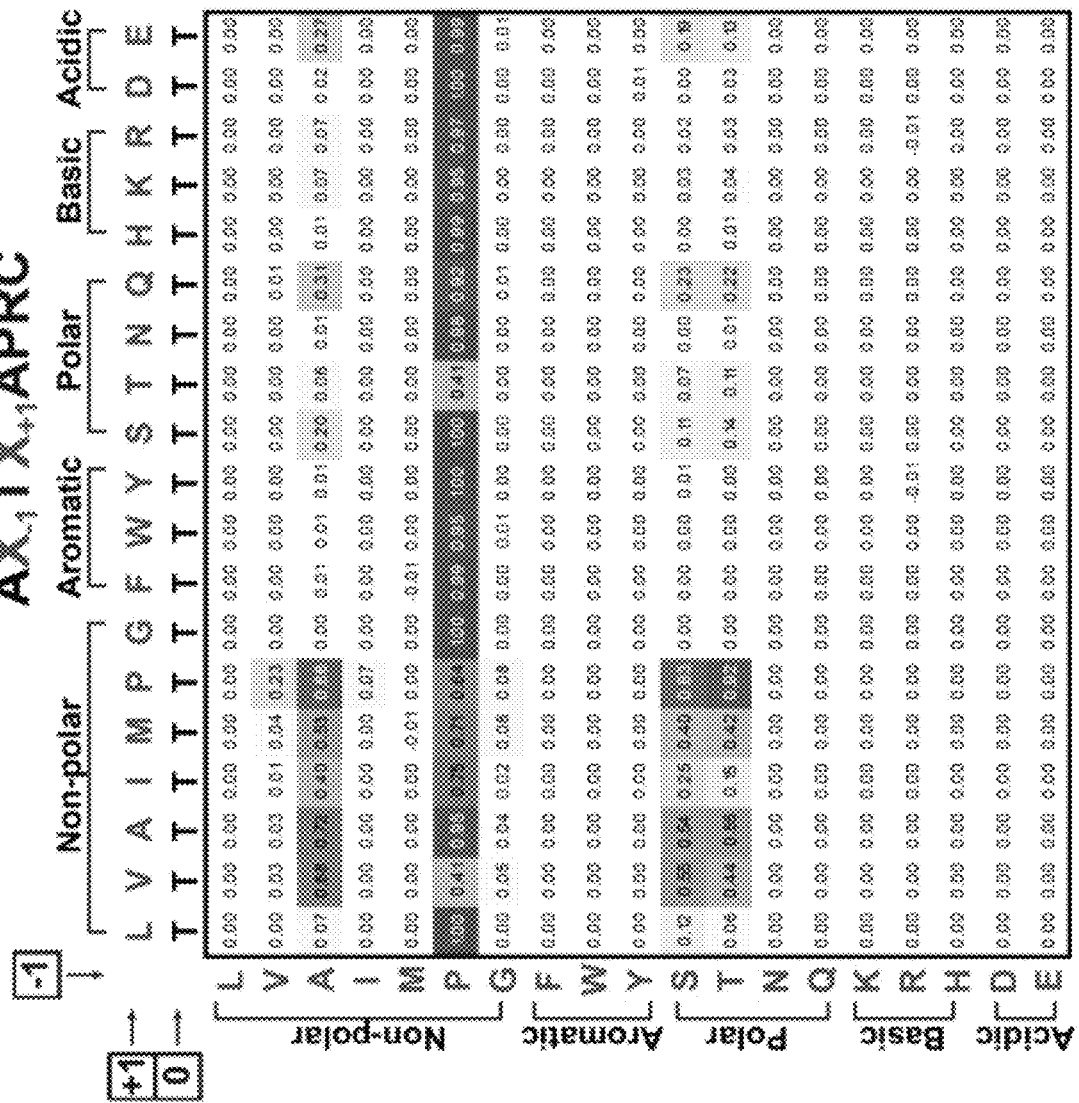
FIG. 13. Peptide specificity maps of ppGalNAcTs annotated with numerical values and peptide control library. (A) Peptide specificity map of CFPS GalNAcT1 shown in FIG. 3a annotated with numerical values of the relative intensities peptide substrates and glycosylated products. (B) The same peptide array and annotations with CFPS ppGalNAcT2 shown in FIG. 3b. (C) Negative control library incubated with CFPS sfGFP showed no GalNAc modification. Reaction conditions: 100 µM peptide, 1 mM UDP-GalNAc, and 0.024 mM CFPS ppGalNAcT1 (A), 0.04 mM CFPS ppGalNAcT2 (B) or CFPS sfGFP (C) incubated at 37° C. for 1 h. Isoforms ppGalNAcT1 and ppGalNAcT2 share 40% (Uniprot Clustal Omega Alignment[15]) sequence identity and showed major differences in peptide preferences. Heat maps show the average of n=2 SAMDI-MS spectra from separate peptide immobilizations.
Figure 13C:
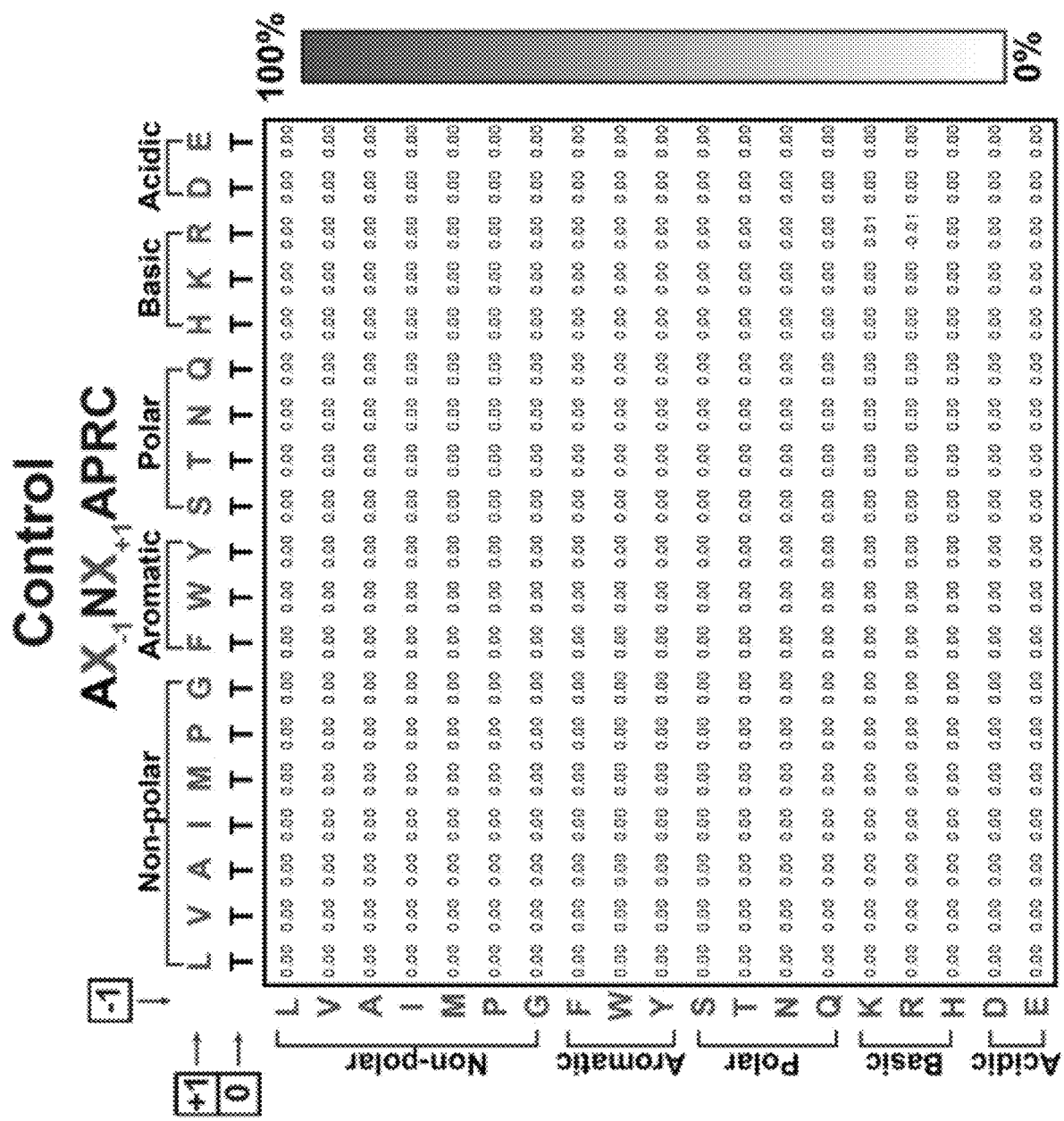

We also applied the GlycoSCORES workflow to determine the peptide specificities of two important O-linked human glycosylation enzymes, ppGalNAcT1 and ppGalNAcT2. These enzymes install the first sugar of mucin-like glycans which effect the development of several cancers[36] and aberrant lipid metabolism[37]. Both ppGalNAcT1 and ppGalNAcT2 were produced in CFPS (data not shown) and characterized with a saturated $X_{-1}$-T-$X_{+1}$-P peptide library (FIG. 3 and FIG. 13). In addition to corroborating previous investigations of the specificity of these enzymes on peptides in vitro[37-40] and on proteins in vivo[37, 41], the throughput of GlycoSCORES allowed us to simultaneously vary both the $X_{-1}$ and $X_{+1}$ positions, which was difficult using conventional strategies, and obtain quantitative readouts for each combination. Our data led to unexpected results in the specificities of ppGalNAcT1 and ppGalNAc2. For example, we discovered that intolerance of aromatic residues adjacent to the glycosylation site of ppGalNAcT2 can be overcome by the presence of a Pro in the $X_{-1}$ position. However, the preference of ppGalNAcT2 for Pro is reduced in the cases of Val and Thr in the $X_{+1}$ position, which themselves would predict relatively good substrates (FIG. 3). The ability to investigate ppGalNAcT specificity at this depth could advance efforts to design of isoform-specific substrates and substrate mimics and enhance glycosylation site prediction.

Figure 14:
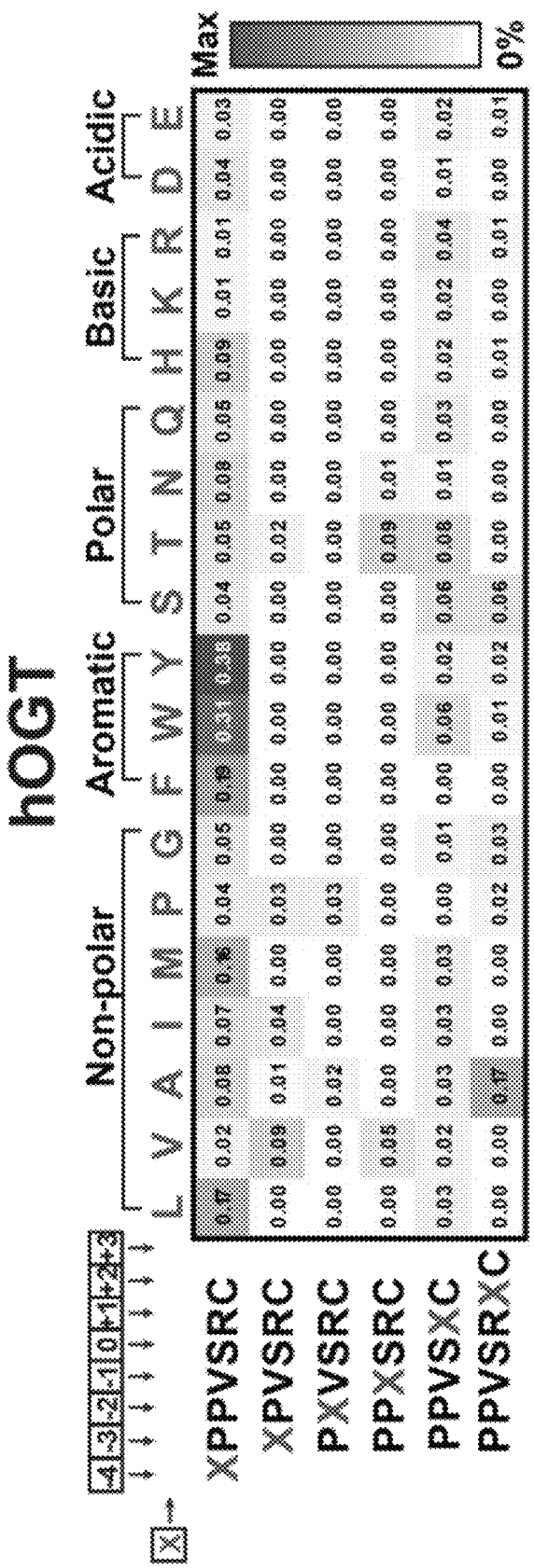
FIG. 14. GlycoSCORES characterization of human OGT. Peptide specificity map of human OGT produced in CFPS. We analyzed 19-amino acid substitutions for each position of a previously proposed OGT targeting sequence of PPVSR and also investigated the specificity at the $X_{-4}$ and $X_{+2}$. This screen shows successful production of active human OGT in CFPS and that GlycoSCORES can be used to probe peptide specificity of hOGT in high throughput. This is the first saturated substitution of this sequence, and specificity results were generally consistent with previous analysis of human glycosylation sites and peptide screens[11, 16, 17], such as the preference for V in the $X_{-3}$ position and A in the $X_{+2}$ position. When we extended the sequence to include an $X_{-4}$ amino acid, we observed an overall increase in modification and a strong preference for aromatic residues. This result indicates that the presence and identity of the $X_{-4}$ position is important for OGT activity. Reaction conditions: 50 µM peptide, 2.5 mM UDP-GlcNAc, and 0.062 µM CFPS hOGT. The heat map shows the average of n=2 SAMDI-MS spectra from separate peptide immobilizations.

We further demonstrated the broad applicability of GlycoSCORES by characterizing the human O-linked GlcNAc transferase (hOGT), which has been implicated in neurodegeneration and insulin resistance disease states[42, 43]. We expressed hOGT in CFPS (Supplementary FIG. 14) and analyzed 19-amino acid substitutions for each position of a proposed OGT targeting sequence of PPVSR[16] (FIG. 14). Specificity results were largely consistent with previous analysis of human glycosylation sites and peptide screens[16, 44-46], such as the preference for V in the $X_{-3}$ position and A in the $X_{+2}$ position. When we extended the sequence to the $X_{-4}$ and $X_{+2}$ position, we discovered an overall increase in modification and a strong preference for aromatic residues. This screen provides proof of concept for future studies of OGT variants, which can be rapidly produced in CFPS and probed for peptide specificity at high depth and throughput.

Figure 4A:
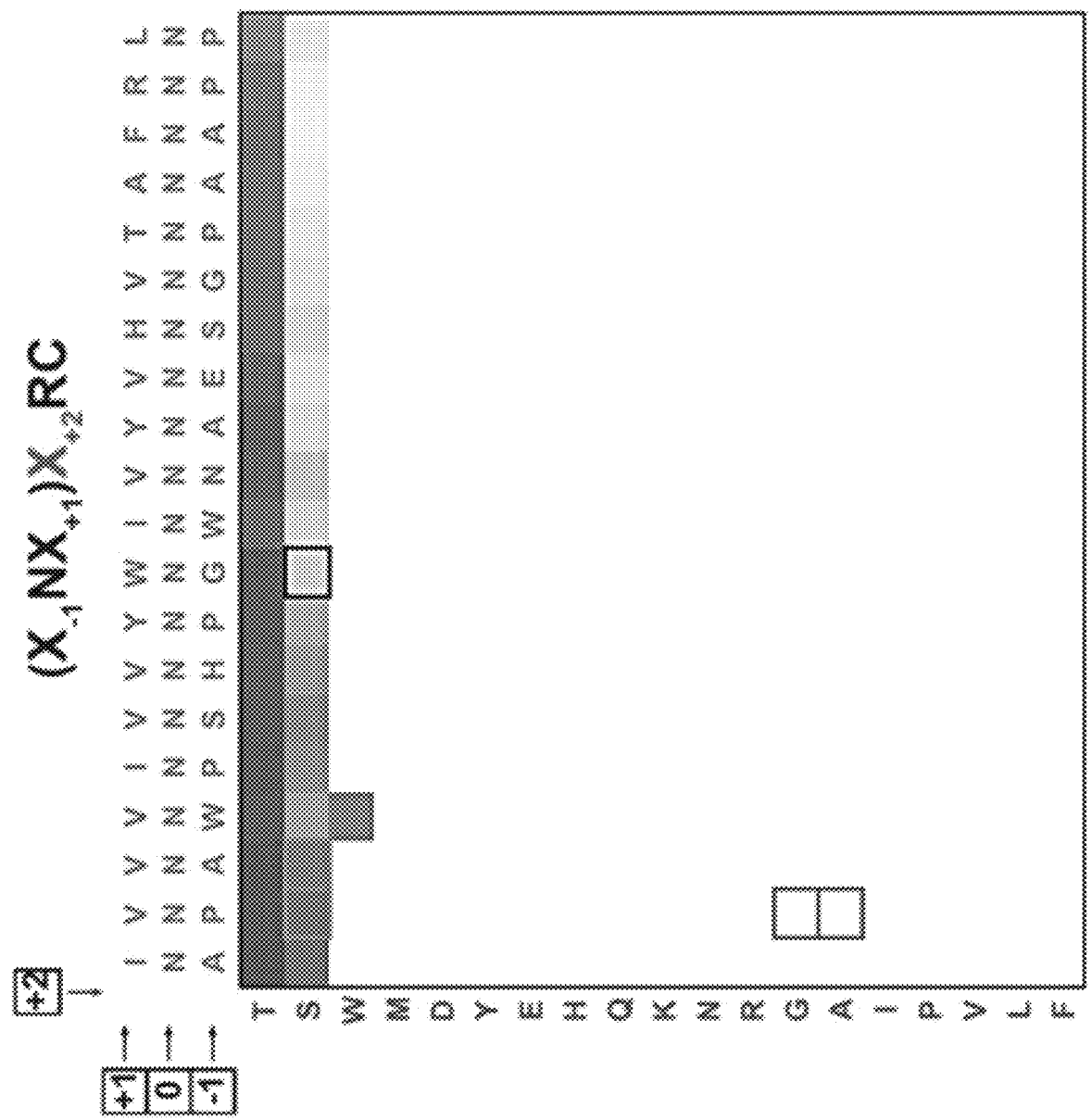
FIG. 4: GlycoSCORES $X_{+2}$, $X_{-2}$, and $X_{+3}$ position peptide specificity screening of NGT. (a) Highly modified peptide sequences from FIG. 2b were tested with 19 amino acids in position $X_{+2}$ relative to modified Asn. Only Thr and Ser showed efficient modification. (b) Sequences from FIGS. 2b and 4a were tested with 19 amino acids in the $X_{-2}$ position. Only the GNWT sequence showed efficient modification with all amino acids at the $X_{-2}$ position. (c) Sequences from 4b were tested with 19 amino acids in the $X_{+3}$ position. Sequences showing high (blue boxes, >66%), medium (black boxes, 33-66%), and low (grey boxes, <3%) modification efficiencies were chosen for subsequent screens towards an optimized GlycTag. Four sequences from (c) with varying levels of modification were selected for installation into proteins in FIGS. 5 and 6. Peptide sequences for which modification efficiencies could not be determined due to poor peptide solubility are shown as filled grey squares in the heat map. Reactions in (a-b) were completed with 0.2 µM NGT for 3 h. Reaction conditions were altered to 0.025 µM NGT for 1 h in (c) to avoid saturation. Peptide maps also were completed using 0.1 µM NGT for 1 h (data not shown). Numerical values of modification efficiencies from SAMDI-MS spectra were acquired from n=2 separate peptide immobilizations (data not shown). Control peptide arrays reacted with CFPS reactions without NGT also were generated (data not shown).
Figure 15A:
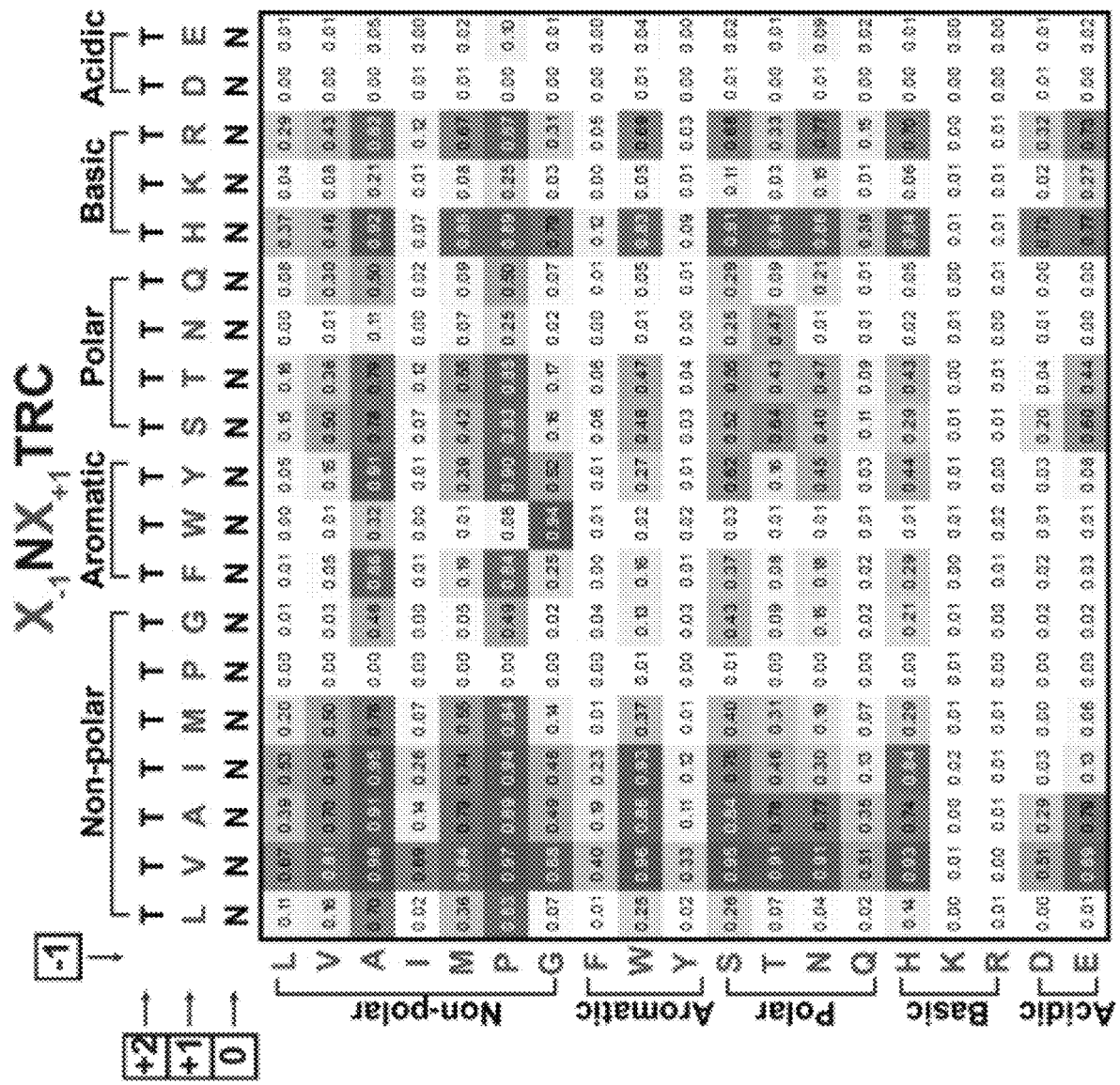
FIG. 15. Amino acids at $X_{+2}$ position weakly influence amino acid selectivity at $X_{-1}$ and $X_{+1}$ positions. (A) Percentage glucose modification map of peptide library $X_{-1}NX_{+1}$TRC using CFPS NGT, the same as FIG. 2b. (B) Percentage glucose modification map of peptide library $X_{-1}NX_{+1}$SRC using CFPS NGT. Modification patterns are nearly identical, but T is preferred over S in the $X_{+2}$ position. Reaction condition: 50 µM peptide, 2.5 mM UDP-Glc, and 0.2 µM CFPS NGT incubated at 30° C. for 3 h. Heat maps show the average of n=2 SAMDI-MS spectra acquired from separate peptide immobilizations.
Figure 15B:
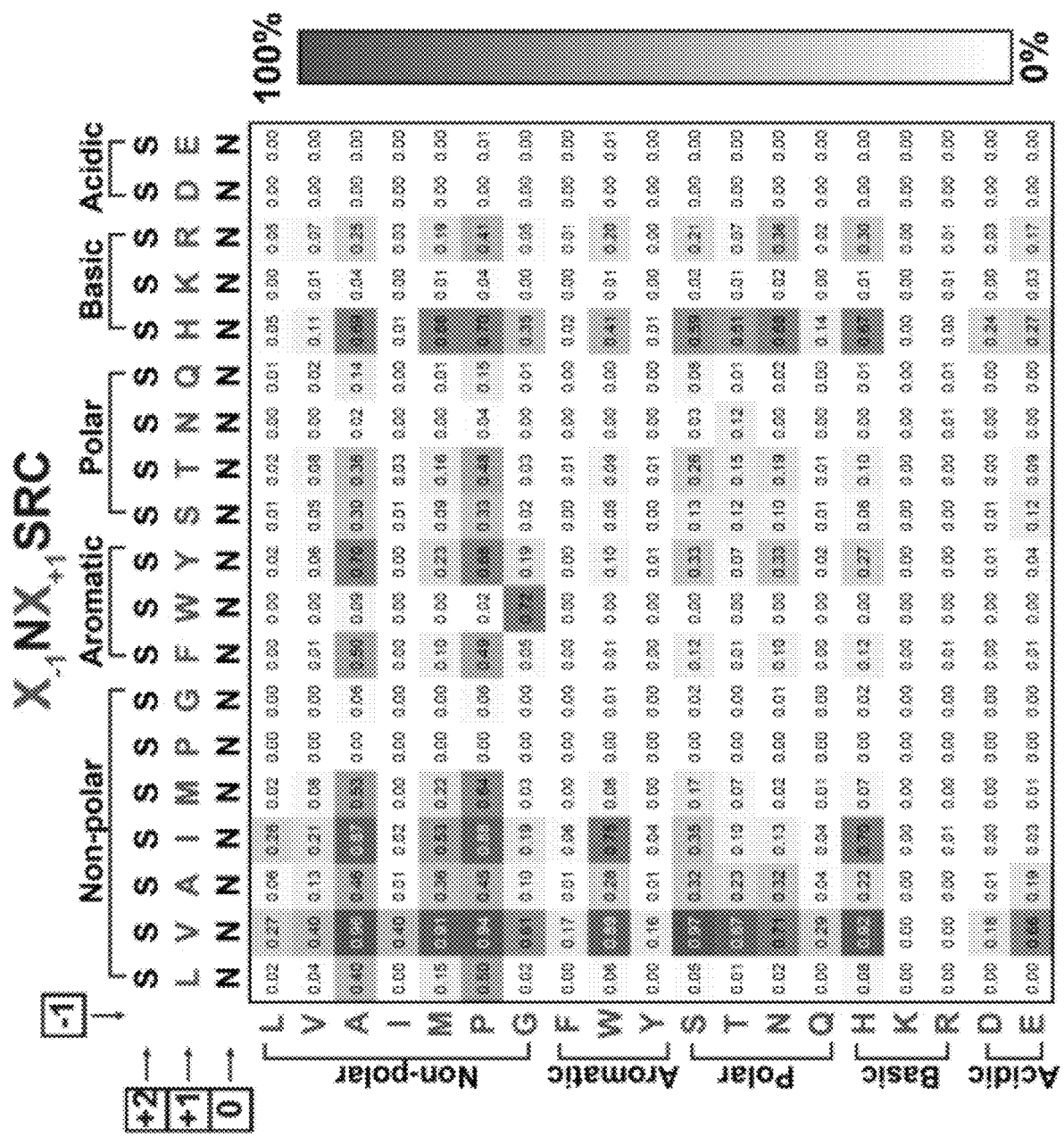

Optimization of NGT peptide acceptor sequences. To show that GlycoSCORES can be used for rigorous acceptor peptide sequence optimization towards increased modification of whole proteins, we sought to develop optimized GlycTag sequences for NGT comprised of 6 amino acids that could be efficiently modified in the context of whole proteins. Because the total number of 6-mer sequences is prohibitively large, we iteratively tested preferences in the $X_{+2}$, $X_{-2}$, and $X_{+3}$ positions across a set of sequences informed by previous libraries (FIG. 4 and data not shown). To determine the preference of NGT for amino acids at the $X_{+2}$ position, we prepared an array of 380 peptides based on the motif $(X_{-1}NX_{+1})X_{+2}RC$, by selecting 20 efficiently glycosylated $X_{-1}NX_{+1}T$ sequences from FIG. 2b and resynthesizing each with 19 amino acids in the $X_{+2}$ position (FIG. 4a). As was previously reported[19, 24], we found Thr or Ser are required in the $X_{+2}$ position for efficient modification by NGT, with Thr preferred over Ser. We also evaluated a complete $X_{-1}NX_{+1}S$ peptide library and did not find significant differences in $X_{-1}$ and $X_{+1}$ residue preferences compared to the $X_{-1}NX_{+1}T$ peptide library (FIG. 15).

Figure 4B:
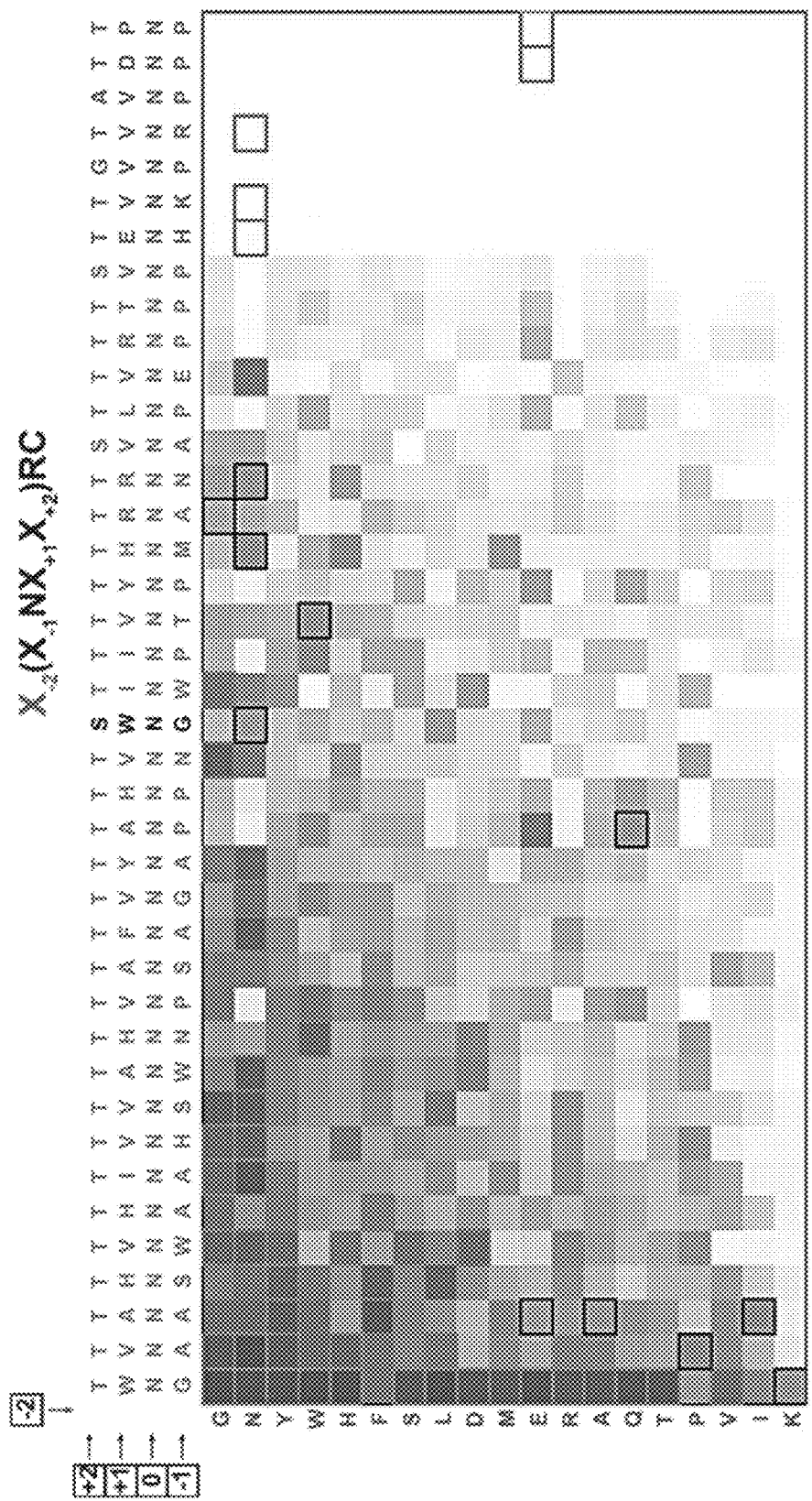
Figure 4C:
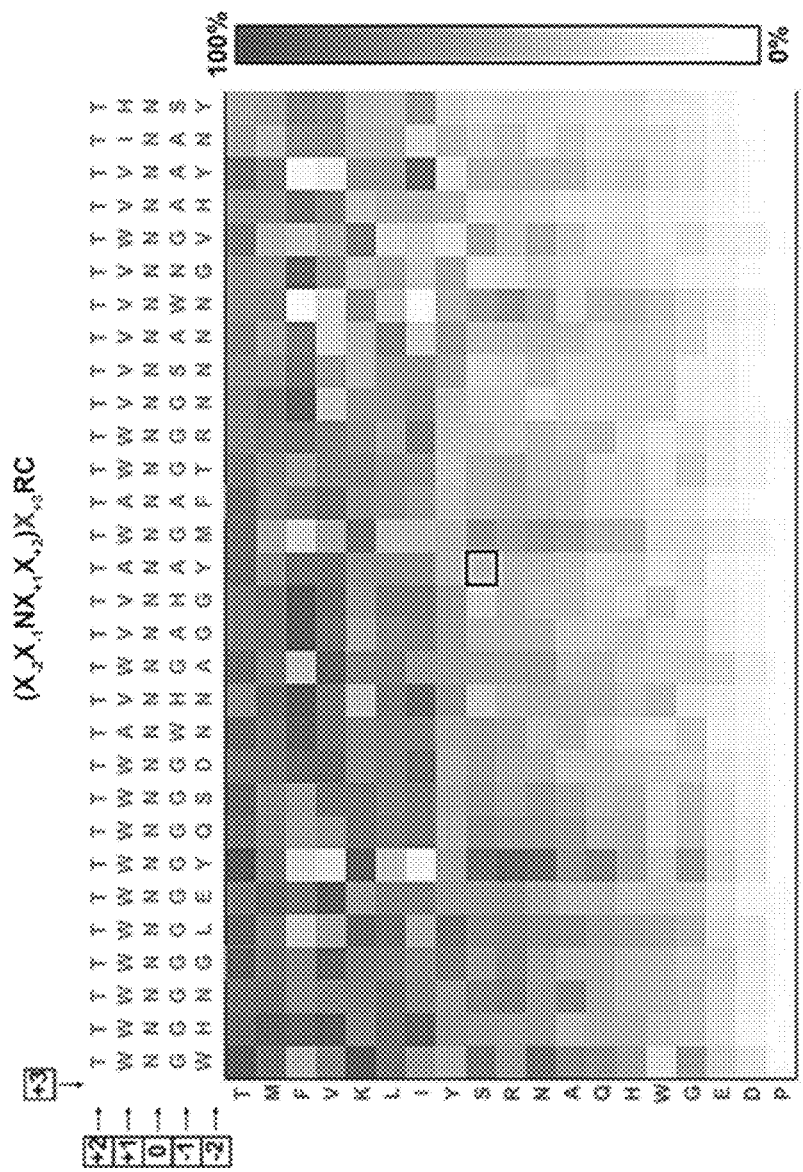
Figure 4C:
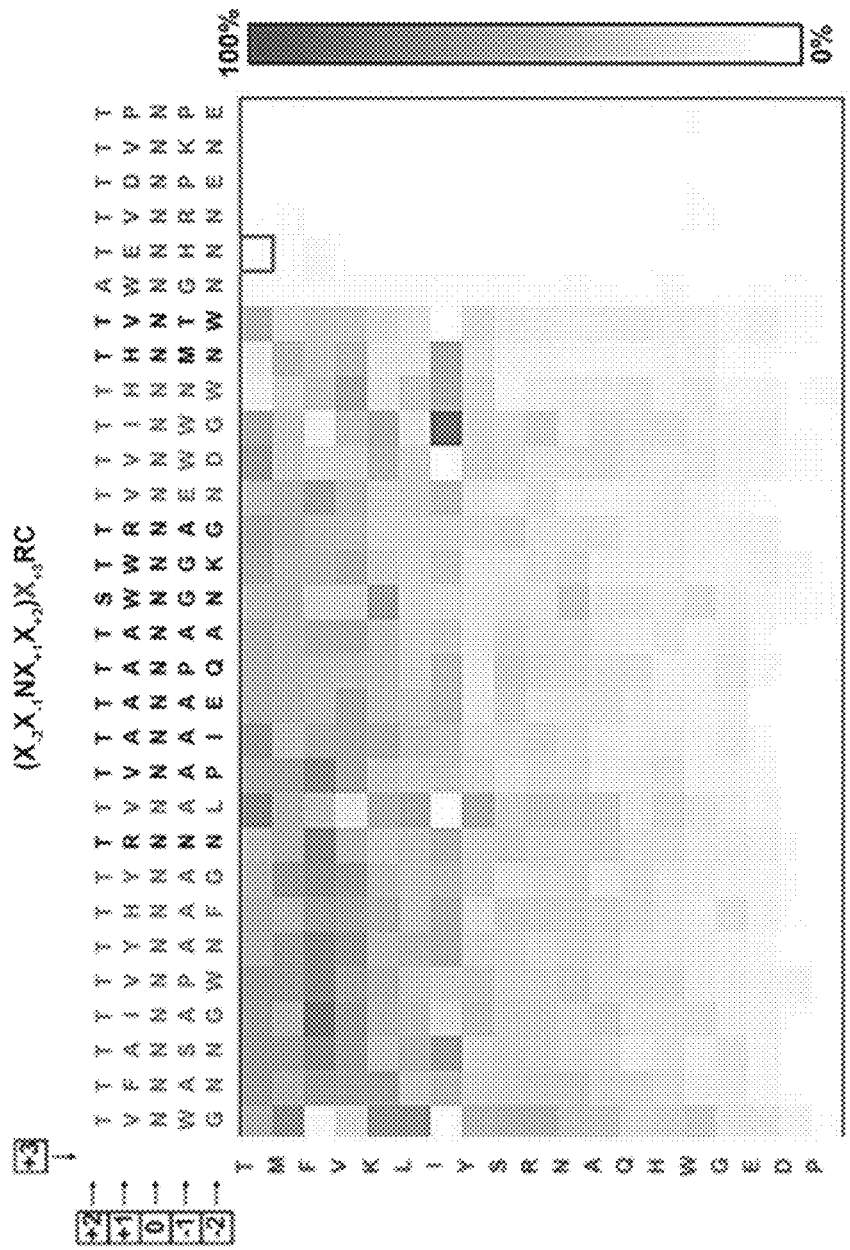

We next evaluated NGT activity for $X_{-2}$ residues using 40 sequences selected from the $X_{-1}NX_{+1}X_{+2}RC$ screens shown in FIG. 2b and FIG. 4a. To allow for synergistic and compensatory mutations leading to overall greater activity in later screens, we balanced preservation of sequence diversity while narrowing our search towards an optimized sequence. This narrowing approach is justified by the observation that sequence modification trends generally matched those predicted by earlier screens (see blue, grey, and black boxes and text in FIGS. 2b and 4). We resynthesized the 40 sequences from FIG. 2b and FIG. 4a with 19 amino acids in the $X_{-2}$ position and performed GlycoSCORES characterization of a 760-peptide library of the form $X_{-2}(X_{-1}NX_{+1}X_{+2})RC$ (FIG. 4b). We found that Gly, Asn, and Tyr were preferred at the $X_{-2}$ position while Lys gave low activity. This library showed robust modification of the GNWT motif even when a non-preferred residue was present in the $X_{-2}$ position. While Pro was a preferred residue in the $X_{-1}$ position of the $X_{-1}NX_{+1}X_{+2}RC$ libraries (FIGS. 2b and 4a and data not shown), we found that most of these sequences were poorly modified with the addition of an $X_{-2}$ residue, especially when the $X_{-2}$ residue was Asn (FIG. 4b and data not shown). This effect is likely related to the conformational constraints of Pro.

Figure 16:
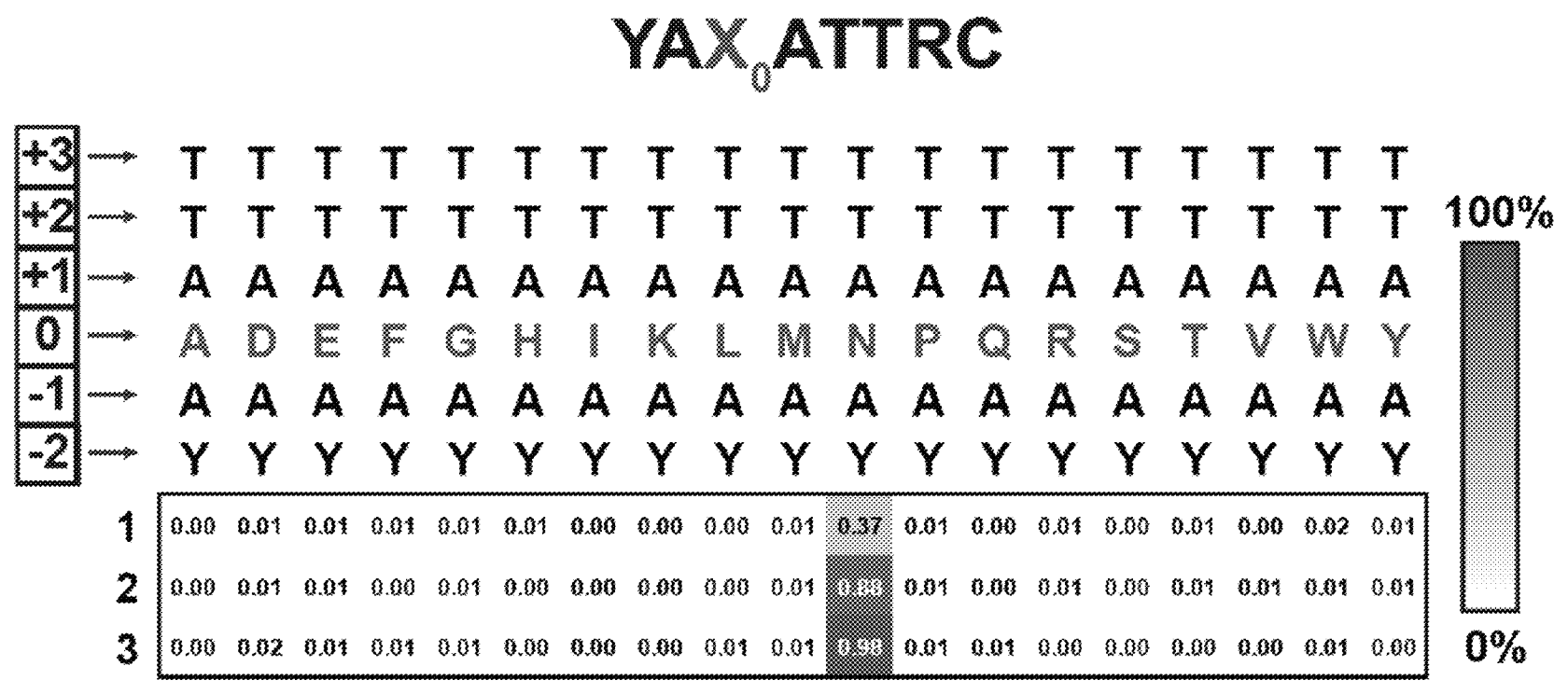

Finally, we synthesized and evaluated a library of 1140 peptides having the sequence $(X_{-2}X_{-1}NX_{+1}X_{+2})X_{+3}RC$ with 19 amino acids in the $X_{+3}$ position (FIG. 4c) based on 60 sequences selected from FIG. 4b. We discovered efficient glycosylation of peptides containing Thr, Met, and Phe in the $X_{+3}$ position, but not peptides with Pro, Asp, and Glu at this position. We found that 59 acceptor peptides had greater than 70% modification efficiency after exposure to just 0.025 µM NGT for 1 h (data not shown). We chose one efficiently modified 6-mer sequence (YANATT (SEQ ID NO:518)) to test NGT preference for the residue that undergoes glycosylation. We found that only peptides with Asn at the $X_0$ position showed detectable modification (FIG. 16).

Figure 5A:
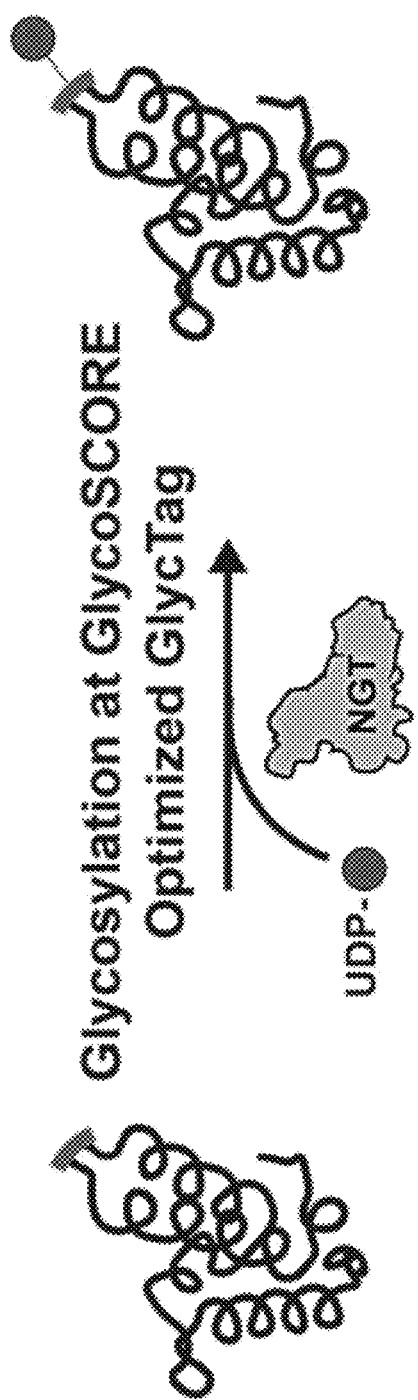
FIG. 5: In vitro synthesis and glycosylation of Im7 with GlycoSCORES identified sequences. Im7 GlycTag variants and NGT were synthesized in CFPS then combined with UDP-glucose in an (IVG) reaction (workflow shown in FIG. 19). (a) Representative LC-TOF spectra from analysis of n=3 IVG reactions generated by maximum entropy deconvolution of the Im7-6 variant containing the GlycoSCORES optimized GlycTag GGNWTT (SEQ ID NO:514) after Ni-NTA purification from IVG reactions with and without NGT. Representative deconvoluted spectra from all sequences and controls are shown in FIG. 19. Deconvolution mass errors as well as chromatogram peak retention times and quantification of relative peak area for all samples were generated and analyzed (data not shown). (b) Relative peak areas of $Glc_1/(Glc_0+Glc_1)$ for Im7 variants containing different GlycTags (NHNETD (SEQ ID NO: 554), DQNATF (SEQ ID NO: 519), GANATA (SEQ ID NO: 515), YANATS (SEQ ID NO: 555), FANATT (SEQ ID NO: 556), and GGNWTT (SEQ ID NO: 514) were analyzed. The results correlate with kinetics data measured by SAMDI for corresponding peptide sequences (inset c). Relative peak areas were calculated from extracted ion chromatograms of the 3 most abundant charge states based on theoretical average masses (see Methods). Mean and S.D. of n=3 IVG reactions are shown. * indicates significance by 2-tailed t-test with p-value of 0.016. Kinetic parameters of six peptide substrates (GGNWTTRC (SEQ ID NO:501), FANATTRC (SEQ ID NO:502), YANATSRC (SEQ ID NO:503), GANATARC (SEQ ID NO:504), DQNATFRC (SEQ ID NO:505), and NHETDRC (SEQ ID NO:506)) were analyzed (data not shown). Sequences positioned at Im7 internal loop are flanked by spacer sequences of the form ATT($X_{-2}X_{-1}NX_{+1}X_{+2}X_{+3}$)AGG. Shading of column graph areas indicates increasing relative peak areas and therefore greater glycosylation efficiencies.
Figure 5A:
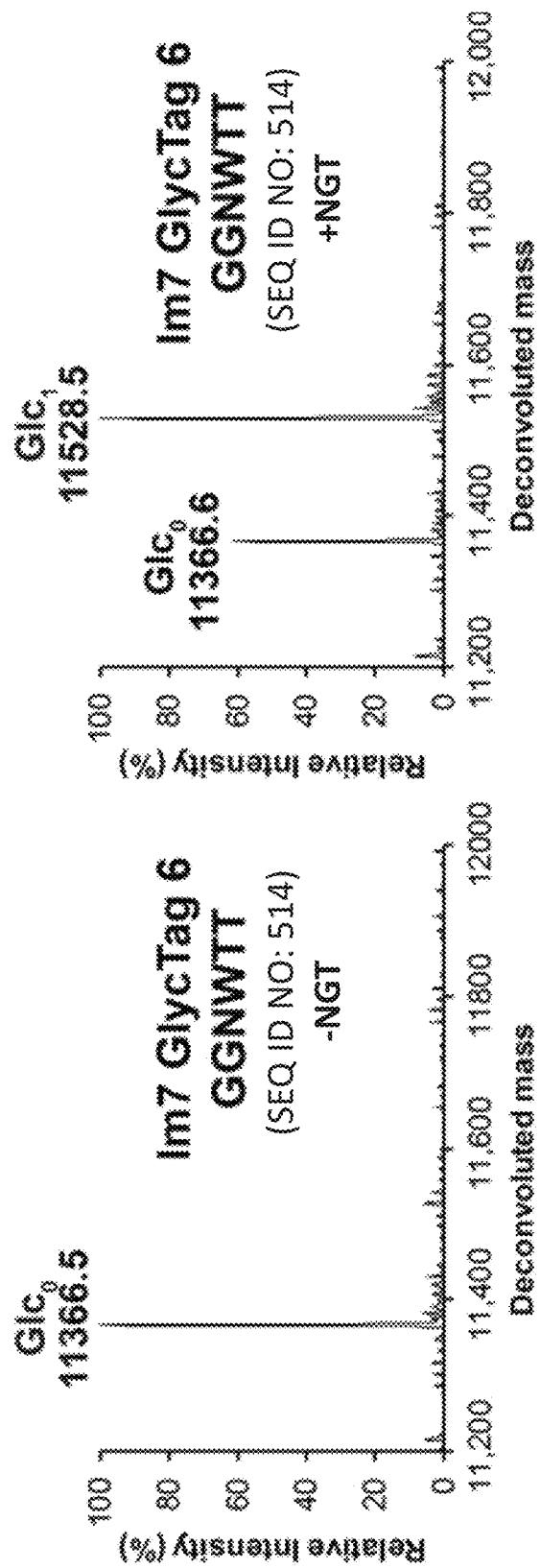
Figure 17A:
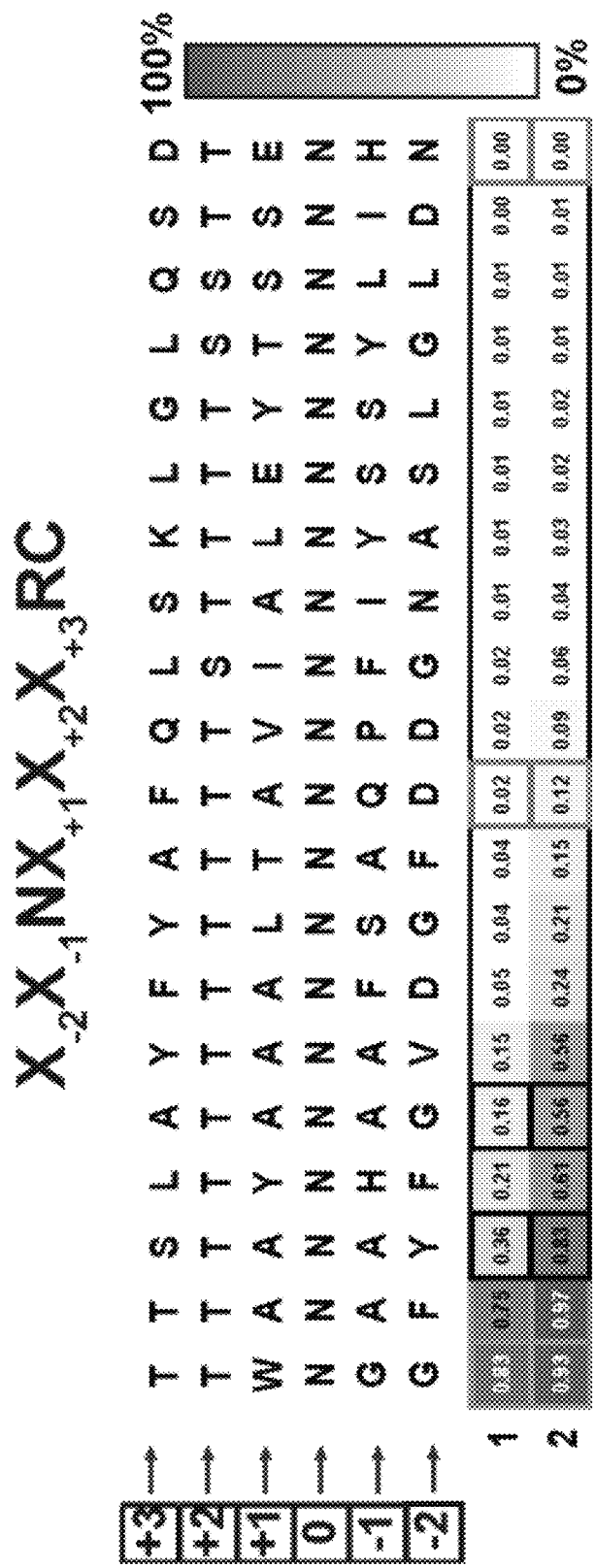
FIG. 17. GlycoSCORES optimized GlycTag peptides are more efficiently modified than previously studied and naturally occurring glycosylation sequences. (A) Comparison of glucose modification of GlycoSCORES identified sequences with high (blue boxes), medium (black boxes), and low (grey boxes) modification efficiency to peptide sequences found to have N-glucose modifications in previous NGT studies[9, 18-20]. (B) Modification efficiencies measured by GlycoSCORES of naturally occurring N-glycosylation sequences used in this study from *H. influenzae* HMW1 protein (NINATS (SEQ ID NO:512)) and *H. sapiens* IgG (QYNSTY (SEQ ID NO:513)). Modification efficiencies for GlycoSCORES optimized GlycTag (GGNWTT, GlycTag ID: 6 (SEQ ID NO:514)) and a biological consensus sequence (GANATA, GlycTag ID: 3 (SEQ ID NO:515)) found in a previous study[18] are also shown on the left. All reactions were conducted with 50 µM peptide and 2.5 mM UDP-Glc, reacted with 0.025 µM NGT synthesized in CFPS incubated at 30° C. for 1 h (1) or 0.1 µM NGT synthesized in CFPS incubated at 30° C. for 1 h (2). Heat maps show the average of n=2 SAMDI-MS spectra acquired from separate peptide immobilizations.
Figure 17B:
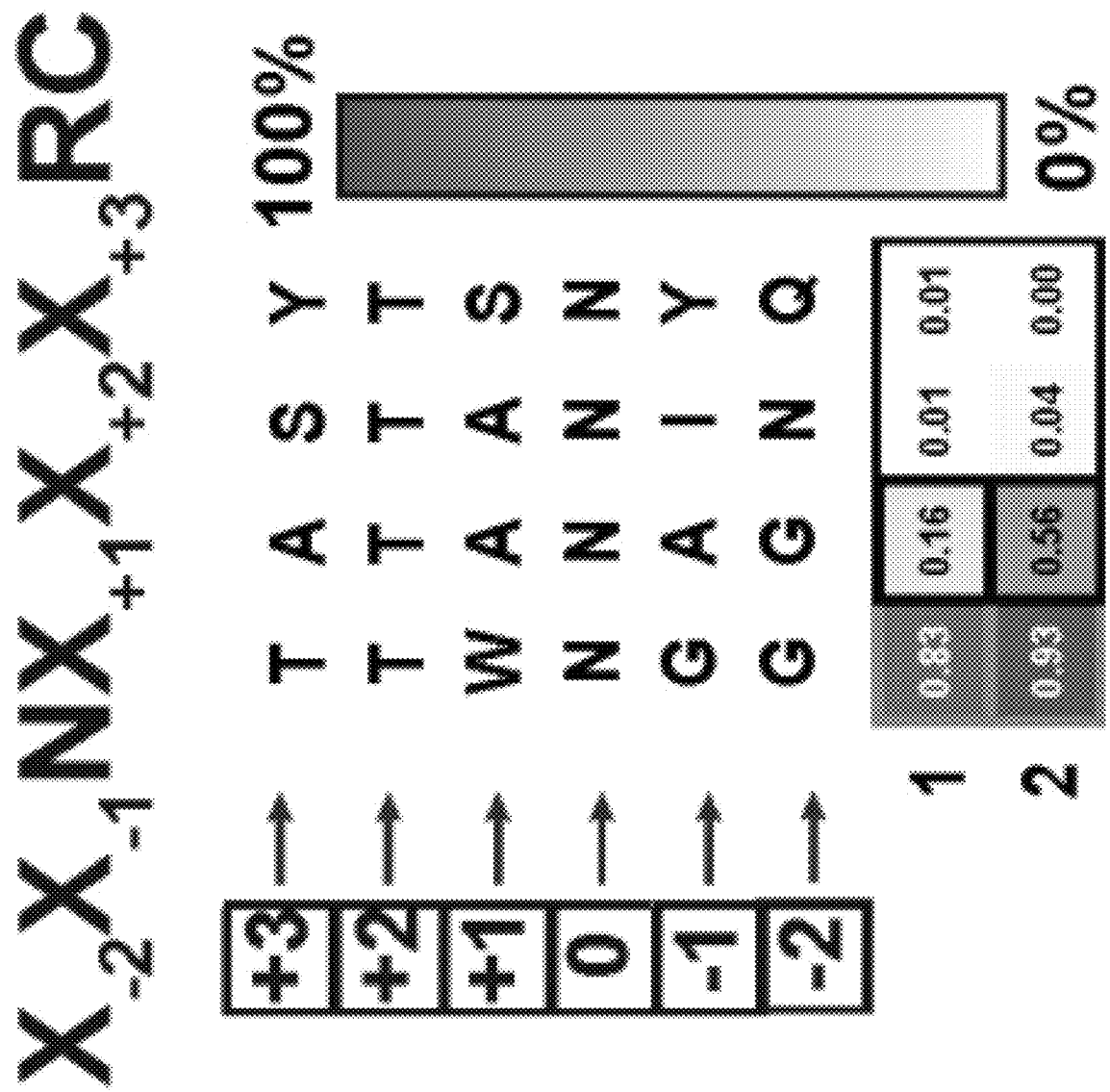
Figure 18A:
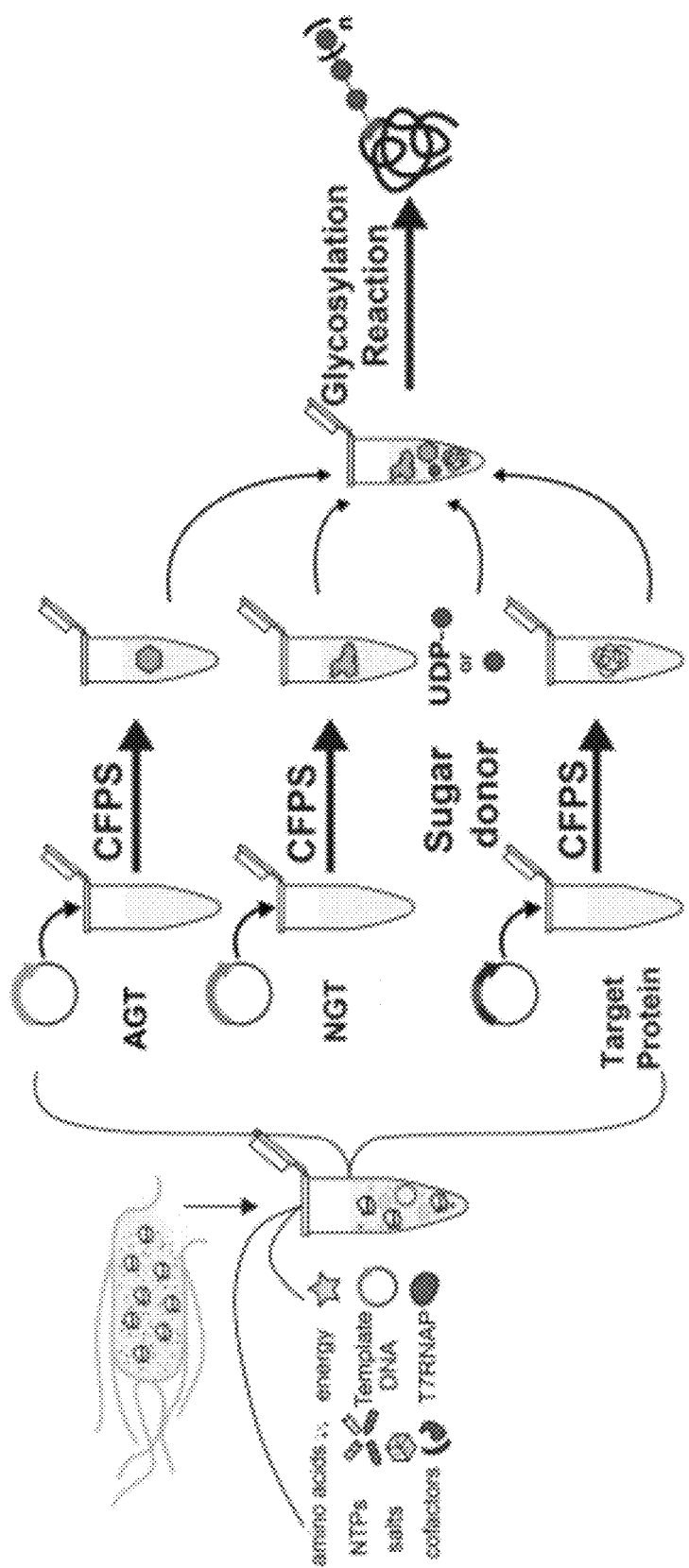
FIG. 18. In vitro recapitulation of *A. pleuropneumoniae* multi-enzyme glycosylation system by synthesis and glycosylation of HMW1ct-WT. (A) Scheme for IVG of HMW1ct-WT by NGT and AGT. HMW1ct-WT, NGT, and AGT were synthesized in separate CFPS reactions for 20 h and combined with UDP-Glc or glucose. IVG reactions were performed with 5 µM HMW1ct-WT, 1 µM NGT, 2 µM AGT, and 2.5 mM UDP-Glc or 200 mM glucose for 16 h. The concentration of soluble HMW1ct-WT in completed CFPS reactions incubated for 20 h at 20° C. was determined by $^{14}$C-leucine incorporation to be 701±32 µg/mL. (B) Reaction scheme for glucose modification of HMW1ct-WT with NGT and AGT. (C) On an α-His western blot representative of n=2 experiments with similar results, we observed small gel mobility shifts in lanes with NGT (indicating single glucose modification of up to 12 available N-X-S/T glycosylation sites) and high molecular weight bands in lanes with NGT and AGT (indicating polyglucose modifications). We found that glycosylation was achieved with both UDP-Glc substrate as well simple glucose, albeit to a lower extent. This is likely due to conversion of glucose to UDP-Glc by endogenous *E. coli* enzymes present in the crude *E. coli* lysate. Poly-α-glucose modifications were confirmed by corresponding signals on ConA blot which specifically binds to terminal α-linked glucose residues. * denotes control lane loaded with CFPS that synthesized sfGFP, ** denotes control lane loaded with CFPS reaction that synthesized sfGFP plus NGT and AGT synthesized in CFPS.
Figure 18B:
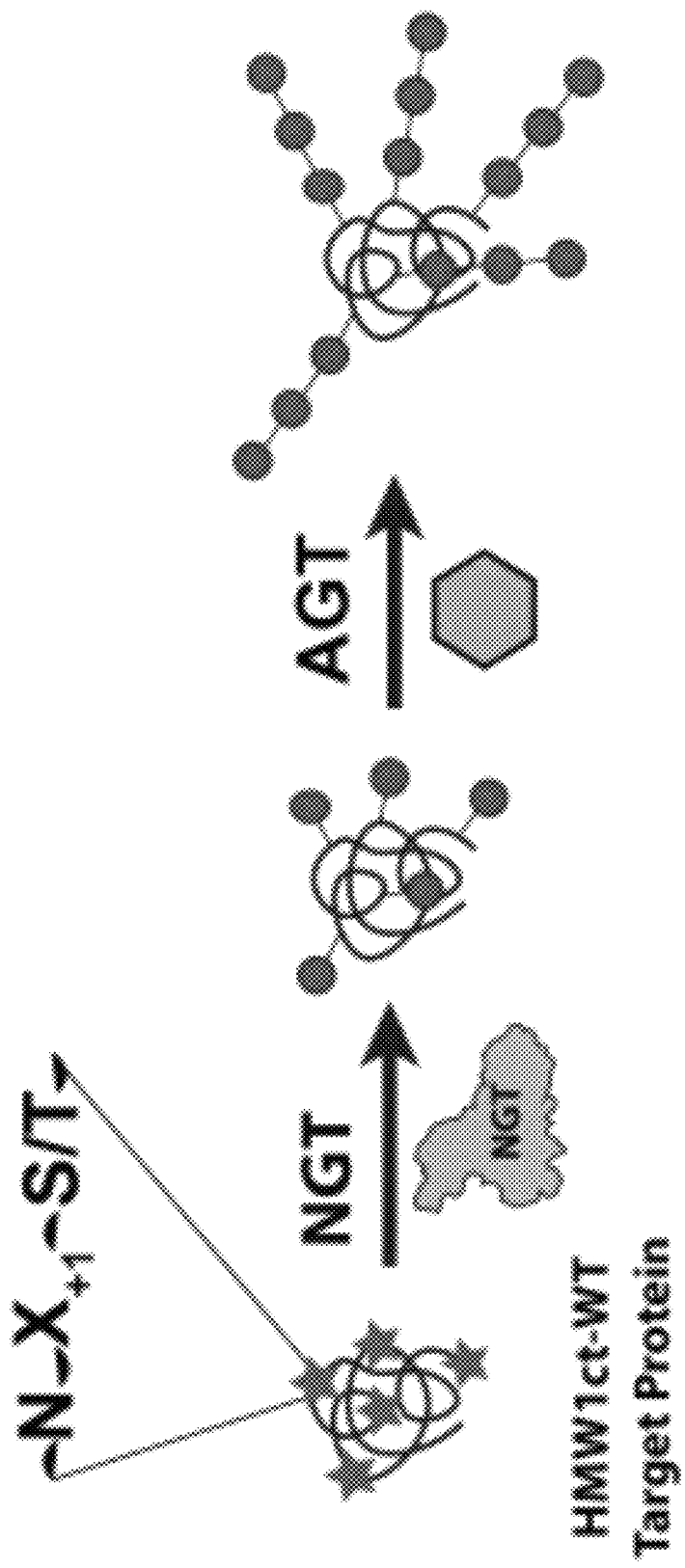
Figure 18C:
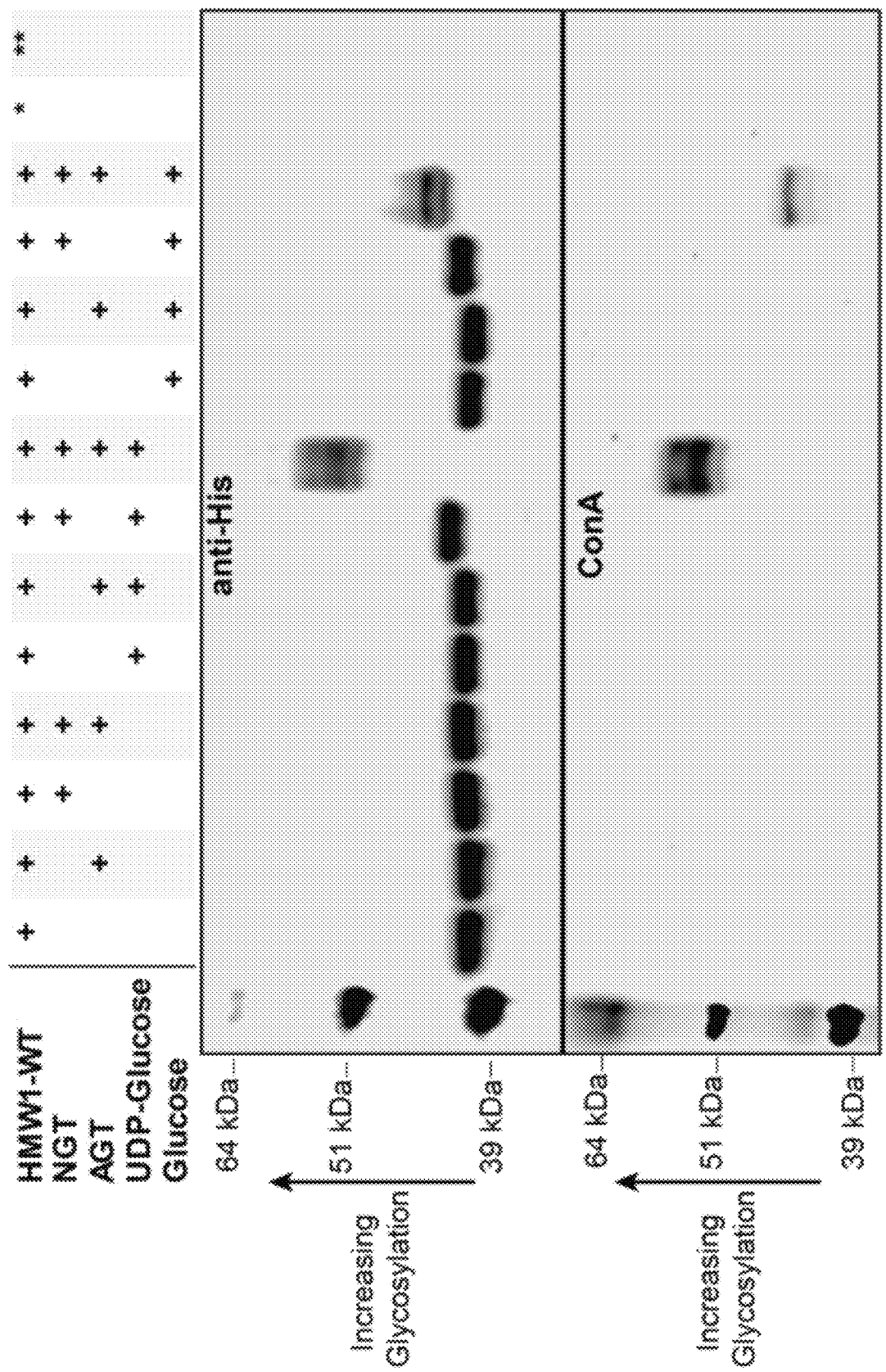
Figure 19A:
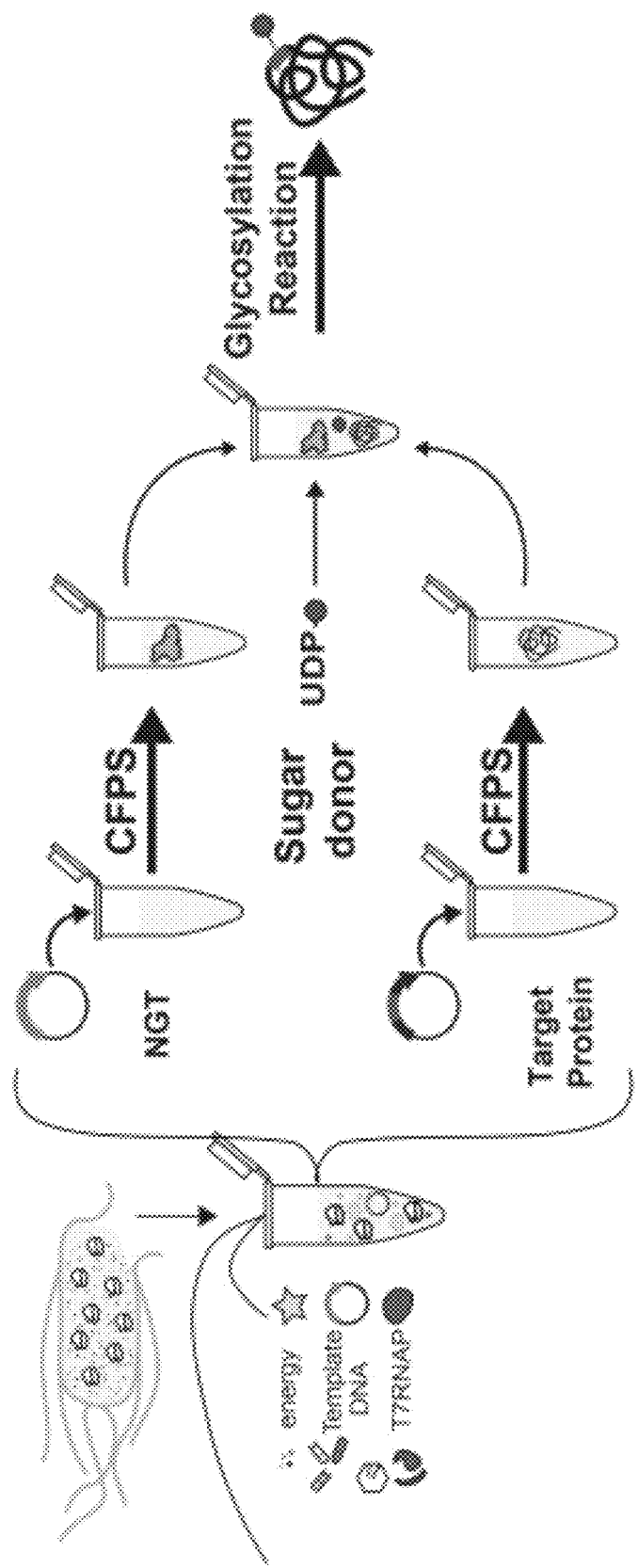
FIG. 19. Scheme and deconvoluted MS spectra from LC-MS analysis of Im7 variants synthesized and glycosylated in vitro. (A) Workflow for rapid synthesis and glycosylation of protein variants. Protein variants and NGT are synthesized in CFPS then assembled into IVG reactions with 5 µM of the indicated Im7 variant produced in CFPS, 0.1 µM NGT produced in CFPS (unless concentration difference is noted; see F), and 2.5 mM UDP-Glc and incubated for 2.5 h at 30° C. Im7 was purified by Ni-NTA and injected into LC-TOF. (B) Representative deconvoluted spectra of proteins (NHNETD (SEQ ID NO: 554), YANATS (SEQ ID NO: 555), DQNATF (SEQ ID NO: 519), FANATT (SEQ ID NO: 556), GANATA (SEQ ID NO: 515), and GGNWTT (SEQ ID NO: 514)) from analysis of n=3 IVG reaction products with indicated GlycTag sequences identified by GlycoSCORES analysis. All sequences were flanked by ATT-($X_{-2}X_{-1}NX_{+1}X_{+2}X_{+3}$)-AGG. Trends of protein glycosylation match observed modification efficiencies and reaction kinetics constants determined by GlycoSCORES at the peptide level. (C) Deconvoluted spectrum of Im7 variant (GGNWTT (SEQ ID NO: 514)) without flanking sequences shows no detectable glycosylation, indicating flanking sequences are required for efficient modification under these conditions. (D) Deconvoluted spectrum of N/Q substituted Im7 variant (DQQATF (SEQ ID NO: 557)) shows no detectable glycosylation, confirming that the redesigned target site was the only site efficiently modified by NGT. (E) Deconvoluted spectrum of Im7 (GGNWTT (SEQ ID NO: 514)) purified from an IVG reaction containing no NGT shows no detectable glycosylation, indicating that the single glucose modification is performed by NGT. (F) Deconvoluted spectrum of Im7 bearing the GlycoSCORES optimized sequence GGNWTT (SEQ ID NO:514) purified from an IVG reaction containing 4 µM NGT with complete glycosylation. (C-F) spectra are representative of n=2 IVGs with similar results. All spectra processed by Agilent Mass Hunter Max Entropy Deconvolution of 700-2000 m/z range into 10,000-15,000 u mass range.
Figure 19B:
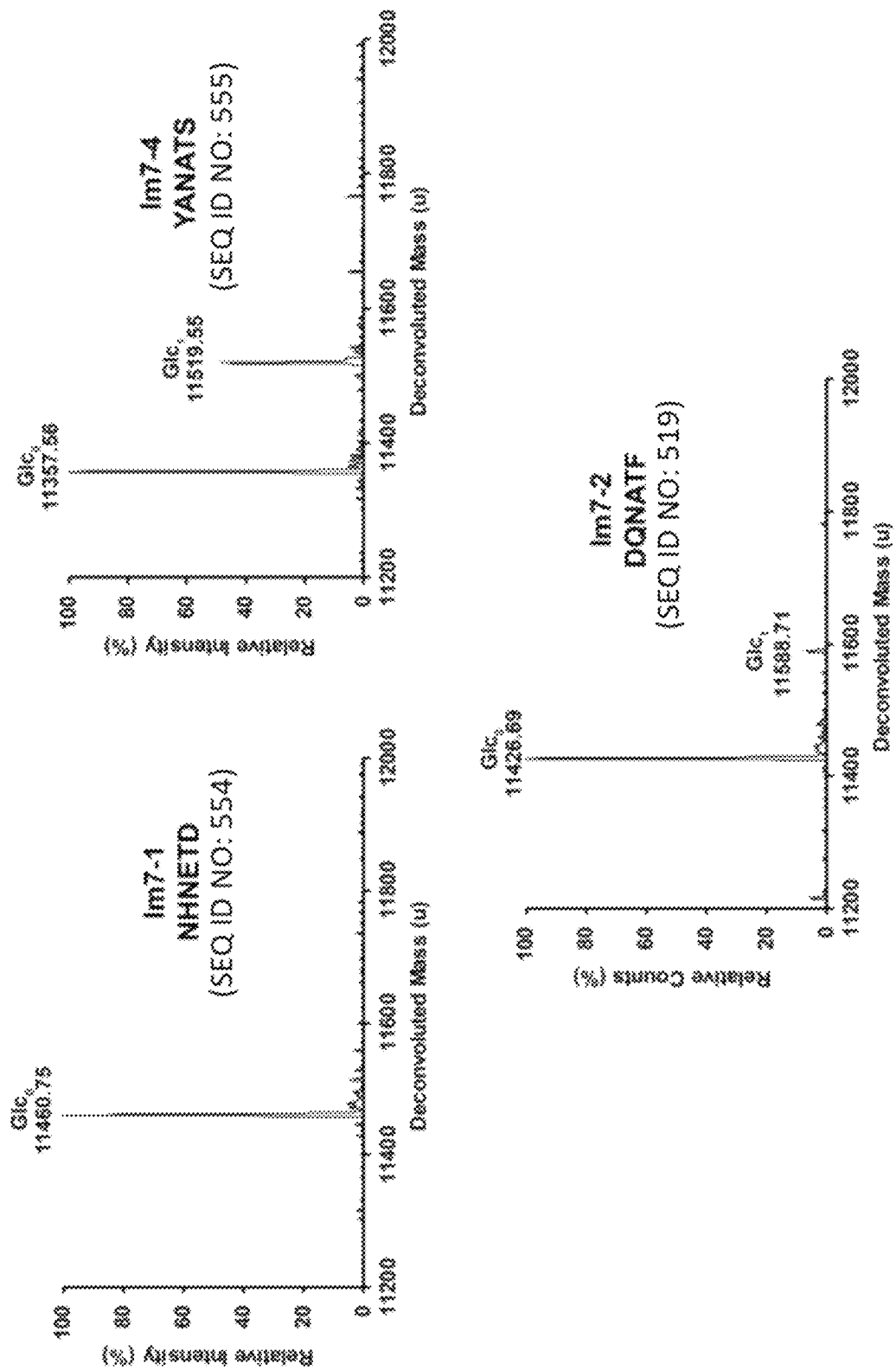
Figure 19B:
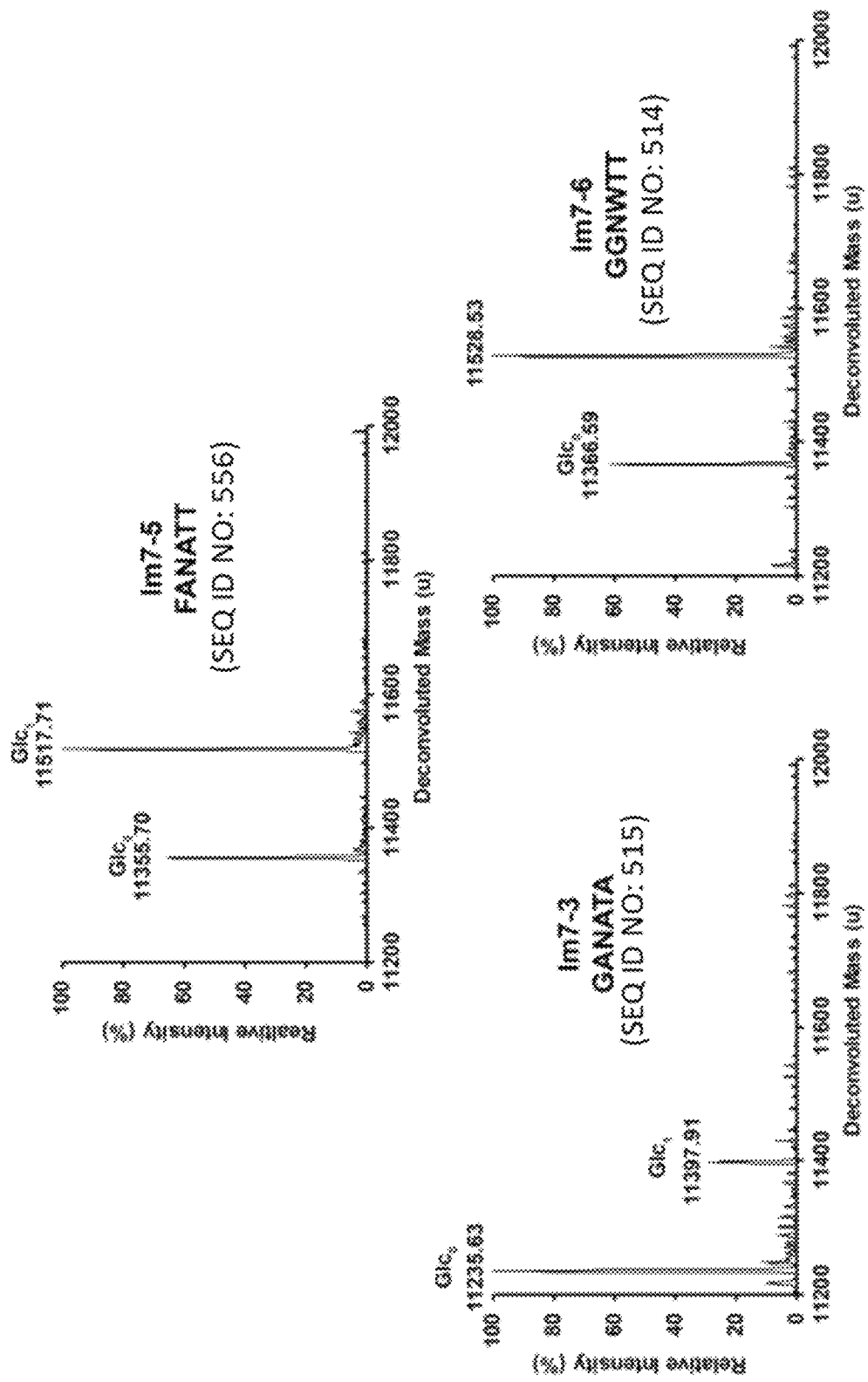
Figure 19C:
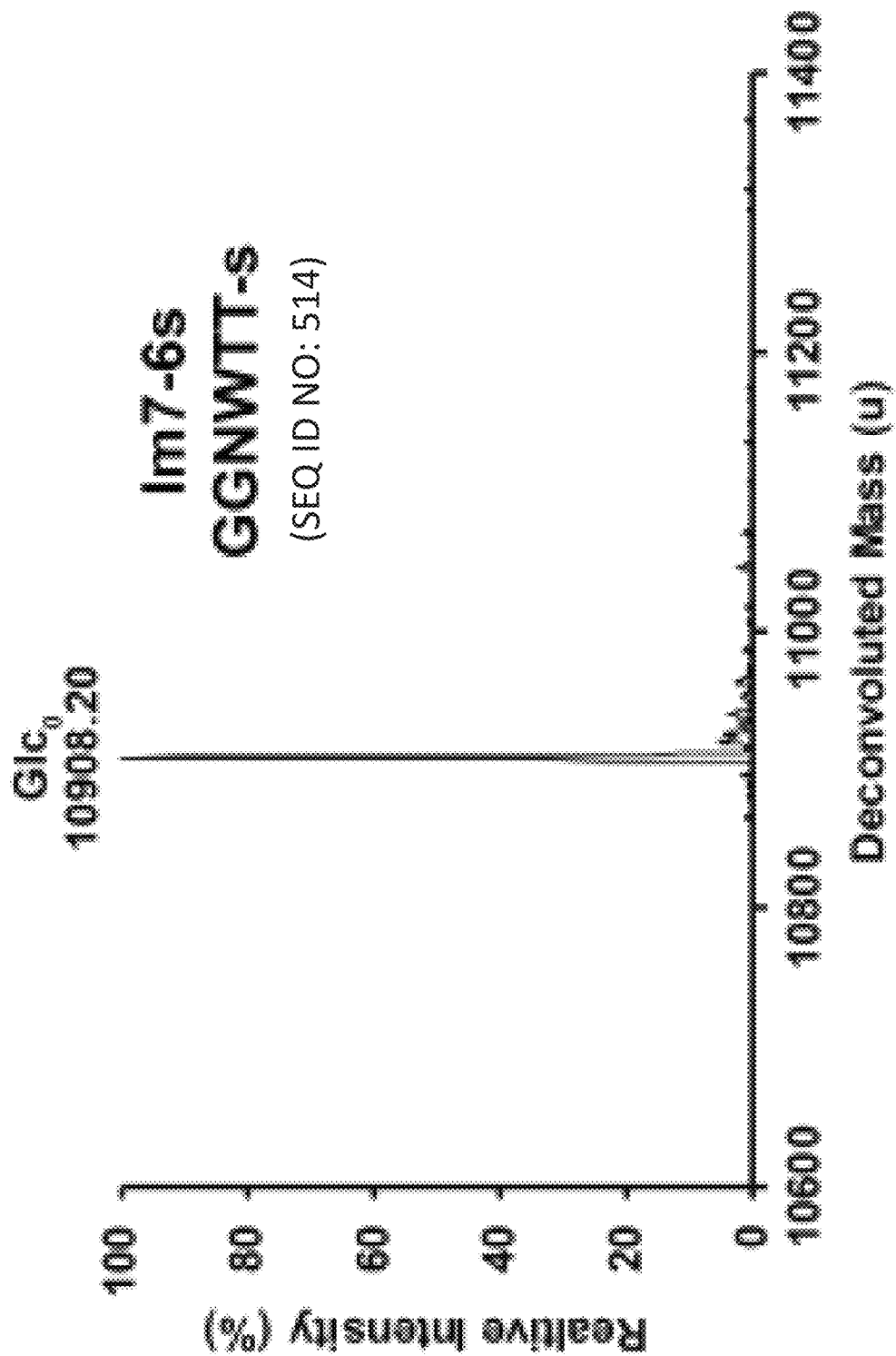
Figure 19D:
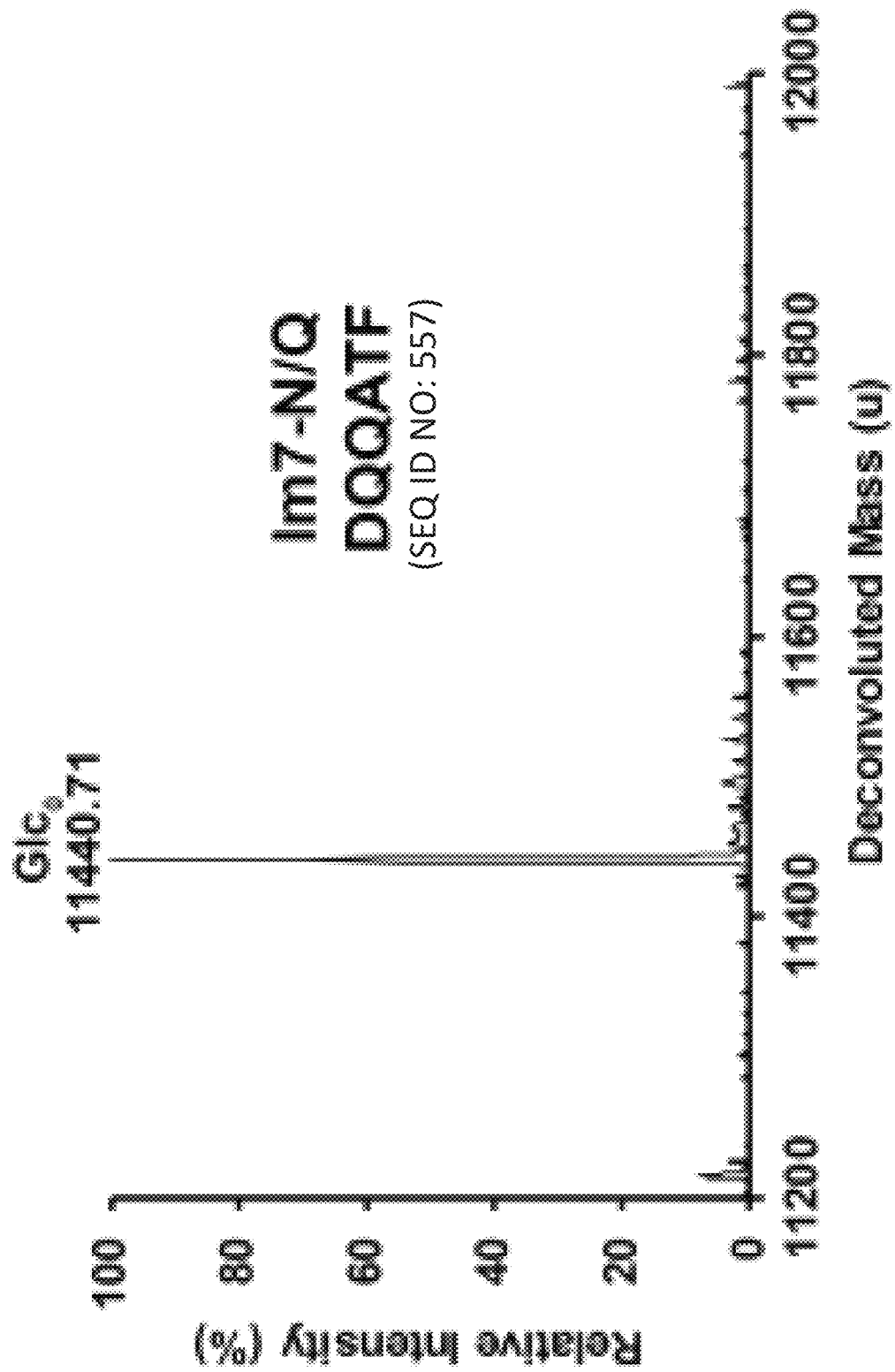
Figure 19E:
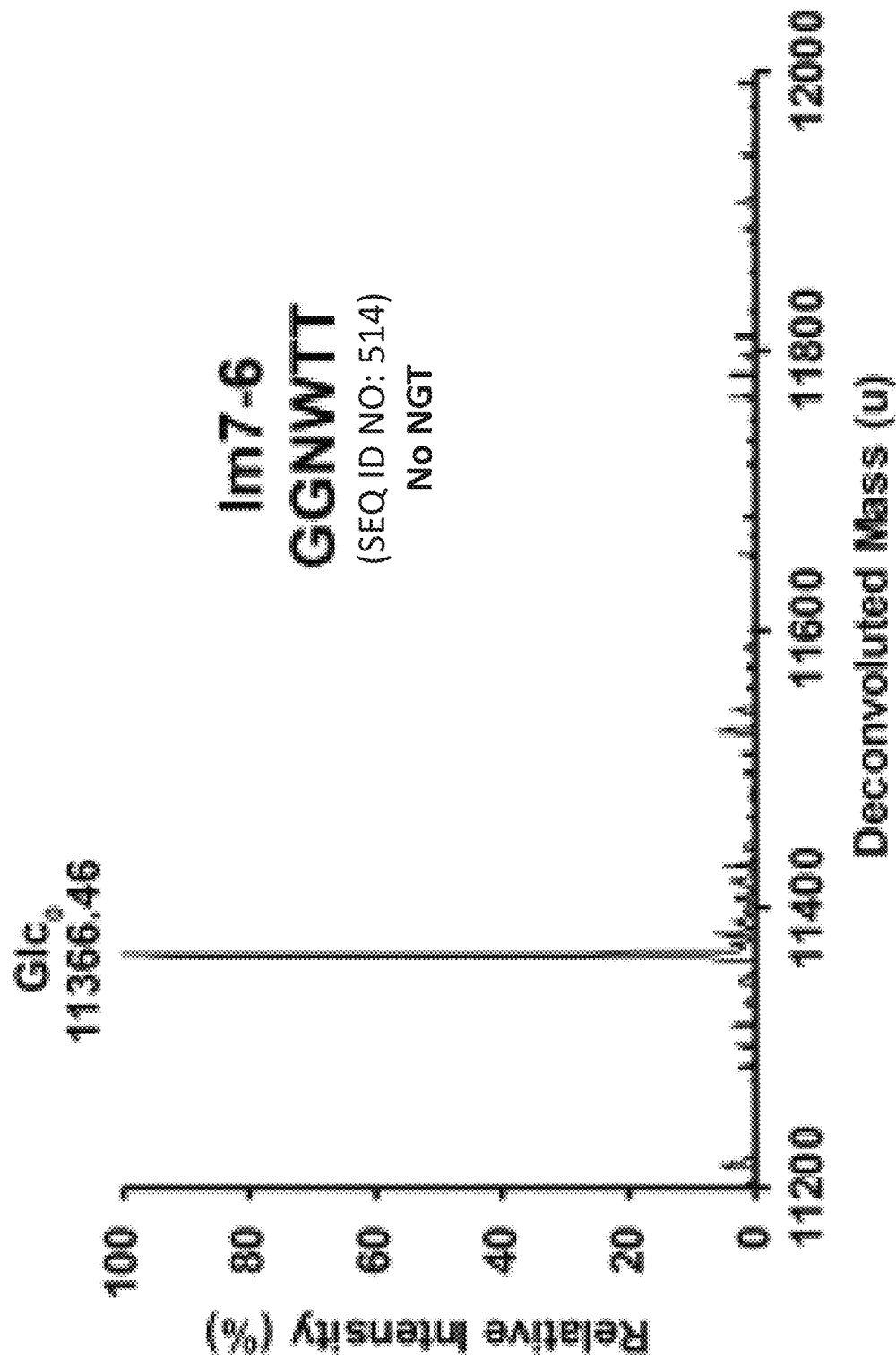
Figure 19F:
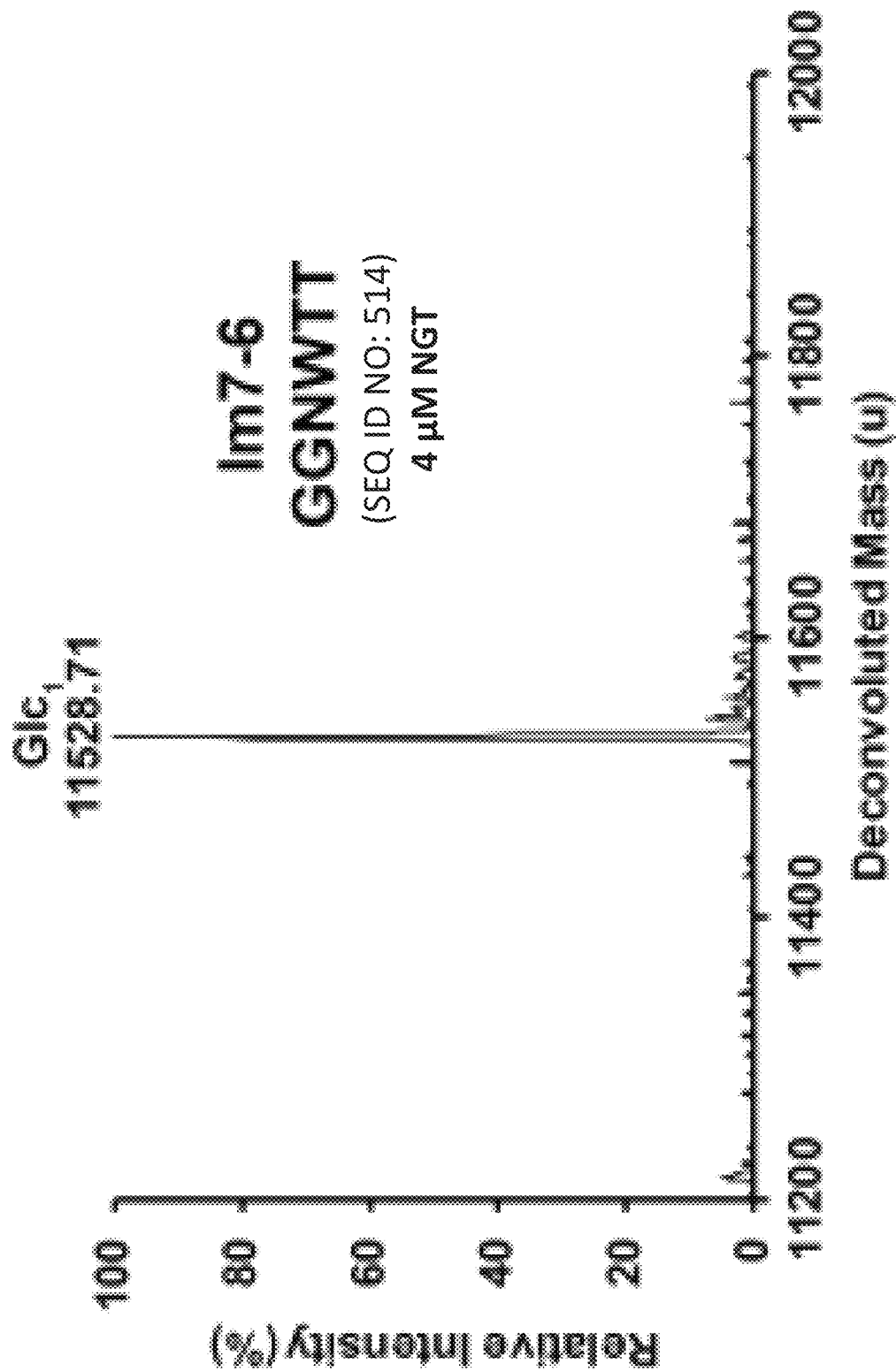
Figure 20A:
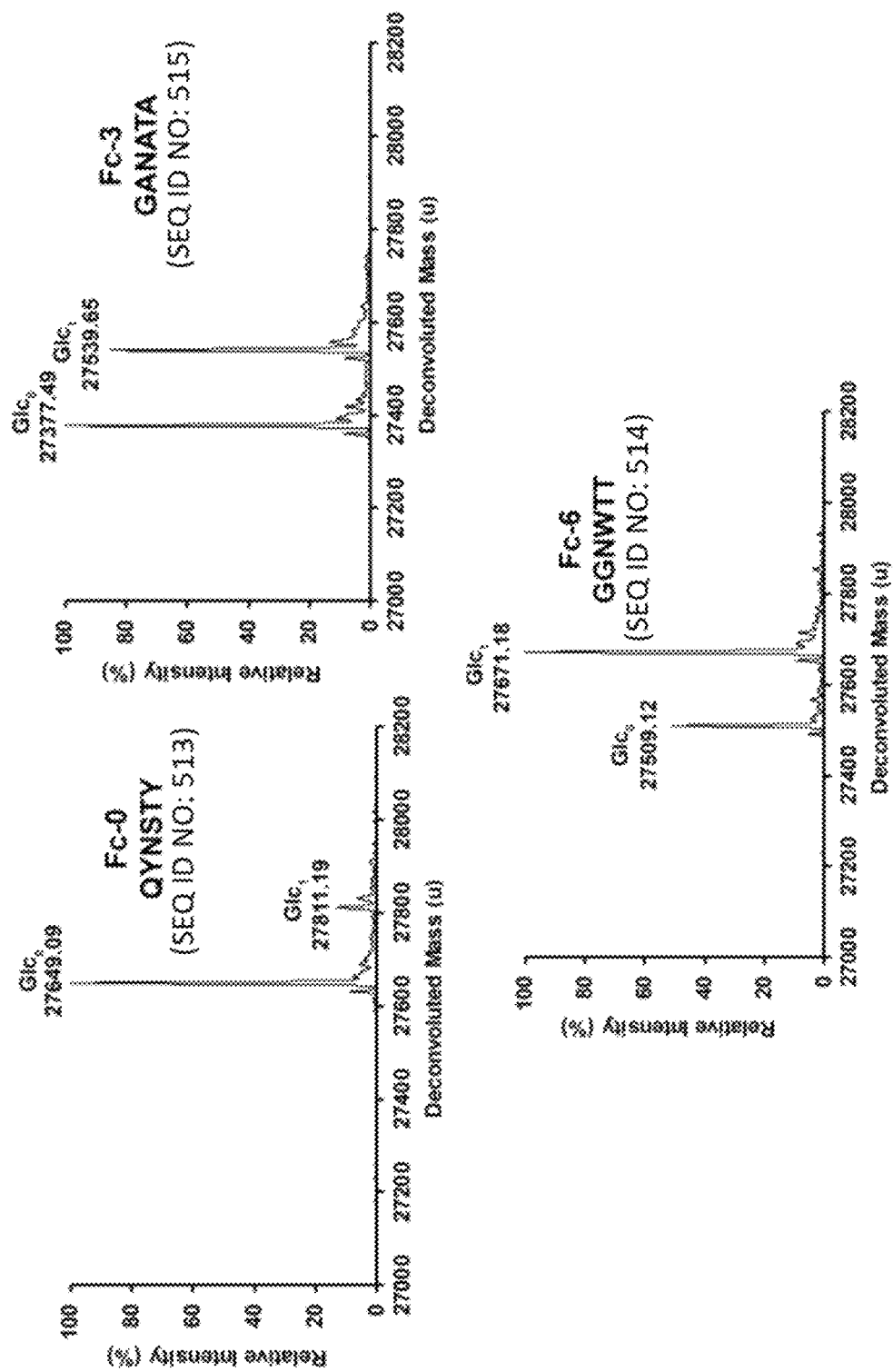
FIG. 20. Deconvoluted mass spectra from LC-TOF analysis of Fc variants synthesized and glycosylated in the cytoplasm of living *E. coli*. Sequence variants of the Fc target protein were coexpressed with NGT in BL21(DE3) *E.* coli, purified by Ni-NTA, reduced by DTT and injected into LC-TOF. The Fc target protein was induced with 400 µM IPTG for 2 h (unless noted; see E), followed by a 30 min induction of NGT with 0.2% arabinose. (A) Representative deconvoluted spectra from n=3 expression cultures of Fc containing the indicated naturally occurring (0), biological consensus[18] (3), and optimized GlycTag (6) sequences (QYNSTY (SEQ ID NO: 513), GANATA (SEQ ID NO: 515), and GGNWTT (SEQ ID NO: 514)) are shown. All glycosylation sequences are flanked by flexible linker sequences of the form ATT-$(X_{-2}X_{-1}NX_{+1}X_{+2}X_{+3})$-AGG. Protein modification trends match those predicted by GlycoSCORES of peptides and show that the protein containing the optimized GlycTag sequence is the most efficiently modified (spectra also shown in FIG. 6). (B) Deconvoluted spectrum of Fc-0s variant (QYNSTY (SEQ ID NO: 513)) without flanking sequences showed no modification, indicating that flanking sequences were required for efficient modification under these conditions. (C) Deconvoluted spectrum of an Fc variant with N/Q substitution (QYQSTY (SEQ ID NO: 558)) to remove the glycosylation site of Fc-0 showed no detectable glycosylation, indicating that only the redesigned site was efficiently modified. (D) Deconvoluted spectrum of Fc-6 expressed in BL21(DE3) *E. coli* (GGNWTT (SEQ ID NO: 514)) with no NGT plasmid present showed no detectable glycosylation, confirming that NGT was responsible for the glucose modification. (E) Deconvoluted spectrum of the Fc variant (GGNWTT (SEQ ID NO: 514)) engineered with the optimized GlycTag co-expressed with NGT for 4 h showed complete glycosylation, indicating that NGT can be used to create homogeneously modified Fc in the cytoplasm of living *E. coli*. (B-E) spectra are representative of analysis of n=2 expression cultures with similar results. All spectra processed by Agilent Mass Hunter Max Entropy Deconvolution of 700-2000 m/z range into mass range of 25,000-30,000 u.
Figure 20B:
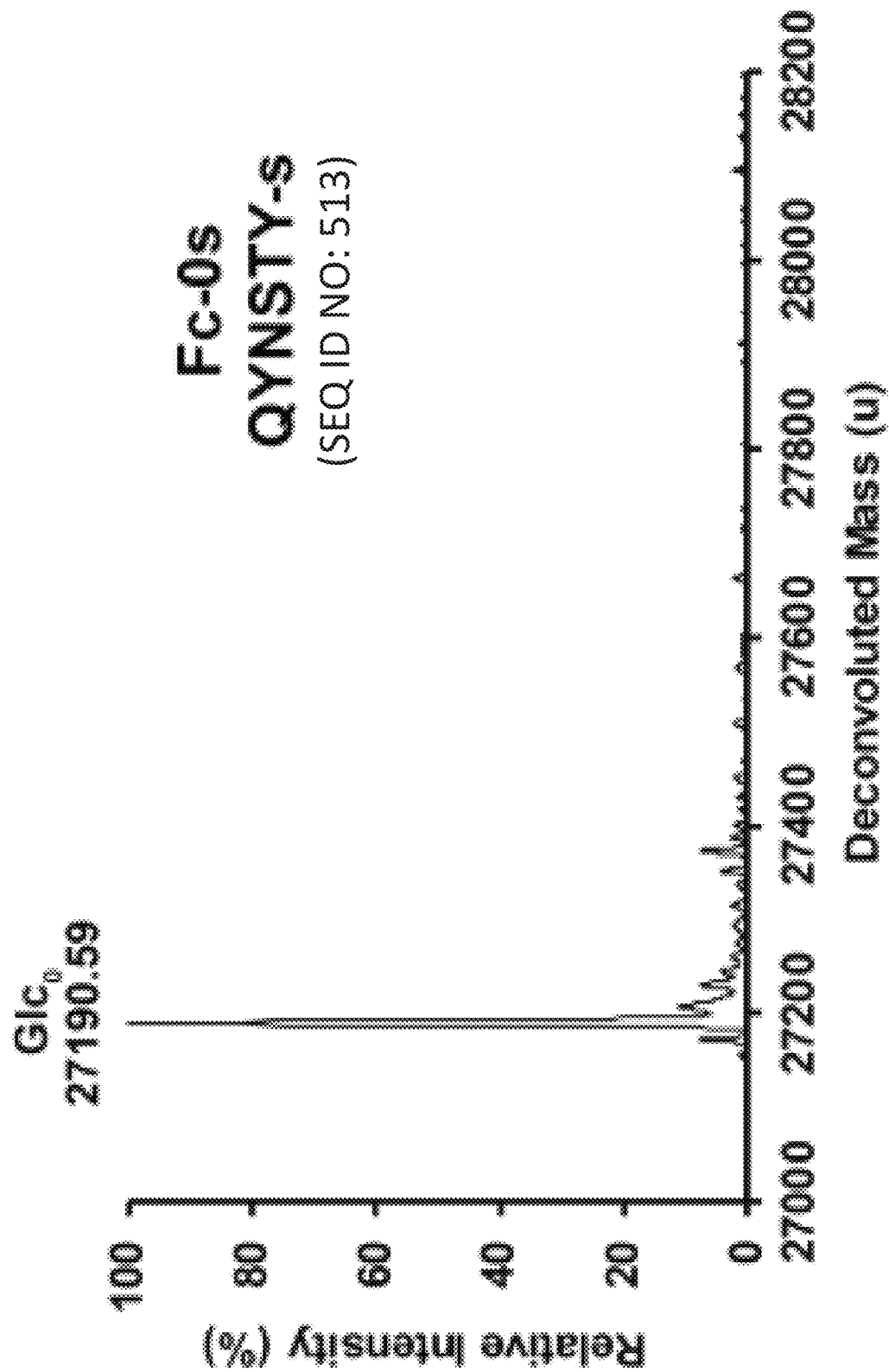
Figure 20C:
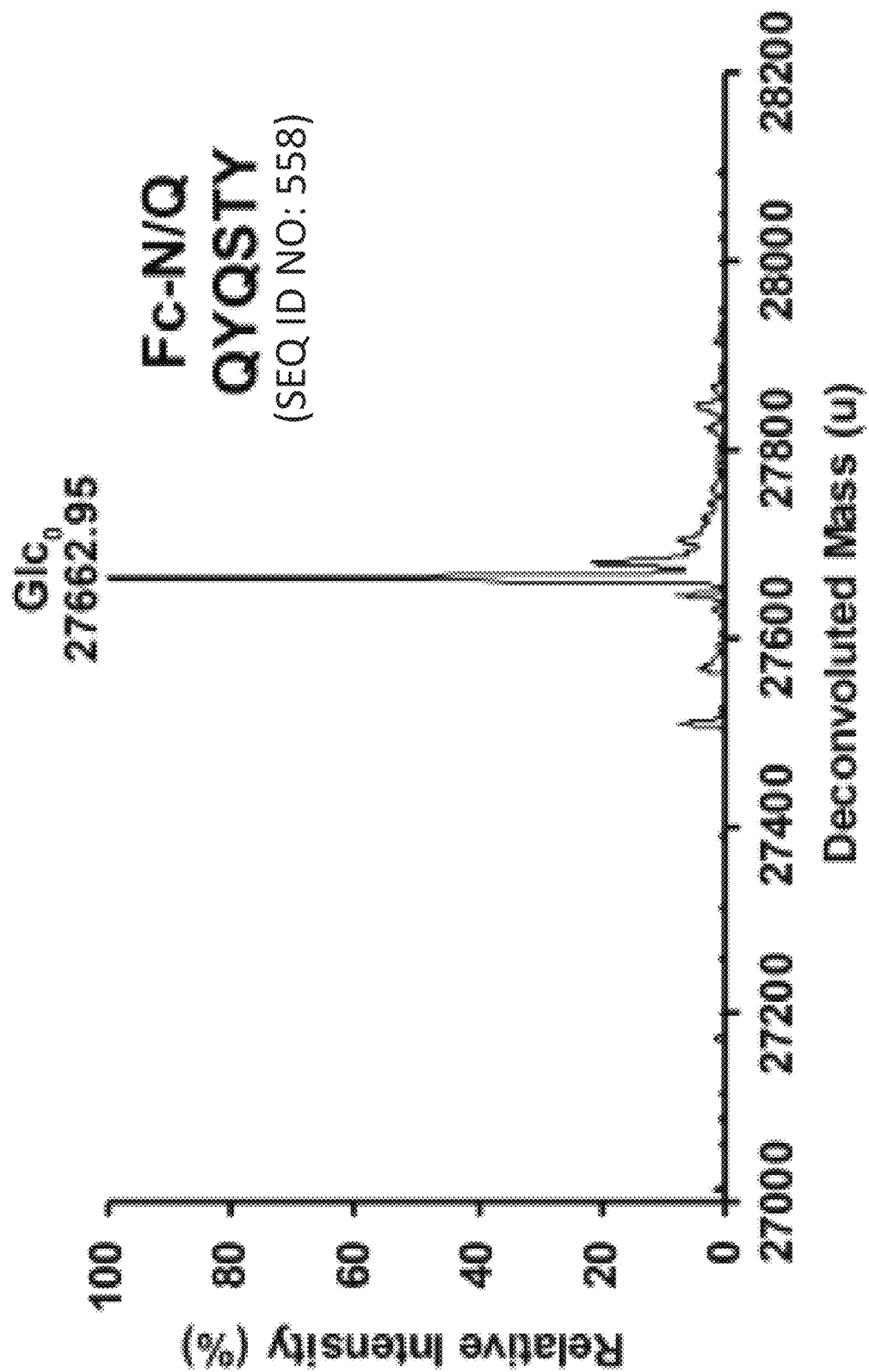
Figure 20D:
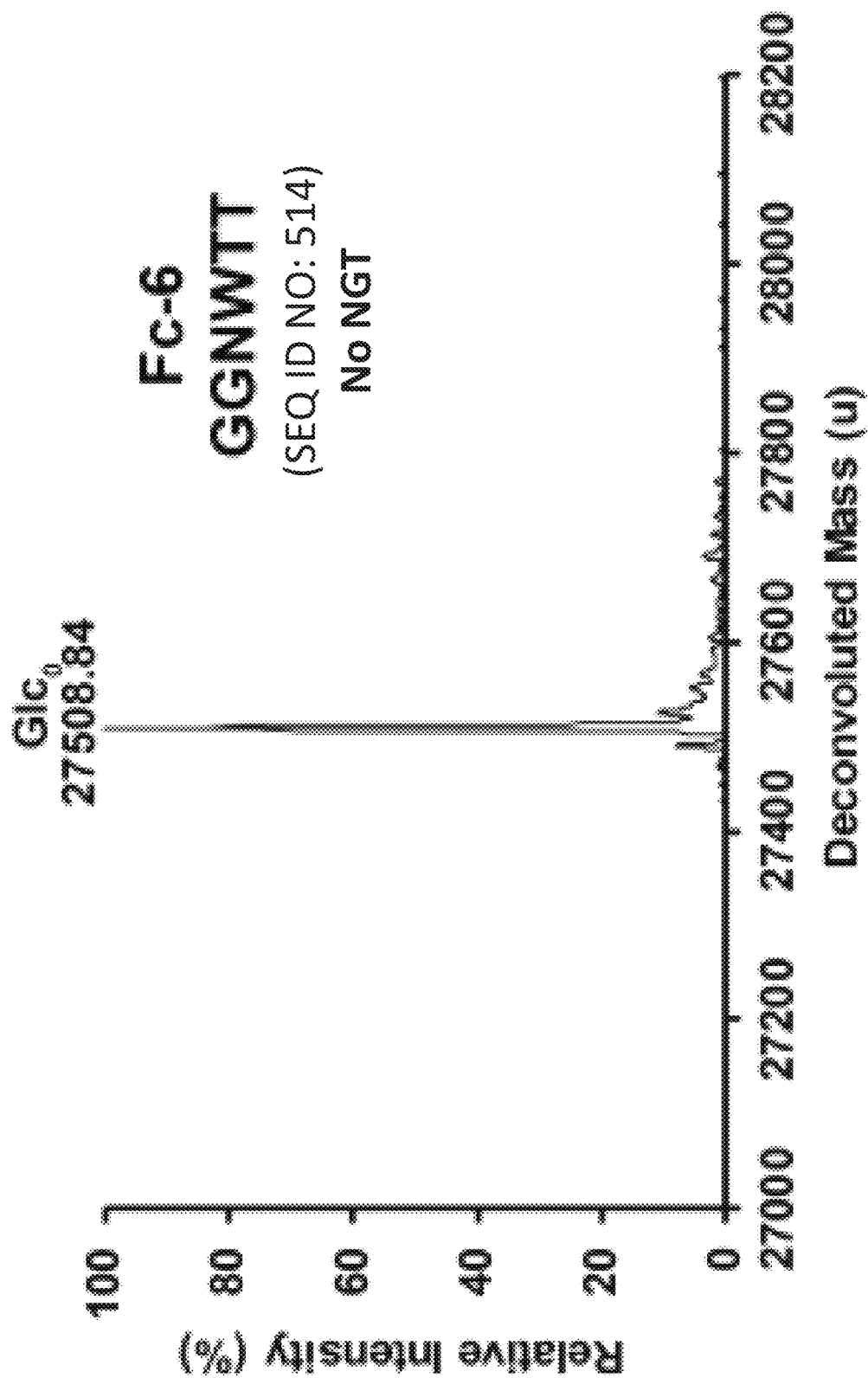
Figure 20E:
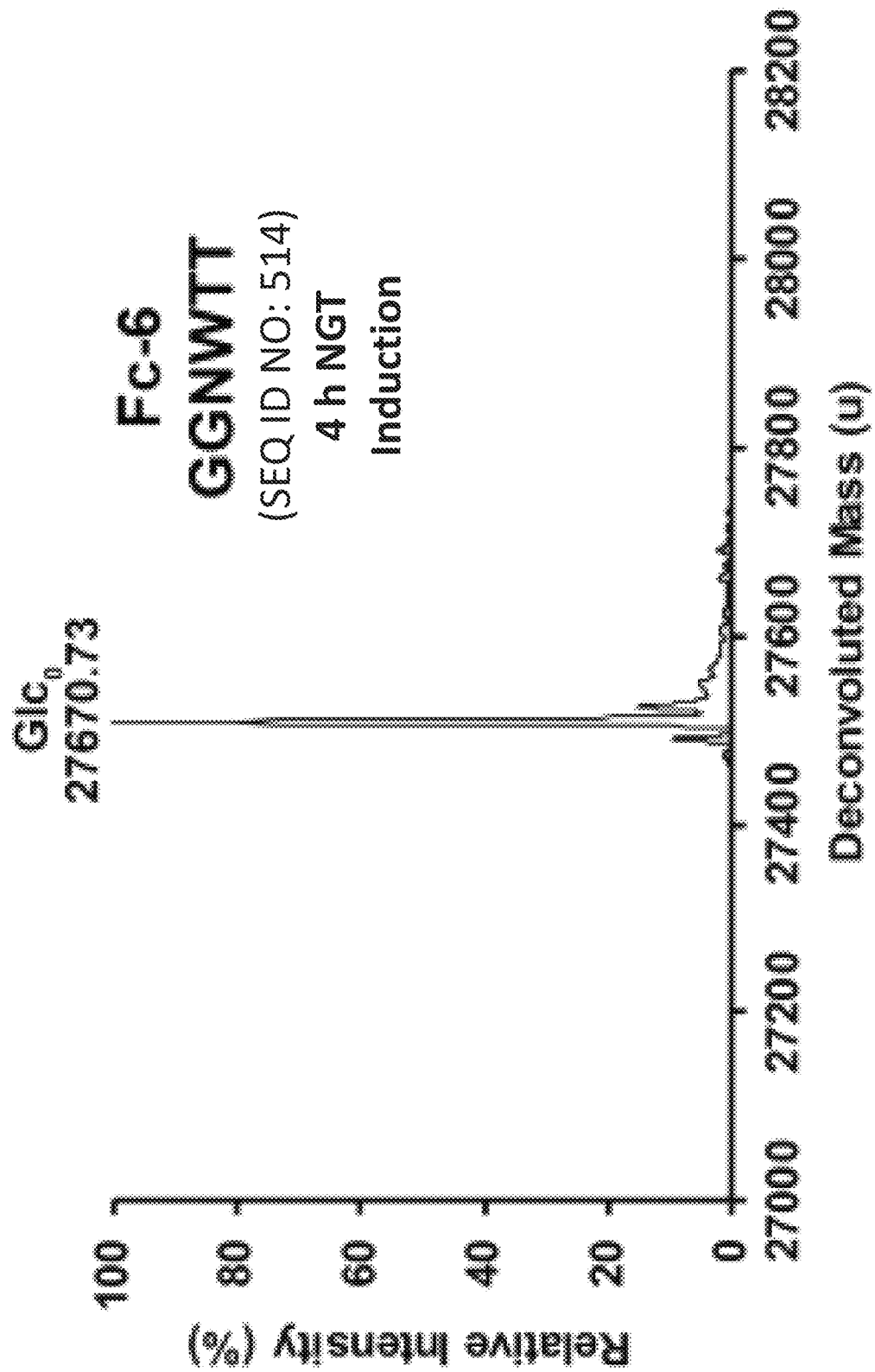
Figure 21A:
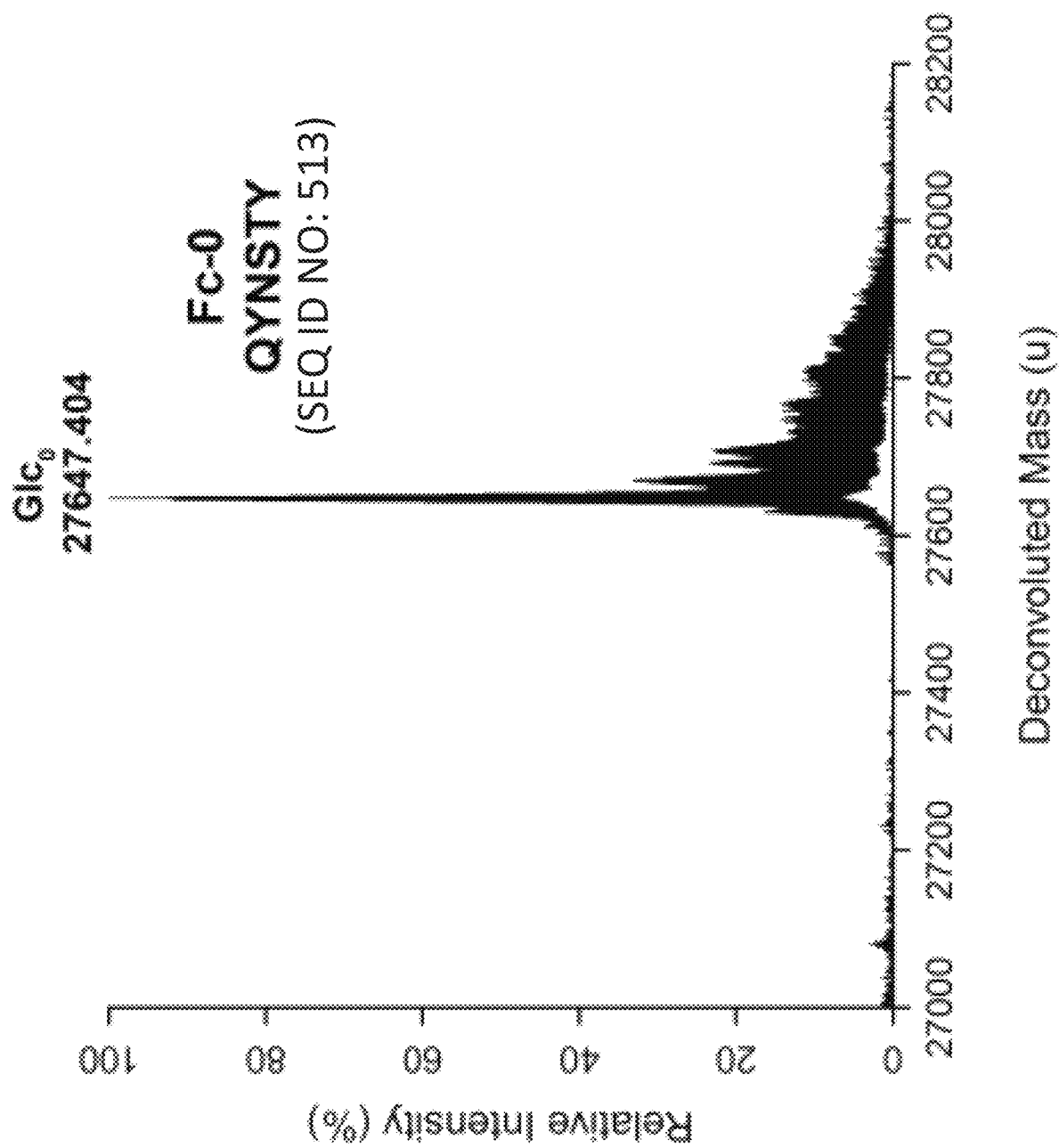
Figure 21B:
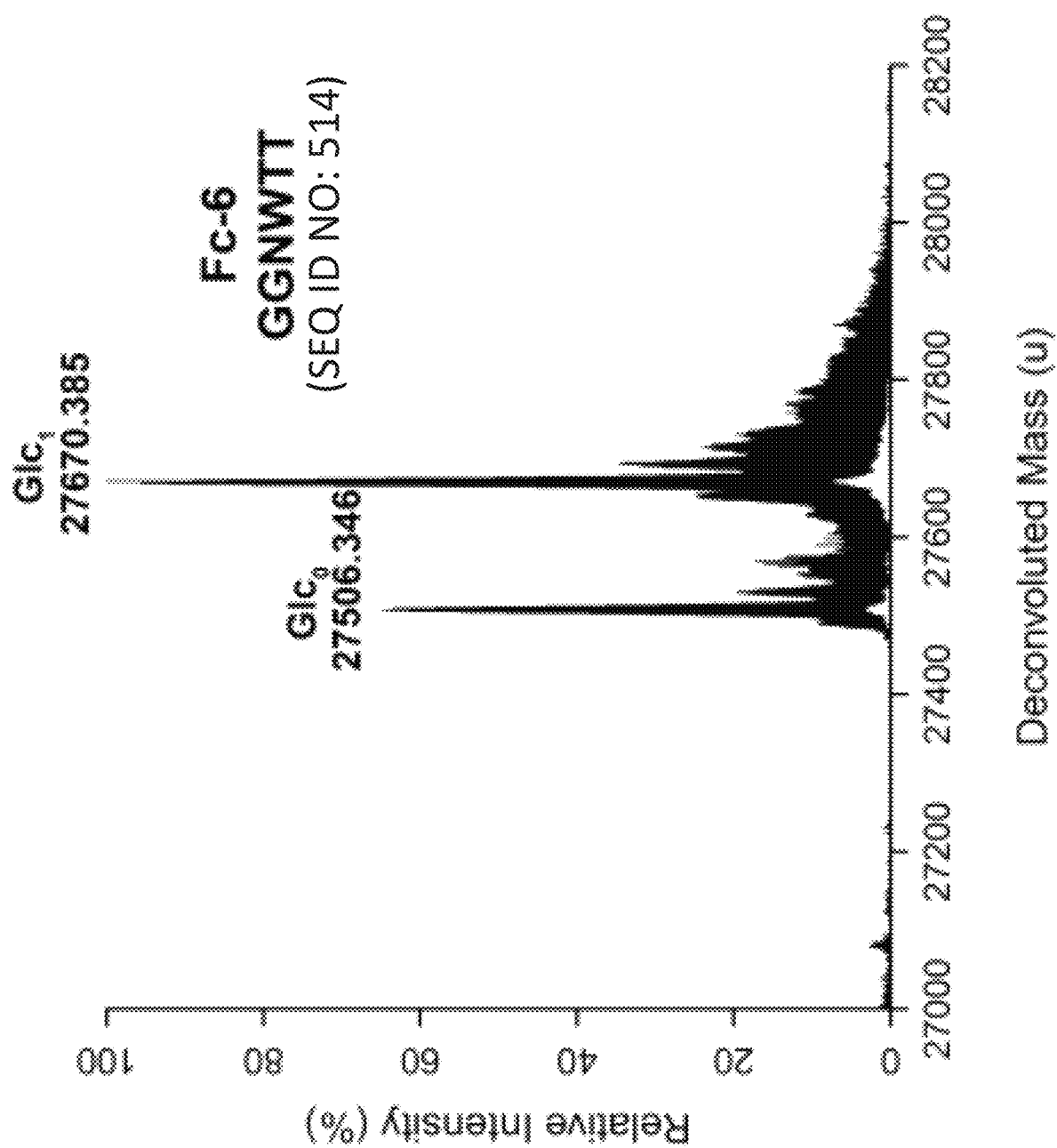
Figure 21C:
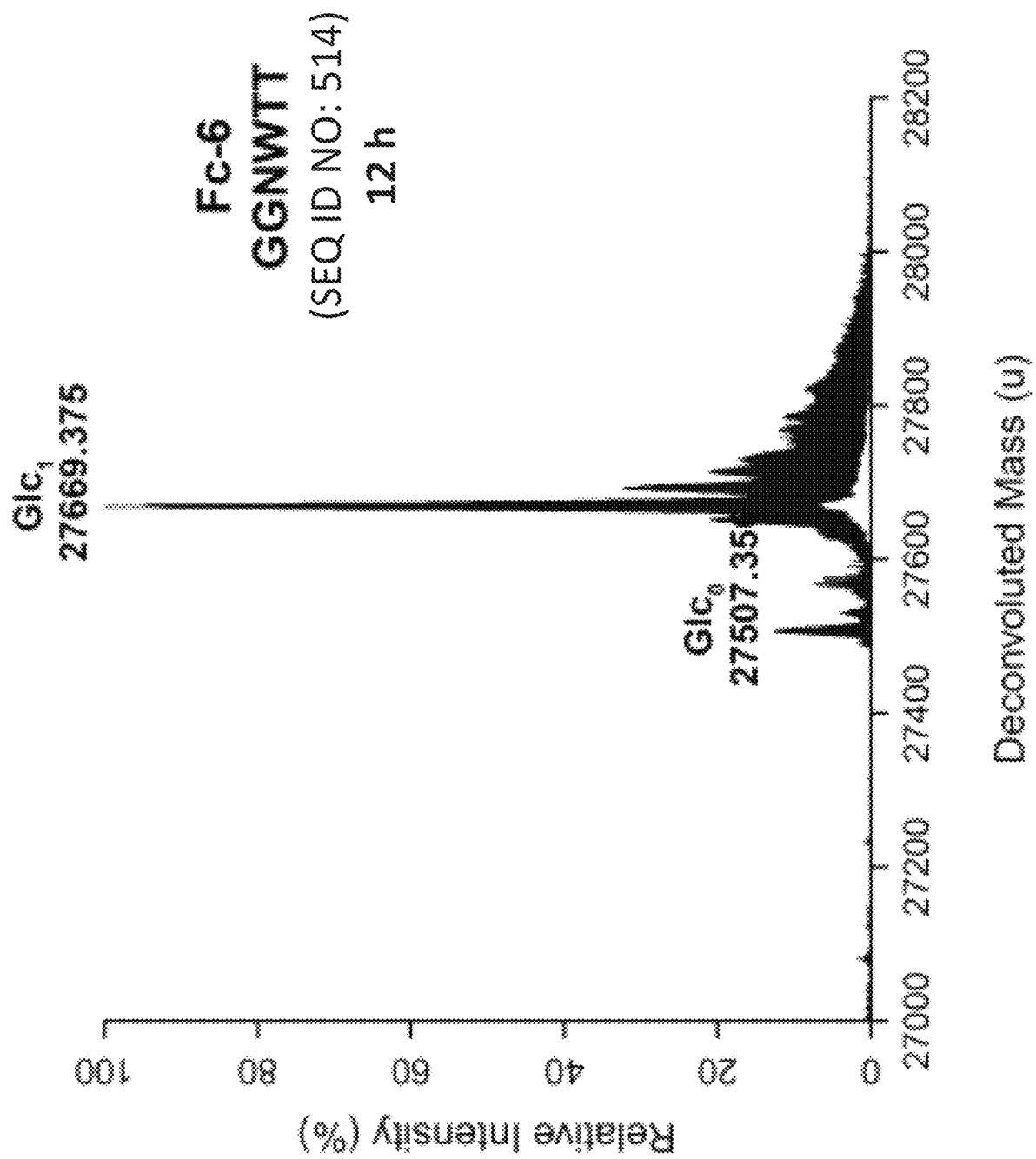
Figure 21D:
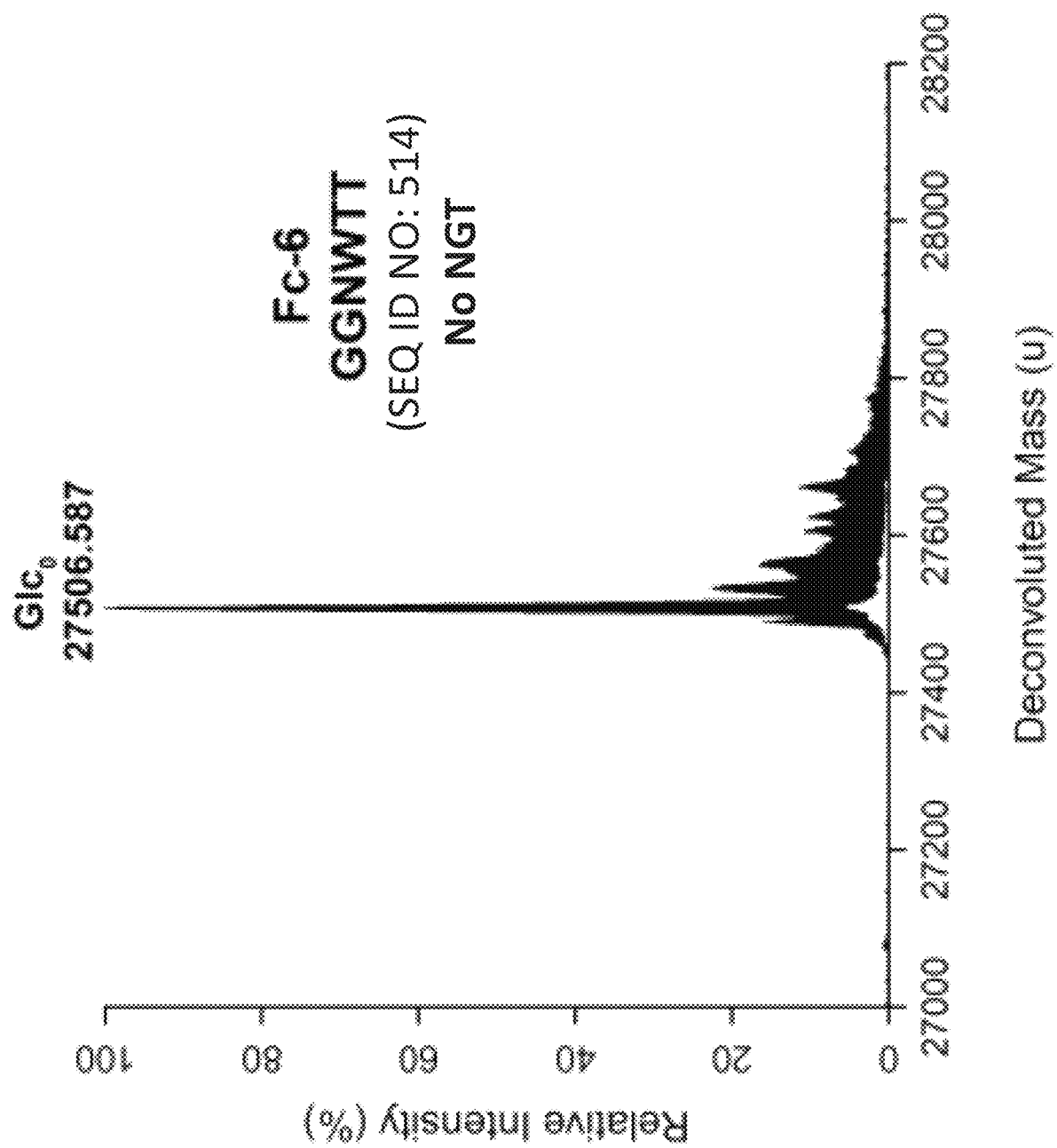
Figure 21E:
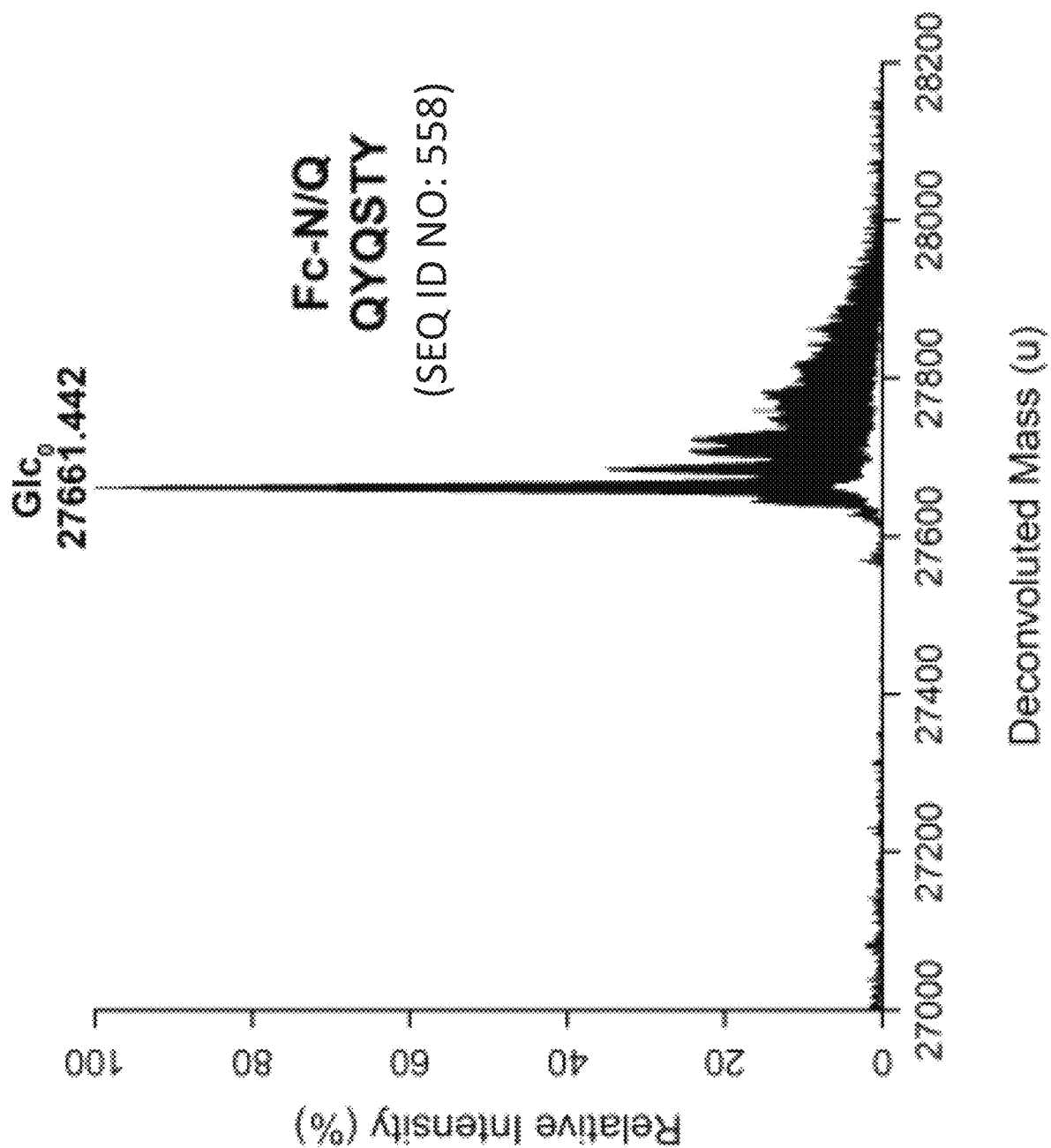
Figure 22A:
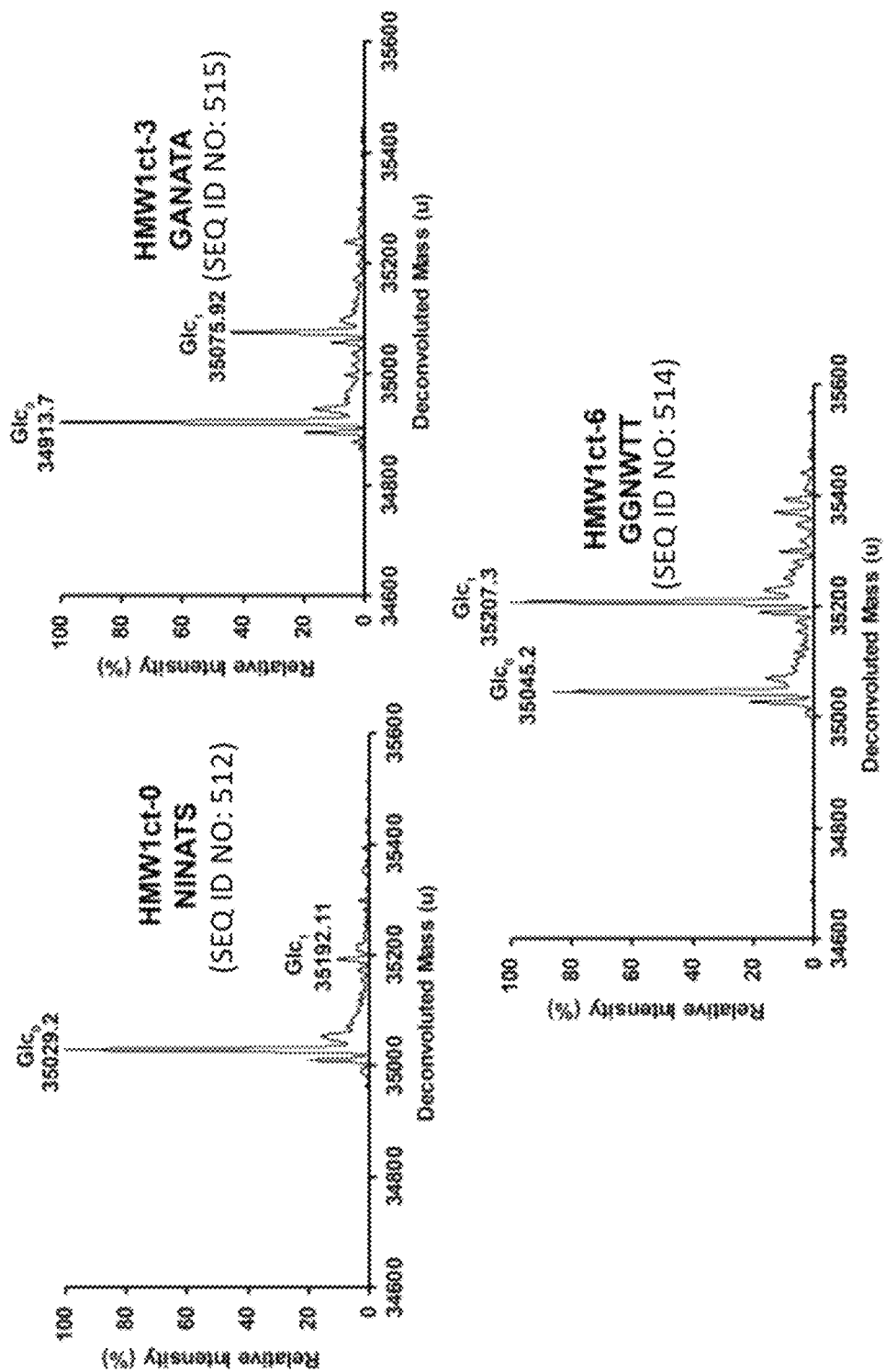
Figure 22B:
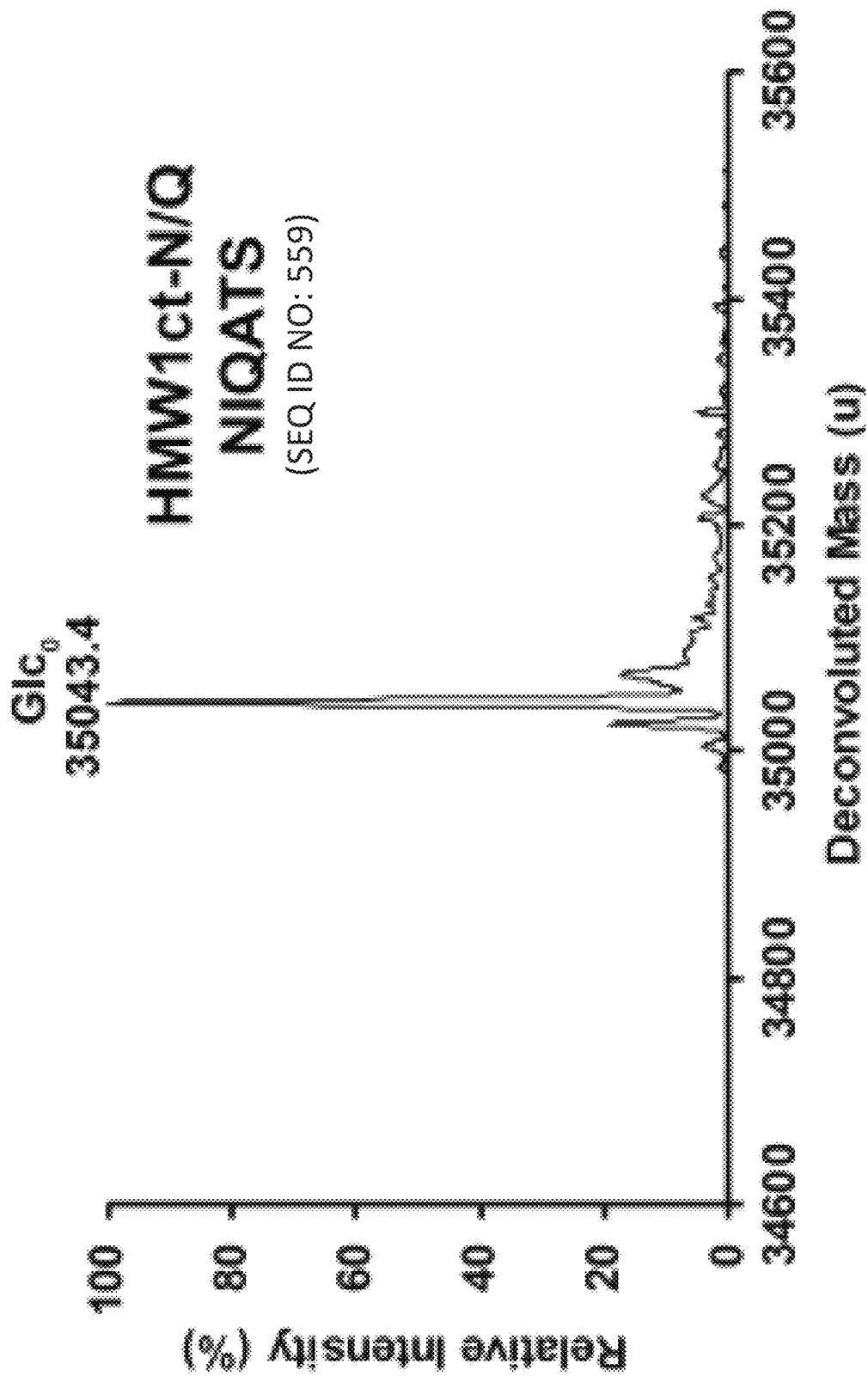
Figure 22C:
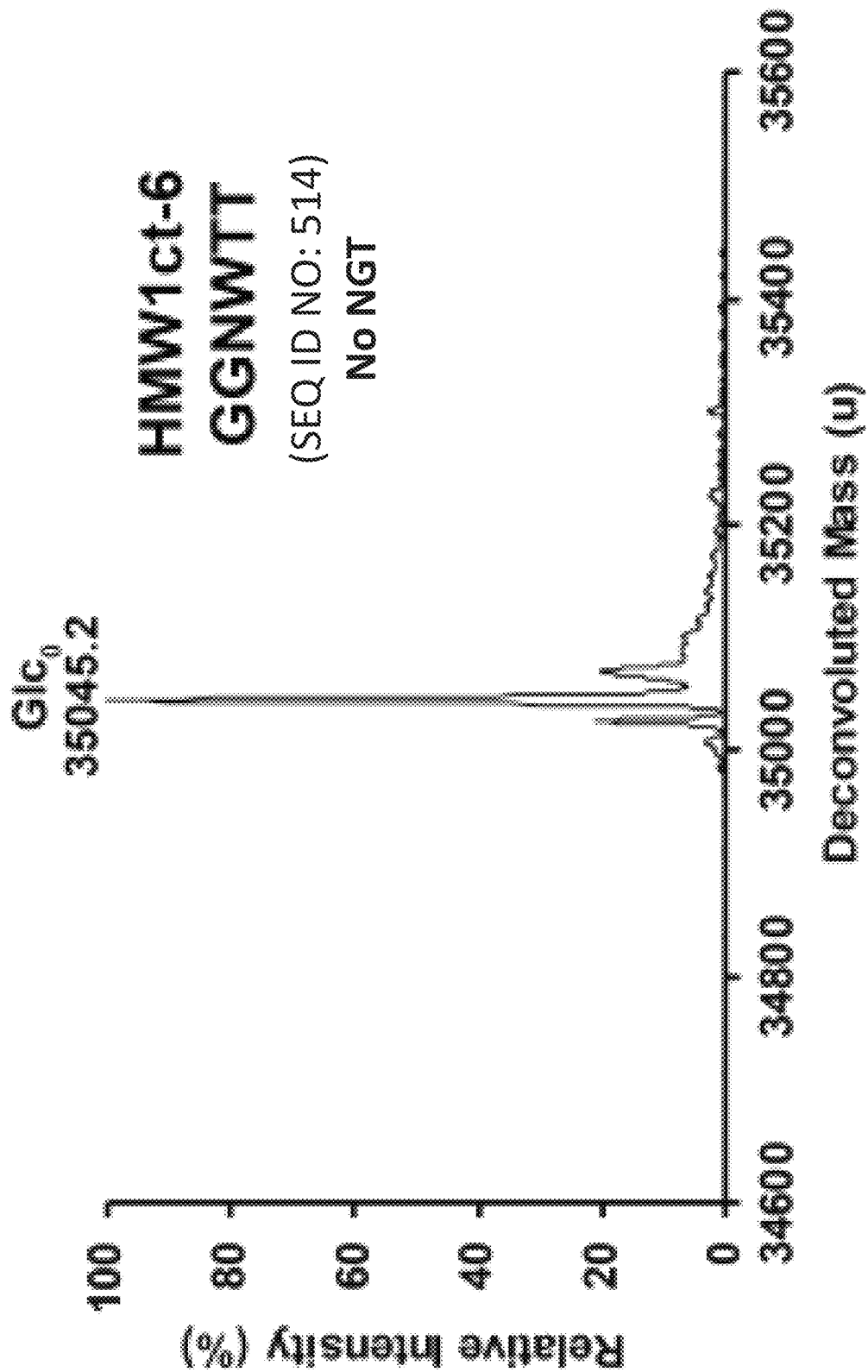
Figure 22D:
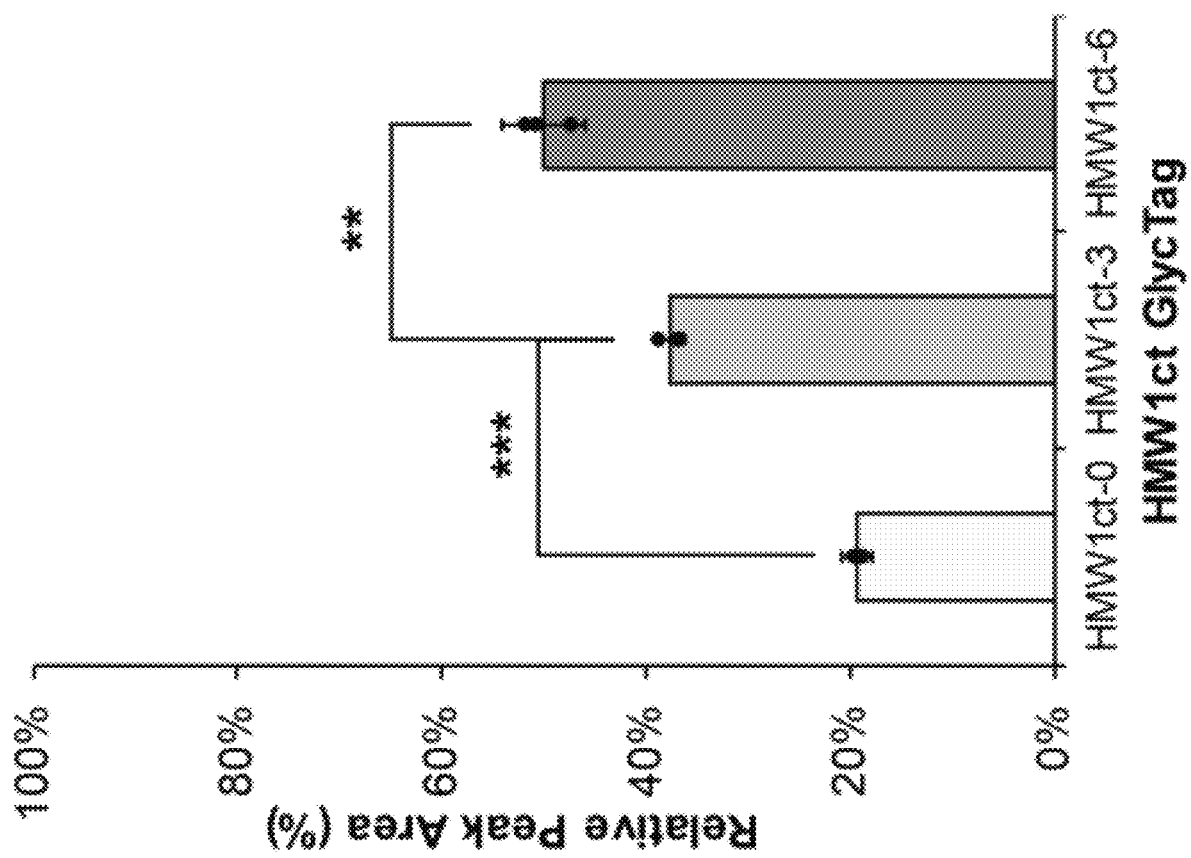

GlycTags enable efficient protein glycosylation in vitro. From the peptide screens described above, we hypothesized that preferred peptide substrates found by GlycoSCORES could be glycosylated by NGT when engineered into whole proteins. We chose the sequence GGNWTT (SEQ ID NO:514) as a model because it was found to be more efficiently glycosylated than any previously studied[19, 20, 23, 47] 6-mer sequences that we tested (FIG. 17). The preference of NGT for the GGNWTT sequence (SEQ ID NO:514) was unexpected due to the presence of Trp (the largest amino acid) in the $X_{+1}$ position at the center of the required N-X-S/T glycosylation motif. We grafted the GGNWTT sequence (SEQ ID NO:514) as a GlycTag into the internal loop of Im7 at Ala28[28] (Im7-6), and developed an in vitro glycosylation (IVG) method using enzymes and target proteins from CFPS (Methods and FIG. 18). We first validated our method by recapitulating the two-enzyme, native glycosylation system of A. pleuropneumoniae on the HMW1ct-WT[47] target protein (FIG. 18). We then assembled IVG reactions containing Im7-6 and NGT synthesized in separate CFPS reactions and a UDP-Glc sugar donor (FIG. 5a and FIG. 21). We purified and analyzed the reaction product with LC-time-of-flight (LC-TOF) mass spectrometry. We found that Im7-6 (containing the GGNWTT GlycTag (SEQ ID NO:514)) was efficiently modified with a single hexose residue (FIG. 5a). Modification was not observed when NGT was absent (FIG. 5a) or when the acceptor residue was mutated from Asn to Gln (FIG. 19).

Figure 5B:
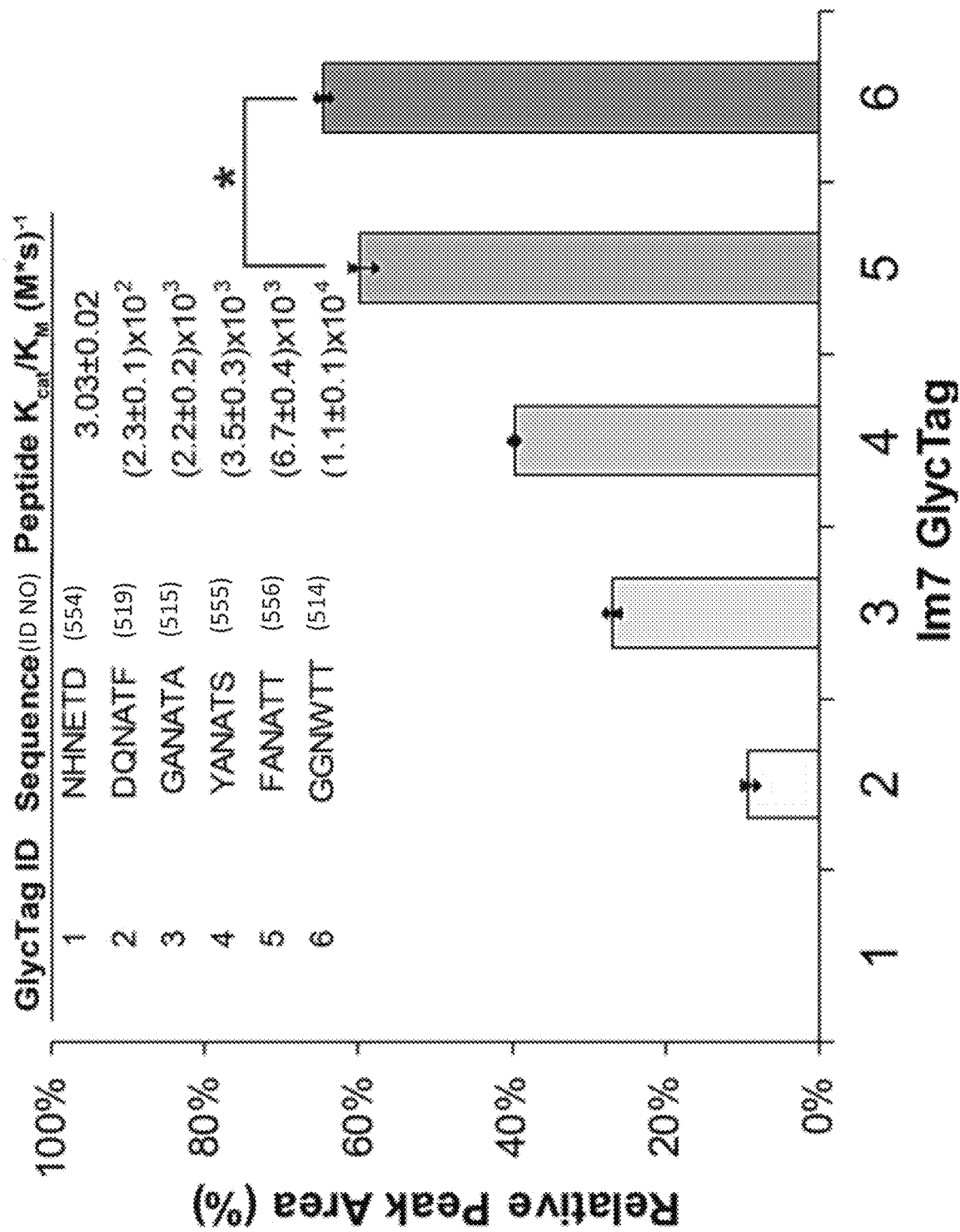

We next investigated how the modification efficiencies of peptides in GlycoSCORES screening correlated with modification efficiencies of these sequences in the context of whole proteins. In addition to GGNWTT (SEQ ID NO:514), we investigated 3 additional sequences from GlycoSCORES peptide screens including FANATT, which showed a high glycosylation efficiency (~75%), YANATS which showed a medium modification efficiency (~36%) and was used in a previous peptide study of NGT[23], and NHNETD which showed no detectable modification (data not shown). For comparison to previous studies, we also analyzed a biological consensus sequence for NGT glycosylation (GANATA (SEQ ID NO:515)) derived from an LC-MS/MS study by Naegeli and coworkers in which NGT was expressed in the cytoplasm of E. coli[20] as well as the optimized PglB GlycTag sequence (DQNATF)[28] (SEQ ID NO:519) which has been used for study of NGT glycosylation at the peptide level[19]. We determined the Michaelis-Menten constants for these sequences along with the GGNWTT sequence (SEQ ID NO:514) used in FIG. 5a using SAMDI (FIG. 5b and data not shown). The relative values of $k_{cat}/K_m$ correlate with GlycoSCORES conversion efficiencies observed in FIG. 4c and FIG. 17. For each of the sequences in FIG. 5b, we synthesized a corresponding Im7 variant containing these sequences at the Ala28 internal loop. To minimize the effects of surrounding amino acids and secondary structure on the glycosylation site, we added flexible flanking sequences around all GlycTags inserted into Im7 based on a biological consensus sequence in the form of ATT-$X_{-2}X_{-1}NX_{+1}X_{+2}X_{+3}$-AGG[20]. The average protein expression yields of all Im7 variants was 624±67 µg/mL (data not shown). We performed IVG reactions and analyzed glycosylation using LC-TOF after purification. Modification was quantified by relative peak areas as in previous literature using dominant charge states of the glycosylated and aglycosylated forms of the protein (FIG. 5b and data not shown). Relative peak areas and deconvoluted mass spectra (FIG. 19) of Im7 variants correlated well with the $k_{cat}/K_m$ values of peptide sequences with identical ranking (FIG. 5b). Of these sequences, GGNWTT (SEQ ID NO:514) showed the highest $k_{cat}/K_M$ value for the peptide substrate and the most efficient modification within the Im7 protein. We also found Im7-6 can be homogeneously glycosylated by increasing the concentration of CFPS-derived NGT in the IVG reaction to 4 µM (FIG. 19). Therefore, we chose GGNWTT (SEQ ID NO:514) as our optimized GlycTag for site-directed protein glycosylation in vivo.

Figure 6A:
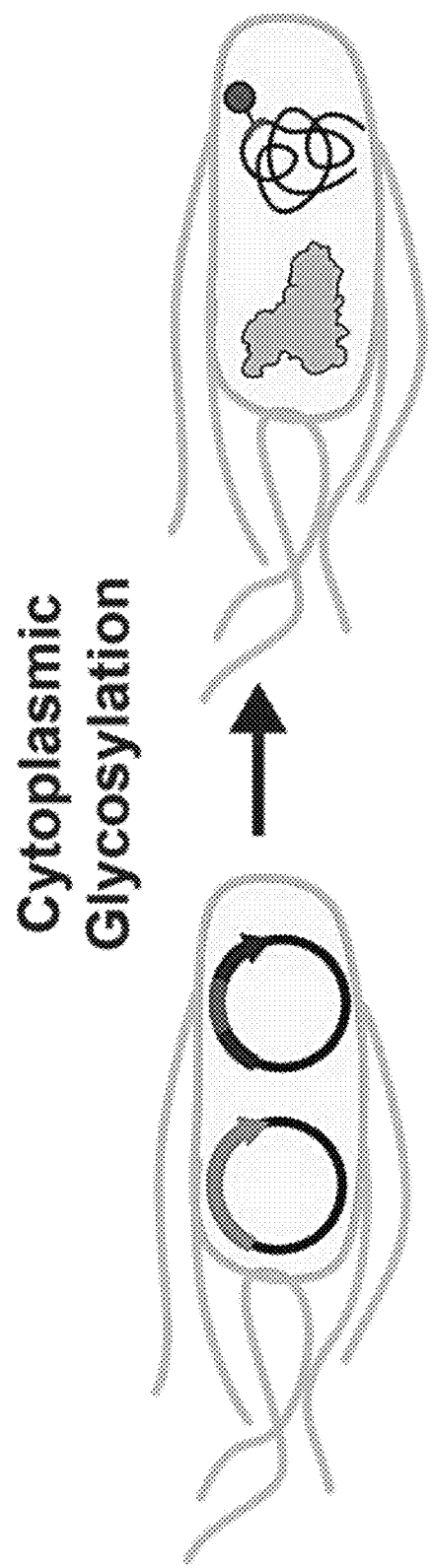
FIG. 6: Site-directed cytoplasmic glycosylation of human Fc using GlycoSCORES optimized sequences. (a) Workflow for cytoplasmic glycosylation in living *E. coli* by coexpression of NGT and target protein GlycTag variants. (b) Relative peak areas of $Glc_1/(Glc_0+Glc_1)$ for Fc containing naturally occurring (0), biological consensus (3), and GlycoSCORES optimized sequence (6) at Asn297 internal loop position with flanking sequences as in ATT($X_{-2}X_{-1}NX_{+1}X_{+2}X_{+3}$)AGG. The GlycoSCORES identified GlycTag (GGNWTT (SEQ ID NO:514)) showed higher relative peak area, indicating greater glycosylation efficiency. Fc was treated with DTT for disulfide reduction before LC-TOF analysis. Relative peak areas calculated from extracted ion chromatograms of the 8 most abundant peaks based on theoretical average masses for Fc (see Methods). Mean and S.D. of n=3 cell cultures are shown. * and *** indicate significances by 2-tailed t-tests of p-values 0.017 and 0.00037, respectively. (c) Representative LC-TOF spectra from analysis of n=3 cell cultures generated by maximum entropy deconvolution are shown on the right (see Methods; QYNSTY (SEQ ID NO: 513), GANATA (SEQ ID NO: 515), GGNWTT (SEQ ID NO: 514)). Representative deconvolution spectra including N/Q and no NGT controls for are shown in FIG. 20. Deconvolution mass errors as well as chromatogram peak retention times and quantification of relative peak area for all samples were generated and analyzed (data not shown). A similar analysis of HMW1ct showed similar results with the GlycoSCORES optimized GlycTag providing more efficient glycosylation (FIG. 22). Shading of bar areas indicates increasing relative peak areas and therefore greater glycosylation efficiencies.
Figure 6B:
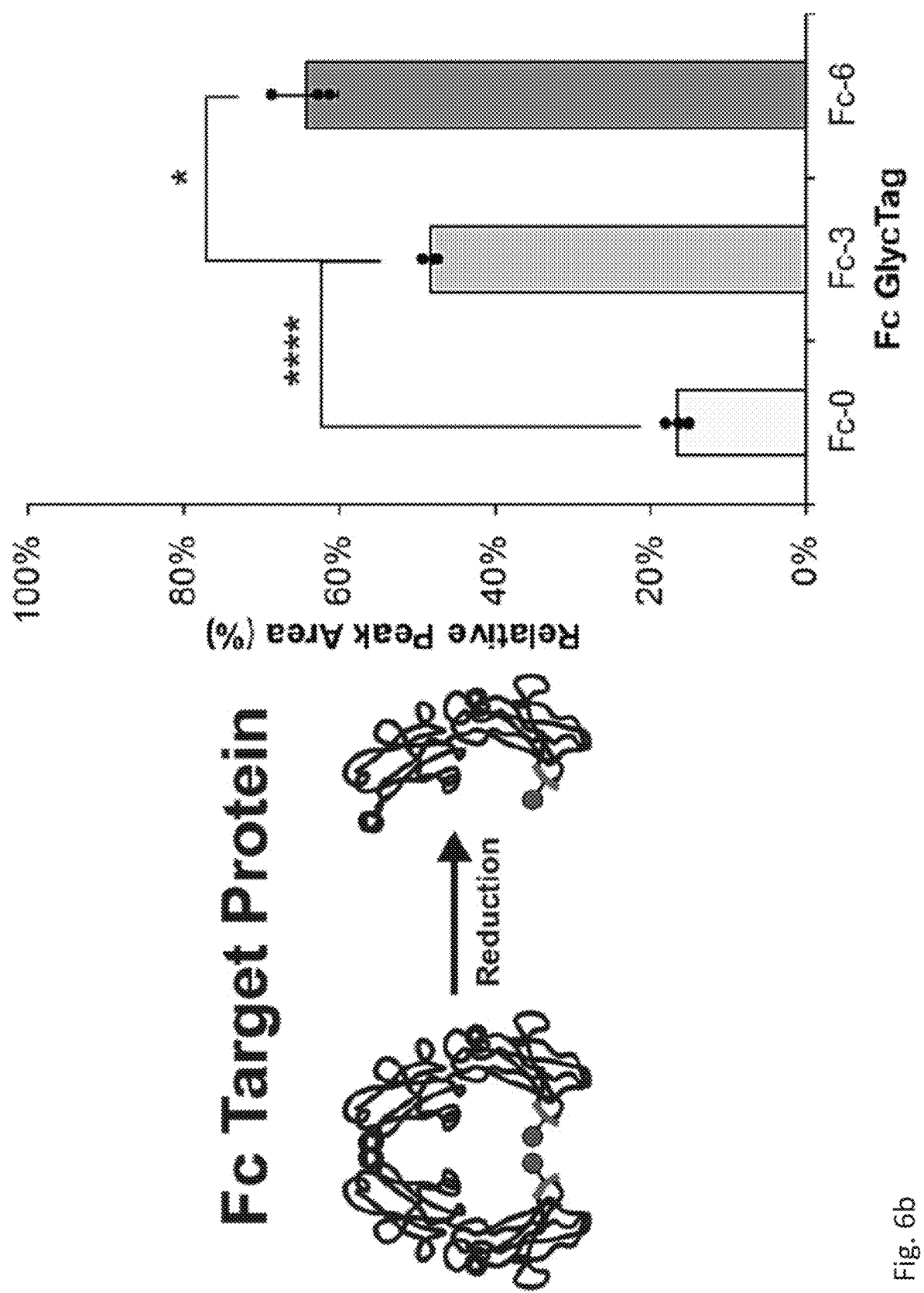
Figure 6C:
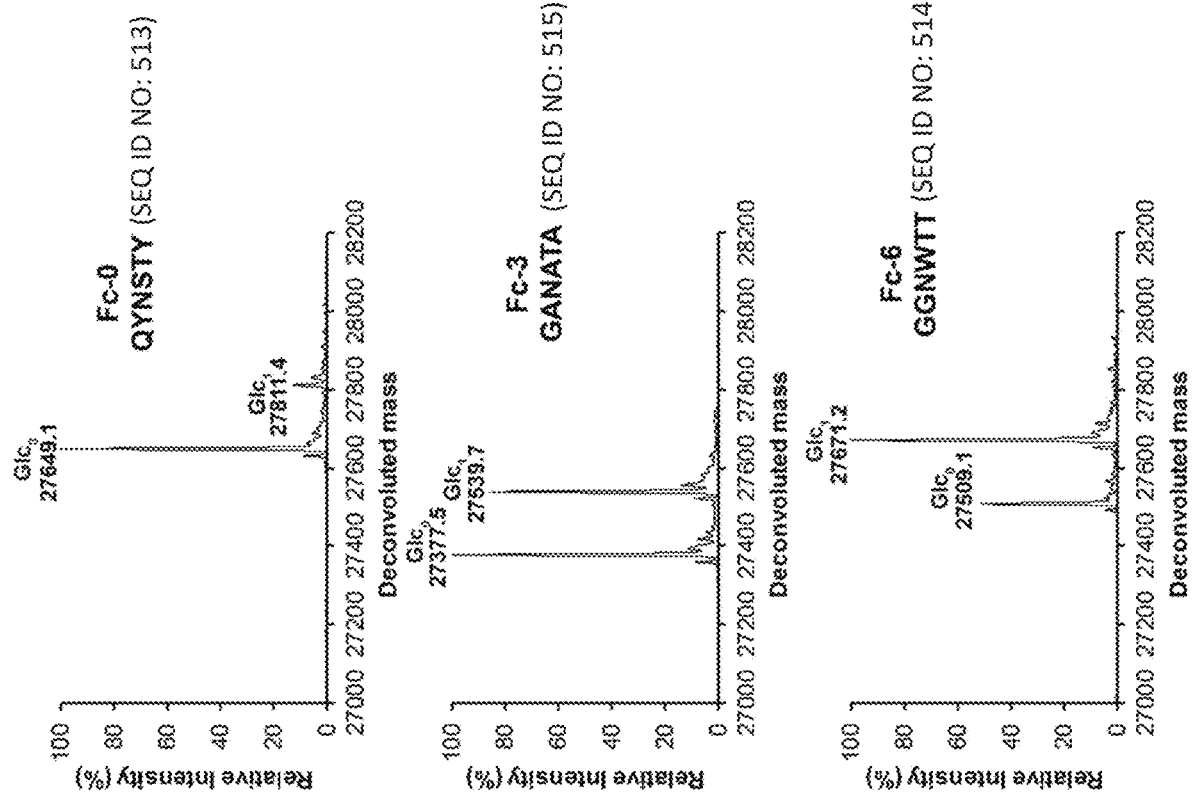

Efficient protein glycosylation in the E. coli cytoplasm. Next, we investigated the use of the GlycoSCORES-derived GGNWTT GlycTag (SEQ ID NO:514) to direct efficient modification of heterologous proteins in the cytoplasm of living E. coli by redesigning the internal protein glycosylation site at Asn297 in human Fc (FIG. 6a). NGT was co-expressed with Fc variants containing the naturally occurring sequence (QYNSTY (SEQ ID NO:513)), the biological consensus sequence (GANATA)[20] (SEQ ID NO:515), and our GlycoSCORES optimized GlycTag (GGNWTT (SEQ ID NO:514)) in vivo. As with Im7, flexible sequences flanked the site. Using a two-plasmid system in BL21(DE3) E. coli, we induced expression of the Fc target protein with IPTG then NGT with arabinose. We found that our GlycoSCORES-derived GlycTag (GGNWTT (SEQ ID NO:514)) enabled the most efficient glycosylation, followed by the biological consensus sequence (GANATA)[20] (SEQ ID NO:515), and the naturally occurring sequence (QYNSTY (SEQ ID NO:513)) in Fc (FIGS. 6b and 6c and FIG. 20). We used this system to produce homogeneously glycosylated Fc in E. coli by extending the co-expression time of the engineered GGNWTT variant with NGT for 4 h (FIG. 20). This same engineered variant of Fc could also be synthesized in CFPS and efficiently glycosylated in vitro (FIG. 21). We completed a similar analysis using a variant of HMW1ct and found that engineered HMW1ct targets also showed trends predicted by GlycoSCORES peptide characterization (FIG. 17) with the optimized GlycTag GGNWTT (SEQ ID NO:514) showing the highest modification followed by GANATA[20] (SEQ ID NO:515) and the naturally occurring NINATS sequence (SEQ ID NO:512) (data not shown). We observed similar expression levels of NGT and Fc or HMW1ct variants across all strains indicating that differences in glycosylation efficiency are due to NGT sequence specificity rather than differences in expression (data not shown).

Discussion

This paper describes the GlycoSCORES platform, a cell-free approach for rapid determination of GT peptide specificity to improve fundamental understanding of glycosylation systems and guide the efficient glycosylation of diverse proteins in vitro and in vivo. By using more than 3,480 unique peptide substrates and 13,903 unique reaction conditions, GlycoSCORES enabled, to our knowledge, the most complete substrate characterization of any ppGT thus far (data not shown). This dataset further facilitated the selection of efficiently modified NGT peptide substrates (FIG. 19 and data not shown), for example GGNWTT (SEQ ID NO:514), which was found to direct efficient glycosylation of Im7, HMW1ct, and Fc proteins. Looking forward, our dataset could also be used to make informed, single mutations to improve modification. Future work could also explore how glycosylation of these optimized sequences is affected by protein structure. We further generalized the GlycoSCORES approach to discover two NGT homologs in pathogenic bacteria with conserved peptide specificities, show complex specificity differences between human ppGalNAcTs, and demonstrate a proof of principle for high-throughput analysis of hOGT specificity. These innovations result from the ability to screen substrate residues more completely and determine synergistic residue combinations that are conventionally not tested.

When combined with recent advancements in the elaboration of the single glucose residue installed by NGT to human-like glycans using chemoenzymatic transglycosylation techniques[13, 27] and polysialic acids using a fully biosynthetic approach[21], the deep specificity data and demonstration of highly efficient GlycTags shown in this work may open the door to diverse applications of NGT-based synthetic glycosylation systems just as the design and implementation of OST GlycTags[28] enabled the improvement of biopharmaceuticals and an array of studies using the bacterial OST, PglB, to produce vaccines and therapeutics in *E. coli*[8, 9]. NGT systems may complement OST-based methods as they do not require export out of the cytoplasm or lipid-associated substrates[9].

Given the versatility of CFPS for rapid, parallelized expression of diverse enzymes and target proteins and the throughput of SAMDI for rapid detection of glycosylation without radioactively or chemically modified sugars or antibodies, we anticipate the application of GlycoSCORES to a broad range of ppGTs investigations of interest to the glycoengineering community including the further characterization of the ppGalNAcTs, OGTs, and OSTs (which have been recently shown to be produced in CFPS using protein nanodiscs[49]). GlycoSCORES is also uniquely suited to the engineering of glycosylation enzymes for alternative specificities in vitro, obviating the need for in vivo selection schemes, which have been challenging to develop for glycan modification. Specifically, CFPS reactions can be performed in 96/384 well plates with linear templates, substrate concentrations can be rigorously controlled, and any peptide mass addition can be detected and quantified by SAMDI. An example application is the synthesis and screening of diverse NGT homologs and engineered variants (building off recent work on NGT mutants[13, 24]) to install GlcNAc onto proteins using a single enzyme or identifying ppGTs that can modify a specific amino acid sequence of interest.

In summary, the GlycoSCORES workflow provides a versatile platform for characterizing and engineering GTs. By allowing for detailed characterization of diverse systems in the current and future studies, we expect this platform to enable a deep, quantitative understanding of glycosylation systems and advance compelling biotechnology applications.

Methods

Solid phase synthesis of peptide arrays. All peptide arrays were synthesized manually using 96-well filter plates (Cat. No. AWFP-F20000, Arctic White LLC) as described previously[31] with some modification. All Fmoc-Amino Acids and Fmoc-Rink Amide MBHA resins were purchased from AnaSpec Inc. All solvents, N,N-dimethylformamide (DMF), dichloromethane (DCM), trifluoroacetic acid (TFA) and piperidine were purchased from Thermo Fisher Scientific. Other chemical reagents used in peptide synthesis were purchased from Sigma-Aldrich unless otherwise noted. Briefly, 10 mg of Fmoc-Rink Amide MBHA resins were placed in each well of 96-well filter plates. Before adding each amino acid, N-terminal fluorenylmethyloxycarbonyl (Fmoc) was deprotected with 300 μL 20% piperidine in DMF, with 600 rpm shaking for 30 min. After 5 washes with DMF, 300 μL 0.1 M Fmoc-Amino Acid, 0.125 M hydroxybenzotriazole (HOBt) and 0.1 M diisopropylcarbodiimide (DIC) were used to add the amino acid onto the resin, with 600 rpm shaking for 2 h. After all amino acids were added onto the resin, Fmoc was deprotected and acetic anhydride (10% in DMF) was used to add an acetyl group on the N-terminal of peptides with 600 rpm shaking for 0.5 h. The resin was washed with DCM 5 times and dried for 1 h, before being cleaved by 500 μL 95% TFA, 2.5% $H_2O$, and 2.5% triethylsilane (TES) with 400 rpm shaking for 2 h. After the solvents were evaporated by flowing nitrogen overnight, remaining solids were dissolved with 600 μL $H_2O$ and transferred to 96-well plates. After lyophilization, the peptides were redissolved in 200 μL 50 mM Tris (pH 8), transferred to 384-well plates (Ref. No. 784201, Greiner Bio One), and stored at −80° C. All peptides had one cysteine to determine the concentration of the peptides and bind to SAMs on gold islands. In most cases, an Arg residue was included N-terminal to the Cys to provide efficient ionization in the mass spectrometry experiments.

Preparation of SAMDI plates. 384 SAMDI plates were prepared as previously described[51] with minor modifications. Briefly, 384 islands with 50 nm Ti and 300 nm Au were prepared by evaporation and rinsed in 0.25 mM ethanolic solution containing 60% of a symmetric disulfide presenting tri(ethylene glycol) (EG3 disulfide from ProChimia Surfaces, Poland) and 40% of an asymmetric disulfide presenting one tri(ethylene glycol) and one maleimide (EG3-Maleimide disulfide from ProChimia Surfaces, Poland) at 4° C. for 2 days. The SAMDI plate was ready for use after washing with ethanol, $H_2O$, and ethanol then drying with flowing nitrogen.

Profiling NGT activity with peptide arrays. A subset of 16-24 peptides were used to measure the average concentration of each peptide library (361 or 380 peptides) using the Ellman test based on manufacture's protocols (Gold Biotechnology). After reduction with tris(2-carboxyethyl) phosphine (TCEP) reducing gel (Thermo Fisher Scientific), 50 µM peptides were reacted with indicated concentrations of NGT purified by Ni-NTA from living *E. coli* or unpurified NGT produced in *E. coli* CFPS, 2.5 mM UDP-Glc in 100 mM 4-(2-hydroxyethyl)-1-piperazineethanesulfonic acid (in HEPES, pH 8) and 500 mM NaCl at 30° C. for indicated times. As a control, the same volume of CFPS after 20 h of sfGFP synthesis was used instead of NGT from CFPS. The reaction was not quenched unless otherwise stated. 2 µL TCEP reducing gel was added to each 10 µL of reaction solutions and incubated at 37° C. for 1 h, before 2 µL reduced solutions were transferred to 384 SAMDI plate using Tecan 96-channel arm and incubated at room temperature for 0.5 h. SAMDI plates were washed with $H_2O$, ethanol, $H_2O$, and ethanol, and dried with flowing nitrogen. After application of 10 mg/mL of 2',4',6'-Trihydroxyacetophenone monohydrate (THAP) matrix (Sigma-Aldrich) in acetone onto the entire SAMDI plate, an Applied Biosystems SciEx MALDI-TOF/TOF 5800 instrument was used to perform mass spectrometry on each spot. Applied Biosystems SciEx Time of Flight Series Explorer Software version 4.1.0 was used to analyze MS spectra. Generally, each 384-well IVG plate was immobilized onto 2 separate 384-well SAMDI plates and analyzed by MALDI separately. The modification efficiency of peptides was calculated using the following equation:

$$\% \text{ modification} = \frac{\frac{I(P)}{RIF(P \text{ to } S)}}{\frac{I(P)}{RIF(P \text{ to } S)} + I(S)}$$

where I(P) is the intensity of product Glc-peptide in mass spectrometry, I(S) is the intensity of substrate peptide in mass spectrometry, and RIF(P to S) is the relative ionization factor of product to substrate. RIFs equal IF(P) IF(S) and were determined as described below. Glucose modification efficiencies for peptides are shown as heat maps in FIGS. 2 and 4 and annotated with numerical values in FIGS. 9-11 and FIGS. 15-17 and data not shown. Heat maps for comparison or characterization are arranged by amino acid properties while heat maps for NGT optimization, are ranked in descending order by average modification of all substrates in each row or column and ranked from left to right and top to bottom. As determined by negative controls peptide arrays using CFPS synthesizing sfGFP rather than NGT (data not shown), glucose modification efficiencies of less than 0.03 were regarded as background. NGT homologs MhNGT and HdNGT were produced in *E. coli* CFPS and profiled with peptide arrays the same way as NGT (FIG. 12 and data not shown).

Measuring relative ionization factors. Relative ionization factors (RIFs) were determined by measurements of mass spectra intensity/concentration for glycosylated and aglycosylated samples. After reduction with TCEP reducing gel, 50 µM peptides were reacted with 2.5 mM UDP-Glc and 10 µM purified NGT or 0.575 µM CFPS NGT in 100 mM HEPES (pH 8) and 500 mM NaCl, at 30° C. for 4 h to achieve more than 70% glucose modification (glycosylated samples). Identical reactions without UDP-Glc were used as control reactions to provide the same total concentration of peptides (aglycosylated samples). The reactions were quenched by placing the reaction plates at 60° C. for 20 min. Glycosylated and aglycosylated samples were mixed at a 1:1 ratio and reduced with TCEP reducing gel, and mass spectra for glycosylated, aglycosylated and mixed samples were collected by SAMDI. The aglycosylated samples always showed no detectable glucose modification. Relative ionization factors were calculated using the equation below.

$$RIF = \frac{\% \ I(Re) * \% \ I(Mix)}{\% \ I(Re) * \% \ I(Mix) + \% \ I(Re) - 2 * \% \ I(Mix)}$$

Where % I(Re) is the intensity of the glycosylated product peptide ($I(P_g)$) divided by the sum of the intensities of the glycosylated product peptide ($I(P_g)$) and aglycosylated substrate peptide ($I(S_g)$) in the glycosylated samples or $I(P_g)$ ($I(P_g)+I(S_g)$). % I(Mix) is the intensity of the glycosylated product peptide ($I(P_m)$) divided by the sum of the intensities of the glycosylated product peptide ($I(P_m)$) and aglycosylated substrate peptide($I(S_m)$) in a 1:1 ratio mixture of glycosylated and aglycosylated samples or $I(P_m)$ ($I(P_m)+I(S_m)$). A subset of 20-24 peptides were used to measure the relative ionization factor (RIF) of each peptide library. The RIFs of peptides for which reaction kinetics data was collected were also determined (data not shown).

Determining sugar donor specificity of NGT. Six peptides were used to profile the monosaccharide selectivity of NGT. 50 µM peptides were reacted with 0.1-0.2 µM purified NGT, 1 mM UDP-Glc, UDP-Gal, GDP-Man, UDP-GlcNAc, UDP-GalNAc or UDP-Xyl in 100 mM HEPES (pH 8) and 500 mM NaCl at 30° C. for 1 h, 4 h or 21 h. After reduction with TCEP reducing gel, the percentage intensity of Glc-peptide was recorded by SAMDI. For testing of sugar donor selectivity of glucose, galactose, or xylose modification with the $X_{-1}NX_{+1}TRC$ peptide library, 1 mM UDP-Glc, UDP-Gal or UDP-Xyl and indicated concentration of purified NGT were used. UDP-Xyl was purchased from Carbosource Services. Other sugar donors were purchased from Sigma-Aldrich.

Measuring reaction kinetics parameters of selected Glyc-Tag peptides. Various (6-8) concentrations of selected HPLC-purified peptides were reacted with indicated concentrations of NGT and 10 mM UDP-Glc in 100 mM HEPES (pH 8) and 500 mM NaCl at 30° C. for a series of reaction times (15 min to 2 h). Reactions were quenched using 2 µL of 2 M HCl per 10 µL of reaction solution. After neutralization with 2 µL 2 M $K_2CO_3$ and reduction with TCEP reducing gel, the modification efficiency was determined by SAMDI. Initial reaction velocities were calculated using the slopes in the linear time-frame of each initial peptide concentration. $K_M$ and $k_{cat}$ and associated errors were then determined by non-linear fitting to the Michaelis-Menten formula using OriginPro 9 software.

Using GlycoSCORES to screen peptide selectivity of human O-linked GTs produced in CFPS. To demonstrate the applicability of GlycoSCORES to the study mammalian O-linked GTs, ppGalNAcT1, ppGalNAcT2, and hOGT were produced in *E. coli* CFPS. While hOGT was synthesized in CFPS the same way as NGT, the ppGalNAcTs were synthesized in CFPS under oxidizing conditions to allow for formation of disulfide bonds. Oxidizing conditions were achieved using standard CFPS reactions were modified as described previously[52], supplemented with 14.3 µM iodoacetamide, 1 mM glutathione, 4 mM glutathione disulfide, and 3.16 µM *E. coli* disulfide bond isomerase (DsbC). For GlycoSCORES screening of ppGalNAcTs, 100 µM of each peptide from peptide array $AX_{-1}TX_{+1}APRC$ was reacted with 0.024 µM CFPS ppGalNAcT1 or 0.04 µM ppGalNAcT2, 1 mM UDP-GalNAc in 100 mM HEPES (pH 7.5), and 3 mM $Mn^{2+}$ at 37° C. for 1 h followed by quenching with 5 mM EDTA. As a control, the same volume of CFPS after 20 h of sfGFP synthesis was used instead of ppGalNAcTs from CFPS. GlycoSCORES screening of hOGT was completed similarly, with 50 µM of each peptide variant of the sequence PPVSRC reacted with 0.62 µM hOGT made in CFPS and 2.5 mM UDP-GlcNAc in 20 mM Tris (pH 7.4), 125 mM NaCl, and 1 mM EDTA for 21 h at 37° C. After reduction with TCEP reducing gel and maleimide capture, the relative percentage intensities of the GalNAc or GlcNAc-modified and unmodified peptides were recorded by SAMDI as described for NGT.

Plasmid construction and molecular cloning. Plasmids used in this study with sources and details are reported in "Design of glycosylation sites by rapid expression and high-throughput characterization of N-glycosyltransferase," by Weston Kightlinger, Liang Lin, Madisen Rosztoczy, Matthew P. DeLisa, Milan Mrksich, and Michael C. Jewett, Nat. Chem. Biol., 2018 May 7, doi: 10.1038/s41589-018-0051-2, which content is incorporated herein by reference in its entirety. The wildtype Im7 coding sequence (Uniprot: IMM7_ECOLX) was PCR amplified from pBR322.Im7 and assembled into the pJL1 CFPS vector between the NdeI and SalI sites using Gibson Assembly to produce pJL1.Im7-0s. Wildtype IgG1 constant Fc region (A1-98 Uniprot: IGHG1_HUMAN) was synthesized by Twist Bioscience and assembled into a variant of pET22b with redesigned restriction sites (pETBCS.NS) using restriction ligation to form pETBCS.NS.Fc-0s. The wildtype sequence for HMW1ct (A1-1203 GenBank: AD096128.1) was synthesized by Life Technologies and assembled into pJL1 between NdeI and SalI sites to form pJL1.HMW1ct-WT. A variant sequence of HMW1ct with N/Q substitutions at all naturally occurring N-X-S/T sites except at N1366 was synthesized by Life Technologies and assembled into pET.BCS.NS to form pET.BCS.NS.HMW1ct-0 using restriction and ligation at NdeI and SalI sites. Variants of the N26_T31 NVAAT loop in Im7-0s, the Q178_Y183 QYN-STY (SEQ ID NO:513) naturally occurring glycosylation sequence in Fc-0s, and the N1364_S1370 naturally occurring glycosylation sequence in HMW1ct-0 were constructed by inverse PCR with 18 bp of overlapping 5' homology and recirculazied by one-piece Gibson Assembly. All variants of Im7, Fc, and HMW1ct contained C-terminal 6×His-tags. Wildtype NGT sequence (Uniprot: NGT_ACTP2) was synthesized by Twist Bioscience and assembled into pJL1 between NdeI and SalI sites, pET.21b between NcoI and XhoI sites with a C-terminal 6×His-tag, and pMAF10 between NcoI and HindIII with a C-terminal 1×FLAG tag by Gibson Assembly. The α-1,6 glucose polymerase from *A. pleuropneumoniae* (AGT, Uniprot: GTF_ACTP7) was ordered from Twist Bioscience in pJL1 with a customized ribosome binding site designed for maximum translation initiation rate using the RBS Calculator v2.0[53]. Codon optimized sequences for MhNGT (Uniprot: A0A0B5BRN9_MANHA) and HdNGT (Uniprot: Q7VKK3_HAEDU) were ordered from Integrated DNA Technologies with C-terminal Strep tags and placed into PJL1 using Gibson assembly. Human ppGalNAcT1 (CGAT1_HUMAN) and ppGalNAcT2 (CGAT2_HUMAN) truncated without the N-terminal 40 aa (Δ40) were also cloned into PJL1 using Gibson Assembly either with or without N-terminal CAT-Strep-Linker fusions. The coding sequence for hOGT (OGT1_HUMANΔ1-313) was PCR amplified from pET42a.hOGT[46] and cloned into PJL1 using Gibson Assembly.

Preparation of cell extracts for CFPS. Crude extracts for CFPS were generated from a genomically recoded release factor 1 (RF1) deficient *E. coli* strain (*E. coli* C321.ΔA.759), based on *E. coli* C321.ΔA[54]. Cell growth, harvest, and lysis were performed as described in Kwon and Jewett[55]. Briefly, *E. coli* cells were grown in 1 L of 2×YTPG (yeast extract 10 g/L, tryptone 16 g/L, NaCl 5 g/L, $K_2HPO_4$ 7 g/L, $KH_2PO_4$ 3 g/L, and glucose 18 g/L, pH 7.2) in a 2.5 L Tunair flask at 34° C. and 250 rpm with initial inoculation to OD600=0.08. At OD600=3.0, cells were pelleted by centrifugation at 5,000×g at 4° C. for 15 min. The pellets were washed three times with cold S30 buffer (10 mM Tris-acetate pH 8.2, 14 mM magnesium acetate, 60 mM potassium acetate, 2 mM dithiothreitol (DTT)) and flash frozen on liquid nitrogen and stored at −80° C. Cells were thawed, resuspended in 0.8 mL of S30 buffer per gram wet weight, and lysed in 1.4 mL aliquots on ice using a Q125 Sonicator (Qsonica) for three pulses (50% amplitude, 45 s on and 59 s off). After sonication, 4 µL of DTT (1 M) was added followed by centrifugation at 12,000×g and 4° C. for 10 min. The supernatant was incubated at 37° C. at 250 rpm for 1 h for a run-off reaction and centrifuged again at 10,000×g at 4° C. for 10 min. The supernatant was flash-frozen on liquid nitrogen and stored at −80° C. until use.

Cell-free protein synthesis. CFPS reactions were conducted using a PANOx-SP crude lysate system[56]. A standard reaction contained 1.2 mM ATP; 0.85 mM each of GTP, UTP, and CTP; 34 µg/mL folinic acid; 170 µg/mL of *E. coli* tRNA mixture; 16 µg/mL purified T7 RNA polymerase; 2 mM for each of the 20 standard amino acids; 0.33 mM nicotinamide adenine dinucleotide (NAD); 0.27 mM coenzyme-A (CoA); 1.5 mM spermidine; 1 mM putrescine; 4 mM sodium oxalate; 130 mM potassium glutamate; 10 mM ammonium glutamate; 12 mM magnesium glutamate; 57 mM HEPES, pH 7.2; 33 mM phosphoenolpyruvate (PEP); 13.3 µg/mL plasmid template of interest; and 27% v/v of *E. coli* cell extract. *E. coli* total tRNA mixture (from strain MRE600) and phosphoenolpyruvate was purchased from Roche Applied Science. ATP, GTP, CTP, UTP, 20 amino acids and other materials were purchased from Sigma-Aldrich. Plasmid DNA for cell-free was purified from DH5-a *E. coli* strain (NEB) using ZymoPURE Midi Kit (Zymo Research). NGT and AGT were synthesized in 50 µL batch reactions in 2.0 mL microtubes and Im7 and HMW1ct-WT target proteins were synthesized in 15 µL batch reactions in 1.5 mL microtubes. The CFPS reactions were carried out at 20° C. for 20 h.

Quantification of CFPS yields. Total and soluble CFPS yields were quantified using CFPS reactions identical to those used for NGT, AGT, Im7, HdNGT, MhNGT, ppGalNAcT1, ppGalNAcT2, and hOGT synthesis supplemented with 10 µM $^{14}$C-leucine (Perkin-Elmer). Protein quantification for triplicate CFPS reactions was completed using trichloroacetic acid (TCA) protein precipitation followed by radioactivity quantification using a Microbeta2 liquid scintillation counter (Perkin Elmer) according to established protocols[57]. Soluble fractions were taken after centrifugation at 12,000×g for 15 min at 4° C. CFPS yields of sfGFP were quantified as described previously[55] using a multi-well fluorimeter (Synergy2, BioTek) and converted to µg/mL yields using a previously determined standard curve based on $^{14}$C leucine incorporation assays[58].

Autoradiograms of CFPS proteins. After synthesis in $^{14}$C-leucine supplemented CFPS reactions, 2 µL of each sample was loaded onto a 4-12% Bolt Bis-Tris Plus SDS-PAGE gels (Invitrogen) and run in MOPS buffer at 150 V for 70 min. The gels were stained using InstantBlue (Expedeon) and destained in water. The gels were incubated in gel drying solution (Bio-rad), dried overnight between cellophane films in a GelAir Dryer (Bio-Rad) without heating, and exposed for 48 h on a Storage Phosphor Screen (GE Healthcare). Autoradiogram images were acquired using Typhoon FLA7000 imager (GE Healthcare). The same coomassie stained gels were imaged using a GelDoc XR+Imager for molecular weight standard references (Bio-rad).

Production and purification of NGT from *E. coli*. NGT was purified as described previously[23] with minor modifications. Briefly, BL21 (DE3) cells were transformed with pET21b.NGT plasmid by electroporation. An overnight culture was inoculated in carbenicillin (CARB) LB media. Fresh CARB LB was inoculated at initial OD600=0.08 and the cells were grown at 37° C. at 250 rpm to 0.6-0.8 OD and induced with 1 mM Isopropyl β-D-1-thiogalactopyranoside (IPTG) for 6 h at 30° C. The cells were pelleted by centrifugation at 8,000×g for 10 min at 4° C., resuspended in Buffer 3 (20 mM Tris-HCl and 250 mM NaCl, pH 8.0), pelleted again by centrifugation at 8,000×g for 10 min at 4° C. and frozen at −80° C. The pellets were then thawed and resuspended in 5 mL Buffer 3 with 20 mM Imidazole per gram wet pellet weight; supplemented with 70 μL of 10 mg/mL lysozyme (Sigma), 1 μL Benzonase (Millipore), and 1× Halt protease inhibitor (Thermo Fisher Scientific); lysed by single pass homogenization at 21,000 psig (Avestin); and centrifuged at 15,000×g for 20 min at 4° C. The supernatant was applied to an Ni-NTA agarose column (Qiagen) equilibrated with Buffer 3 with 20 mM imidazole, washed with 10 column volumes of Buffer 3 with 40 mM imidazole, and eluted with 4 column volumes of Buffer 3 with 500 mM Imidazole. The elution was dialyzed against 50 mM HEPES 200 mM NaCl, pH 7.0, supplemented with 5% glycerol, and flash frozen at −80° C. NGT concentration was quantified using Image Lab software version 6.0.0 densitometry with BSA standard curve after separation by SDS-PAGE, staining with InstantBlue coomassie stain, and destaining in water.

In vitro glycosylation of protein substrates. IVG reactions were assembled in standard 0.2 mL tubes from completed CFPS reactions containing targets and enzymes at concentrations determined by $^{14}$C-leucine incorporation. Im7 glycosylation reactions contained 5 μM of one Im7 variant, 0.1 μM NGT, and 2.5 mM UDP-Glc in the final reaction. Each reaction contained a total of 5 μL UDP-Glc and 25 μL CFPS reaction (remaining CFPS reaction volume up to 25 μL was filled by a completed CFPS reaction which synthesized sfGFP). Similarly, HMW1ct-WT IVG reactions contained 5 μM HMW1ct-WT, 0.1 μM NGT, and 2 μM AGT and 2.5 mM UDP-Glc in the final reaction. Each IVG reaction contained 10 μL completed CFPS reaction and 2 μL UDP-Glc. IVG reactions for Im7 and HMW1ct-WT were performed at 30° C. for 2.5 h and 16 h, respectively.

Western blotting of HMW1ct-WT. Completed HMW1ct-WT IVG reactions (1 μL) were loaded onto a 4-12% Bolt Bis-Tris SDS-PAGE gel in MOPS buffer and run at 130 V for 100 min. The gel was then transferred onto a 0.2 μM PVDF membrane (Bio-Rad) using the Trans-Blot SD semi-dry blotting system (Bio-Rad) using 80% MOPS and 20% Methanol buffer. The target protein was detected by blocking the membrane in 5% milk in PBS with 0.1% Tween 20 and then incubating with a polyclonal His antibody (Abcam, ab1187) diluted 1:7,500 in PBS with 1% milk for 45 min. The poly-α-Glucose moiety installed by NGT and AGT was detected using a ConA lectin blot using an identical gel with identical membrane and transfer conditions. The ConA blot was blocked with Carbo-free solution (Vector Laboratories) for 1 h and probed with 5 μg/mL ConA-HRP (Sigma, L6397-1MG) diluted in Carbo-free solution supplemented with 1 mM $MgCl_2$, 1 mM $MnCl_2$, 0.1% Tween, and 1 mM $CaCl_2$) for 1 h. Blots were imaged using Western-Sure Chemiluminescent substrate on an Odessey Fc (Li-Cor) imager.

Purification from in vitro glycosylation reactions. Purification of Im7 from IVG reactions was completed using Dyna-His tag beads (Thermo Fisher Scientific). The 30 μL IVGs were diluted to 120 μL in Buffer 1 (50 mM $NaH_2PO_4$ and 300 mM NaCl, pH 8.0) with a final concentration of 10 mM imidazole and incubated at room temperature for 5 min on a roller with 20 μL of beads. The beads were then washed with 120 μL of 20 mM imidazole in Buffer 1 four times using a 96 well plate magnetic tube rack (Life Technologies) for separations. The samples were then eluted using 30 μL of 500 mM imidazole in Buffer 1. The samples were dialyzed against Buffer 2 (20 mM $NaH_2PO_4$ and 150 mM NaCl, pH 7.5) in 3.5 kDa MWCO 96-well plate dialysis cassettes (Thermo Fisher Scientific). After dialysis, 10 μL was injected into LC-TOF for analysis.

Production of glycosylated proteins in cells. *E. coli* BL21 (DE3) cells were transformed first with pMAF10.NGT by electroporation and selected on trimethoprim (TMP) LB agar plates. A colony was picked and prepared for calcium-choloride transformation and transformed with pETBCS.NS vectors containing Fc or HMW1ct target proteins and selected on TMP+CARB LB agar plates. Colonies were grown to mid-exponential phase and glycerol stocked. The glycerol stocks were used to inoculate overnight cultures in TMP+CARB LB media. Fresh cultures in TMP+CARB were inoculated at initial OD600=0.08 and grown at 37° C. at 250 rpm. For HMW1ct sequence variants, the target protein was induced at 0.6-0.8 OD for 1 h with 400 μM IPTG at 30° C. followed by NGT induction with 0.2% arabinose for 2 h at 30° C. For Fc sequence variants, the target protein was induced for 2 h followed by NGT induction for 30 min (unless otherwise noted) at identical inducer concentrations. The cells were then pelleted by centrifugation at 4° C. for 2 min at 10,000×g, resuspended in Buffer 1, centrifuged at 4° C. for 2 min at 10,000×g, frozen on liquid nitrogen, and stored at −80° C. The pellets were thawed and resuspended in 630 μL of Buffer 1 with 10 mM imidazole and supplemented with 70 μL of 10 mg/mL lysozyme (Sigma), 1 μL Benzonase (Millipore), and 1× Halt protease inhibitor (Thermo Fisher Scientific). After 15 min of thawing and resuspension, the cells were incubated for 15 min on ice and sonicated for 45 s at 50% amplitude and then spun at 12,000×g for 15 min. The supernatant was then loaded onto Ni-NTA His-tag spin columns (Qiagen) pre-equilibrated with 10 mM imidazole in Buffer 1. The columns were washed 3 times with 30 mM imidazole and eluted with 2×100 μL 500 mM imidazole. Samples were then dialyzed with 10 kDa MWCO MINI slide-a-lyzers (Thermo Fisher Scientific) overnight. Protein concentrations were quantified using Image Lab software densitometry with BSA ladder standard after separation by SDS-PAGE, 1 h stain with InstantBlue, and 1 h destain in water. Prior to injection into LC-TOF, purified Fc was incubated with 50 mM DTT for 1 h at room temperature to reduce disulfide linkages.

LC-TOF Analysis of Glycoprotein Modification. Purified proteins from CFPS of Im7 or in vivo expression of Fc and HMW1ct were injected onto an Agilent 1200 HPLC equipped with an XBridge BEH300 Å C4 3.5 μm 2.1 mm×50 mm reverse-phase column (186004498 Waters Corporation) with a 10 mm guard column of identical packing (186007230 Waters Corporation) coupled to an Agilent 6210A ESI-TOF mass spectrometer. The chromatographic separation method was based on manufacturer instructions for XBridge column with minor modifications. Solvent A was 95% $H_2O$ and 5% acetonitrile (ACN) with 0.1% formic acid and solvent B was 100% ACN with 0.1% formic acid.

The separation was completed at a flow rate of 0.4 mL/min with a column temperature of 50° C. Solvent conditions were held at 15.8% B for 1 min, then the target protein of interest was eluted during a 12 min gradient from 15.8% to 65.8% B. The column was then washed and re-equilibrated using a 2 min gradient from 65.8-69.9% B, a 2 min hold at 100% B, and a 6 min hold at 15.8% B. Purified Fc after in vitro synthesis and glycosylation was injected into a Bruker Elute UPLC system, separated using the same chromatography methods as listed above, and analyzed by an Impact-II UHR TOF-MS system (Bruker Daltonics, Inc.). External calibration was completed prior to analysis of all proteins.

LC-TOF Data Analysis. Data from Agilent 6210A was processed using Agilent Mass Hunter software version B.04.00. Methods for quantification of relative peak areas for glycosylated and aglycosylated glycoforms were adapted from previous works[48, 59]. Extracted ion chromatograms (EICs) were created using theoretical values for the most dominant charge states from the glycosylated and aglycosylated samples±0.5 Da. Protonated charge states +12 to +14, +29 to +36, and +34 to +43 were used to quantify the relative peak areas for Im7, Fc, and HMW1ct, respectively. EIC peaks corresponding with retention times of each protein (data not shown) were then integrated and used for quantification of relative peak areas, defined as $Glc_1/(Glc_0+Glc_1)$. Deconvoluted spectra were produced using Agilent Mass Hunter maximum entropy deconvolution using MS peaks within m/z range 700-2000 into mass ranges of 10,000-15,000 u; 25,000-30,000 u; and 32,500-37,500 u for Im7, Fc, and HMW1ct, respectively. Isotope widths were calculated by Mass Hunter for deconvolution mass ranges at 7.1, 10.5, and 11.6 u for Im7, Fc, and HMW1ct, respectively. Data from Impact-II UHR TOF-MS was performed using Bruker Compass Hystar software version 4.1. Deconvolution was performed using maximum entropy deconvolution using MS peaks within m/z range 700-2000 into a mass range of 20,000-30,000 u. Raw data was then plotted and annotated using R Studio. Deconvolutions used full mass spectra averaged across the entire peak width of the proteins of interest (encompassing the full elution of the glycosylated and aglycosylated glycoforms). Deconvoluted masses and errors compared to calculated values also were generated and analyzed (data not shown).

Statistical Analysis. Two-tailed Student's t-tests and resulting p-values were calculated in Microsoft Excel 2016 assuming unequal variances and two-tailed distributions to assign significance to observed differences in relative peak areas for GlycTag variants of Im7, HMW1, and Fc. In these cases, n=3 independent IVG reactions were performed for analysis of Im7 while n=3 independent *E. coli* expression cultures were completed for analysis of HMW1 and Fc.

Example 3—Modification Efficiencies

Using the methods disclosure herein, the efficiency of modification of various peptide sequences comprising 4-mers by different prokaryotic N-glycosyltransferases was tested. The results are presented in Tables 1-5 below.

TABLE 1

Modification Efficiencies for 4-mer Peptides by the N-glycosyltransferase from *Actinobacillus pleuropneumoniae*

| SEQ ID NO | SEQUENCE | MODIFICATION EFFICIENCY |
|---|---|---|
| 1 | ANVT | 0.984415739 |
| 2 | PNVT | 0.974081648 |
| 3 | SNVS | 0.970991647 |
| 4 | ANVS | 0.961116293 |
| 5 | WNVT | 0.959477963 |
| 6 | ANIT | 0.949681393 |
| 7 | SNVT | 0.948773939 |
| 8 | GNWT | 0.940868639 |
| 9 | PNVS | 0.937421199 |
| 10 | PNIT | 0.935753551 |
| 11 | HNVT | 0.92947334 |
| 12 | WNIT | 0.927501013 |
| 13 | ANHT | 0.92009282 |
| 11 | HNVS | 0.918469123 |
| 15 | NNVT | 0.912108093 |
| 16 | MNVS | 0.911819033 |
| 17 | ANAT | 0.910075484 |
| 18 | ANYT | 0.90999696 |
| 19 | TNVT | 0.909628783 |
| 20 | SNHT | 0.905957216 |
| 21 | PNYT | 0.89630672 |
| 22 | PNHT | 0.893750169 |
| 23 | PNAT | 0.89193703 |
| 24 | WNVS | 0.891025101 |
| 25 | ENVT | 0.890314969 |
| 26 | GNVT | 0.884287478 |
| 27 | PNIS | 0.882098631 |
| 28 | TNVS | 0.869468635 |
| 29 | ANIS | 0.86938912 |
| 30 | PNRT | 0.866193568 |
| 31 | ANFT | 0.863314885 |
| 32 | NNHT | 0.86237279 |
| 33 | WNAT | 0.85991535 |
| 34 | MNHT | 0.854975457 |
| 35 | PNTT | 0.853226526 |
| 36 | TNHT | 0.844442897 |
| 37 | HNHT | 0.842703071 |
| 38 | HNIT | 0.841062558 |
| 39 | PNFT | 0.840189685 |
| 40 | PNMT | 0.839913026 |

TABLE 1-continued

Modification Efficiencies for 4-mer Peptides by the N-glycosyltransferase from *Actinobacillus pleuropneumoniae*

| | | |
|---|---|---|
| 41 | SNAT | 0.838341214 |
| 42 | MNVT | 0.837446553 |
| 43 | WNHT | 0.83348684 |
| 44 | PNST | 0.827083781 |
| 45 | PNLT | 0.82541612 |
| 46 | ANRT | 0.820621518 |
| 47 | VNVT | 0.808053372 |
| 48 | MNAT | 0.790260086 |
| 49 | ANTT | 0.787236781 |
| 50 | ENAT | 0.787179032 |
| 51 | GNHT | 0.785556357 |
| 52 | ANST | 0.784629132 |
| 53 | TNAT | 0.776112522 |
| 54 | NNRT | 0.767139721 |
| 55 | NNAT | 0.766385598 |
| 56 | ENHT | 0.76559028 |
| 57 | ANMT | 0.762942447 |
| 58 | WNIS | 0.746004631 |
| 59 | SNIT | 0.745271788 |
| 60 | HNAT | 0.742714018 |
| 61 | MNIT | 0.73927687 |
| 62 | DNHT | 0.728678043 |
| 63 | ENRT | 0.727085969 |
| 64 | GNWS | 0.720023034 |
| 65 | NNVS | 0.714661402 |
| 66 | HNIS | 0.70396499 |
| 67 | PNHS | 0.698764486 |
| 68 | VNAT | 0.698207647 |
| 69 | ANYS | 0.697516068 |
| 70 | HNRT | 0.696238004 |
| 71 | ANLT | 0.695723705 |
| 72 | WNRT | 0.693312013 |
| 73 | ANHS | 0.691828284 |
| 74 | INVT | 0.689347628 |
| 75 | VNIT | 0.687272402 |
| 76 | NNHS | 0.684843747 |
| 77 | SNRT | 0.682056263 |
| 78 | MNHS | 0.681569621 |

TABLE 1-continued

Modification Efficiencies for 4-mer Peptides by the N-glycosyltransferase from *Actinobacillus pleuropneumoniae*

| | | |
|---|---|---|
| 79 | PNYS | 0.676235848 |
| 80 | HNHS | 0.674735108 |
| 81 | MNRT | 0.672379595 |
| 82 | LNVT | 0.672374083 |
| 83 | ENVS | 0.658378162 |
| 84 | TNST | 0.642444026 |
| 85 | PNMS | 0.635956603 |
| 86 | SNYT | 0.617741657 |
| 87 | GNVS | 0.611666564 |
| 88 | ENST | 0.604165847 |
| 89 | SNHS | 0.59371954 |
| 90 | MNMT | 0.554727063 |
| 91 | MNTT | 0.550210797 |
| 92 | SNTT | 0.549557128 |
| 93 | ANMS | 0.533618588 |
| 94 | LNIT | 0.528844233 |
| 95 | MNIS | 0.528587676 |
| 96 | GNYT | 0.519494028 |
| 97 | SNST | 0.515592117 |
| 98 | TNHS | 0.509141636 |
| 99 | DNVT | 0.507296409 |
| 100 | QNVT | 0.505578004 |

| BIN | FREQUENCY |
|---|---|
| 0 | 9 |
| 0.05 | 395 |
| 0.1 | 55 |
| 0.15 | 37 |
| 0.2 | 24 |
| 0.25 | 19 |
| 0.3 | 20 |
| 0.35 | 15 |
| 0.4 | 13 |
| 0.45 | 16 |
| 0.5 | 13 |
| 0.55 | 15 |
| 0.6 | 3 |
| 0.65 | 5 |
| 0.7 | 17 |

TABLE 1-continued

Modification Efficiencies for 4-mer Peptides by the N-glycosyltransferase from *Actinobacillus pleuropneumoniae*

| | |
|---|---|
| 0.75 | 9 |
| 0.8 | 10 |
| 0.85 | 12 |
| 0.9 | 15 |
| 0.95 | 15 |
| 1 | 5 |
| More | 0 |

TABLE 2

Modification Efficiencies for 4-mer Peptides by the N-glycosyltransferase from *Escherichia coli*

| SEQ ID NO | SEQUENCE | MODIFICATION EFFICIENCY |
|---|---|---|
| 101 | VNIS | 0.82796747 |
| 102 | PNMS | 0.753577002 |
| 103 | PNYS | 0.735004331 |
| 104 | LNIS | 0.731581868 |
| 105 | PNFS | 0.698269083 |
| 106 | PNIS | 0.668808087 |
| 107 | PNLS | 0.627359189 |
| 108 | PNIT | 0.60279085 |
| 109 | SNIS | 0.59009408 |
| 110 | WNGS | 0.584266436 |
| 111 | GNIS | 0.566026277 |
| 112 | ANVS | 0.564339393 |
| 113 | GNVS | 0.561344135 |
| 114 | LNVS | 0.550034231 |
| 115 | PNVS | 0.544920711 |
| 116 | INVS | 0.541576458 |
| 117 | TNIS | 0.532404343 |
| 118 | YNAT | 0.528232857 |
| 119 | LNHS | 0.528190841 |
| 120 | ANIT | 0.523701957 |
| 121 | SNVS | 0.519382814 |
| 122 | VNMS | 0.51810446 |
| 123 | PNYT | 0.517274136 |
| 124 | VNVS | 0.516905557 |
| 125 | PNGS | 0.512088764 |

TABLE 2-continued

Modification Efficiencies for 4-mer Peptides by the N-glycosyltransferase from *Escherichia coli*

| 126 | PNFT | 0.507277631 |
|---|---|---|
| 127 | MNHS | 0.492958628 |
| 128 | ANIS | 0.49169052 |
| 129 | MNIS | 0.477399865 |
| 130 | WNGT | 0.475704948 |
| 131 | PNMT | 0.452623408 |
| 132 | ANMS | 0.446947415 |
| 133 | PNVT | 0.441515986 |
| 134 | PNHS | 0.43719687 |
| 135 | MNVS | 0.434864046 |
| 136 | NNIS | 0.408557928 |
| 137 | INIT | 0.40016673 |
| 138 | VNIT | 0.398343399 |
| 139 | FNGS | 0.383438044 |
| 140 | VNYS | 0.381618237 |
| 141 | TNVS | 0.380089456 |
| 142 | GNIT | 0.375939233 |
| 143 | VNMT | 0.371775726 |
| 144 | INHS | 0.359828438 |
| 145 | LNIT | 0.358718641 |
| 146 | ANVT | 0.351004095 |
| 147 | ANFS | 0.346182732 |
| 148 | VNLS | 0.341726397 |
| 149 | LNFS | 0.339966784 |
| 150 | PNWS | 0.334806728 |
| 151 | ANGS | 0.332428339 |
| 152 | VNFS | 0.325367326 |
| 153 | ANYS | 0.321482329 |
| 154 | PNLT | 0.317538849 |
| 155 | LNVT | 0.307874944 |
| 156 | VNVT | 0.300283512 |
| 157 | YNGS | 0.291752903 |
| 158 | ANLS | 0.279786094 |
| 159 | INIS | 0.270744696 |
| 160 | GNVT | 0.269651995 |
| 161 | FNHS | 0.266061219 |
| 162 | PNRS | 0.265194227 |
| 163 | TNIT | 0.25866238 |

TABLE 2-continued

Modification Efficiencies for 4-mer Peptides by the N-glycosyltransferase from *Escherichia coli*

| | | |
|---|---|---|
| 164 | SNMS | 0.253083662 |
| 165 | GNLS | 0.251946642 |
| 166 | NNIT | 0.250115306 |
| 167 | SNIT | 0.234106222 |
| 168 | TNMS | 0.221310026 |
| 169 | ANHS | 0.217808703 |
| 170 | PNRT | 0.216307802 |
| 171 | MNIT | 0.215031456 |
| 172 | SNVT | 0.213276944 |
| 173 | LNMS | 0.21284054 |
| 174 | PNHT | 0.211595482 |
| 175 | INVT | 0.208814402 |
| 176 | VNHS | 0.207103204 |
| 177 | NNVS | 0.205011148 |
| 178 | LNYS | 0.203604231 |
| 179 | VNLT | 0.199226218 |
| 180 | LNHT | 0.199037207 |
| 181 | ANMT | 0.195434618 |
| 182 | GNHS | 0.194483535 |
| 183 | FNGT | 0.193875356 |
| 184 | PNGT | 0.1929585 |
| 185 | SNYS | 0.189229065 |
| 186 | LNAT | 0.187349711 |
| 187 | PNAT | 0.183334397 |
| 188 | PNAS | 0.179737178 |
| 189 | SNGS | 0.17860807 |
| 190 | YNGT | 0.176243637 |
| 191 | MNHT | 0.165755541 |
| 192 | GNMS | 0.165211568 |
| 193 | VNAT | 0.164566376 |
| 194 | VNFT | 0.164431729 |
| 195 | FNHT | 0.159144461 |
| 196 | ANRS | 0.158149197 |
| 197 | LNYT | 0.15697147 |
| 198 | TNVT | 0.156446198 |
| 199 | GNYS | 0.155766768 |
| 200 | GNFS | 0.152854107 |

TABLE 2-continued

Modification Efficiencies for 4-mer Peptides by the N-glycosyltransferase from *Escherichia coli*

| BIN | FREQUENCY |
|---|---|
| 0 | 29 |
| 0.05 | 518 |
| 0.1 | 45 |
| 0.15 | 27 |
| 0.2 | 25 |
| 0.25 | 12 |
| 0.3 | 10 |
| 0.35 | 10 |
| 0.4 | 9 |
| 0.45 | 6 |
| 0.5 | 5 |
| 0.55 | 12 |
| 0.6 | 6 |
| 0.65 | 2 |
| 0.7 | 2 |
| 0.75 | 2 |
| 0.8 | 1 |
| 0.85 | 1 |
| 0.9 | 0 |
| 0.95 | 0 |
| 1 | 0 |
| More | 0 |

TABLE 3

Modification Efficiencies for 4-mer Peptides by the N-glycosyltransferase from *Haemophilus dureyi*

| SEQ ID NO | SEQUENCE | MODIFICATION EFFICIENCY |
|---|---|---|
| 201 | ANVT | 0.900743 |
| 202 | PNVT | 0.888506 |
| 203 | ANIT | 0.82341 |
| 204 | PNIT | 0.819559 |
| 205 | SNVT | 0.7806 |
| 206 | PNAT | 0.750574 |
| 207 | ANAT | 0.735488 |
| 208 | PNTT | 0.662328 |
| 209 | PNMT | 0.658102 |

TABLE 3-continued

Modification Efficiencies for 4-mer Peptides by the N-glycosyltransferase from *Haemophilus dureyi*

| | | |
|---|---|---|
| 210 | ANHT | 0.623851 |
| 211 | GNWT | 0.623028 |
| 212 | PNST | 0.622506 |
| 213 | NNVT | 0.612493 |
| 214 | ANST | 0.606666 |
| 215 | PNYT | 0.605621 |
| 216 | NNAT | 0.601921 |
| 217 | ANTT | 0.580212 |
| 218 | SNHT | 0.573231 |
| 219 | ANYT | 0.56827 |
| 220 | ANVS | 0.566734 |
| 221 | ANMT | 0.558359 |
| 222 | TNVT | 0.537524 |
| 223 | PNLT | 0.533925 |
| 224 | PNHT | 0.524854 |
| 225 | PNFT | 0.514359 |
| 226 | TNHT | 0.491842 |
| 227 | SNAT | 0.485772 |
| 228 | PNRT | 0.472573 |
| 229 | ANFT | 0.466985 |
| 230 | PNVS | 0.45746 |
| 231 | PNIS | 0.426112 |
| 232 | ANLT | 0.425127 |
| 233 | NNHT | 0.413605 |
| 234 | SNIT | 0.409056 |
| 235 | ANRT | 0.407949 |
| 236 | WNHT | 0.398551 |
| 237 | HNVT | 0.380896 |
| 238 | GNVT | 0.380446 |
| 239 | WNAT | 0.366419 |
| 240 | HNHT | 0.348211 |
| 241 | SNVS | 0.334165 |
| 242 | WNVT | 0.323861 |
| 243 | VNVT | 0.315139 |
| 244 | VNAT | 0.304739 |
| 245 | TNAT | 0.304363 |
| 246 | TNST | 0.2587 |
| 247 | ANHS | 0.254992 |
| 248 | VNIT | 0.242711 |
| 249 | ANIS | 0.241908 |
| 250 | GNHT | 0.232812 |
| 251 | NNRT | 0.231829 |
| 252 | NNTT | 0.229518 |
| 253 | SNTT | 0.22013 |
| 254 | MNVT | 0.214801 |
| 255 | SNST | 0.214257 |
| 256 | VNMT | 0.204642 |
| 257 | TNIT | 0.19798 |
| 258 | NNST | 0.187755 |
| 259 | MNIT | 0.17966 |
| 260 | WNRT | 0.179016 |
| 261 | SNRT | 0.178091 |
| 262 | GNIT | 0.17171 |
| 263 | MNHT | 0.168865 |
| 264 | HNAT | 0.162251 |
| 265 | SNMT | 0.157808 |
| 266 | PNHS | 0.156218 |
| 267 | SNYT | 0.152193 |
| 268 | ANGT | 0.138123 |
| 269 | ENST | 0.137658 |
| 270 | TNNT | 0.136027 |
| 271 | PNMS | 0.132182 |
| 272 | TNTT | 0.13073 |
| 273 | PNGT | 0.130558 |
| 274 | VNST | 0.123327 |
| 275 | LNVT | 0.119945 |
| 276 | GNAT | 0.119761 |
| 277 | PNYS | 0.118633 |
| 278 | PNKT | 0.118554 |
| 279 | ENVT | 0.113663 |
| 280 | VNHT | 0.109097 |
| 281 | NNHS | 0.107909 |
| 282 | ENAT | 0.105764 |
| 283 | SNGT | 0.105569 |
| 284 | SNHS | 0.104335 |
| 285 | NNYT | 0.103967 |

TABLE 3-continued

Modification Efficiencies for 4-mer Peptides by the N-glycosyltransferase from *Haemophilus dureyi*

| | | |
|---|---|---|
| 286 | MNAT | 0.103538 |
| 287 | PNTS | 0.09756 |
| 288 | ANAS | 0.095155 |
| 289 | GNYT | 0.093017 |
| 290 | LNAT | 0.092369 |
| 291 | NNVS | 0.088442 |
| 292 | ANQT | 0.088372 |
| 293 | TNVS | 0.087944 |
| 294 | PNAS | 0.086776 |
| 295 | GNVS | 0.086098 |
| 296 | PNQT | 0.086057 |
| 297 | ANKT | 0.0857 |
| 298 | SNLT | 0.085519 |
| 299 | TNMT | 0.084772 |
| 300 | TNHS | 0.082042 |

| BIN | FREQUENCY |
|---|---|
| 0 | 61 |
| 0.05 | 529 |
| 0.1 | 46 |
| 0.15 | 19 |
| 0.2 | 11 |
| 0.25 | 9 |
| 0.3 | 2 |
| 0.35 | 6 |
| 0.4 | 4 |
| 0.45 | 5 |
| 0.5 | 5 |
| 0.55 | 4 |
| 0.6 | 5 |
| 0.65 | 7 |
| 0.7 | 2 |
| 0.75 | 1 |
| 0.8 | 2 |
| 0.85 | 2 |
| 0.9 | 1 |
| 0.95 | 1 |
| 1 | 0 |
| More | 0 |

TABLE 4

Modification Efficiencies for 4-mer Peptides by the N-glycosyltransferase from *Mannheimia haemolytica*

| SEQ ID NO | SEQUENCE | MODIFICATION EFFICIENCY |
|---|---|---|
| 301 | ANYT | 0.96465 |
| 302 | ANVT | 0.958746 |
| 303 | SNVT | 0.930745 |
| 304 | PNVT | 0.920004 |
| 305 | WNVT | 0.908308 |
| 306 | GNWT | 0.882545 |
| 307 | PNMT | 0.87976 |
| 308 | ANIT | 0.878841 |
| 309 | WNAT | 0.878522 |
| 310 | NNVT | 0.873659 |
| 311 | ANAT | 0.873087 |
| 312 | PNIT | 0.868744 |
| 313 | ANFT | 0.866228 |
| 314 | PNAT | 0.86522 |
| 315 | PNYT | 0.8592 |
| 316 | PNFT | 0.858603 |
| 317 | ANRT | 0.853493 |
| 318 | SNAT | 0.850271 |
| 319 | HNVT | 0.844279 |
| 320 | GNVT | 0.843273 |
| 321 | PNST | 0.839726 |
| 322 | PNRT | 0.838078 |
| 323 | TNVT | 0.835131 |
| 324 | SNHT | 0.83346 |
| 325 | PNTT | 0.830543 |
| 326 | ANST | 0.824501 |
| 327 | PNLT | 0.823914 |
| 328 | ANMT | 0.821819 |
| 329 | NNAT | 0.817938 |
| 330 | ANTT | 0.811151 |
| 331 | WNHT | 0.810613 |
| 332 | NNRT | 0.810094 |
| 333 | WNRT | 0.80212 |
| 334 | ANHT | 0.787241 |
| 335 | MNIT | 0.764916 |
| 336 | MNHT | 0.756672 |
| 337 | SNVS | 0.753741 |

TABLE 4-continued

Modification Efficiencies for 4-mer Peptides by the N-glycosyltransferase from *Mannheimia haemolytica*

| | | |
|---|---|---|
| 338 | SNIT | 0.753394 |
| 339 | HNHT | 0.74824 |
| 340 | GNHT | 0.743891 |
| 341 | TNHT | 0.739773 |
| 342 | WNIT | 0.738131 |
| 343 | TNAT | 0.733502 |
| 344 | MNVT | 0.73061 |
| 345 | ANLT | 0.724314 |
| 346 | SNRT | 0.722217 |
| 347 | NNHT | 0.719883 |
| 348 | VNVT | 0.710196 |
| 349 | MNAT | 0.706852 |
| 350 | PNHT | 0.69745 |
| 351 | HNAT | 0.688339 |
| 352 | SNYT | 0.687115 |
| 353 | VNAT | 0.672586 |
| 354 | ANVS | 0.672556 |
| 355 | ENVT | 0.663018 |
| 356 | SNTT | 0.661821 |
| 357 | NNST | 0.660101 |
| 358 | SNST | 0.648362 |
| 359 | VNMT | 0.644028 |
| 360 | NNTT | 0.641425 |
| 361 | TNST | 0.624424 |
| 362 | PNVS | 0.624348 |
| 363 | HNRT | 0.612555 |
| 364 | WNST | 0.610847 |
| 365 | ENST | 0.59463 |
| 366 | ENRT | 0.584351 |
| 367 | SNMT | 0.581497 |
| 368 | HNIT | 0.57906 |
| 369 | GNYT | 0.574794 |
| 370 | WNMT | 0.560978 |
| 371 | WNTT | 0.558826 |
| 372 | INVT | 0.554687 |
| 373 | ENAT | 0.554528 |
| 374 | ANQT | 0.550673 |
| 375 | GNAT | 0.549155 |
| 376 | MNLT | 0.549058 |
| 377 | TNVS | 0.546237 |
| 378 | PNQT | 0.545224 |
| 379 | MNRT | 0.545093 |
| 380 | NNYT | 0.540375 |
| 381 | SNFT | 0.53759 |
| 382 | LNVT | 0.53582 |
| 383 | PNIS | 0.530673 |
| 384 | QNVT | 0.523167 |
| 385 | VNST | 0.522874 |
| 386 | VNIT | 0.521194 |
| 387 | GNIT | 0.511218 |
| 388 | ANIS | 0.507664 |
| 389 | HNTT | 0.495843 |
| 390 | YNVT | 0.490232 |
| 391 | FNVT | 0.486868 |
| 392 | VNRT | 0.47939 |
| 393 | WNYT | 0.476276 |
| 394 | ANWT | 0.474853 |
| 395 | LNAT | 0.472108 |
| 396 | ENHT | 0.469099 |
| 397 | ANGT | 0.463129 |
| 398 | MNST | 0.461919 |
| 399 | TNIT | 0.461009 |
| 400 | LNRT | 0.457687 |

| BIN | FREQUENCY |
|---|---|
| 0 | 11 |
| 0.05 | 431 |
| 0.1 | 49 |
| 0.15 | 22 |
| 0.2 | 27 |
| 0.25 | 21 |
| 0.3 | 15 |
| 0.35 | 13 |
| 0.4 | 15 |
| 0.45 | 17 |
| 0.5 | 13 |
| 0.55 | 14 |

TABLE 4-continued

Modification Efficiencies for 4-mer Peptides by the N-glycosyltransferase from *Mannheimia haemolytica*

| | |
|---|---|
| 0.6 | 10 |
| 0.65 | 7 |
| 0.7 | 8 |
| 0.75 | 11 |
| 0.8 | 5 |
| 0.85 | 15 |
| 0.9 | 13 |
| 0.95 | 3 |
| 1 | 2 |
| More | 0 |

TABLE 5

Modification Efficiencies for 4-mer Peptides by the N-glycosyltransferase from *Haemophilus influenza*

| SEQ ID NO | SEQUENCE | MODIFICATION EFFICIENCY |
|---|---|---|
| 401 | PNIT | 0.872492503 |
| 402 | ANAT | 0.857052653 |
| 403 | PNVT | 0.795394559 |
| 404 | PNMT | 0.718961169 |
| 405 | PNAT | 0.603312989 |
| 406 | PNLT | 0.590978057 |
| 407 | ANVT | 0.58963897 |
| 408 | ANMT | 0.588036414 |
| 409 | ANIT | 0.570257163 |
| 410 | HNVT | 0.554514307 |
| 411 | PNFT | 0.464502861 |
| 412 | ANFT | 0.461944104 |
| 413 | PNVS | 0.442701706 |
| 414 | PNYT | 0.433228465 |
| 415 | MNIT | 0.432644327 |
| 416 | PNRT | 0.421151455 |
| 417 | ANRT | 0.41573846 |
| 418 | PNIS | 0.392207849 |
| 419 | SNVT | 0.38329666 |
| 420 | NNAT | 0.381109213 |
| 421 | ANVS | 0.3782757 |
| 422 | VNMT | 0.373309945 |

TABLE 5-continued

Modification Efficiencies for 4-mer Peptides by the N-glycosyltransferase from *Haemophilus influenza*

| 423 | INVT | 0.373104823 |
|---|---|---|
| 424 | ANHT | 0.355689212 |
| 425 | NNVT | 0.336341478 |
| 426 | PNHT | 0.329569969 |
| 427 | HNHT | 0.321026995 |
| 428 | WNVT | 0.311422801 |
| 429 | ANLT | 0.295331218 |
| 430 | PNTT | 0.279773705 |
| 431 | MNVT | 0.257204301 |
| 432 | ANYT | 0.251127086 |
| 433 | MNLT | 0.247786488 |
| 434 | VNIT | 0.24240979 |
| 435 | PNST | 0.226010829 |
| 436 | WNAT | 0.221585505 |
| 437 | FNAT | 0.221034299 |
| 438 | ANIS | 0.20792148 |
| 439 | TNVT | 0.190595546 |
| 440 | INMT | 0.179126526 |
| 441 | HNVS | 0.177090897 |
| 442 | HNRT | 0.167363107 |
| 443 | PNLS | 0.165777071 |
| 444 | PNMS | 0.1617613 |
| 445 | VNVT | 0.160963364 |
| 446 | ANST | 0.159600972 |
| 447 | HNAT | 0.157573446 |
| 448 | ANTT | 0.141177856 |
| 449 | WNHT | 0.14031522 |
| 450 | NNHT | 0.140082578 |
| 451 | PNYS | 0.136122223 |
| 452 | HNIT | 0.134601969 |
| 453 | SNHT | 0.134282522 |
| 454 | TNHT | 0.127849126 |
| 455 | GNWT | 0.126267091 |
| 456 | SNVS | 0.126264092 |
| 457 | FNVT | 0.121700545 |
| 458 | SNAT | 0.121390895 |
| 459 | VNAT | 0.117290489 |
| 460 | PNKT | 0.110401803 |

TABLE 5-continued

Modification Efficiencies for 4-mer Peptides by the N-glycosyltransferase from *Haemophilus influenza*

| | | |
|---|---|---|
| 461 | NNRT | 0.106761729 |
| 462 | WNMT | 0.102229077 |
| 463 | VNRT | 0.095070318 |
| 464 | LNLT | 0.095068093 |
| 465 | PNHS | 0.094654507 |
| 466 | LNMT | 0.089964838 |
| 467 | HNMT | 0.089441554 |
| 468 | ANHS | 0.089162334 |
| 469 | INIT | 0.082852649 |
| 470 | HNTT | 0.080023423 |
| 471 | SNIT | 0.079360519 |
| 472 | YNRT | 0.079177876 |
| 473 | INTVS | 0.077276724 |
| 474 | YNVT | 0.076140663 |
| 475 | SNYT | 0.074808805 |
| 476 | LNRT | 0.071432067 |
| 477 | NNMT | 0.071361253 |
| 478 | LNVT | 0.069067056 |
| 479 | HNHS | 0.068650466 |
| 480 | ANKT | 0.066420398 |
| 481 | ANYS | 0.065983037 |
| 482 | VNLT | 0.065024642 |
| 483 | TNAT | 0.064442386 |
| 484 | LNIT | 0.062291989 |
| 485 | PNQT | 0.06199128 |
| 486 | LNAT | 0.060627653 |
| 487 | ANLS | 0.060442633 |
| 488 | FNHT | 0.060271 |
| 489 | NNVS | 0.060003436 |
| 490 | PNFS | 0.059684221 |
| 491 | GNVT | 0.058773849 |
| 492 | ANQT | 0.057167365 |
| 493 | RNHT | 0.054084953 |
| 494 | PNTS | 0.052231141 |
| 495 | WNVS | 0.051913903 |
| 496 | ANAS | 0.051662869 |
| 497 | MNAT | 0.050851556 |
| 498 | HNYT | 0.04898975 |
| 499 | SNLT | 0.048372175 |
| 500 | TNIT | 0.048052479 |

| BIN | FREQUENCY |
|---|---|
| 0 | 99 |
| 0.05 | 526 |
| 0.1 | 35 |
| 0.15 | 15 |
| 0.2 | 9 |
| 0.25 | 6 |
| 0.3 | 4 |
| 0.35 | 4 |
| 0.4 | 7 |
| 0.45 | 5 |
| 0.5 | 2 |
| 0.55 | 0 |
| 0.6 | 5 |
| 0.65 | 1 |
| 0.7 | 0 |
| 0.75 | 1 |
| 0.8 | 1 |
| 0.85 | 0 |
| 0.9 | 2 |
| 0.95 | 0 |
| 1 | 0 |
| More | 0 |

Example 4—Site-Specific Control of Multiple Glycosylation Sites Using Unique Enzyme Specificities Introduction Glycosylation, the attachment of sugar moieties to amino acid side-chains, is one of the most common post-translational modifications found in nature[1] and is known to endow proteins with new functions and profoundly affect stability, potency, and half-life of protein therapeutics[3,4,6]. However, glycoproteins derived from living cells are usually a complex mixture of glycosylation structures at varying levels at multiple glycosylation sites[3]. This complexity is one of the core challenges to the systematic understanding of the activity and properties of specific glycoforms (bearing specific glycosylation structures at specific points within proteins) and therefore the development and optimization of glycoproteins for biotechnological applications[3]. While significant advances have been made in glycoengineering bacterial[8], yeast[12], and mammalian[11] cells for more homogeneous glycoprotein expression, a generalizable technique for obtaining user-defined glycoforms from cells remains elusive[60].

New developments in chemical and chemoenzymatic methods for in vitro construction of homogeneous glycoproteins have enabled the synthesis and study of diverse glycoproteins with rigorously defined glycan structures[60]. For example, total chemical synthesis has been used to produce human EPO and test the function of each glycan by assembling constituent peptides and glycopeptides[61,62]. However, total chemical synthesis is very costly, requires specialized expertise, and is difficult for large proteins[60]. Recently, great strides have been made in the use of chemoenzymatic methods to remodel or install homogeneous glycans at monosaccharide modified proteins[60]. The Wang group has developed a suite of endoglycosidases to remodel glycans and used them to carefully study the function of human antibodies with defined glycosylation structures[60], these enzymes have been used to find that the S2G2 or G2 modification provides the most efficient antibody dependent cell-killing[6,63]. The Davis group and others have combined this method with the incorporation of non-standard amino acids and modification of cysteine residues to install glycans using site-directed mutagenesis[64-67].

However, because only one unique non-standard amino acid can be reliably incorporated into a protein and current chemoenzymatic methods cannot distinguish between modification sites which are chemically nearly identical[60], they are limited to the synthesis of proteins with the same, at most two, glycosylation structures at all sites[60,68]. In contrast, glycoproteins often contain multiple glycosylation sites with distinct glycosylation structures at each position which can interact synergistically to effect protein function[61,69-71]. New methods are needed to site-specifically control glycosylation so that glycoproteins with defined combinations of glycans and the interactions between them can be studied and optimized to engineer precise or multifunctional glycoprotein therapeutics and vaccines[60]. A set of glycosyltransferases which could distinguish between multiple glycosylation sites and make the first monosaccharide modification would permit the controlled construction of each glycosylation site afterwards by well-established chemoenzymatic methods in a sequential fashion. However, due to insufficient characterization of glycosyltransferase peptide substrate preferences, such a system has not been realized.

Here we report a strategy to site-specifically control the glycosylation of up to four sites within a single target, which we developed by discovering and rigorously characterizing the unique peptide acceptor specificities of N-linked glycosyltransferase (NGT) enzymes (FIG. 23). Because existing characterization of N-linked glycosyltransferases are insufficient to enable the selection of specifically interacting sequence-enzyme pairs within the canonical N-linked glycosylation sequences N-X-S/T-X (where X is not P), we employed our recently developed method called "GlycoSCORES" to rapidly test the activity of 41 putative N-linked GTs and rigorously characterize the activities of three NGTs, combining with a ApNGT mutants, exhibiting strong activity and differences in peptide specificity. We then optimized 6-mer peptide sequences (called GlycTags) which are differentially modified by these four enzymes. We show that when these GlycTags are placed into a single target protein, glycosylation can be site-specifically controlled at up to four sites by the sequential addition of specific NGTs. When combined with existing technologies for chemoenzymatic elaboration of single monosaccharide to homogeneous glycans, our method for site-specific control of glycosylation could significantly advance our understanding of how multiple glycans interact within a single protein and our ability to engineer glycoproteins for specific purposes.

Results

Phylogenetic screening for NGT activity. In order to find NGTs that may possess different peptide preferences and could enable specific targeting of multiple glycosylation sites within a single protein, we sought out previously uncharacterized NGT homologs. We performed a phylogenetic analysis of the CAZY database family 41[14], which is known to contain N-linked polypeptide glucosyltransferases (NGTs) and O-linked N-Acetylglucosaminyltransferases (OGTs). From this phylogenetic analysis, we selected 41 putative N-linked glycosyltransferases from bacteria. In selecting enzymes for our screen, we sought to balance sequence diversity with likelihood of possessing NGT activity by selecting enzymes that are both closely and distantly related to previously characterized NGTs, such as ApNGT.

Site-specific control of glycosylation by rapid enzyme characterization and sequential addition of enzymes. Four NGT homologs were selected from the phylogenetic screen of putative NGT enzymes and characterized using GlycoSCORES to find differences in peptide specificity. (See FIG. 23). Peptide sequences showing conditional orthogonality which would enable site-specific glycosylation when applied in the correct order, were discovered by further GlycoSCORES optimization. Optimized GlycTags were incorporated into a single glycoprotein and NGTs were added sequentially to site-specifically control glycosylation at up to four glycosylation sites within one protein. Sugars, modification sites, and NGTs have been color coded for illustration purposes.

GlycoSCORES screening of NGT homologs for unique peptide activities. Six representative N-linked glycosylation peptide substrates were screened with 41 putative GTs from CAZY database (GT family 41). (See FIG. 24). The phylogenetic tree uses human OGT as the outgroup due to its sequence divergence and eukaryotic origin. Six enzymes were found to have NGT activity, with strong activity (*Actinobacillus pleuropneumoniae* NGT (ApNGT), *Escherichia coli* NGT (EcNGT), *Haemophilus influenza* NGT (HiNGT), *Mannheimia haemolytica* NGT (MhNGT), and *Haemophilus dureyi* NGT (HdNGT)). GlycoSCORES screening was performing similarly as disclosed in Examples 1 and 2. NGTs were produced in CFPS and mixed with UDP-glucose sugar donor and cysteine-containing peptide substrates which were immobilized to a maleimide self-assembled monolayer and characterized by SAMDI-MS. Some NGTs were found to have differences in peptide selectivity (MS spectra). In particular, the specificity of HiNGT, EcNGT, ApNGT and ApNGT$^{Q469A}$ for a peptide substrate library of the form $X_{-1}NX_{+1}TRC$ was analyzed. These four NGTs showed differences in peptide selectivity from each other, but not from MhNGT or HdNGT (data not shown). Experimental conditions: 0.42 µM CFPS HiNGT or 0.75 µM CFPS EcNGT, 30° C. for 21 h; 0.055 µM CFPS ApNGT or 0.014 µM CFPS ApNGT$^{Q469A}$ 30° C. for 1 h. Expression of HiNGT, EcNGT, ApNGT and ApNGT$^{Q469A}$ by CFPS was verified (data not shown).

Optimization of Differentially Modified Sequences to Obtain Conditionally Orthogonal GlycTags A peptide library was generated in order to identify optimally conditional orthogonal GlycTag sequences for HiNGT, EcNGT, ApNGT and ApNGT$^{Q469A}$. The generated library generally had the sequence $X_{-1}NX_{+1}(T/S)RC$ where $X_{-1}$ and $X_{+1}$ independently were any amino acid. The C-terminal cysteine of the peptide library was used to immobilize the peptides on a SAMDI plate for GlycoSCORE analysis and screening as described in Examples 1 and 2. The analysis and screening revealed that each of HiNGT, EcNGT, ApNGT and ApNGT$^{Q469A}$ exhibited differential sequence preferences in regard to N-glycosylation (e.g., FNQT (SEQ ID NO:520), YNLT (SEQ ID NO:521), YNRT (SEQ ID NO:472), INWT (SEQ ID NO:522), WNWT (SEQ ID NO:523), INQT (SEQ ID NO:524) only for ApNGT$^{Q469A}$; ENVT (SEQ ID NOs:25,279,355) for ApNGT but not for EcNGT or HiNGT; WNGS (SEQ ID NO:110), LNHS (SEQ ID NO:119), and GNIS (SEQ ID NO:111) for EcNGT but not for HiNGT; and PNLT (SEQ ID NOs:45,154,223,327,406), ANVT (SEQ ID NOs:1,146,201, 302,407), PNIT (SEQ ID NOs:10,108,204,312,401) and PNVT (SEQ ID NOs:2, 133,202,304,403) for HiNGT).

Selected sequences with differential modification patterns were resynthesized and screened with 19 amino acids in the $X_{-2}$ position in an X-member $X_{-2}(X_{-1}NX_{+1}T/S)RC$ library using all four enzymes. Several sequences that exhibited differential modification patterns between the four enzymes were identified (e.g., AFNQT (SEQ ID NO:525), SYNLT (SEQ ID NO:526), AYNLT (SEQ ID NO:527), DFNQT (SEQ ID NO:528), SFNQT (SEQ ID NO:529), and DYNLT (SEQ ID NO:530) only for ApNGT$^{Q469A}$; NENVT (SEQ ID NO:531) for ApNGT but not for EcNGT or HiNGT; FGNWS (SEQ ID NO:531), WGNWS (SEQ ID NO:532), FGNIS (SEQ ID NO:533), YGNWS (SEQ ID NO:534), TGNIS (SEQ ID NO:535), LGNIS (SEQ ID NO:536), AGNIS (SEQ ID NO:537), VGNIS (SEQ ID NO:538), MGNIS (SEQ ID NO:539), and IGNIS (SEQ ID NO:540) for EcNGT but not for HiNGT; and YGNWT (SEQ ID NO:541), WPNLT (SEQ ID NO:542), WGNWT (SEQ ID NO:543), WPNIT (SEQ ID NO:544), and WPNVT (SEQ ID NO:545) for HiNGT).

Selected peptide sequences again were resynthesized and screened with 19 amino acids in the $X_{-3}$ positions in an X-member $X_{-3}(X_{-2}(X_{-1}NX_{+1}T/S)RC$ library using all four NGTs. Several sequences that exhibited differential modification patterns between the four enzymes were identified (e.g., WDYNLT (SEQ ID NO:546) only for ApNGT$^{Q469A}$; LNENVT (SEQ ID NO:547) for ApNGT but not for EcNGT or HiNGT; YMGNIS (SEQ ID NO:548) for EcNGT but not for HiNGT; and WYANVT (SEQ ID NO:549) for HiNGT).

Optimized GlycTag sequences show conditional orthogonality at peptide level and enable differential targeting of glycosylation sites within protein. Conditional orthogonality of optimized 6-mer GlycTags. Selected GlycTags were screened for HiNGT, EcNGT, ApNGT and ApNGT$^{Q469A}$ modification by SAMDI in triplicate experiments. (See FIG. 25a). Optimized 6-mer GlycTags were inserted into the N-terminus, C-terminus, and two exposed loops of the glycosylation model protein Im7, with flanking sequences of RATT (SEQ ID NO:516)-GlycTag-AGGR (SEQ ID NO:517) to facilitate trypsinization and quantitative LC-MS analysis. (See FIG. 25b). Differential targeting of four optimized GlycTags within a single Im7 target protein. Im7 bearing the four optimized GlycTags was reacted with 2.5 mM UDP-Glucose and various concentrations of each purified NGT for 4 hrs. After the modification, Im7 was purified using Ni-NTA functionalized magnetic beads, treated with trypsin and analyzed by LC-qTOF. (See FIG. 25c). Conditional orthogonality of each NGT for 6-mer GlycTags within Im7 under optimized conditions was observed. (See FIG. 25d).

Site-specific control of glycosylation at four distinct GlycTag sequences within one target protein. Site-specific control of glycosylation at the four distinct GlycTag sequences within one target protein was tested and observed. (See FIGS. 26a and 26b).

Discussion

Here, we report the discovery of unique N-glucosyltransferases (NGTs) and specificities for corresponding peptide targets (GlycTag) and optimization of conditionally orthogonal NGT-GlycTag pairs. Importantly, we demonstrate that conditional orthogonality behavior observed at the peptide level was also achieved at the protein level. We also demonstrate a system and workflow for site-specific control using four different NGTs and four different GlycTags when the different GlycTags were fused into a protein at four locations. Now that we have overcome the critical challenge of site-specificity, our sequential glycosylation technique can be combined with well-established chemo-enzymatic methods to install multiple, distinct N-linked glycans onto a single protein using endoglycosidases or other glycosyltranferases during each modification step. Future work will be directed to rigorously characterizing ApNGT mutants to expand the available repertoire of enzymes and develop more highly orthogonal NGT and GlycTag pairs.

Now that we have overcome the challenge of site-specificity, our sequential glycosylation technique can be combined with well-established chemo-enzymatic methods[60] to install multiple, distinct N-linked glycans onto a single protein using endoglycosidases or other glycosyltranferases during each modification step. With the depth of characterization data found in this work and our continuing efforts to rigorously understand NGT specificities, we can modify any therapeutic target protein with multiple glycans with minimal change of the amino acid sequence by strategically using known enzymes with specific activities. Towards this goal, we are currently working to rigorously characterize ApNGT mutants to expand the available repertoire of enzymes and develop more highly orthogonal NGT and GlycTag pairs. We note that at present the NGTs used in this work install a reducing end Glc rather than a GlcNAc. If a reducing end GlcNAc is required, previous work has shown that GlcN can be installed by ApNGT$^{Q469A}$ and AaNGT and then further converted to GlcNAc by an acetyltranferase[13]. We are also working to engineer ApNGT$^{Q469A}$ to directly install GlcNAc.

Conclusion

We have described the first systematic and generalizable method to site-specifically control glycosylation at multiple sites within the same protein, and that the development of enzymatic tools that can distinguish between chemically identical glycosylation sites described and demonstrated here overcomes the major limitation in achieving multiple, distinct, site-specifically defined glycoforms for basic science and biotechnological applications.

Methods

Phylogenetic analysis was performed using RaxmL, MUSCLE, and iTol. Peptide synthesis and SAMDI was performed similarly as Examples 1 and 2 and as described in the art[72]. Cell free protein synthesis was performed similarly as Examples 1 and 2 and as described in the art[72]. Peptide synthesis was performed using Wang-resin and purification was performed by HPLC. NGT purification was performed using a strept tag. The Im7 target was purified using a His tag. Modified protein and Glycoprotein with Glc, prepare for samples for LC-qTOF.

Special consideration for sequential modification of Im7 with NGTs including the following: To facilitate sequential purification steps, the Im7 sequence bearing four optimized GlycTags was fused to the C-terminus of an N-terminally polyhistidine-tagged SUMO protein. After reaction with HiNGT, the His-SUMO-Im7 protein was immobilized to magnetic beads then sequentially reacted with each subsequent NGT with wash steps in between NGT treatments. Finally, the Im7 was eluted and released from the SUMO fusion protein by cleavage with Ulp1 protease.

REFERENCES

1. Khoury, G. A., Baliban, R. C. & Floudas, C. A. Proteome-wide post-translational modification statistics: frequency analysis and curation of the swiss-prot database. Sci. Rep. 1, 90 (2011).
2. Helenius, A. & Aebi, M. Intracellular functions of N-linked glycans. Science 291, 2364-2369 (2001).
3. Sethuraman, N. & Stadheim, T. A. Challenges in therapeutic glycoprotein production. Curr. Opin. Biotechnol. 17, 341-346 (2006).
4. Elliott, S. et al. Enhancement of therapeutic protein in vivo activities through glycoengineering. Nat. Biotechnol. 21, 414-421 (2003).
5. Chung, C. H. et al. Cetuximab-Induced Anaphylaxis and IgE Specific for Galactose-a-1,3-Galactose. New Engl. J. Med. 358, 1109-1117 (2008).
6. Lin, C.-W. et al. A common glycan structure on immunoglobulin G for enhancement of effector functions. Proc. Natl. Acad. Sci. U.S.A. 112, 10611-10616 (2015).
7. Clausen, H., Wandall, H. H., Steentoft, C., Stanley, P. & Schnaar, R. L. in Essentials of Glycobiology. (eds. A. Varki et al.) 713-728 (Cold Spring Harbor Laboratory Press, Cold Spring Harbor (NY); 2015).
8. Valderrama-Rincon, J. D. et al. An engineered eukaryotic protein glycosylation pathway in *Escherichia coli*. Nat. Chem. Biol. 8, 434-436 (2012).
9. Keys, T. G. & Aebi, M. Engineering protein glycosylation in prokaryotes. Curr. Opin. Syst. Biol. 5, 23-31 (2017).
10. Wang, L.-X. & Davis, B. G. Realizing the promise of chemical glycobiology. Chem. Sci. 4, 3381-3394 (2013).
11. Yang, Z. et al. Engineered CHO cells for production of diverse, homogeneous glycoproteins. Nat. Biotechnol. 33, 842-844 (2015).
12. Li, H. et al. Optimization of humanized IgGs in glycoengineered *Pichia pastoris*. Nat. Biotechnol. 24, 210-215 (2006).
13. Xu, Y. et al. A novel enzymatic method for synthesis of glycopeptides carrying natural eukaryotic N-glycans. Chem. Commun. 53, 9075-9077 (2017).
14. Lombard, V., Golaconda Ramulu, H., Drula, E., Coutinho, P. M. & Henrissat, B. The carbohydrate-active enzymes database (CAZy) in 2013. Nucleic Acids Res. 42, D490-495 (2014).
15. Ban, L. et al. Discovery of glycosyltransferases using carbohydrate arrays and mass spectrometry. Nat. Chem. Biol. 8, 769-773 (2012).
16. Pathak, S. et al. The active site of O-GlcNAc transferase imposes constraints on substrate sequence. Nat. Struct. Mol. Biol. 22, 744-750 (2015).
17. Ortiz-Meoz, R. F., Merbl, Y., Kirschner, M. W. & Walker, S. Microarray discovery of new OGT substrates: the medulloblastoma oncogene OTX2 is O-GlcNAcylated. J. Am. Chem. Soc. 136, 4845-4848 (2014).
18. Robinson, P. V., Tsai, C.-t., de Groot, A. E., McKechnie, J. L. & Bertozzi, C. R. Glyco-seek: Ultrasensitive Detection of Protein-Specific Glycosylation by Proximity Ligation Polymerase Chain Reaction. J. Am. Chem. Soc. 138, 10722-10725 (2016).
19. Naegeli, A. et al. Substrate Specificity of Cytoplasmic N-Glycosyltransferase. J. Biol. Chem. 289, 24521-24532 (2014).
20. Naegeli, A. et al. Molecular analysis of an alternative N-glycosylation machinery by functional transfer from *Actinobacillus pleuropneumoniae* to *Escherichia coli*. J. Biol. Chem. 289, 2170-2179 (2014).
21. Keys, T. G. et al. A biosynthetic route for polysialylating proteins in *Escherichia coli*. Metab. Eng. 44, 293-301 (2017).
22. Cuccui, J. et al. The N-linking glycosylation system from *Actinobacillus pleuropneumoniae* is required for adhesion and has potential use in glycoengineering. Open Biol. 7 (2017).
23. Schwarz, F., Fan, Y. Y., Schubert, M. & Aebi, M. Cytoplasmic N-glycosyltransferase of *Actinobacillus pleuropneumoniae* is an inverting enzyme and recognizes the NX(S/T) consensus sequence. J. Biol. Chem. 286, 35267-35274 (2011).
24. Song, Q. et al. Production of homogeneous glycoprotein with multi-site modifications by an engineered N-glycosyltransferase mutant. J. Biol. Chem. (2017).
25. Gross, J. et al. The *Haemophilus influenzae* HMW1 Adhesin Is a Glycoprotein with an Unusual N-Linked Carbohydrate Modification. J. Biol. Chem. 283, 26010-26015 (2008).
26. Kawai, F. et al. Structural insights into the glycosyltransferase activity of the *Actinobacillus pleuropneumoniae* HMW1C-like protein. J. Biol. Chem. 286, 38546-38557 (2011).
27. Lomino, J. V. et al. A two-step enzymatic glycosylation of polypeptides with complex N-glycans. Biorg. Med. Chem. 21, 2262-2270 (2013).
28. Chen, M. M., Glover, K. J. & Imperiali, B. From Peptide to Protein:?Comparative Analysis of the Substrate Specificity of N-Linked Glycosylation in *C. jejuni*. Biochemistry 46, 5579-5585 (2007).
29. Fisher, A. C. et al. Production of secretory and extracellular N-linked glycoproteins in *Escherichia coli*. Appl. Environ. Microbiol. 77, 871-881 (2011).
30. Carlson, E. D., Gan, R., Hodgman, C. E. & Jewett, M. C. Cell-free protein synthesis: applications come of age. Biotechnol. Adv. 30, 1185-1194 (2012).
31. Kuo, H. Y., DeLuca, T. A., Miller, W. M. & Mrksich, M. Profiling deacetylase activities in cell lysates with peptide arrays and SAMDI mass spectrometry. Anal. Chem. 85, 10635-10642 (2013).
32. Kornacki, J. R., Stuparu, A. D. & Mrksich, M. Acetyltransferase p300/CBP Associated Factor (PCAF) Regulates Crosstalk-Dependent Acetylation of Histone H3 by Distal Site Recognition. ACS Chem. Biol. 10, 157-164 (2015).
33. Kim, J. & Mrksich, M. Profiling the selectivity of DNA ligases in an array format with mass spectrometry. Nucleic Acids Res. 38, e2 (2010).
34. Laurent, N. et al. Enzymatic Glycosylation of Peptide Arrays on Gold Surfaces. ChemBioChem 9, 883-887 (2008).
35. Laurent, N. et al. SPOT Synthesis of Peptide Arrays on Self-Assembled Monolayers and their Evaluation as Enzyme Substrates. ChemBioChem 9, 2592-2596 (2008).
36. Hussain, M. R., Hoessli, D. C. & Fang, M. N-acetylgalactosaminyltransferases in cancer. Oncotarget 7, 54067-54081 (2016).
37. Schjoldager, K. T. et al. Probing isoform-specific functions of polypeptide GalNAc-transferases using zinc 37. finger nuclease glycoengineered SimpleCells. Proc. Natl. Acad. Sci. U.S.A. 109, 9893-9898 (2012).

38. Yoshida, A., Suzuki, M., Ikenaga, H. & Takeuchi, M. Discovery of the shortest sequence motif for high level mucin-type O-glycosylation. J. Biol. Chem. 272, 16884-16888 (1997).

39. Gerken, T. A., Raman, J., Fritz, T. A. & Jamison, O. Identification of Common and Unique Peptide Substrate Preferences for the UDP-GalNAc:Polypeptide a-N-acetyl-galactosaminyltransferases T1 and T2 Derived from Oriented Random Peptide Substrates. J. Biol. Chem. 281, 32403-32416 (2006).

40. Kong, Y. et al. Probing polypeptide GalNAc-transferase isoform substrate specificities by in vitro analysis. Glycobiology 25, 55-65 (2015).

41. Steentoft, C. et al. Precision mapping of the human O-GalNAc glycoproteome through SimpleCell technology. EMBO J. 32, 1478-1488 (2013).

42. Wang, A. C., Jensen, E. H., Rexach, J. E., Vinters, H. V. & Hsieh-Wilson, L. C. Loss of O-GlcNAc glycosylation in forebrain excitatory neurons induces neurodegeneration. Proc. Natl. Acad. Sci. U.S.A. 113, 15120-15125 (2016).

43. Yang, X. et al. Phosphoinositide signalling links O-GlcNAc transferase to insulin resistance. Nature 451, 964-969 (2008).

44. Liu, X. et al. A peptide panel investigation reveals the acceptor specificity of O-GlcNAc transferase. FASEB J. 28, 3362-3372 (2014).

45. Chalkley, R. J., Thalhammer, A., Schoepfer, R. & Burlingame, A. L. Identification of protein O-GlcNAcylation sites using electron transfer dissociation mass spectrometry on native peptides. Proc. Natl. Acad. Sci. U.S.A. 106, 8894-8899 (2009).

46. Lazarus, M. B., Nam, Y., Jiang, J., Sliz, P. & Walker, S. Structure of human O-GlcNAc transferase and its complex with a peptide substrate. Nature 469, 564-567 (2011).

47. Choi, K. J., Grass, S., Paek, S., St Geme, J. W., 3rd & Yeo, H. J. The *Actinobacillus pleuropneumoniae* HMW1C-like glycosyltransferase mediates N-linked glycosylation of the *Haemophilus influenzae* HMW1 adhesin. PLoS ONE 5, e15888 (2010).

48. Haselberg, R., de Jong, G. J. & Somsen, G. W. Low-Flow Sheathless Capillary Electrophoresis-Mass Spectrometry for Sensitive Glycoform Profiling of Intact Pharmaceutical Proteins. Anal. Chem. 85, 2289-2296 (2013).

49. Schoborg, J. A. et al. A cell-free platform for rapid synthesis and testing of active oligosaccharyltransferases. Biotechnol. Bioeng. (2017).

50. Sievers, F. et al. Fast, scalable generation of high-quality protein multiple sequence alignments using Clustal Omega. Mol. Syst. Biol. 7 (2011).

51. Gurard-Levin, Z. A., Scholle, M. D., Eisenberg, A. H. & Mrksich, M. High-Throughput Screening of Small Molecule Libraries using SAMDI Mass Spectrometry. ACS Comb. Sci. 13, 347-350 (2011).

52. Goerke, A. R. & Swartz, J. R. Development of cell-free protein synthesis platforms for disulfide bonded proteins. Biotechnol. Bioeng. 99, 351-367 (2008).

53. Espah Borujeni, A., Channarasappa, A. S. & Salis, H. M. Translation rate is controlled by coupled trade-offs between site accessibility, selective RNA unfolding and sliding at upstream standby sites. Nucleic Acids Res. 42, 2646-2659 (2014).

54. Lajoie, M. J. et al. Genomically Recoded Organisms Expand Biological Functions. Science 342, 357-360 (2013).

55. Kwon, Y.-C. & Jewett, M. C. High-throughput preparation methods of crude extract for robust cell-free protein synthesis. Sci. Rep. 5, 8663 (2015).

56. Jewett, M. C. & Swartz, J. R. Mimicking the *Escherichia coli* cytoplasmic environment activates long-lived and efficient cell-free protein synthesis. Biotechnol. Bioeng. 86, 19-26 (2004).

57. Jewett, M. C. & Swartz, J. R. Rapid Expression and Purification of 100 nmol Quantities of Active Protein Using Cell-Free Protein Synthesis. Biotechnol. Prog. 20, 102-109 (2004).

58. Hong, S. H. et al. Cell-free Protein Synthesis from a Release Factor 1 Deficient *Escherichia coli* Activates Efficient and Multiple Site-specific Nonstandard Amino Acid Incorporation. ACS Synth. Biol. 3, 398-409 (2014).

59. Jian, W., Edom, R. W., Wang, D., Weng, N. & Zhang, S. Relative Quantitation of Glycoisoforms of Intact Apolipoprotein C3 in Human Plasma by Liquid Chromatography-High-Resolution Mass Spectrometry. Anal. Chem. 85, 2867-2874 (2013).

60. Wang, L.-X. & Amin, M. N. Chemical and Chemoenzymatic Synthesis of Glycoproteins for Deciphering Functions. Chemistry & biology 21, 51-66 (2014).

61. Fernindez-Tejada, A. et al. Total Synthesis of Glycosylated Proteins. Topics in current chemistry 362, 1-26 (2015).

62. Murakami, M. et al. Chemical synthesis of erythropoietin glycoforms for insights into the relationship between glycosylation pattern and bioactivity. Science Advances 2, e1500678 (2016).

63. Li, T. et al. Modulating IgG effector function by Fc glycan engineering. Proceedings of the National Academy of Sciences 114, 3485-3490 (2017).

64. van Kasteren, S. I., Kramer, H. B., Gamblin, D. P. & Davis, B. G. Site-selective glycosylation of proteins: creating synthetic glycoproteins. Nature protocols 2, 3185 (2007).

65. van Kasteren, S. I. et al. Expanding the diversity of chemical protein modification allows post-translational mimicry. Nature 446, 1105 (2007).

66. Wright, T. H. et al. Posttranslational mutagenesis: A chemical strategy for exploring protein side-chain diversity. Science (New York, N.Y.) 354 (2016).

67. Yang, A. et al. A chemical biology route to site-specific authentic protein modifications. Science (New York, N.Y.) 354, 623-626 (2016).

68. Yang, Q. et al. Glycan Remodeling of Human Erythropoietin (EPO) Through Combined Mammalian Cell Engineering and Chemoenzymatic Transglycosylation. ACS Chemical Biology 12, 1665-1673 (2017).

69. Hang, I. et al. Analysis of site-specific N-glycan remodeling in the endoplasmic reticulum and the Golgi. Glycobiology 25, 1335-1349 (2015).

70. Losfeld, M.-E. et al. Influence of protein/glycan interaction on site-specific glycan heterogeneity. The FASEB Journal 31, 4623-4635 (2017).

71. Go, E. P. et al. Glycosylation Site-Specific Analysis of HIV Envelope Proteins (JR-FL and CON-S) Reveals Major Differences in Glycosylation Site Occupancy, Glycoform Profiles, and Antigenic Epitopes' Accessibility. Journal of proteome research 7, 1660-1674 (2008).

72. Kightlinger, W. et al. Design of glycosylation sites by rapid synthesis and analysis of glycosyltransferases. Nature Chemical Biology 14, 627-635 (2018).

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

All methods described herein can be performed in any suitable order unless otherwise indicated herein or otherwise clearly contradicted by context. The use of any and all examples provided herein, is intended merely to better illuminate the invention and does not pose a limitation on the scope of the invention unless otherwise claimed. No language in the specification should be construed as indicating any non-claimed element as essential to the practice of the invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A method for synthesizing a glycoprotein or recombinant glycoprotein, the method comprising:
   (a) expressing in a cell or in a cell-free protein synthesis (CFPS) reaction, a polypeptide comprising the amino acid sequence of a target protein which includes naturally an amino acid motif that includes an asparagine that is glycosylated by N-glycosyltransferase from *Actinobacillus pleuropneumoniae* (ApNGT) or that has been modified to include a heterologous amino acid motif that includes an asparagine that is glycosylated by ApNGT, the amino acid motif or heterologous amino acid motif comprises $X_{-2}$-$X_{-1}$-N-$X_{+1}$-S/T-$X_{+3}$, wherein $X_{-2}$ is selected from Gly, Asn, and Tyr; $X_{-1}$ is selected from Gly and Ala; $X_{+1}$ is selected from Trp, Val, His, Ala, and Ile; and $X_{+3}$ is selected from Thr, Met, and Phe;
   (b) expressing ApNGT in a cell or in a CFPS reaction; and
   (c) reacting the polypeptide and ApNGT in the presence of a sugar donor, wherein ApNGT glycosylates the amino acid motif or heterologous amino acid motif of the polypeptide with the sugar of the sugar donor to synthesize the glycoprotein or recombinant glycoprotein.

2. The method of claim 1, wherein the target protein is a eukaryotic protein.

3. The method of claim 1, wherein the target protein is a prokaryotic protein.

4. The method of claim 1, wherein step (a) is performed in a prokaryotic cell; step (b) is performed in a prokaryotic cell; or both of step (a) and step (b) are performed in the same prokaryotic cell.

5. The method of claim 1, wherein step (a) is performed in a eukaryotic cell; step (b) is performed in a eukaryotic cell; or both of step (a) and step (b) are performed in the same eukaryotic cell.

6. The method of claim 1, wherein step (a) is performed in a prokaryotic-based CFPS reaction; step (b) is performed in a prokaryotic-based CFPS reaction; or both of step (a) and step (b) are performed in the same prokaryotic-based CFPS reaction.

7. The method of claim 6, wherein step (c) is performed in the same prokaryotic-based CFPS reaction.

8. The method of claim 1, wherein step (b) further comprises expressing in the cell an additional N-glycosyltransferase selected from one of *Actinobacillus* spp., *Escherichia* spp., *Haemophilus* spp., or *Mannheimia* spp.

9. The method of claim 1, wherein multiple identical, multiple distinct, and/or non-naturally occurring glycans are introduced to a protein by specifically choosing unique sequence:enzyme pairs that allow for orthogonal, and/or parallel and/or independent glycosylation.

10. The method of claim 1, wherein prior to performing step (c), the polypeptide is immobilized on a solid support.

11. A method for synthesizing a glycoprotein or recombinant glycoprotein, the method comprising:
(a) expressing in a cell or in a cell-free protein synthesis (CFPS) reaction a polypeptide comprising the amino acid sequence of a target protein which includes naturally two or more different amino acid motifs that includes an asparagine that is glycosylated by two or more different N-glycosyltransferases from *Actinobacillus* spp., *Escherichia* spp., *Haemophilus* spp., or *Mannheimia* spp., wherein at least one of the different N-glycosyltransferases comprises N-glycosyltransferase from *Actinobacillus pleuropneumoniae* (ApNGT), or that has been modified to include two or more different heterologous amino acid motifs that includes an asparagine that is glycosylated by two or more different N-glycosyltransferases from *Actinobacillus* spp., *Escherichia* spp., *Haemophilus* spp., or *Mannheimia* spp., wherein at least one of the different N-glycosyltransferases comprises ApNGT, the amino acid motifs or heterologous amino acid motifs comprising an amino acid sequence selected from the amino acid sequences of SEQ ID NOs:1-549, wherein at least one of the amino acid motifs or heterologous amino acid motifs comprises $X_{-2}$-$X_{-1}$-N-$X_{+1}$-S/T-$X_{+3}$, wherein $X_{-2}$ is selected from Gly, Asn, and Tyr: $X_{-1}$ is selected from Gly and Ala: $X_{+1}$ is selected from Trp, Val, His, Ala, and Ile; and $X_{+3}$ is selected from Thr, Met, and Phe;
(b) expressing in one or more cells or in one or more CFPS reactions the two or more different N-glycosyltransferases from *Actinobacillus* spp., *Escherichia* spp., *Haemophilus* spp., or *Mannheimia* spp., wherein at least one of the different N-glycosyltransferases comprises ApNGT, wherein the two or more different N-glycosyltransferases selected from *Actinobacillus* spp., *Escherichia* spp., *Haemophilus* spp., or *Mannheimia* spp., wherein at least one of the different N-glycosyltransferases comprises ApNGT, are expressed simultaneously in the same cell or CFPS reaction or sequentially in two or more different cells or two or more different CFPS reactions; and
(c) reacting the polypeptide and the two or more different N-glycosyltransferases selected from *Actinobacillus* spp., *Escherichia* spp., *Haemophilus* spp., or *Mannheimia* spp., wherein at least one of the different N-glycosyltransferases comprises ApNGT, in the presence of two or more sugar donors which are the same or different, wherein the polypeptide is reacted with the two or more different N-glycosyltransferases selected from *Actinobacillus* spp., *Escherichia* spp., *Haemophilus* spp., or *Mannheimia* spp., wherein at least one of the different N-glycosyltransferases comprises ApNGT, simultaneously in the same cell or CFPS reaction, or sequentially in two or more different cells or two or more different CFPS reactions, and wherein the two or more different N-glycosyltransferases selected from *Actinobacillus* spp., *Escherichia* spp., *Haemophilus* spp., or *Mannheimia* spp., wherein at least one of the different N-glycosyltransferases comprises ApNGT, glycosylate the two or more different amino acid motifs or heterologous amino acid motifs of the polypeptide with the sugar of the two or more sugar donors to synthesize the glycoprotein or recombinant glycoprotein.

12. The method of claim 11, wherein prior to performing step (c), the polypeptide is immobilized on a solid support.

13. A method for selecting an amino acid motif that is glycosylated by an N-glycosyltransferase, the method comprising:
(a) reacting a library of peptides with an N-glycosyltransferase in the presence of a sugar donor, wherein the N-glycosyltransferase glycosylates one or more of the peptides, and wherein the peptides comprise at least 6 amino acids and have a sequence $X_{-2}$-$X_{-1}$-N-$X_{+1}$-S/T-R-C wherein X is any amino acid;
(b) detecting glycosylation of the reacted peptides by immobilizing the reacted peptides on a substrate comprising self-assembled monolayers, and performing matrix-assisted laser desorption/ionization mass spectrometry of the immobilized reacted peptides to select the amino acid motif that is glycosylated by the N-glycosyltransferase.

14. The method of claim 13, wherein the library comprises at least 500 peptides.

15. The method of claim 13, wherein the peptides are covalently immobilized on the substrate comprising the self-assembled monolayers.

16. The method of claim 15, wherein the library of peptides comprise a C-terminal Cys, the self-assembled monolayers comprise free maleimides, and the C-terminal Cys of the peptides reacts with the free maleimides to form a bond and covalently immobilize the peptide.

17. The method of claim 16, wherein the self-assembled monolayers comprise alkylthiolates which provide the free maleimides.

18. The method of claim 13, wherein:
(i) the library of peptides comprise a C-terminal alkyne, the self-assembled monolayers comprise free azides, and the C-terminal alkyne of the peptides reacts with the free azides to form a bond and covalently immobilize the peptide; or
(ii) the library of peptides comprise a C-terminal azide, the self-assembled monolayers comprise free alkynes, and the C-terminal azide of the peptides reacts with the free alkynes to form a bond and covalently immobilize the peptide.

19. The method of claim 13, wherein the bonds formed in (i) and (ii) comprise a 1,2,3-triazole bond.

20. The method of claim 1, wherein the amino acid motif comprises the amino acid sequence of SEQ ID NO: 1 or the amino acid sequence of SEQ ID NO: 8.

21. The method of claim 11, wherein $X_{-2}$-$X_{-1}$-N-$X_{+1}$-S/T-$X_{+3}$ comprises the amino acid sequence of SEQ ID NO: 1 or the amino acid sequence of SEQ ID NO: 8.

* * * * *

SEQUENCE LISTING

```
<160> NUMBER OF SEQ ID NOS: 553

<210> SEQ ID NO 1
<211> LENGTH: 4
<212> TYPE: PRT
<213> ORGANISM: Artificial Sequence
<220> FEATURE:
<223> OTHER INFORMATION: Synthetic

<400> SEQUENCE: 1

Ala Asn Val Thr
1

<210> SEQ ID NO 2
<211> LENGTH: 4
<212> TYPE: PRT
<213> ORGANISM: Artificial Sequence
<220> FEATURE:
<223> OTHER INFORMATION: Synthetic

<400> SEQUENCE: 2

Pro Asn Val Thr
1

<210> SEQ ID NO 3
<211> LENGTH: 4
<212> TYPE: PRT
<213> ORGANISM: Artificial Sequence
<220> FEATURE:
<223> OTHER INFORMATION: Synthetic

<400> SEQUENCE: 3

Ser Asn Val Ser
1

<210> SEQ ID NO 4
<211> LENGTH: 4
<212> TYPE: PRT
<213> ORGANISM: Artificial Sequence
<220> FEATURE:
<223> OTHER INFORMATION: Synthetic

<400> SEQUENCE: 4

Ala Asn Val Ser
1

<210> SEQ ID NO 5
<211> LENGTH: 4
```

```
<212> TYPE: PRT
<213> ORGANISM: Artificial Sequence
<220> FEATURE:
<223> OTHER INFORMATION: Synthetic

<400> SEQUENCE: 5

Trp Asn Val Thr
1

<210> SEQ ID NO 6
<211> LENGTH: 4
<212> TYPE: PRT
<213> ORGANISM: Artificial Sequence
<220> FEATURE:
<223> OTHER INFORMATION: Synthetic

<400> SEQUENCE: 6

Ala Asn Ile Thr
1

<210> SEQ ID NO 7
<211> LENGTH: 4
<212> TYPE: PRT
<213> ORGANISM: Artificial Sequence
<220> FEATURE:
<223> OTHER INFORMATION: Synthetic

<400> SEQUENCE: 7

Ser Asn Val Thr
1

<210> SEQ ID NO 8
<211> LENGTH: 4
<212> TYPE: PRT
<213> ORGANISM: Artificial Sequence
<220> FEATURE:
<223> OTHER INFORMATION: Synthetic

<400> SEQUENCE: 8

Gly Asn Trp Thr
1

<210> SEQ ID NO 9
<211> LENGTH: 4
<212> TYPE: PRT
<213> ORGANISM: Artificial Sequence
<220> FEATURE:
<223> OTHER INFORMATION: Synthetic

<400> SEQUENCE: 9

Pro Asn Val Ser
1

<210> SEQ ID NO 10
<211> LENGTH: 4
<212> TYPE: PRT
<213> ORGANISM: Artificial Sequence
<220> FEATURE:
<223> OTHER INFORMATION: Synthetic

<400> SEQUENCE: 10

Pro Asn Ile Thr
1

<210> SEQ ID NO 11
<211> LENGTH: 4
<212> TYPE: PRT
```

```
<213> ORGANISM: Artificial Sequence
<220> FEATURE:
<223> OTHER INFORMATION: Synthetic

<400> SEQUENCE: 11

His Asn Val Thr
1

<210> SEQ ID NO 12
<211> LENGTH: 4
<212> TYPE: PRT
<213> ORGANISM: Artificial Sequence
<220> FEATURE:
<223> OTHER INFORMATION: Synthetic

<400> SEQUENCE: 12

Trp Asn Ile Thr
1

<210> SEQ ID NO 13
<211> LENGTH: 4
<212> TYPE: PRT
<213> ORGANISM: Artificial Sequence
<220> FEATURE:
<223> OTHER INFORMATION: Synthetic

<400> SEQUENCE: 13

Ala Asn His Thr
1

<210> SEQ ID NO 14
<211> LENGTH: 4
<212> TYPE: PRT
<213> ORGANISM: Artificial Sequence
<220> FEATURE:
<223> OTHER INFORMATION: Synthetic

<400> SEQUENCE: 14

His Asn Val Ser
1

<210> SEQ ID NO 15
<211> LENGTH: 4
<212> TYPE: PRT
<213> ORGANISM: Artificial Sequence
<220> FEATURE:
<223> OTHER INFORMATION: Synthetic

<400> SEQUENCE: 15

Asn Asn Val Thr
1

<210> SEQ ID NO 16
<211> LENGTH: 4
<212> TYPE: PRT
<213> ORGANISM: Artificial Sequence
<220> FEATURE:
<223> OTHER INFORMATION: Synthetic

<400> SEQUENCE: 16

Met Asn Val Ser
1

<210> SEQ ID NO 17
<211> LENGTH: 4
<212> TYPE: PRT
<213> ORGANISM: Artificial Sequence
```

```
<220> FEATURE:
<223> OTHER INFORMATION: Synthetic

<400> SEQUENCE: 17

Ala Asn Ala Thr
1

<210> SEQ ID NO 18
<211> LENGTH: 4
<212> TYPE: PRT
<213> ORGANISM: Artificial Sequence
<220> FEATURE:
<223> OTHER INFORMATION: Synthetic

<400> SEQUENCE: 18

Ala Asn Tyr Thr
1

<210> SEQ ID NO 19
<211> LENGTH: 4
<212> TYPE: PRT
<213> ORGANISM: Artificial Sequence
<220> FEATURE:
<223> OTHER INFORMATION: Synthetic

<400> SEQUENCE: 19

Thr Asn Val Thr
1

<210> SEQ ID NO 20
<211> LENGTH: 4
<212> TYPE: PRT
<213> ORGANISM: Artificial Sequence
<220> FEATURE:
<223> OTHER INFORMATION: Synthetic

<400> SEQUENCE: 20

Ser Asn His Thr
1

<210> SEQ ID NO 21
<211> LENGTH: 4
<212> TYPE: PRT
<213> ORGANISM: Artificial Sequence
<220> FEATURE:
<223> OTHER INFORMATION: Synthetic

<400> SEQUENCE: 21

Pro Asn Tyr Thr
1

<210> SEQ ID NO 22
<211> LENGTH: 4
<212> TYPE: PRT
<213> ORGANISM: Artificial Sequence
<220> FEATURE:
<223> OTHER INFORMATION: Synthetic

<400> SEQUENCE: 22

Pro Asn His Thr
1

<210> SEQ ID NO 23
<211> LENGTH: 4
<212> TYPE: PRT
<213> ORGANISM: Artificial Sequence
<220> FEATURE:
```

```
<223> OTHER INFORMATION: Synthetic

<400> SEQUENCE: 23

Pro Asn Ala Thr
1

<210> SEQ ID NO 24
<211> LENGTH: 4
<212> TYPE: PRT
<213> ORGANISM: Artificial Sequence
<220> FEATURE:
<223> OTHER INFORMATION: Synthetic

<400> SEQUENCE: 24

Trp Asn Val Ser
1

<210> SEQ ID NO 25
<211> LENGTH: 4
<212> TYPE: PRT
<213> ORGANISM: Artificial Sequence
<220> FEATURE:
<223> OTHER INFORMATION: Synthetic

<400> SEQUENCE: 25

Glu Asn Val Thr
1

<210> SEQ ID NO 26
<211> LENGTH: 4
<212> TYPE: PRT
<213> ORGANISM: Artificial Sequence
<220> FEATURE:
<223> OTHER INFORMATION: Synthetic

<400> SEQUENCE: 26

Gly Asn Val Thr
1

<210> SEQ ID NO 27
<211> LENGTH: 4
<212> TYPE: PRT
<213> ORGANISM: Artificial Sequence
<220> FEATURE:
<223> OTHER INFORMATION: Synthetic

<400> SEQUENCE: 27

Pro Asn Ile Ser
1

<210> SEQ ID NO 28
<211> LENGTH: 4
<212> TYPE: PRT
<213> ORGANISM: Artificial Sequence
<220> FEATURE:
<223> OTHER INFORMATION: Synthetic

<400> SEQUENCE: 28

Thr Asn Val Ser
1

<210> SEQ ID NO 29
<211> LENGTH: 4
<212> TYPE: PRT
<213> ORGANISM: Artificial Sequence
<220> FEATURE:
<223> OTHER INFORMATION: Synthetic
```

<400> SEQUENCE: 29

Ala Asn Ile Ser
1

<210> SEQ ID NO 30
<211> LENGTH: 4
<212> TYPE: PRT
<213> ORGANISM: Artificial Sequence
<220> FEATURE:
<223> OTHER INFORMATION: Synthetic

<400> SEQUENCE: 30

Pro Asn Arg Thr
1

<210> SEQ ID NO 31
<211> LENGTH: 4
<212> TYPE: PRT
<213> ORGANISM: Artificial Sequence
<220> FEATURE:
<223> OTHER INFORMATION: Synthetic

<400> SEQUENCE: 31

Ala Asn Phe Thr
1

<210> SEQ ID NO 32
<211> LENGTH: 4
<212> TYPE: PRT
<213> ORGANISM: Artificial Sequence
<220> FEATURE:
<223> OTHER INFORMATION: Synthetic

<400> SEQUENCE: 32

Asn Asn His Thr
1

<210> SEQ ID NO 33
<211> LENGTH: 4
<212> TYPE: PRT
<213> ORGANISM: Artificial Sequence
<220> FEATURE:
<223> OTHER INFORMATION: Synthetic

<400> SEQUENCE: 33

Trp Asn Ala Thr
1

<210> SEQ ID NO 34
<211> LENGTH: 4
<212> TYPE: PRT
<213> ORGANISM: Artificial Sequence
<220> FEATURE:
<223> OTHER INFORMATION: Synthetic

<400> SEQUENCE: 34

Met Asn His Thr
1

<210> SEQ ID NO 35
<211> LENGTH: 4
<212> TYPE: PRT
<213> ORGANISM: Artificial Sequence
<220> FEATURE:
<223> OTHER INFORMATION: Synthetic

```
<400> SEQUENCE: 35

Pro Asn Thr Thr
1

<210> SEQ ID NO 36
<211> LENGTH: 4
<212> TYPE: PRT
<213> ORGANISM: Artificial Sequence
<220> FEATURE:
<223> OTHER INFORMATION: Synthetic

<400> SEQUENCE: 36

Thr Asn His Thr
1

<210> SEQ ID NO 37
<211> LENGTH: 4
<212> TYPE: PRT
<213> ORGANISM: Artificial Sequence
<220> FEATURE:
<223> OTHER INFORMATION: Synthetic

<400> SEQUENCE: 37

His Asn His Thr
1

<210> SEQ ID NO 38
<211> LENGTH: 4
<212> TYPE: PRT
<213> ORGANISM: Artificial Sequence
<220> FEATURE:
<223> OTHER INFORMATION: Synthetic

<400> SEQUENCE: 38

His Asn Ile Thr
1

<210> SEQ ID NO 39
<211> LENGTH: 4
<212> TYPE: PRT
<213> ORGANISM: Artificial Sequence
<220> FEATURE:
<223> OTHER INFORMATION: Synthetic

<400> SEQUENCE: 39

Pro Asn Phe Thr
1

<210> SEQ ID NO 40
<211> LENGTH: 4
<212> TYPE: PRT
<213> ORGANISM: Artificial Sequence
<220> FEATURE:
<223> OTHER INFORMATION: Synthetic

<400> SEQUENCE: 40

Pro Asn Met Thr
1

<210> SEQ ID NO 41
<211> LENGTH: 4
<212> TYPE: PRT
<213> ORGANISM: Artificial Sequence
<220> FEATURE:
<223> OTHER INFORMATION: Synthetic

<400> SEQUENCE: 41
```

Ser Asn Ala Thr
1

<210> SEQ ID NO 42
<211> LENGTH: 4
<212> TYPE: PRT
<213> ORGANISM: Artificial Sequence
<220> FEATURE:
<223> OTHER INFORMATION: Synthetic

<400> SEQUENCE: 42

Met Asn Val Thr
1

<210> SEQ ID NO 43
<211> LENGTH: 4
<212> TYPE: PRT
<213> ORGANISM: Artificial Sequence
<220> FEATURE:
<223> OTHER INFORMATION: Synthetic

<400> SEQUENCE: 43

Trp Asn His Thr
1

<210> SEQ ID NO 44
<211> LENGTH: 4
<212> TYPE: PRT
<213> ORGANISM: Artificial Sequence
<220> FEATURE:
<223> OTHER INFORMATION: Synthetic

<400> SEQUENCE: 44

Pro Asn Ser Thr
1

<210> SEQ ID NO 45
<211> LENGTH: 4
<212> TYPE: PRT
<213> ORGANISM: Artificial Sequence
<220> FEATURE:
<223> OTHER INFORMATION: Synthetic

<400> SEQUENCE: 45

Pro Asn Leu Thr
1

<210> SEQ ID NO 46
<211> LENGTH: 4
<212> TYPE: PRT
<213> ORGANISM: Artificial Sequence
<220> FEATURE:
<223> OTHER INFORMATION: Synthetic

<400> SEQUENCE: 46

Ala Asn Arg Thr
1

<210> SEQ ID NO 47
<211> LENGTH: 4
<212> TYPE: PRT
<213> ORGANISM: Artificial Sequence
<220> FEATURE:
<223> OTHER INFORMATION: Synthetic

<400> SEQUENCE: 47

Val Asn Val Thr
1

<210> SEQ ID NO 48
<211> LENGTH: 4
<212> TYPE: PRT
<213> ORGANISM: Artificial Sequence
<220> FEATURE:
<223> OTHER INFORMATION: Synthetic

<400> SEQUENCE: 48

Met Asn Ala Thr
1

<210> SEQ ID NO 49
<211> LENGTH: 4
<212> TYPE: PRT
<213> ORGANISM: Artificial Sequence
<220> FEATURE:
<223> OTHER INFORMATION: Synthetic

<400> SEQUENCE: 49

Ala Asn Thr Thr
1

<210> SEQ ID NO 50
<211> LENGTH: 4
<212> TYPE: PRT
<213> ORGANISM: Artificial Sequence
<220> FEATURE:
<223> OTHER INFORMATION: Synthetic

<400> SEQUENCE: 50

Glu Asn Ala Thr
1

<210> SEQ ID NO 51
<211> LENGTH: 4
<212> TYPE: PRT
<213> ORGANISM: Artificial Sequence
<220> FEATURE:
<223> OTHER INFORMATION: Synthetic

<400> SEQUENCE: 51

Gly Asn His Thr
1

<210> SEQ ID NO 52
<211> LENGTH: 4
<212> TYPE: PRT
<213> ORGANISM: Artificial Sequence
<220> FEATURE:
<223> OTHER INFORMATION: Synthetic

<400> SEQUENCE: 52

Ala Asn Ser Thr
1

<210> SEQ ID NO 53
<211> LENGTH: 4
<212> TYPE: PRT
<213> ORGANISM: Artificial Sequence
<220> FEATURE:
<223> OTHER INFORMATION: Synthetic

<400> SEQUENCE: 53

Thr Asn Ala Thr

```
<210> SEQ ID NO 54
<211> LENGTH: 4
<212> TYPE: PRT
<213> ORGANISM: Artificial Sequence
<220> FEATURE:
<223> OTHER INFORMATION: Synthetic

<400> SEQUENCE: 54

Asn Asn Arg Thr
1

<210> SEQ ID NO 55
<211> LENGTH: 4
<212> TYPE: PRT
<213> ORGANISM: Artificial Sequence
<220> FEATURE:
<223> OTHER INFORMATION: Synthetic

<400> SEQUENCE: 55

Asn Asn Ala Thr
1

<210> SEQ ID NO 56
<211> LENGTH: 4
<212> TYPE: PRT
<213> ORGANISM: Artificial Sequence
<220> FEATURE:
<223> OTHER INFORMATION: Synthetic

<400> SEQUENCE: 56

Glu Asn His Thr
1

<210> SEQ ID NO 57
<211> LENGTH: 4
<212> TYPE: PRT
<213> ORGANISM: Artificial Sequence
<220> FEATURE:
<223> OTHER INFORMATION: Synthetic

<400> SEQUENCE: 57

Ala Asn Met Thr
1

<210> SEQ ID NO 58
<211> LENGTH: 4
<212> TYPE: PRT
<213> ORGANISM: Artificial Sequence
<220> FEATURE:
<223> OTHER INFORMATION: Synthetic

<400> SEQUENCE: 58

Trp Asn Ile Ser
1

<210> SEQ ID NO 59
<211> LENGTH: 4
<212> TYPE: PRT
<213> ORGANISM: Artificial Sequence
<220> FEATURE:
<223> OTHER INFORMATION: Synthetic

<400> SEQUENCE: 59

Ser Asn Ile Thr
1
```

```
<210> SEQ ID NO 60
<211> LENGTH: 4
<212> TYPE: PRT
<213> ORGANISM: Artificial Sequence
<220> FEATURE:
<223> OTHER INFORMATION: Synthetic

<400> SEQUENCE: 60

His Asn Ala Thr
1

<210> SEQ ID NO 61
<211> LENGTH: 4
<212> TYPE: PRT
<213> ORGANISM: Artificial Sequence
<220> FEATURE:
<223> OTHER INFORMATION: Synthetic

<400> SEQUENCE: 61

Met Asn Ile Thr
1

<210> SEQ ID NO 62
<211> LENGTH: 4
<212> TYPE: PRT
<213> ORGANISM: Artificial Sequence
<220> FEATURE:
<223> OTHER INFORMATION: Synthetic

<400> SEQUENCE: 62

Asp Asn His Thr
1

<210> SEQ ID NO 63
<211> LENGTH: 4
<212> TYPE: PRT
<213> ORGANISM: Artificial Sequence
<220> FEATURE:
<223> OTHER INFORMATION: Synthetic

<400> SEQUENCE: 63

Glu Asn Arg Thr
1

<210> SEQ ID NO 64
<211> LENGTH: 4
<212> TYPE: PRT
<213> ORGANISM: Artificial Sequence
<220> FEATURE:
<223> OTHER INFORMATION: Synthetic

<400> SEQUENCE: 64

Gly Asn Trp Ser
1

<210> SEQ ID NO 65
<211> LENGTH: 4
<212> TYPE: PRT
<213> ORGANISM: Artificial Sequence
<220> FEATURE:
<223> OTHER INFORMATION: Synthetic

<400> SEQUENCE: 65

Asn Asn Val Ser
1
```

```
<210> SEQ ID NO 66
<211> LENGTH: 4
<212> TYPE: PRT
<213> ORGANISM: Artificial Sequence
<220> FEATURE:
<223> OTHER INFORMATION: Synthetic

<400> SEQUENCE: 66

His Asn Ile Ser
1

<210> SEQ ID NO 67
<211> LENGTH: 4
<212> TYPE: PRT
<213> ORGANISM: Artificial Sequence
<220> FEATURE:
<223> OTHER INFORMATION: Synthetic

<400> SEQUENCE: 67

Pro Asn His Ser
1

<210> SEQ ID NO 68
<211> LENGTH: 4
<212> TYPE: PRT
<213> ORGANISM: Artificial Sequence
<220> FEATURE:
<223> OTHER INFORMATION: Synthetic

<400> SEQUENCE: 68

Val Asn Ala Thr
1

<210> SEQ ID NO 69
<211> LENGTH: 4
<212> TYPE: PRT
<213> ORGANISM: Artificial Sequence
<220> FEATURE:
<223> OTHER INFORMATION: Synthetic

<400> SEQUENCE: 69

Ala Asn Tyr Ser
1

<210> SEQ ID NO 70
<211> LENGTH: 4
<212> TYPE: PRT
<213> ORGANISM: Artificial Sequence
<220> FEATURE:
<223> OTHER INFORMATION: Synthetic

<400> SEQUENCE: 70

His Asn Arg Thr
1

<210> SEQ ID NO 71
<211> LENGTH: 4
<212> TYPE: PRT
<213> ORGANISM: Artificial Sequence
<220> FEATURE:
<223> OTHER INFORMATION: Synthetic

<400> SEQUENCE: 71

Ala Asn Leu Thr
1
```

```
<210> SEQ ID NO 72
<211> LENGTH: 4
<212> TYPE: PRT
<213> ORGANISM: Artificial Sequence
<220> FEATURE:
<223> OTHER INFORMATION: Synthetic

<400> SEQUENCE: 72

Trp Asn Arg Thr
1

<210> SEQ ID NO 73
<211> LENGTH: 4
<212> TYPE: PRT
<213> ORGANISM: Artificial Sequence
<220> FEATURE:
<223> OTHER INFORMATION: Synthetic

<400> SEQUENCE: 73

Ala Asn His Ser
1

<210> SEQ ID NO 74
<211> LENGTH: 4
<212> TYPE: PRT
<213> ORGANISM: Artificial Sequence
<220> FEATURE:
<223> OTHER INFORMATION: Synthetic

<400> SEQUENCE: 74

Ile Asn Val Thr
1

<210> SEQ ID NO 75
<211> LENGTH: 4
<212> TYPE: PRT
<213> ORGANISM: Artificial Sequence
<220> FEATURE:
<223> OTHER INFORMATION: Synthetic

<400> SEQUENCE: 75

Val Asn Ile Thr
1

<210> SEQ ID NO 76
<211> LENGTH: 4
<212> TYPE: PRT
<213> ORGANISM: Artificial Sequence
<220> FEATURE:
<223> OTHER INFORMATION: Synthetic

<400> SEQUENCE: 76

Asn Asn His Ser
1

<210> SEQ ID NO 77
<211> LENGTH: 4
<212> TYPE: PRT
<213> ORGANISM: Artificial Sequence
<220> FEATURE:
<223> OTHER INFORMATION: Synthetic

<400> SEQUENCE: 77

Ser Asn Arg Thr
1

<210> SEQ ID NO 78
```

```
<211> LENGTH: 4
<212> TYPE: PRT
<213> ORGANISM: Artificial Sequence
<220> FEATURE:
<223> OTHER INFORMATION: Synthetic

<400> SEQUENCE: 78

Met Asn His Ser
1

<210> SEQ ID NO 79
<211> LENGTH: 4
<212> TYPE: PRT
<213> ORGANISM: Artificial Sequence
<220> FEATURE:
<223> OTHER INFORMATION: Synthetic

<400> SEQUENCE: 79

Pro Asn Tyr Ser
1

<210> SEQ ID NO 80
<211> LENGTH: 4
<212> TYPE: PRT
<213> ORGANISM: Artificial Sequence
<220> FEATURE:
<223> OTHER INFORMATION: Synthetic

<400> SEQUENCE: 80

His Asn His Ser
1

<210> SEQ ID NO 81
<211> LENGTH: 4
<212> TYPE: PRT
<213> ORGANISM: Artificial Sequence
<220> FEATURE:
<223> OTHER INFORMATION: Synthetic

<400> SEQUENCE: 81

Met Asn Arg Thr
1

<210> SEQ ID NO 82
<211> LENGTH: 4
<212> TYPE: PRT
<213> ORGANISM: Artificial Sequence
<220> FEATURE:
<223> OTHER INFORMATION: Synthetic

<400> SEQUENCE: 82

Leu Asn Val Thr
1

<210> SEQ ID NO 83
<211> LENGTH: 4
<212> TYPE: PRT
<213> ORGANISM: Artificial Sequence
<220> FEATURE:
<223> OTHER INFORMATION: Synthetic

<400> SEQUENCE: 83

Glu Asn Val Ser
1

<210> SEQ ID NO 84
<211> LENGTH: 4
```

```
<212> TYPE: PRT
<213> ORGANISM: Artificial Sequence
<220> FEATURE:
<223> OTHER INFORMATION: Synthetic

<400> SEQUENCE: 84

Thr Asn Ser Thr
1

<210> SEQ ID NO 85
<211> LENGTH: 4
<212> TYPE: PRT
<213> ORGANISM: Artificial Sequence
<220> FEATURE:
<223> OTHER INFORMATION: Synthetic

<400> SEQUENCE: 85

Pro Asn Met Ser
1

<210> SEQ ID NO 86
<211> LENGTH: 4
<212> TYPE: PRT
<213> ORGANISM: Artificial Sequence
<220> FEATURE:
<223> OTHER INFORMATION: Synthetic

<400> SEQUENCE: 86

Ser Asn Tyr Thr
1

<210> SEQ ID NO 87
<211> LENGTH: 4
<212> TYPE: PRT
<213> ORGANISM: Artificial Sequence
<220> FEATURE:
<223> OTHER INFORMATION: Synthetic

<400> SEQUENCE: 87

Gly Asn Val Ser
1

<210> SEQ ID NO 88
<211> LENGTH: 4
<212> TYPE: PRT
<213> ORGANISM: Artificial Sequence
<220> FEATURE:
<223> OTHER INFORMATION: Synthetic

<400> SEQUENCE: 88

Glu Asn Ser Thr
1

<210> SEQ ID NO 89
<211> LENGTH: 4
<212> TYPE: PRT
<213> ORGANISM: Artificial Sequence
<220> FEATURE:
<223> OTHER INFORMATION: Synthetic

<400> SEQUENCE: 89

Ser Asn His Ser
1

<210> SEQ ID NO 90
<211> LENGTH: 4
<212> TYPE: PRT
```

```
<213> ORGANISM: Artificial Sequence
<220> FEATURE:
<223> OTHER INFORMATION: Synthetic

<400> SEQUENCE: 90

Met Asn Met Thr
1

<210> SEQ ID NO 91
<211> LENGTH: 4
<212> TYPE: PRT
<213> ORGANISM: Artificial Sequence
<220> FEATURE:
<223> OTHER INFORMATION: Synthetic

<400> SEQUENCE: 91

Met Asn Thr Thr
1

<210> SEQ ID NO 92
<211> LENGTH: 4
<212> TYPE: PRT
<213> ORGANISM: Artificial Sequence
<220> FEATURE:
<223> OTHER INFORMATION: Synthetic

<400> SEQUENCE: 92

Ser Asn Thr Thr
1

<210> SEQ ID NO 93
<211> LENGTH: 4
<212> TYPE: PRT
<213> ORGANISM: Artificial Sequence
<220> FEATURE:
<223> OTHER INFORMATION: Synthetic

<400> SEQUENCE: 93

Ala Asn Met Ser
1

<210> SEQ ID NO 94
<211> LENGTH: 4
<212> TYPE: PRT
<213> ORGANISM: Artificial Sequence
<220> FEATURE:
<223> OTHER INFORMATION: Synthetic

<400> SEQUENCE: 94

Leu Asn Ile Thr
1

<210> SEQ ID NO 95
<211> LENGTH: 4
<212> TYPE: PRT
<213> ORGANISM: Artificial Sequence
<220> FEATURE:
<223> OTHER INFORMATION: Synthetic

<400> SEQUENCE: 95

Met Asn Ile Ser
1

<210> SEQ ID NO 96
<211> LENGTH: 4
<212> TYPE: PRT
<213> ORGANISM: Artificial Sequence
```

```
<220> FEATURE:
<223> OTHER INFORMATION: Synthetic

<400> SEQUENCE: 96

Gly Asn Tyr Thr
1

<210> SEQ ID NO 97
<211> LENGTH: 4
<212> TYPE: PRT
<213> ORGANISM: Artificial Sequence
<220> FEATURE:
<223> OTHER INFORMATION: Synthetic

<400> SEQUENCE: 97

Ser Asn Ser Thr
1

<210> SEQ ID NO 98
<211> LENGTH: 4
<212> TYPE: PRT
<213> ORGANISM: Artificial Sequence
<220> FEATURE:
<223> OTHER INFORMATION: Synthetic

<400> SEQUENCE: 98

Thr Asn His Ser
1

<210> SEQ ID NO 99
<211> LENGTH: 4
<212> TYPE: PRT
<213> ORGANISM: Artificial Sequence
<220> FEATURE:
<223> OTHER INFORMATION: Synthetic

<400> SEQUENCE: 99

Asp Asn Val Thr
1

<210> SEQ ID NO 100
<211> LENGTH: 4
<212> TYPE: PRT
<213> ORGANISM: Artificial Sequence
<220> FEATURE:
<223> OTHER INFORMATION: Synthetic

<400> SEQUENCE: 100

Gln Asn Val Thr
1

<210> SEQ ID NO 101
<211> LENGTH: 4
<212> TYPE: PRT
<213> ORGANISM: Artificial Sequence
<220> FEATURE:
<223> OTHER INFORMATION: Synthetic

<400> SEQUENCE: 101

Val Asn Ile Ser
1

<210> SEQ ID NO 102
<211> LENGTH: 4
<212> TYPE: PRT
<213> ORGANISM: Artificial Sequence
<220> FEATURE:
```

<223> OTHER INFORMATION: Synthetic

<400> SEQUENCE: 102

Pro Asn Met Ser
1

<210> SEQ ID NO 103
<211> LENGTH: 4
<212> TYPE: PRT
<213> ORGANISM: Artificial Sequence
<220> FEATURE:
<223> OTHER INFORMATION: Synthetic

<400> SEQUENCE: 103

Pro Asn Tyr Ser
1

<210> SEQ ID NO 104
<211> LENGTH: 4
<212> TYPE: PRT
<213> ORGANISM: Artificial Sequence
<220> FEATURE:
<223> OTHER INFORMATION: Synthetic

<400> SEQUENCE: 104

Leu Asn Ile Ser
1

<210> SEQ ID NO 105
<211> LENGTH: 4
<212> TYPE: PRT
<213> ORGANISM: Artificial Sequence
<220> FEATURE:
<223> OTHER INFORMATION: Synthetic

<400> SEQUENCE: 105

Pro Asn Phe Ser
1

<210> SEQ ID NO 106
<211> LENGTH: 4
<212> TYPE: PRT
<213> ORGANISM: Artificial Sequence
<220> FEATURE:
<223> OTHER INFORMATION: Synthetic

<400> SEQUENCE: 106

Pro Asn Ile Ser
1

<210> SEQ ID NO 107
<211> LENGTH: 4
<212> TYPE: PRT
<213> ORGANISM: Artificial Sequence
<220> FEATURE:
<223> OTHER INFORMATION: Synthetic

<400> SEQUENCE: 107

Pro Asn Leu Ser
1

<210> SEQ ID NO 108
<211> LENGTH: 4
<212> TYPE: PRT
<213> ORGANISM: Artificial Sequence
<220> FEATURE:
<223> OTHER INFORMATION: Synthetic

<400> SEQUENCE: 108

Pro Asn Ile Thr
1

<210> SEQ ID NO 109
<211> LENGTH: 4
<212> TYPE: PRT
<213> ORGANISM: Artificial Sequence
<220> FEATURE:
<223> OTHER INFORMATION: Synthetic

<400> SEQUENCE: 109

Ser Asn Ile Ser
1

<210> SEQ ID NO 110
<211> LENGTH: 4
<212> TYPE: PRT
<213> ORGANISM: Artificial Sequence
<220> FEATURE:
<223> OTHER INFORMATION: Synthetic

<400> SEQUENCE: 110

Trp Asn Gly Ser
1

<210> SEQ ID NO 111
<211> LENGTH: 4
<212> TYPE: PRT
<213> ORGANISM: Artificial Sequence
<220> FEATURE:
<223> OTHER INFORMATION: Synthetic

<400> SEQUENCE: 111

Gly Asn Ile Ser
1

<210> SEQ ID NO 112
<211> LENGTH: 4
<212> TYPE: PRT
<213> ORGANISM: Artificial Sequence
<220> FEATURE:
<223> OTHER INFORMATION: Synthetic

<400> SEQUENCE: 112

Ala Asn Val Ser
1

<210> SEQ ID NO 113
<211> LENGTH: 4
<212> TYPE: PRT
<213> ORGANISM: Artificial Sequence
<220> FEATURE:
<223> OTHER INFORMATION: Synthetic

<400> SEQUENCE: 113

Gly Asn Val Ser
1

<210> SEQ ID NO 114
<211> LENGTH: 4
<212> TYPE: PRT
<213> ORGANISM: Artificial Sequence
<220> FEATURE:
<223> OTHER INFORMATION: Synthetic

```
<400> SEQUENCE: 114

Leu Asn Val Ser
1

<210> SEQ ID NO 115
<211> LENGTH: 4
<212> TYPE: PRT
<213> ORGANISM: Artificial Sequence
<220> FEATURE:
<223> OTHER INFORMATION: Synthetic

<400> SEQUENCE: 115

Pro Asn Val Ser
1

<210> SEQ ID NO 116
<211> LENGTH: 4
<212> TYPE: PRT
<213> ORGANISM: Artificial Sequence
<220> FEATURE:
<223> OTHER INFORMATION: Synthetic

<400> SEQUENCE: 116

Ile Asn Val Ser
1

<210> SEQ ID NO 117
<211> LENGTH: 4
<212> TYPE: PRT
<213> ORGANISM: Artificial Sequence
<220> FEATURE:
<223> OTHER INFORMATION: Synthetic

<400> SEQUENCE: 117

Thr Asn Ile Ser
1

<210> SEQ ID NO 118
<211> LENGTH: 4
<212> TYPE: PRT
<213> ORGANISM: Artificial Sequence
<220> FEATURE:
<223> OTHER INFORMATION: Synthetic

<400> SEQUENCE: 118

Tyr Asn Ala Thr
1

<210> SEQ ID NO 119
<211> LENGTH: 4
<212> TYPE: PRT
<213> ORGANISM: Artificial Sequence
<220> FEATURE:
<223> OTHER INFORMATION: Synthetic

<400> SEQUENCE: 119

Leu Asn His Ser
1

<210> SEQ ID NO 120
<211> LENGTH: 4
<212> TYPE: PRT
<213> ORGANISM: Artificial Sequence
<220> FEATURE:
<223> OTHER INFORMATION: Synthetic

<400> SEQUENCE: 120
```

Ala Asn Ile Thr
1

<210> SEQ ID NO 121
<211> LENGTH: 4
<212> TYPE: PRT
<213> ORGANISM: Artificial Sequence
<220> FEATURE:
<223> OTHER INFORMATION: Synthetic

<400> SEQUENCE: 121

Ser Asn Val Ser
1

<210> SEQ ID NO 122
<211> LENGTH: 4
<212> TYPE: PRT
<213> ORGANISM: Artificial Sequence
<220> FEATURE:
<223> OTHER INFORMATION: Synthetic

<400> SEQUENCE: 122

Val Asn Met Ser
1

<210> SEQ ID NO 123
<211> LENGTH: 4
<212> TYPE: PRT
<213> ORGANISM: Artificial Sequence
<220> FEATURE:
<223> OTHER INFORMATION: Synthetic

<400> SEQUENCE: 123

Pro Asn Tyr Thr
1

<210> SEQ ID NO 124
<211> LENGTH: 4
<212> TYPE: PRT
<213> ORGANISM: Artificial Sequence
<220> FEATURE:
<223> OTHER INFORMATION: Synthetic

<400> SEQUENCE: 124

Val Asn Val Ser
1

<210> SEQ ID NO 125
<211> LENGTH: 4
<212> TYPE: PRT
<213> ORGANISM: Artificial Sequence
<220> FEATURE:
<223> OTHER INFORMATION: Synthetic

<400> SEQUENCE: 125

Pro Asn Gly Ser
1

<210> SEQ ID NO 126
<211> LENGTH: 4
<212> TYPE: PRT
<213> ORGANISM: Artificial Sequence
<220> FEATURE:
<223> OTHER INFORMATION: Synthetic

<400> SEQUENCE: 126

Pro Asn Phe Thr
1

<210> SEQ ID NO 127
<211> LENGTH: 4
<212> TYPE: PRT
<213> ORGANISM: Artificial Sequence
<220> FEATURE:
<223> OTHER INFORMATION: Synthetic

<400> SEQUENCE: 127

Met Asn His Ser
1

<210> SEQ ID NO 128
<211> LENGTH: 4
<212> TYPE: PRT
<213> ORGANISM: Artificial Sequence
<220> FEATURE:
<223> OTHER INFORMATION: Synthetic

<400> SEQUENCE: 128

Ala Asn Ile Ser
1

<210> SEQ ID NO 129
<211> LENGTH: 4
<212> TYPE: PRT
<213> ORGANISM: Artificial Sequence
<220> FEATURE:
<223> OTHER INFORMATION: Synthetic

<400> SEQUENCE: 129

Met Asn Ile Ser
1

<210> SEQ ID NO 130
<211> LENGTH: 4
<212> TYPE: PRT
<213> ORGANISM: Artificial Sequence
<220> FEATURE:
<223> OTHER INFORMATION: Synthetic

<400> SEQUENCE: 130

Trp Asn Gly Thr
1

<210> SEQ ID NO 131
<211> LENGTH: 4
<212> TYPE: PRT
<213> ORGANISM: Artificial Sequence
<220> FEATURE:
<223> OTHER INFORMATION: Synthetic

<400> SEQUENCE: 131

Pro Asn Met Thr
1

<210> SEQ ID NO 132
<211> LENGTH: 4
<212> TYPE: PRT
<213> ORGANISM: Artificial Sequence
<220> FEATURE:
<223> OTHER INFORMATION: Synthetic

<400> SEQUENCE: 132

Ala Asn Met Ser

<210> SEQ ID NO 133
<211> LENGTH: 4
<212> TYPE: PRT
<213> ORGANISM: Artificial Sequence
<220> FEATURE:
<223> OTHER INFORMATION: Synthetic

<400> SEQUENCE: 133

Pro Asn Val Thr
1

<210> SEQ ID NO 134
<211> LENGTH: 4
<212> TYPE: PRT
<213> ORGANISM: Artificial Sequence
<220> FEATURE:
<223> OTHER INFORMATION: Synthetic

<400> SEQUENCE: 134

Pro Asn His Ser
1

<210> SEQ ID NO 135
<211> LENGTH: 4
<212> TYPE: PRT
<213> ORGANISM: Artificial Sequence
<220> FEATURE:
<223> OTHER INFORMATION: Synthetic

<400> SEQUENCE: 135

Met Asn Val Ser
1

<210> SEQ ID NO 136
<211> LENGTH: 4
<212> TYPE: PRT
<213> ORGANISM: Artificial Sequence
<220> FEATURE:
<223> OTHER INFORMATION: Synthetic

<400> SEQUENCE: 136

Asn Asn Ile Ser
1

<210> SEQ ID NO 137
<211> LENGTH: 4
<212> TYPE: PRT
<213> ORGANISM: Artificial Sequence
<220> FEATURE:
<223> OTHER INFORMATION: Synthetic

<400> SEQUENCE: 137

Ile Asn Ile Thr
1

<210> SEQ ID NO 138
<211> LENGTH: 4
<212> TYPE: PRT
<213> ORGANISM: Artificial Sequence
<220> FEATURE:
<223> OTHER INFORMATION: Synthetic

<400> SEQUENCE: 138

Val Asn Ile Thr
1

```
<210> SEQ ID NO 139
<211> LENGTH: 4
<212> TYPE: PRT
<213> ORGANISM: Artificial Sequence
<220> FEATURE:
<223> OTHER INFORMATION: Synthetic

<400> SEQUENCE: 139

Phe Asn Gly Ser
1

<210> SEQ ID NO 140
<211> LENGTH: 4
<212> TYPE: PRT
<213> ORGANISM: Artificial Sequence
<220> FEATURE:
<223> OTHER INFORMATION: Synthetic

<400> SEQUENCE: 140

Val Asn Tyr Ser
1

<210> SEQ ID NO 141
<211> LENGTH: 4
<212> TYPE: PRT
<213> ORGANISM: Artificial Sequence
<220> FEATURE:
<223> OTHER INFORMATION: Synthetic

<400> SEQUENCE: 141

Thr Asn Val Ser
1

<210> SEQ ID NO 142
<211> LENGTH: 4
<212> TYPE: PRT
<213> ORGANISM: Artificial Sequence
<220> FEATURE:
<223> OTHER INFORMATION: Synthetic

<400> SEQUENCE: 142

Gly Asn Ile Thr
1

<210> SEQ ID NO 143
<211> LENGTH: 4
<212> TYPE: PRT
<213> ORGANISM: Artificial Sequence
<220> FEATURE:
<223> OTHER INFORMATION: Synthetic

<400> SEQUENCE: 143

Val Asn Met Thr
1

<210> SEQ ID NO 144
<211> LENGTH: 4
<212> TYPE: PRT
<213> ORGANISM: Artificial Sequence
<220> FEATURE:
<223> OTHER INFORMATION: Synthetic

<400> SEQUENCE: 144

Ile Asn His Ser
1
```

```
<210> SEQ ID NO 145
<211> LENGTH: 4
<212> TYPE: PRT
<213> ORGANISM: Artificial Sequence
<220> FEATURE:
<223> OTHER INFORMATION: Synthetic

<400> SEQUENCE: 145

Leu Asn Ile Thr
1

<210> SEQ ID NO 146
<211> LENGTH: 4
<212> TYPE: PRT
<213> ORGANISM: Artificial Sequence
<220> FEATURE:
<223> OTHER INFORMATION: Synthetic

<400> SEQUENCE: 146

Ala Asn Val Thr
1

<210> SEQ ID NO 147
<211> LENGTH: 4
<212> TYPE: PRT
<213> ORGANISM: Artificial Sequence
<220> FEATURE:
<223> OTHER INFORMATION: Synthetic

<400> SEQUENCE: 147

Ala Asn Phe Ser
1

<210> SEQ ID NO 148
<211> LENGTH: 4
<212> TYPE: PRT
<213> ORGANISM: Artificial Sequence
<220> FEATURE:
<223> OTHER INFORMATION: Synthetic

<400> SEQUENCE: 148

Val Asn Leu Ser
1

<210> SEQ ID NO 149
<211> LENGTH: 4
<212> TYPE: PRT
<213> ORGANISM: Artificial Sequence
<220> FEATURE:
<223> OTHER INFORMATION: Synthetic

<400> SEQUENCE: 149

Leu Asn Phe Ser
1

<210> SEQ ID NO 150
<211> LENGTH: 4
<212> TYPE: PRT
<213> ORGANISM: Artificial Sequence
<220> FEATURE:
<223> OTHER INFORMATION: Synthetic

<400> SEQUENCE: 150

Pro Asn Trp Ser
1
```

```
<210> SEQ ID NO 151
<211> LENGTH: 4
<212> TYPE: PRT
<213> ORGANISM: Artificial Sequence
<220> FEATURE:
<223> OTHER INFORMATION: Synthetic

<400> SEQUENCE: 151

Ala Asn Gly Ser
1

<210> SEQ ID NO 152
<211> LENGTH: 4
<212> TYPE: PRT
<213> ORGANISM: Artificial Sequence
<220> FEATURE:
<223> OTHER INFORMATION: Synthetic

<400> SEQUENCE: 152

Val Asn Phe Ser
1

<210> SEQ ID NO 153
<211> LENGTH: 4
<212> TYPE: PRT
<213> ORGANISM: Artificial Sequence
<220> FEATURE:
<223> OTHER INFORMATION: Synthetic

<400> SEQUENCE: 153

Ala Asn Tyr Ser
1

<210> SEQ ID NO 154
<211> LENGTH: 4
<212> TYPE: PRT
<213> ORGANISM: Artificial Sequence
<220> FEATURE:
<223> OTHER INFORMATION: Synthetic

<400> SEQUENCE: 154

Pro Asn Leu Thr
1

<210> SEQ ID NO 155
<211> LENGTH: 4
<212> TYPE: PRT
<213> ORGANISM: Artificial Sequence
<220> FEATURE:
<223> OTHER INFORMATION: Synthetic

<400> SEQUENCE: 155

Leu Asn Val Thr
1

<210> SEQ ID NO 156
<211> LENGTH: 4
<212> TYPE: PRT
<213> ORGANISM: Artificial Sequence
<220> FEATURE:
<223> OTHER INFORMATION: Synthetic

<400> SEQUENCE: 156

Val Asn Val Thr
1

<210> SEQ ID NO 157
```

```
<211> LENGTH: 4
<212> TYPE: PRT
<213> ORGANISM: Artificial Sequence
<220> FEATURE:
<223> OTHER INFORMATION: Synthetic

<400> SEQUENCE: 157

Tyr Asn Gly Ser
1

<210> SEQ ID NO 158
<211> LENGTH: 4
<212> TYPE: PRT
<213> ORGANISM: Artificial Sequence
<220> FEATURE:
<223> OTHER INFORMATION: Synthetic

<400> SEQUENCE: 158

Ala Asn Leu Ser
1

<210> SEQ ID NO 159
<211> LENGTH: 4
<212> TYPE: PRT
<213> ORGANISM: Artificial Sequence
<220> FEATURE:
<223> OTHER INFORMATION: Synthetic

<400> SEQUENCE: 159

Ile Asn Ile Ser
1

<210> SEQ ID NO 160
<211> LENGTH: 4
<212> TYPE: PRT
<213> ORGANISM: Artificial Sequence
<220> FEATURE:
<223> OTHER INFORMATION: Synthetic

<400> SEQUENCE: 160

Gly Asn Val Thr
1

<210> SEQ ID NO 161
<211> LENGTH: 4
<212> TYPE: PRT
<213> ORGANISM: Artificial Sequence
<220> FEATURE:
<223> OTHER INFORMATION: Synthetic

<400> SEQUENCE: 161

Phe Asn His Ser
1

<210> SEQ ID NO 162
<211> LENGTH: 4
<212> TYPE: PRT
<213> ORGANISM: Artificial Sequence
<220> FEATURE:
<223> OTHER INFORMATION: Synthetic

<400> SEQUENCE: 162

Pro Asn Arg Ser
1

<210> SEQ ID NO 163
<211> LENGTH: 4
```

```
<212> TYPE: PRT
<213> ORGANISM: Artificial Sequence
<220> FEATURE:
<223> OTHER INFORMATION: Synthetic

<400> SEQUENCE: 163

Thr Asn Ile Thr
1

<210> SEQ ID NO 164
<211> LENGTH: 4
<212> TYPE: PRT
<213> ORGANISM: Artificial Sequence
<220> FEATURE:
<223> OTHER INFORMATION: Synthetic

<400> SEQUENCE: 164

Ser Asn Met Ser
1

<210> SEQ ID NO 165
<211> LENGTH: 4
<212> TYPE: PRT
<213> ORGANISM: Artificial Sequence
<220> FEATURE:
<223> OTHER INFORMATION: Synthetic

<400> SEQUENCE: 165

Gly Asn Leu Ser
1

<210> SEQ ID NO 166
<211> LENGTH: 4
<212> TYPE: PRT
<213> ORGANISM: Artificial Sequence
<220> FEATURE:
<223> OTHER INFORMATION: Synthetic

<400> SEQUENCE: 166

Asn Asn Ile Thr
1

<210> SEQ ID NO 167
<211> LENGTH: 4
<212> TYPE: PRT
<213> ORGANISM: Artificial Sequence
<220> FEATURE:
<223> OTHER INFORMATION: Synthetic

<400> SEQUENCE: 167

Ser Asn Ile Thr
1

<210> SEQ ID NO 168
<211> LENGTH: 4
<212> TYPE: PRT
<213> ORGANISM: Artificial Sequence
<220> FEATURE:
<223> OTHER INFORMATION: Synthetic

<400> SEQUENCE: 168

Thr Asn Met Ser
1

<210> SEQ ID NO 169
<211> LENGTH: 4
<212> TYPE: PRT
```

```
<213> ORGANISM: Artificial Sequence
<220> FEATURE:
<223> OTHER INFORMATION: Synthetic

<400> SEQUENCE: 169

Ala Asn His Ser
1

<210> SEQ ID NO 170
<211> LENGTH: 4
<212> TYPE: PRT
<213> ORGANISM: Artificial Sequence
<220> FEATURE:
<223> OTHER INFORMATION: Synthetic

<400> SEQUENCE: 170

Pro Asn Arg Thr
1

<210> SEQ ID NO 171
<211> LENGTH: 4
<212> TYPE: PRT
<213> ORGANISM: Artificial Sequence
<220> FEATURE:
<223> OTHER INFORMATION: Synthetic

<400> SEQUENCE: 171

Met Asn Ile Thr
1

<210> SEQ ID NO 172
<211> LENGTH: 4
<212> TYPE: PRT
<213> ORGANISM: Artificial Sequence
<220> FEATURE:
<223> OTHER INFORMATION: Synthetic

<400> SEQUENCE: 172

Ser Asn Val Thr
1

<210> SEQ ID NO 173
<211> LENGTH: 4
<212> TYPE: PRT
<213> ORGANISM: Artificial Sequence
<220> FEATURE:
<223> OTHER INFORMATION: Synthetic

<400> SEQUENCE: 173

Leu Asn Met Ser
1

<210> SEQ ID NO 174
<211> LENGTH: 4
<212> TYPE: PRT
<213> ORGANISM: Artificial Sequence
<220> FEATURE:
<223> OTHER INFORMATION: Synthetic

<400> SEQUENCE: 174

Pro Asn His Thr
1

<210> SEQ ID NO 175
<211> LENGTH: 4
<212> TYPE: PRT
<213> ORGANISM: Artificial Sequence
```

```
<220> FEATURE:
<223> OTHER INFORMATION: Synthetic

<400> SEQUENCE: 175

Ile Asn Val Thr
1

<210> SEQ ID NO 176
<211> LENGTH: 4
<212> TYPE: PRT
<213> ORGANISM: Artificial Sequence
<220> FEATURE:
<223> OTHER INFORMATION: Synthetic

<400> SEQUENCE: 176

Val Asn His Ser
1

<210> SEQ ID NO 177
<211> LENGTH: 4
<212> TYPE: PRT
<213> ORGANISM: Artificial Sequence
<220> FEATURE:
<223> OTHER INFORMATION: Synthetic

<400> SEQUENCE: 177

Asn Asn Val Ser
1

<210> SEQ ID NO 178
<211> LENGTH: 4
<212> TYPE: PRT
<213> ORGANISM: Artificial Sequence
<220> FEATURE:
<223> OTHER INFORMATION: Synthetic

<400> SEQUENCE: 178

Leu Asn Tyr Ser
1

<210> SEQ ID NO 179
<211> LENGTH: 4
<212> TYPE: PRT
<213> ORGANISM: Artificial Sequence
<220> FEATURE:
<223> OTHER INFORMATION: Synthetic

<400> SEQUENCE: 179

Val Asn Leu Thr
1

<210> SEQ ID NO 180
<211> LENGTH: 4
<212> TYPE: PRT
<213> ORGANISM: Artificial Sequence
<220> FEATURE:
<223> OTHER INFORMATION: Synthetic

<400> SEQUENCE: 180

Leu Asn His Thr
1

<210> SEQ ID NO 181
<211> LENGTH: 4
<212> TYPE: PRT
<213> ORGANISM: Artificial Sequence
<220> FEATURE:
```

```
<223> OTHER INFORMATION: Synthetic

<400> SEQUENCE: 181

Ala Asn Met Thr
 1

<210> SEQ ID NO 182
<211> LENGTH: 4
<212> TYPE: PRT
<213> ORGANISM: Artificial Sequence
<220> FEATURE:
<223> OTHER INFORMATION: Synthetic

<400> SEQUENCE: 182

Gly Asn His Ser
 1

<210> SEQ ID NO 183
<211> LENGTH: 4
<212> TYPE: PRT
<213> ORGANISM: Artificial Sequence
<220> FEATURE:
<223> OTHER INFORMATION: Synthetic

<400> SEQUENCE: 183

Phe Asn Gly Thr
 1

<210> SEQ ID NO 184
<211> LENGTH: 4
<212> TYPE: PRT
<213> ORGANISM: Artificial Sequence
<220> FEATURE:
<223> OTHER INFORMATION: Synthetic

<400> SEQUENCE: 184

Pro Asn Gly Thr
 1

<210> SEQ ID NO 185
<211> LENGTH: 4
<212> TYPE: PRT
<213> ORGANISM: Artificial Sequence
<220> FEATURE:
<223> OTHER INFORMATION: Synthetic

<400> SEQUENCE: 185

Ser Asn Tyr Ser
 1

<210> SEQ ID NO 186
<211> LENGTH: 4
<212> TYPE: PRT
<213> ORGANISM: Artificial Sequence
<220> FEATURE:
<223> OTHER INFORMATION: Synthetic

<400> SEQUENCE: 186

Leu Asn Ala Thr
 1

<210> SEQ ID NO 187
<211> LENGTH: 4
<212> TYPE: PRT
<213> ORGANISM: Artificial Sequence
<220> FEATURE:
<223> OTHER INFORMATION: Synthetic
```

```
<400> SEQUENCE: 187

Pro Asn Ala Thr
1

<210> SEQ ID NO 188
<211> LENGTH: 4
<212> TYPE: PRT
<213> ORGANISM: Artificial Sequence
<220> FEATURE:
<223> OTHER INFORMATION: Synthetic

<400> SEQUENCE: 188

Pro Asn Ala Ser
1

<210> SEQ ID NO 189
<211> LENGTH: 4
<212> TYPE: PRT
<213> ORGANISM: Artificial Sequence
<220> FEATURE:
<223> OTHER INFORMATION: Synthetic

<400> SEQUENCE: 189

Ser Asn Gly Ser
1

<210> SEQ ID NO 190
<211> LENGTH: 4
<212> TYPE: PRT
<213> ORGANISM: Artificial Sequence
<220> FEATURE:
<223> OTHER INFORMATION: Synthetic

<400> SEQUENCE: 190

Tyr Asn Gly Thr
1

<210> SEQ ID NO 191
<211> LENGTH: 4
<212> TYPE: PRT
<213> ORGANISM: Artificial Sequence
<220> FEATURE:
<223> OTHER INFORMATION: Synthetic

<400> SEQUENCE: 191

Met Asn His Thr
1

<210> SEQ ID NO 192
<211> LENGTH: 4
<212> TYPE: PRT
<213> ORGANISM: Artificial Sequence
<220> FEATURE:
<223> OTHER INFORMATION: Synthetic

<400> SEQUENCE: 192

Gly Asn Met Ser
1

<210> SEQ ID NO 193
<211> LENGTH: 4
<212> TYPE: PRT
<213> ORGANISM: Artificial Sequence
<220> FEATURE:
<223> OTHER INFORMATION: Synthetic
```

```
<400> SEQUENCE: 193

Val Asn Ala Thr
1

<210> SEQ ID NO 194
<211> LENGTH: 4
<212> TYPE: PRT
<213> ORGANISM: Artificial Sequence
<220> FEATURE:
<223> OTHER INFORMATION: Synthetic

<400> SEQUENCE: 194

Val Asn Phe Thr
1

<210> SEQ ID NO 195
<211> LENGTH: 4
<212> TYPE: PRT
<213> ORGANISM: Artificial Sequence
<220> FEATURE:
<223> OTHER INFORMATION: Synthetic

<400> SEQUENCE: 195

Phe Asn His Thr
1

<210> SEQ ID NO 196
<211> LENGTH: 4
<212> TYPE: PRT
<213> ORGANISM: Artificial Sequence
<220> FEATURE:
<223> OTHER INFORMATION: Synthetic

<400> SEQUENCE: 196

Ala Asn Arg Ser
1

<210> SEQ ID NO 197
<211> LENGTH: 4
<212> TYPE: PRT
<213> ORGANISM: Artificial Sequence
<220> FEATURE:
<223> OTHER INFORMATION: Synthetic

<400> SEQUENCE: 197

Leu Asn Tyr Thr
1

<210> SEQ ID NO 198
<211> LENGTH: 4
<212> TYPE: PRT
<213> ORGANISM: Artificial Sequence
<220> FEATURE:
<223> OTHER INFORMATION: Synthetic

<400> SEQUENCE: 198

Thr Asn Val Thr
1

<210> SEQ ID NO 199
<211> LENGTH: 4
<212> TYPE: PRT
<213> ORGANISM: Artificial Sequence
<220> FEATURE:
<223> OTHER INFORMATION: Synthetic

<400> SEQUENCE: 199
```

Gly Asn Tyr Ser
1

<210> SEQ ID NO 200
<211> LENGTH: 4
<212> TYPE: PRT
<213> ORGANISM: Artificial Sequence
<220> FEATURE:
<223> OTHER INFORMATION: Synthetic

<400> SEQUENCE: 200

Gly Asn Phe Ser
1

<210> SEQ ID NO 201
<211> LENGTH: 4
<212> TYPE: PRT
<213> ORGANISM: Artificial Sequence
<220> FEATURE:
<223> OTHER INFORMATION: Synthetic

<400> SEQUENCE: 201

Ala Asn Val Thr
1

<210> SEQ ID NO 202
<211> LENGTH: 4
<212> TYPE: PRT
<213> ORGANISM: Artificial Sequence
<220> FEATURE:
<223> OTHER INFORMATION: Synthetic

<400> SEQUENCE: 202

Pro Asn Val Thr
1

<210> SEQ ID NO 203
<211> LENGTH: 4
<212> TYPE: PRT
<213> ORGANISM: Artificial Sequence
<220> FEATURE:
<223> OTHER INFORMATION: Synthetic

<400> SEQUENCE: 203

Ala Asn Ile Thr
1

<210> SEQ ID NO 204
<211> LENGTH: 4
<212> TYPE: PRT
<213> ORGANISM: Artificial Sequence
<220> FEATURE:
<223> OTHER INFORMATION: Synthetic

<400> SEQUENCE: 204

Pro Asn Ile Thr
1

<210> SEQ ID NO 205
<211> LENGTH: 4
<212> TYPE: PRT
<213> ORGANISM: Artificial Sequence
<220> FEATURE:
<223> OTHER INFORMATION: Synthetic

<400> SEQUENCE: 205

```
Ser Asn Val Thr
1

<210> SEQ ID NO 206
<211> LENGTH: 4
<212> TYPE: PRT
<213> ORGANISM: Artificial Sequence
<220> FEATURE:
<223> OTHER INFORMATION: Synthetic

<400> SEQUENCE: 206

Pro Asn Ala Thr
1

<210> SEQ ID NO 207
<211> LENGTH: 4
<212> TYPE: PRT
<213> ORGANISM: Artificial Sequence
<220> FEATURE:
<223> OTHER INFORMATION: Synthetic

<400> SEQUENCE: 207

Ala Asn Ala Thr
1

<210> SEQ ID NO 208
<211> LENGTH: 4
<212> TYPE: PRT
<213> ORGANISM: Artificial Sequence
<220> FEATURE:
<223> OTHER INFORMATION: Synthetic

<400> SEQUENCE: 208

Pro Asn Thr Thr
1

<210> SEQ ID NO 209
<211> LENGTH: 4
<212> TYPE: PRT
<213> ORGANISM: Artificial Sequence
<220> FEATURE:
<223> OTHER INFORMATION: Synthetic

<400> SEQUENCE: 209

Pro Asn Met Thr
1

<210> SEQ ID NO 210
<211> LENGTH: 4
<212> TYPE: PRT
<213> ORGANISM: Artificial Sequence
<220> FEATURE:
<223> OTHER INFORMATION: Synthetic

<400> SEQUENCE: 210

Ala Asn His Thr
1

<210> SEQ ID NO 211
<211> LENGTH: 4
<212> TYPE: PRT
<213> ORGANISM: Artificial Sequence
<220> FEATURE:
<223> OTHER INFORMATION: Synthetic

<400> SEQUENCE: 211

Gly Asn Trp Thr
```

<210> SEQ ID NO 212
<211> LENGTH: 4
<212> TYPE: PRT
<213> ORGANISM: Artificial Sequence
<220> FEATURE:
<223> OTHER INFORMATION: Synthetic

<400> SEQUENCE: 212

Pro Asn Ser Thr
1

<210> SEQ ID NO 213
<211> LENGTH: 4
<212> TYPE: PRT
<213> ORGANISM: Artificial Sequence
<220> FEATURE:
<223> OTHER INFORMATION: Synthetic

<400> SEQUENCE: 213

Asn Asn Val Thr
1

<210> SEQ ID NO 214
<211> LENGTH: 4
<212> TYPE: PRT
<213> ORGANISM: Artificial Sequence
<220> FEATURE:
<223> OTHER INFORMATION: Synthetic

<400> SEQUENCE: 214

Ala Asn Ser Thr
1

<210> SEQ ID NO 215
<211> LENGTH: 4
<212> TYPE: PRT
<213> ORGANISM: Artificial Sequence
<220> FEATURE:
<223> OTHER INFORMATION: Synthetic

<400> SEQUENCE: 215

Pro Asn Tyr Thr
1

<210> SEQ ID NO 216
<211> LENGTH: 4
<212> TYPE: PRT
<213> ORGANISM: Artificial Sequence
<220> FEATURE:
<223> OTHER INFORMATION: Synthetic

<400> SEQUENCE: 216

Asn Asn Ala Thr
1

<210> SEQ ID NO 217
<211> LENGTH: 4
<212> TYPE: PRT
<213> ORGANISM: Artificial Sequence
<220> FEATURE:
<223> OTHER INFORMATION: Synthetic

<400> SEQUENCE: 217

Ala Asn Thr Thr
1

<210> SEQ ID NO 218
<211> LENGTH: 4
<212> TYPE: PRT
<213> ORGANISM: Artificial Sequence
<220> FEATURE:
<223> OTHER INFORMATION: Synthetic

<400> SEQUENCE: 218

Ser Asn His Thr
1

<210> SEQ ID NO 219
<211> LENGTH: 4
<212> TYPE: PRT
<213> ORGANISM: Artificial Sequence
<220> FEATURE:
<223> OTHER INFORMATION: Synthetic

<400> SEQUENCE: 219

Ala Asn Tyr Thr
1

<210> SEQ ID NO 220
<211> LENGTH: 4
<212> TYPE: PRT
<213> ORGANISM: Artificial Sequence
<220> FEATURE:
<223> OTHER INFORMATION: Synthetic

<400> SEQUENCE: 220

Ala Asn Val Ser
1

<210> SEQ ID NO 221
<211> LENGTH: 4
<212> TYPE: PRT
<213> ORGANISM: Artificial Sequence
<220> FEATURE:
<223> OTHER INFORMATION: Synthetic

<400> SEQUENCE: 221

Ala Asn Met Thr
1

<210> SEQ ID NO 222
<211> LENGTH: 4
<212> TYPE: PRT
<213> ORGANISM: Artificial Sequence
<220> FEATURE:
<223> OTHER INFORMATION: Synthetic

<400> SEQUENCE: 222

Thr Asn Val Thr
1

<210> SEQ ID NO 223
<211> LENGTH: 4
<212> TYPE: PRT
<213> ORGANISM: Artificial Sequence
<220> FEATURE:
<223> OTHER INFORMATION: Synthetic

<400> SEQUENCE: 223

Pro Asn Leu Thr
1

```
<210> SEQ ID NO 224
<211> LENGTH: 4
<212> TYPE: PRT
<213> ORGANISM: Artificial Sequence
<220> FEATURE:
<223> OTHER INFORMATION: Synthetic

<400> SEQUENCE: 224

Pro Asn His Thr
1

<210> SEQ ID NO 225
<211> LENGTH: 4
<212> TYPE: PRT
<213> ORGANISM: Artificial Sequence
<220> FEATURE:
<223> OTHER INFORMATION: Synthetic

<400> SEQUENCE: 225

Pro Asn Phe Thr
1

<210> SEQ ID NO 226
<211> LENGTH: 4
<212> TYPE: PRT
<213> ORGANISM: Artificial Sequence
<220> FEATURE:
<223> OTHER INFORMATION: Synthetic

<400> SEQUENCE: 226

Thr Asn His Thr
1

<210> SEQ ID NO 227
<211> LENGTH: 4
<212> TYPE: PRT
<213> ORGANISM: Artificial Sequence
<220> FEATURE:
<223> OTHER INFORMATION: Synthetic

<400> SEQUENCE: 227

Ser Asn Ala Thr
1

<210> SEQ ID NO 228
<211> LENGTH: 4
<212> TYPE: PRT
<213> ORGANISM: Artificial Sequence
<220> FEATURE:
<223> OTHER INFORMATION: Synthetic

<400> SEQUENCE: 228

Pro Asn Arg Thr
1

<210> SEQ ID NO 229
<211> LENGTH: 4
<212> TYPE: PRT
<213> ORGANISM: Artificial Sequence
<220> FEATURE:
<223> OTHER INFORMATION: Synthetic

<400> SEQUENCE: 229

Ala Asn Phe Thr
1
```

```
<210> SEQ ID NO 230
<211> LENGTH: 4
<212> TYPE: PRT
<213> ORGANISM: Artificial Sequence
<220> FEATURE:
<223> OTHER INFORMATION: Synthetic

<400> SEQUENCE: 230

Pro Asn Val Ser
1

<210> SEQ ID NO 231
<211> LENGTH: 4
<212> TYPE: PRT
<213> ORGANISM: Artificial Sequence
<220> FEATURE:
<223> OTHER INFORMATION: Synthetic

<400> SEQUENCE: 231

Pro Asn Ile Ser
1

<210> SEQ ID NO 232
<211> LENGTH: 4
<212> TYPE: PRT
<213> ORGANISM: Artificial Sequence
<220> FEATURE:
<223> OTHER INFORMATION: Synthetic

<400> SEQUENCE: 232

Ala Asn Leu Thr
1

<210> SEQ ID NO 233
<211> LENGTH: 4
<212> TYPE: PRT
<213> ORGANISM: Artificial Sequence
<220> FEATURE:
<223> OTHER INFORMATION: Synthetic

<400> SEQUENCE: 233

Asn Asn His Thr
1

<210> SEQ ID NO 234
<211> LENGTH: 4
<212> TYPE: PRT
<213> ORGANISM: Artificial Sequence
<220> FEATURE:
<223> OTHER INFORMATION: Synthetic

<400> SEQUENCE: 234

Ser Asn Ile Thr
1

<210> SEQ ID NO 235
<211> LENGTH: 4
<212> TYPE: PRT
<213> ORGANISM: Artificial Sequence
<220> FEATURE:
<223> OTHER INFORMATION: Synthetic

<400> SEQUENCE: 235

Ala Asn Arg Thr
1

<210> SEQ ID NO 236
```

```
<211> LENGTH: 4
<212> TYPE: PRT
<213> ORGANISM: Artificial Sequence
<220> FEATURE:
<223> OTHER INFORMATION: Synthetic

<400> SEQUENCE: 236

Trp Asn His Thr
1

<210> SEQ ID NO 237
<211> LENGTH: 4
<212> TYPE: PRT
<213> ORGANISM: Artificial Sequence
<220> FEATURE:
<223> OTHER INFORMATION: Synthetic

<400> SEQUENCE: 237

His Asn Val Thr
1

<210> SEQ ID NO 238
<211> LENGTH: 4
<212> TYPE: PRT
<213> ORGANISM: Artificial Sequence
<220> FEATURE:
<223> OTHER INFORMATION: Synthetic

<400> SEQUENCE: 238

Gly Asn Val Thr
1

<210> SEQ ID NO 239
<211> LENGTH: 4
<212> TYPE: PRT
<213> ORGANISM: Artificial Sequence
<220> FEATURE:
<223> OTHER INFORMATION: Synthetic

<400> SEQUENCE: 239

Trp Asn Ala Thr
1

<210> SEQ ID NO 240
<211> LENGTH: 4
<212> TYPE: PRT
<213> ORGANISM: Artificial Sequence
<220> FEATURE:
<223> OTHER INFORMATION: Synthetic

<400> SEQUENCE: 240

His Asn His Thr
1

<210> SEQ ID NO 241
<211> LENGTH: 4
<212> TYPE: PRT
<213> ORGANISM: Artificial Sequence
<220> FEATURE:
<223> OTHER INFORMATION: Synthetic

<400> SEQUENCE: 241

Ser Asn Val Ser
1

<210> SEQ ID NO 242
<211> LENGTH: 4
```

```
<212> TYPE: PRT
<213> ORGANISM: Artificial Sequence
<220> FEATURE:
<223> OTHER INFORMATION: Synthetic

<400> SEQUENCE: 242

Trp Asn Val Thr
1

<210> SEQ ID NO 243
<211> LENGTH: 4
<212> TYPE: PRT
<213> ORGANISM: Artificial Sequence
<220> FEATURE:
<223> OTHER INFORMATION: Synthetic

<400> SEQUENCE: 243

Val Asn Val Thr
1

<210> SEQ ID NO 244
<211> LENGTH: 4
<212> TYPE: PRT
<213> ORGANISM: Artificial Sequence
<220> FEATURE:
<223> OTHER INFORMATION: Synthetic

<400> SEQUENCE: 244

Val Asn Ala Thr
1

<210> SEQ ID NO 245
<211> LENGTH: 4
<212> TYPE: PRT
<213> ORGANISM: Artificial Sequence
<220> FEATURE:
<223> OTHER INFORMATION: Synthetic

<400> SEQUENCE: 245

Thr Asn Ala Thr
1

<210> SEQ ID NO 246
<211> LENGTH: 4
<212> TYPE: PRT
<213> ORGANISM: Artificial Sequence
<220> FEATURE:
<223> OTHER INFORMATION: Synthetic

<400> SEQUENCE: 246

Thr Asn Ser Thr
1

<210> SEQ ID NO 247
<211> LENGTH: 4
<212> TYPE: PRT
<213> ORGANISM: Artificial Sequence
<220> FEATURE:
<223> OTHER INFORMATION: Synthetic

<400> SEQUENCE: 247

Ala Asn His Ser
1

<210> SEQ ID NO 248
<211> LENGTH: 4
<212> TYPE: PRT
```

```
<213> ORGANISM: Artificial Sequence
<220> FEATURE:
<223> OTHER INFORMATION: Synthetic

<400> SEQUENCE: 248

Val Asn Ile Thr
1

<210> SEQ ID NO 249
<211> LENGTH: 4
<212> TYPE: PRT
<213> ORGANISM: Artificial Sequence
<220> FEATURE:
<223> OTHER INFORMATION: Synthetic

<400> SEQUENCE: 249

Ala Asn Ile Ser
1

<210> SEQ ID NO 250
<211> LENGTH: 4
<212> TYPE: PRT
<213> ORGANISM: Artificial Sequence
<220> FEATURE:
<223> OTHER INFORMATION: Synthetic

<400> SEQUENCE: 250

Gly Asn His Thr
1

<210> SEQ ID NO 251
<211> LENGTH: 4
<212> TYPE: PRT
<213> ORGANISM: Artificial Sequence
<220> FEATURE:
<223> OTHER INFORMATION: Synthetic

<400> SEQUENCE: 251

Asn Asn Arg Thr
1

<210> SEQ ID NO 252
<211> LENGTH: 4
<212> TYPE: PRT
<213> ORGANISM: Artificial Sequence
<220> FEATURE:
<223> OTHER INFORMATION: Synthetic

<400> SEQUENCE: 252

Asn Asn Thr Thr
1

<210> SEQ ID NO 253
<211> LENGTH: 4
<212> TYPE: PRT
<213> ORGANISM: Artificial Sequence
<220> FEATURE:
<223> OTHER INFORMATION: Synthetic

<400> SEQUENCE: 253

Ser Asn Thr Thr
1

<210> SEQ ID NO 254
<211> LENGTH: 4
<212> TYPE: PRT
<213> ORGANISM: Artificial Sequence
```

```
<220> FEATURE:
<223> OTHER INFORMATION: Synthetic

<400> SEQUENCE: 254

Met Asn Val Thr
1

<210> SEQ ID NO 255
<211> LENGTH: 4
<212> TYPE: PRT
<213> ORGANISM: Artificial Sequence
<220> FEATURE:
<223> OTHER INFORMATION: Synthetic

<400> SEQUENCE: 255

Ser Asn Ser Thr
1

<210> SEQ ID NO 256
<211> LENGTH: 4
<212> TYPE: PRT
<213> ORGANISM: Artificial Sequence
<220> FEATURE:
<223> OTHER INFORMATION: Synthetic

<400> SEQUENCE: 256

Val Asn Met Thr
1

<210> SEQ ID NO 257
<211> LENGTH: 4
<212> TYPE: PRT
<213> ORGANISM: Artificial Sequence
<220> FEATURE:
<223> OTHER INFORMATION: Synthetic

<400> SEQUENCE: 257

Thr Asn Ile Thr
1

<210> SEQ ID NO 258
<211> LENGTH: 4
<212> TYPE: PRT
<213> ORGANISM: Artificial Sequence
<220> FEATURE:
<223> OTHER INFORMATION: Synthetic

<400> SEQUENCE: 258

Asn Asn Ser Thr
1

<210> SEQ ID NO 259
<211> LENGTH: 4
<212> TYPE: PRT
<213> ORGANISM: Artificial Sequence
<220> FEATURE:
<223> OTHER INFORMATION: Synthetic

<400> SEQUENCE: 259

Met Asn Ile Thr
1

<210> SEQ ID NO 260
<211> LENGTH: 4
<212> TYPE: PRT
<213> ORGANISM: Artificial Sequence
<220> FEATURE:
```

<223> OTHER INFORMATION: Synthetic

<400> SEQUENCE: 260

Trp Asn Arg Thr
1

<210> SEQ ID NO 261
<211> LENGTH: 4
<212> TYPE: PRT
<213> ORGANISM: Artificial Sequence
<220> FEATURE:
<223> OTHER INFORMATION: Synthetic

<400> SEQUENCE: 261

Ser Asn Arg Thr
1

<210> SEQ ID NO 262
<211> LENGTH: 4
<212> TYPE: PRT
<213> ORGANISM: Artificial Sequence
<220> FEATURE:
<223> OTHER INFORMATION: Synthetic

<400> SEQUENCE: 262

Gly Asn Ile Thr
1

<210> SEQ ID NO 263
<211> LENGTH: 4
<212> TYPE: PRT
<213> ORGANISM: Artificial Sequence
<220> FEATURE:
<223> OTHER INFORMATION: Synthetic

<400> SEQUENCE: 263

Met Asn His Thr
1

<210> SEQ ID NO 264
<211> LENGTH: 4
<212> TYPE: PRT
<213> ORGANISM: Artificial Sequence
<220> FEATURE:
<223> OTHER INFORMATION: Synthetic

<400> SEQUENCE: 264

His Asn Ala Thr
1

<210> SEQ ID NO 265
<211> LENGTH: 4
<212> TYPE: PRT
<213> ORGANISM: Artificial Sequence
<220> FEATURE:
<223> OTHER INFORMATION: Synthetic

<400> SEQUENCE: 265

Ser Asn Met Thr
1

<210> SEQ ID NO 266
<211> LENGTH: 4
<212> TYPE: PRT
<213> ORGANISM: Artificial Sequence
<220> FEATURE:
<223> OTHER INFORMATION: Synthetic

<400> SEQUENCE: 266

Pro Asn His Ser
1

<210> SEQ ID NO 267
<211> LENGTH: 4
<212> TYPE: PRT
<213> ORGANISM: Artificial Sequence
<220> FEATURE:
<223> OTHER INFORMATION: Synthetic

<400> SEQUENCE: 267

Ser Asn Tyr Thr
1

<210> SEQ ID NO 268
<211> LENGTH: 4
<212> TYPE: PRT
<213> ORGANISM: Artificial Sequence
<220> FEATURE:
<223> OTHER INFORMATION: Synthetic

<400> SEQUENCE: 268

Ala Asn Gly Thr
1

<210> SEQ ID NO 269
<211> LENGTH: 4
<212> TYPE: PRT
<213> ORGANISM: Artificial Sequence
<220> FEATURE:
<223> OTHER INFORMATION: Synthetic

<400> SEQUENCE: 269

Glu Asn Ser Thr
1

<210> SEQ ID NO 270
<211> LENGTH: 4
<212> TYPE: PRT
<213> ORGANISM: Artificial Sequence
<220> FEATURE:
<223> OTHER INFORMATION: Synthetic

<400> SEQUENCE: 270

Thr Asn Asn Thr
1

<210> SEQ ID NO 271
<211> LENGTH: 4
<212> TYPE: PRT
<213> ORGANISM: Artificial Sequence
<220> FEATURE:
<223> OTHER INFORMATION: Synthetic

<400> SEQUENCE: 271

Pro Asn Met Ser
1

<210> SEQ ID NO 272
<211> LENGTH: 4
<212> TYPE: PRT
<213> ORGANISM: Artificial Sequence
<220> FEATURE:
<223> OTHER INFORMATION: Synthetic

<400> SEQUENCE: 272

Thr Asn Thr Thr
1

<210> SEQ ID NO 273
<211> LENGTH: 4
<212> TYPE: PRT
<213> ORGANISM: Artificial Sequence
<220> FEATURE:
<223> OTHER INFORMATION: Synthetic

<400> SEQUENCE: 273

Pro Asn Gly Thr
1

<210> SEQ ID NO 274
<211> LENGTH: 4
<212> TYPE: PRT
<213> ORGANISM: Artificial Sequence
<220> FEATURE:
<223> OTHER INFORMATION: Synthetic

<400> SEQUENCE: 274

Val Asn Ser Thr
1

<210> SEQ ID NO 275
<211> LENGTH: 4
<212> TYPE: PRT
<213> ORGANISM: Artificial Sequence
<220> FEATURE:
<223> OTHER INFORMATION: Synthetic

<400> SEQUENCE: 275

Leu Asn Val Thr
1

<210> SEQ ID NO 276
<211> LENGTH: 4
<212> TYPE: PRT
<213> ORGANISM: Artificial Sequence
<220> FEATURE:
<223> OTHER INFORMATION: Synthetic

<400> SEQUENCE: 276

Gly Asn Ala Thr
1

<210> SEQ ID NO 277
<211> LENGTH: 4
<212> TYPE: PRT
<213> ORGANISM: Artificial Sequence
<220> FEATURE:
<223> OTHER INFORMATION: Synthetic

<400> SEQUENCE: 277

Pro Asn Tyr Ser
1

<210> SEQ ID NO 278
<211> LENGTH: 4
<212> TYPE: PRT
<213> ORGANISM: Artificial Sequence
<220> FEATURE:
<223> OTHER INFORMATION: Synthetic

<400> SEQUENCE: 278

```
Pro Asn Lys Thr
1

<210> SEQ ID NO 279
<211> LENGTH: 4
<212> TYPE: PRT
<213> ORGANISM: Artificial Sequence
<220> FEATURE:
<223> OTHER INFORMATION: Synthetic

<400> SEQUENCE: 279

Glu Asn Val Thr
1

<210> SEQ ID NO 280
<211> LENGTH: 4
<212> TYPE: PRT
<213> ORGANISM: Artificial Sequence
<220> FEATURE:
<223> OTHER INFORMATION: Synthetic

<400> SEQUENCE: 280

Val Asn His Thr
1

<210> SEQ ID NO 281
<211> LENGTH: 4
<212> TYPE: PRT
<213> ORGANISM: Artificial Sequence
<220> FEATURE:
<223> OTHER INFORMATION: Synthetic

<400> SEQUENCE: 281

Asn Asn His Ser
1

<210> SEQ ID NO 282
<211> LENGTH: 4
<212> TYPE: PRT
<213> ORGANISM: Artificial Sequence
<220> FEATURE:
<223> OTHER INFORMATION: Synthetic

<400> SEQUENCE: 282

Glu Asn Ala Thr
1

<210> SEQ ID NO 283
<211> LENGTH: 4
<212> TYPE: PRT
<213> ORGANISM: Artificial Sequence
<220> FEATURE:
<223> OTHER INFORMATION: Synthetic

<400> SEQUENCE: 283

Ser Asn Gly Thr
1

<210> SEQ ID NO 284
<211> LENGTH: 4
<212> TYPE: PRT
<213> ORGANISM: Artificial Sequence
<220> FEATURE:
<223> OTHER INFORMATION: Synthetic

<400> SEQUENCE: 284
```

Ser Asn His Ser
1

<210> SEQ ID NO 285
<211> LENGTH: 4
<212> TYPE: PRT
<213> ORGANISM: Artificial Sequence
<220> FEATURE:
<223> OTHER INFORMATION: Synthetic

<400> SEQUENCE: 285

Asn Asn Tyr Thr
1

<210> SEQ ID NO 286
<211> LENGTH: 4
<212> TYPE: PRT
<213> ORGANISM: Artificial Sequence
<220> FEATURE:
<223> OTHER INFORMATION: Synthetic

<400> SEQUENCE: 286

Met Asn Ala Thr
1

<210> SEQ ID NO 287
<211> LENGTH: 4
<212> TYPE: PRT
<213> ORGANISM: Artificial Sequence
<220> FEATURE:
<223> OTHER INFORMATION: Synthetic

<400> SEQUENCE: 287

Pro Asn Thr Ser
1

<210> SEQ ID NO 288
<211> LENGTH: 4
<212> TYPE: PRT
<213> ORGANISM: Artificial Sequence
<220> FEATURE:
<223> OTHER INFORMATION: Synthetic

<400> SEQUENCE: 288

Ala Asn Ala Ser
1

<210> SEQ ID NO 289
<211> LENGTH: 4
<212> TYPE: PRT
<213> ORGANISM: Artificial Sequence
<220> FEATURE:
<223> OTHER INFORMATION: Synthetic

<400> SEQUENCE: 289

Gly Asn Tyr Thr
1

<210> SEQ ID NO 290
<211> LENGTH: 4
<212> TYPE: PRT
<213> ORGANISM: Artificial Sequence
<220> FEATURE:
<223> OTHER INFORMATION: Synthetic

<400> SEQUENCE: 290

Leu Asn Ala Thr

<210> SEQ ID NO 291
<211> LENGTH: 4
<212> TYPE: PRT
<213> ORGANISM: Artificial Sequence
<220> FEATURE:
<223> OTHER INFORMATION: Synthetic

<400> SEQUENCE: 291

Asn Asn Val Ser
1

<210> SEQ ID NO 292
<211> LENGTH: 4
<212> TYPE: PRT
<213> ORGANISM: Artificial Sequence
<220> FEATURE:
<223> OTHER INFORMATION: Synthetic

<400> SEQUENCE: 292

Ala Asn Gln Thr
1

<210> SEQ ID NO 293
<211> LENGTH: 4
<212> TYPE: PRT
<213> ORGANISM: Artificial Sequence
<220> FEATURE:
<223> OTHER INFORMATION: Synthetic

<400> SEQUENCE: 293

Thr Asn Val Ser
1

<210> SEQ ID NO 294
<211> LENGTH: 4
<212> TYPE: PRT
<213> ORGANISM: Artificial Sequence
<220> FEATURE:
<223> OTHER INFORMATION: Synthetic

<400> SEQUENCE: 294

Pro Asn Ala Ser
1

<210> SEQ ID NO 295
<211> LENGTH: 4
<212> TYPE: PRT
<213> ORGANISM: Artificial Sequence
<220> FEATURE:
<223> OTHER INFORMATION: Synthetic

<400> SEQUENCE: 295

Gly Asn Val Ser
1

<210> SEQ ID NO 296
<211> LENGTH: 4
<212> TYPE: PRT
<213> ORGANISM: Artificial Sequence
<220> FEATURE:
<223> OTHER INFORMATION: Synthetic

<400> SEQUENCE: 296

Pro Asn Gln Thr
1

<210> SEQ ID NO 297
<211> LENGTH: 4
<212> TYPE: PRT
<213> ORGANISM: Artificial Sequence
<220> FEATURE:
<223> OTHER INFORMATION: Synthetic

<400> SEQUENCE: 297

Ala Asn Lys Thr
1

<210> SEQ ID NO 298
<211> LENGTH: 4
<212> TYPE: PRT
<213> ORGANISM: Artificial Sequence
<220> FEATURE:
<223> OTHER INFORMATION: Synthetic

<400> SEQUENCE: 298

Ser Asn Leu Thr
1

<210> SEQ ID NO 299
<211> LENGTH: 4
<212> TYPE: PRT
<213> ORGANISM: Artificial Sequence
<220> FEATURE:
<223> OTHER INFORMATION: Synthetic

<400> SEQUENCE: 299

Thr Asn Met Thr
1

<210> SEQ ID NO 300
<211> LENGTH: 4
<212> TYPE: PRT
<213> ORGANISM: Artificial Sequence
<220> FEATURE:
<223> OTHER INFORMATION: Synthetic

<400> SEQUENCE: 300

Thr Asn His Ser
1

<210> SEQ ID NO 301
<211> LENGTH: 4
<212> TYPE: PRT
<213> ORGANISM: Artificial Sequence
<220> FEATURE:
<223> OTHER INFORMATION: Synthetic

<400> SEQUENCE: 301

Ala Asn Tyr Thr
1

<210> SEQ ID NO 302
<211> LENGTH: 4
<212> TYPE: PRT
<213> ORGANISM: Artificial Sequence
<220> FEATURE:
<223> OTHER INFORMATION: Synthetic

<400> SEQUENCE: 302

Ala Asn Val Thr
1

```
<210> SEQ ID NO 303
<211> LENGTH: 4
<212> TYPE: PRT
<213> ORGANISM: Artificial Sequence
<220> FEATURE:
<223> OTHER INFORMATION: Synthetic

<400> SEQUENCE: 303

Ser Asn Val Thr
1

<210> SEQ ID NO 304
<211> LENGTH: 4
<212> TYPE: PRT
<213> ORGANISM: Artificial Sequence
<220> FEATURE:
<223> OTHER INFORMATION: Synthetic

<400> SEQUENCE: 304

Pro Asn Val Thr
1

<210> SEQ ID NO 305
<211> LENGTH: 4
<212> TYPE: PRT
<213> ORGANISM: Artificial Sequence
<220> FEATURE:
<223> OTHER INFORMATION: Synthetic

<400> SEQUENCE: 305

Trp Asn Val Thr
1

<210> SEQ ID NO 306
<211> LENGTH: 4
<212> TYPE: PRT
<213> ORGANISM: Artificial Sequence
<220> FEATURE:
<223> OTHER INFORMATION: Synthetic

<400> SEQUENCE: 306

Gly Asn Trp Thr
1

<210> SEQ ID NO 307
<211> LENGTH: 4
<212> TYPE: PRT
<213> ORGANISM: Artificial Sequence
<220> FEATURE:
<223> OTHER INFORMATION: Synthetic

<400> SEQUENCE: 307

Pro Asn Met Thr
1

<210> SEQ ID NO 308
<211> LENGTH: 4
<212> TYPE: PRT
<213> ORGANISM: Artificial Sequence
<220> FEATURE:
<223> OTHER INFORMATION: Synthetic

<400> SEQUENCE: 308

Ala Asn Ile Thr
1
```

```
<210> SEQ ID NO 309
<211> LENGTH: 4
<212> TYPE: PRT
<213> ORGANISM: Artificial Sequence
<220> FEATURE:
<223> OTHER INFORMATION: Synthetic

<400> SEQUENCE: 309

Trp Asn Ala Thr
1

<210> SEQ ID NO 310
<211> LENGTH: 4
<212> TYPE: PRT
<213> ORGANISM: Artificial Sequence
<220> FEATURE:
<223> OTHER INFORMATION: Synthetic

<400> SEQUENCE: 310

Asn Asn Val Thr
1

<210> SEQ ID NO 311
<211> LENGTH: 4
<212> TYPE: PRT
<213> ORGANISM: Artificial Sequence
<220> FEATURE:
<223> OTHER INFORMATION: Synthetic

<400> SEQUENCE: 311

Ala Asn Ala Thr
1

<210> SEQ ID NO 312
<211> LENGTH: 4
<212> TYPE: PRT
<213> ORGANISM: Artificial Sequence
<220> FEATURE:
<223> OTHER INFORMATION: Synthetic

<400> SEQUENCE: 312

Pro Asn Ile Thr
1

<210> SEQ ID NO 313
<211> LENGTH: 4
<212> TYPE: PRT
<213> ORGANISM: Artificial Sequence
<220> FEATURE:
<223> OTHER INFORMATION: Synthetic

<400> SEQUENCE: 313

Ala Asn Phe Thr
1

<210> SEQ ID NO 314
<211> LENGTH: 4
<212> TYPE: PRT
<213> ORGANISM: Artificial Sequence
<220> FEATURE:
<223> OTHER INFORMATION: Synthetic

<400> SEQUENCE: 314

Pro Asn Ala Thr
1

<210> SEQ ID NO 315
```

```
<211> LENGTH: 4
<212> TYPE: PRT
<213> ORGANISM: Artificial Sequence
<220> FEATURE:
<223> OTHER INFORMATION: Synthetic

<400> SEQUENCE: 315

Pro Asn Tyr Thr
1

<210> SEQ ID NO 316
<211> LENGTH: 4
<212> TYPE: PRT
<213> ORGANISM: Artificial Sequence
<220> FEATURE:
<223> OTHER INFORMATION: Synthetic

<400> SEQUENCE: 316

Pro Asn Phe Thr
1

<210> SEQ ID NO 317
<211> LENGTH: 4
<212> TYPE: PRT
<213> ORGANISM: Artificial Sequence
<220> FEATURE:
<223> OTHER INFORMATION: Synthetic

<400> SEQUENCE: 317

Ala Asn Arg Thr
1

<210> SEQ ID NO 318
<211> LENGTH: 4
<212> TYPE: PRT
<213> ORGANISM: Artificial Sequence
<220> FEATURE:
<223> OTHER INFORMATION: Synthetic

<400> SEQUENCE: 318

Ser Asn Ala Thr
1

<210> SEQ ID NO 319
<211> LENGTH: 4
<212> TYPE: PRT
<213> ORGANISM: Artificial Sequence
<220> FEATURE:
<223> OTHER INFORMATION: Synthetic

<400> SEQUENCE: 319

His Asn Val Thr
1

<210> SEQ ID NO 320
<211> LENGTH: 4
<212> TYPE: PRT
<213> ORGANISM: Artificial Sequence
<220> FEATURE:
<223> OTHER INFORMATION: Synthetic

<400> SEQUENCE: 320

Gly Asn Val Thr
1

<210> SEQ ID NO 321
<211> LENGTH: 4
```

```
<212> TYPE: PRT
<213> ORGANISM: Artificial Sequence
<220> FEATURE:
<223> OTHER INFORMATION: Synthetic

<400> SEQUENCE: 321

Pro Asn Ser Thr
1

<210> SEQ ID NO 322
<211> LENGTH: 4
<212> TYPE: PRT
<213> ORGANISM: Artificial Sequence
<220> FEATURE:
<223> OTHER INFORMATION: Synthetic

<400> SEQUENCE: 322

Pro Asn Arg Thr
1

<210> SEQ ID NO 323
<211> LENGTH: 4
<212> TYPE: PRT
<213> ORGANISM: Artificial Sequence
<220> FEATURE:
<223> OTHER INFORMATION: Synthetic

<400> SEQUENCE: 323

Thr Asn Val Thr
1

<210> SEQ ID NO 324
<211> LENGTH: 4
<212> TYPE: PRT
<213> ORGANISM: Artificial Sequence
<220> FEATURE:
<223> OTHER INFORMATION: Synthetic

<400> SEQUENCE: 324

Ser Asn His Thr
1

<210> SEQ ID NO 325
<211> LENGTH: 4
<212> TYPE: PRT
<213> ORGANISM: Artificial Sequence
<220> FEATURE:
<223> OTHER INFORMATION: Synthetic

<400> SEQUENCE: 325

Pro Asn Thr Thr
1

<210> SEQ ID NO 326
<211> LENGTH: 4
<212> TYPE: PRT
<213> ORGANISM: Artificial Sequence
<220> FEATURE:
<223> OTHER INFORMATION: Synthetic

<400> SEQUENCE: 326

Ala Asn Ser Thr
1

<210> SEQ ID NO 327
<211> LENGTH: 4
<212> TYPE: PRT
```

```
<213> ORGANISM: Artificial Sequence
<220> FEATURE:
<223> OTHER INFORMATION: Synthetic

<400> SEQUENCE: 327

Pro Asn Leu Thr
1

<210> SEQ ID NO 328
<211> LENGTH: 4
<212> TYPE: PRT
<213> ORGANISM: Artificial Sequence
<220> FEATURE:
<223> OTHER INFORMATION: Synthetic

<400> SEQUENCE: 328

Ala Asn Met Thr
1

<210> SEQ ID NO 329
<211> LENGTH: 4
<212> TYPE: PRT
<213> ORGANISM: Artificial Sequence
<220> FEATURE:
<223> OTHER INFORMATION: Synthetic

<400> SEQUENCE: 329

Asn Asn Ala Thr
1

<210> SEQ ID NO 330
<211> LENGTH: 4
<212> TYPE: PRT
<213> ORGANISM: Artificial Sequence
<220> FEATURE:
<223> OTHER INFORMATION: Synthetic

<400> SEQUENCE: 330

Ala Asn Thr Thr
1

<210> SEQ ID NO 331
<211> LENGTH: 4
<212> TYPE: PRT
<213> ORGANISM: Artificial Sequence
<220> FEATURE:
<223> OTHER INFORMATION: Synthetic

<400> SEQUENCE: 331

Trp Asn His Thr
1

<210> SEQ ID NO 332
<211> LENGTH: 4
<212> TYPE: PRT
<213> ORGANISM: Artificial Sequence
<220> FEATURE:
<223> OTHER INFORMATION: Synthetic

<400> SEQUENCE: 332

Asn Asn Arg Thr
1

<210> SEQ ID NO 333
<211> LENGTH: 4
<212> TYPE: PRT
<213> ORGANISM: Artificial Sequence
```

```
<220> FEATURE:
<223> OTHER INFORMATION: Synthetic

<400> SEQUENCE: 333

Trp Asn Arg Thr
1

<210> SEQ ID NO 334
<211> LENGTH: 4
<212> TYPE: PRT
<213> ORGANISM: Artificial Sequence
<220> FEATURE:
<223> OTHER INFORMATION: Synthetic

<400> SEQUENCE: 334

Ala Asn His Thr
1

<210> SEQ ID NO 335
<211> LENGTH: 4
<212> TYPE: PRT
<213> ORGANISM: Artificial Sequence
<220> FEATURE:
<223> OTHER INFORMATION: Synthetic

<400> SEQUENCE: 335

Met Asn Ile Thr
1

<210> SEQ ID NO 336
<211> LENGTH: 4
<212> TYPE: PRT
<213> ORGANISM: Artificial Sequence
<220> FEATURE:
<223> OTHER INFORMATION: Synthetic

<400> SEQUENCE: 336

Met Asn His Thr
1

<210> SEQ ID NO 337
<211> LENGTH: 4
<212> TYPE: PRT
<213> ORGANISM: Artificial Sequence
<220> FEATURE:
<223> OTHER INFORMATION: Synthetic

<400> SEQUENCE: 337

Ser Asn Val Ser
1

<210> SEQ ID NO 338
<211> LENGTH: 4
<212> TYPE: PRT
<213> ORGANISM: Artificial Sequence
<220> FEATURE:
<223> OTHER INFORMATION: Synthetic

<400> SEQUENCE: 338

Ser Asn Ile Thr
1

<210> SEQ ID NO 339
<211> LENGTH: 4
<212> TYPE: PRT
<213> ORGANISM: Artificial Sequence
<220> FEATURE:
```

<223> OTHER INFORMATION: Synthetic

<400> SEQUENCE: 339

His Asn His Thr
1

<210> SEQ ID NO 340
<211> LENGTH: 4
<212> TYPE: PRT
<213> ORGANISM: Artificial Sequence
<220> FEATURE:
<223> OTHER INFORMATION: Synthetic

<400> SEQUENCE: 340

Gly Asn His Thr
1

<210> SEQ ID NO 341
<211> LENGTH: 4
<212> TYPE: PRT
<213> ORGANISM: Artificial Sequence
<220> FEATURE:
<223> OTHER INFORMATION: Synthetic

<400> SEQUENCE: 341

Thr Asn His Thr
1

<210> SEQ ID NO 342
<211> LENGTH: 4
<212> TYPE: PRT
<213> ORGANISM: Artificial Sequence
<220> FEATURE:
<223> OTHER INFORMATION: Synthetic

<400> SEQUENCE: 342

Trp Asn Ile Thr
1

<210> SEQ ID NO 343
<211> LENGTH: 4
<212> TYPE: PRT
<213> ORGANISM: Artificial Sequence
<220> FEATURE:
<223> OTHER INFORMATION: Synthetic

<400> SEQUENCE: 343

Thr Asn Ala Thr
1

<210> SEQ ID NO 344
<211> LENGTH: 4
<212> TYPE: PRT
<213> ORGANISM: Artificial Sequence
<220> FEATURE:
<223> OTHER INFORMATION: Synthetic

<400> SEQUENCE: 344

Met Asn Val Thr
1

<210> SEQ ID NO 345
<211> LENGTH: 4
<212> TYPE: PRT
<213> ORGANISM: Artificial Sequence
<220> FEATURE:
<223> OTHER INFORMATION: Synthetic

<400> SEQUENCE: 345

Ala Asn Leu Thr
1

<210> SEQ ID NO 346
<211> LENGTH: 4
<212> TYPE: PRT
<213> ORGANISM: Artificial Sequence
<220> FEATURE:
<223> OTHER INFORMATION: Synthetic

<400> SEQUENCE: 346

Ser Asn Arg Thr
1

<210> SEQ ID NO 347
<211> LENGTH: 4
<212> TYPE: PRT
<213> ORGANISM: Artificial Sequence
<220> FEATURE:
<223> OTHER INFORMATION: Synthetic

<400> SEQUENCE: 347

Asn Asn His Thr
1

<210> SEQ ID NO 348
<211> LENGTH: 4
<212> TYPE: PRT
<213> ORGANISM: Artificial Sequence
<220> FEATURE:
<223> OTHER INFORMATION: Synthetic

<400> SEQUENCE: 348

Val Asn Val Thr
1

<210> SEQ ID NO 349
<211> LENGTH: 4
<212> TYPE: PRT
<213> ORGANISM: Artificial Sequence
<220> FEATURE:
<223> OTHER INFORMATION: Synthetic

<400> SEQUENCE: 349

Met Asn Ala Thr
1

<210> SEQ ID NO 350
<211> LENGTH: 4
<212> TYPE: PRT
<213> ORGANISM: Artificial Sequence
<220> FEATURE:
<223> OTHER INFORMATION: Synthetic

<400> SEQUENCE: 350

Pro Asn His Thr
1

<210> SEQ ID NO 351
<211> LENGTH: 4
<212> TYPE: PRT
<213> ORGANISM: Artificial Sequence
<220> FEATURE:
<223> OTHER INFORMATION: Synthetic

<400> SEQUENCE: 351

His Asn Ala Thr
1

<210> SEQ ID NO 352
<211> LENGTH: 4
<212> TYPE: PRT
<213> ORGANISM: Artificial Sequence
<220> FEATURE:
<223> OTHER INFORMATION: Synthetic

<400> SEQUENCE: 352

Ser Asn Tyr Thr
1

<210> SEQ ID NO 353
<211> LENGTH: 4
<212> TYPE: PRT
<213> ORGANISM: Artificial Sequence
<220> FEATURE:
<223> OTHER INFORMATION: Synthetic

<400> SEQUENCE: 353

Val Asn Ala Thr
1

<210> SEQ ID NO 354
<211> LENGTH: 4
<212> TYPE: PRT
<213> ORGANISM: Artificial Sequence
<220> FEATURE:
<223> OTHER INFORMATION: Synthetic

<400> SEQUENCE: 354

Ala Asn Val Ser
1

<210> SEQ ID NO 355
<211> LENGTH: 4
<212> TYPE: PRT
<213> ORGANISM: Artificial Sequence
<220> FEATURE:
<223> OTHER INFORMATION: Synthetic

<400> SEQUENCE: 355

Glu Asn Val Thr
1

<210> SEQ ID NO 356
<211> LENGTH: 4
<212> TYPE: PRT
<213> ORGANISM: Artificial Sequence
<220> FEATURE:
<223> OTHER INFORMATION: Synthetic

<400> SEQUENCE: 356

Ser Asn Thr Thr
1

<210> SEQ ID NO 357
<211> LENGTH: 4
<212> TYPE: PRT
<213> ORGANISM: Artificial Sequence
<220> FEATURE:
<223> OTHER INFORMATION: Synthetic

<400> SEQUENCE: 357

Asn Asn Ser Thr
1

<210> SEQ ID NO 358
<211> LENGTH: 4
<212> TYPE: PRT
<213> ORGANISM: Artificial Sequence
<220> FEATURE:
<223> OTHER INFORMATION: Synthetic

<400> SEQUENCE: 358

Ser Asn Ser Thr
1

<210> SEQ ID NO 359
<211> LENGTH: 4
<212> TYPE: PRT
<213> ORGANISM: Artificial Sequence
<220> FEATURE:
<223> OTHER INFORMATION: Synthetic

<400> SEQUENCE: 359

Val Asn Met Thr
1

<210> SEQ ID NO 360
<211> LENGTH: 4
<212> TYPE: PRT
<213> ORGANISM: Artificial Sequence
<220> FEATURE:
<223> OTHER INFORMATION: Synthetic

<400> SEQUENCE: 360

Asn Asn Thr Thr
1

<210> SEQ ID NO 361
<211> LENGTH: 4
<212> TYPE: PRT
<213> ORGANISM: Artificial Sequence
<220> FEATURE:
<223> OTHER INFORMATION: Synthetic

<400> SEQUENCE: 361

Thr Asn Ser Thr
1

<210> SEQ ID NO 362
<211> LENGTH: 4
<212> TYPE: PRT
<213> ORGANISM: Artificial Sequence
<220> FEATURE:
<223> OTHER INFORMATION: Synthetic

<400> SEQUENCE: 362

Pro Asn Val Ser
1

<210> SEQ ID NO 363
<211> LENGTH: 4
<212> TYPE: PRT
<213> ORGANISM: Artificial Sequence
<220> FEATURE:
<223> OTHER INFORMATION: Synthetic

<400> SEQUENCE: 363

His Asn Arg Thr
1

<210> SEQ ID NO 364
<211> LENGTH: 4
<212> TYPE: PRT
<213> ORGANISM: Artificial Sequence
<220> FEATURE:
<223> OTHER INFORMATION: Synthetic

<400> SEQUENCE: 364

Trp Asn Ser Thr
1

<210> SEQ ID NO 365
<211> LENGTH: 4
<212> TYPE: PRT
<213> ORGANISM: Artificial Sequence
<220> FEATURE:
<223> OTHER INFORMATION: Synthetic

<400> SEQUENCE: 365

Glu Asn Ser Thr
1

<210> SEQ ID NO 366
<211> LENGTH: 4
<212> TYPE: PRT
<213> ORGANISM: Artificial Sequence
<220> FEATURE:
<223> OTHER INFORMATION: Synthetic

<400> SEQUENCE: 366

Glu Asn Arg Thr
1

<210> SEQ ID NO 367
<211> LENGTH: 4
<212> TYPE: PRT
<213> ORGANISM: Artificial Sequence
<220> FEATURE:
<223> OTHER INFORMATION: Synthetic

<400> SEQUENCE: 367

Ser Asn Met Thr
1

<210> SEQ ID NO 368
<211> LENGTH: 4
<212> TYPE: PRT
<213> ORGANISM: Artificial Sequence
<220> FEATURE:
<223> OTHER INFORMATION: Synthetic

<400> SEQUENCE: 368

His Asn Ile Thr
1

<210> SEQ ID NO 369
<211> LENGTH: 4
<212> TYPE: PRT
<213> ORGANISM: Artificial Sequence
<220> FEATURE:
<223> OTHER INFORMATION: Synthetic

<400> SEQUENCE: 369

Gly Asn Tyr Thr

```
<210> SEQ ID NO 370
<211> LENGTH: 4
<212> TYPE: PRT
<213> ORGANISM: Artificial Sequence
<220> FEATURE:
<223> OTHER INFORMATION: Synthetic

<400> SEQUENCE: 370

Trp Asn Met Thr
1

<210> SEQ ID NO 371
<211> LENGTH: 4
<212> TYPE: PRT
<213> ORGANISM: Artificial Sequence
<220> FEATURE:
<223> OTHER INFORMATION: Synthetic

<400> SEQUENCE: 371

Trp Asn Thr Thr
1

<210> SEQ ID NO 372
<211> LENGTH: 4
<212> TYPE: PRT
<213> ORGANISM: Artificial Sequence
<220> FEATURE:
<223> OTHER INFORMATION: Synthetic

<400> SEQUENCE: 372

Ile Asn Val Thr
1

<210> SEQ ID NO 373
<211> LENGTH: 4
<212> TYPE: PRT
<213> ORGANISM: Artificial Sequence
<220> FEATURE:
<223> OTHER INFORMATION: Synthetic

<400> SEQUENCE: 373

Glu Asn Ala Thr
1

<210> SEQ ID NO 374
<211> LENGTH: 4
<212> TYPE: PRT
<213> ORGANISM: Artificial Sequence
<220> FEATURE:
<223> OTHER INFORMATION: Synthetic

<400> SEQUENCE: 374

Ala Asn Gln Thr
1

<210> SEQ ID NO 375
<211> LENGTH: 4
<212> TYPE: PRT
<213> ORGANISM: Artificial Sequence
<220> FEATURE:
<223> OTHER INFORMATION: Synthetic

<400> SEQUENCE: 375

Gly Asn Ala Thr
1
```

<210> SEQ ID NO 376
<211> LENGTH: 4
<212> TYPE: PRT
<213> ORGANISM: Artificial Sequence
<220> FEATURE:
<223> OTHER INFORMATION: Synthetic

<400> SEQUENCE: 376

Met Asn Leu Thr
1

<210> SEQ ID NO 377
<211> LENGTH: 4
<212> TYPE: PRT
<213> ORGANISM: Artificial Sequence
<220> FEATURE:
<223> OTHER INFORMATION: Synthetic

<400> SEQUENCE: 377

Thr Asn Val Ser
1

<210> SEQ ID NO 378
<211> LENGTH: 4
<212> TYPE: PRT
<213> ORGANISM: Artificial Sequence
<220> FEATURE:
<223> OTHER INFORMATION: Synthetic

<400> SEQUENCE: 378

Pro Asn Gln Thr
1

<210> SEQ ID NO 379
<211> LENGTH: 4
<212> TYPE: PRT
<213> ORGANISM: Artificial Sequence
<220> FEATURE:
<223> OTHER INFORMATION: Synthetic

<400> SEQUENCE: 379

Met Asn Arg Thr
1

<210> SEQ ID NO 380
<211> LENGTH: 4
<212> TYPE: PRT
<213> ORGANISM: Artificial Sequence
<220> FEATURE:
<223> OTHER INFORMATION: Synthetic

<400> SEQUENCE: 380

Asn Asn Tyr Thr
1

<210> SEQ ID NO 381
<211> LENGTH: 4
<212> TYPE: PRT
<213> ORGANISM: Artificial Sequence
<220> FEATURE:
<223> OTHER INFORMATION: Synthetic

<400> SEQUENCE: 381

Ser Asn Phe Thr
1

```
<210> SEQ ID NO 382
<211> LENGTH: 4
<212> TYPE: PRT
<213> ORGANISM: Artificial Sequence
<220> FEATURE:
<223> OTHER INFORMATION: Synthetic

<400> SEQUENCE: 382

Leu Asn Val Thr
1

<210> SEQ ID NO 383
<211> LENGTH: 4
<212> TYPE: PRT
<213> ORGANISM: Artificial Sequence
<220> FEATURE:
<223> OTHER INFORMATION: Synthetic

<400> SEQUENCE: 383

Pro Asn Ile Ser
1

<210> SEQ ID NO 384
<211> LENGTH: 4
<212> TYPE: PRT
<213> ORGANISM: Artificial Sequence
<220> FEATURE:
<223> OTHER INFORMATION: Synthetic

<400> SEQUENCE: 384

Gln Asn Val Thr
1

<210> SEQ ID NO 385
<211> LENGTH: 4
<212> TYPE: PRT
<213> ORGANISM: Artificial Sequence
<220> FEATURE:
<223> OTHER INFORMATION: Synthetic

<400> SEQUENCE: 385

Val Asn Ser Thr
1

<210> SEQ ID NO 386
<211> LENGTH: 4
<212> TYPE: PRT
<213> ORGANISM: Artificial Sequence
<220> FEATURE:
<223> OTHER INFORMATION: Synthetic

<400> SEQUENCE: 386

Val Asn Ile Thr
1

<210> SEQ ID NO 387
<211> LENGTH: 4
<212> TYPE: PRT
<213> ORGANISM: Artificial Sequence
<220> FEATURE:
<223> OTHER INFORMATION: Synthetic

<400> SEQUENCE: 387

Gly Asn Ile Thr
1
```

```
<210> SEQ ID NO 388
<211> LENGTH: 4
<212> TYPE: PRT
<213> ORGANISM: Artificial Sequence
<220> FEATURE:
<223> OTHER INFORMATION: Synthetic

<400> SEQUENCE: 388

Ala Asn Ile Ser
1

<210> SEQ ID NO 389
<211> LENGTH: 4
<212> TYPE: PRT
<213> ORGANISM: Artificial Sequence
<220> FEATURE:
<223> OTHER INFORMATION: Synthetic

<400> SEQUENCE: 389

His Asn Thr Thr
1

<210> SEQ ID NO 390
<211> LENGTH: 4
<212> TYPE: PRT
<213> ORGANISM: Artificial Sequence
<220> FEATURE:
<223> OTHER INFORMATION: Synthetic

<400> SEQUENCE: 390

Tyr Asn Val Thr
1

<210> SEQ ID NO 391
<211> LENGTH: 4
<212> TYPE: PRT
<213> ORGANISM: Artificial Sequence
<220> FEATURE:
<223> OTHER INFORMATION: Synthetic

<400> SEQUENCE: 391

Phe Asn Val Thr
1

<210> SEQ ID NO 392
<211> LENGTH: 4
<212> TYPE: PRT
<213> ORGANISM: Artificial Sequence
<220> FEATURE:
<223> OTHER INFORMATION: Synthetic

<400> SEQUENCE: 392

Val Asn Arg Thr
1

<210> SEQ ID NO 393
<211> LENGTH: 4
<212> TYPE: PRT
<213> ORGANISM: Artificial Sequence
<220> FEATURE:
<223> OTHER INFORMATION: Synthetic

<400> SEQUENCE: 393

Trp Asn Tyr Thr
1

<210> SEQ ID NO 394
```

```
<211> LENGTH: 4
<212> TYPE: PRT
<213> ORGANISM: Artificial Sequence
<220> FEATURE:
<223> OTHER INFORMATION: Synthetic

<400> SEQUENCE: 394

Ala Asn Trp Thr
1

<210> SEQ ID NO 395
<211> LENGTH: 4
<212> TYPE: PRT
<213> ORGANISM: Artificial Sequence
<220> FEATURE:
<223> OTHER INFORMATION: Synthetic

<400> SEQUENCE: 395

Leu Asn Ala Thr
1

<210> SEQ ID NO 396
<211> LENGTH: 4
<212> TYPE: PRT
<213> ORGANISM: Artificial Sequence
<220> FEATURE:
<223> OTHER INFORMATION: Synthetic

<400> SEQUENCE: 396

Glu Asn His Thr
1

<210> SEQ ID NO 397
<211> LENGTH: 4
<212> TYPE: PRT
<213> ORGANISM: Artificial Sequence
<220> FEATURE:
<223> OTHER INFORMATION: Synthetic

<400> SEQUENCE: 397

Ala Asn Gly Thr
1

<210> SEQ ID NO 398
<211> LENGTH: 4
<212> TYPE: PRT
<213> ORGANISM: Artificial Sequence
<220> FEATURE:
<223> OTHER INFORMATION: Synthetic

<400> SEQUENCE: 398

Met Asn Ser Thr
1

<210> SEQ ID NO 399
<211> LENGTH: 4
<212> TYPE: PRT
<213> ORGANISM: Artificial Sequence
<220> FEATURE:
<223> OTHER INFORMATION: Synthetic

<400> SEQUENCE: 399

Thr Asn Ile Thr
1

<210> SEQ ID NO 400
<211> LENGTH: 4
```

```
<212> TYPE: PRT
<213> ORGANISM: Artificial Sequence
<220> FEATURE:
<223> OTHER INFORMATION: Synthetic

<400> SEQUENCE: 400

Leu Asn Arg Thr
1

<210> SEQ ID NO 401
<211> LENGTH: 4
<212> TYPE: PRT
<213> ORGANISM: Artificial Sequence
<220> FEATURE:
<223> OTHER INFORMATION: Synthetic

<400> SEQUENCE: 401

Pro Asn Ile Thr
1

<210> SEQ ID NO 402
<211> LENGTH: 4
<212> TYPE: PRT
<213> ORGANISM: Artificial Sequence
<220> FEATURE:
<223> OTHER INFORMATION: Synthetic

<400> SEQUENCE: 402

Ala Asn Ala Thr
1

<210> SEQ ID NO 403
<211> LENGTH: 4
<212> TYPE: PRT
<213> ORGANISM: Artificial Sequence
<220> FEATURE:
<223> OTHER INFORMATION: Synthetic

<400> SEQUENCE: 403

Pro Asn Val Thr
1

<210> SEQ ID NO 404
<211> LENGTH: 4
<212> TYPE: PRT
<213> ORGANISM: Artificial Sequence
<220> FEATURE:
<223> OTHER INFORMATION: Synthetic

<400> SEQUENCE: 404

Pro Asn Met Thr
1

<210> SEQ ID NO 405
<211> LENGTH: 4
<212> TYPE: PRT
<213> ORGANISM: Artificial Sequence
<220> FEATURE:
<223> OTHER INFORMATION: Synthetic

<400> SEQUENCE: 405

Pro Asn Ala Thr
1

<210> SEQ ID NO 406
<211> LENGTH: 4
<212> TYPE: PRT
```

```
<213> ORGANISM: Artificial Sequence
<220> FEATURE:
<223> OTHER INFORMATION: Synthetic

<400> SEQUENCE: 406

Pro Asn Leu Thr
1

<210> SEQ ID NO 407
<211> LENGTH: 4
<212> TYPE: PRT
<213> ORGANISM: Artificial Sequence
<220> FEATURE:
<223> OTHER INFORMATION: Synthetic

<400> SEQUENCE: 407

Ala Asn Val Thr
1

<210> SEQ ID NO 408
<211> LENGTH: 4
<212> TYPE: PRT
<213> ORGANISM: Artificial Sequence
<220> FEATURE:
<223> OTHER INFORMATION: Synthetic

<400> SEQUENCE: 408

Ala Asn Met Thr
1

<210> SEQ ID NO 409
<211> LENGTH: 4
<212> TYPE: PRT
<213> ORGANISM: Artificial Sequence
<220> FEATURE:
<223> OTHER INFORMATION: Synthetic

<400> SEQUENCE: 409

Ala Asn Ile Thr
1

<210> SEQ ID NO 410
<211> LENGTH: 4
<212> TYPE: PRT
<213> ORGANISM: Artificial Sequence
<220> FEATURE:
<223> OTHER INFORMATION: Synthetic

<400> SEQUENCE: 410

His Asn Val Thr
1

<210> SEQ ID NO 411
<211> LENGTH: 4
<212> TYPE: PRT
<213> ORGANISM: Artificial Sequence
<220> FEATURE:
<223> OTHER INFORMATION: Synthetic

<400> SEQUENCE: 411

Pro Asn Phe Thr
1

<210> SEQ ID NO 412
<211> LENGTH: 4
<212> TYPE: PRT
<213> ORGANISM: Artificial Sequence
```

```
<220> FEATURE:
<223> OTHER INFORMATION: Synthetic

<400> SEQUENCE: 412

Ala Asn Phe Thr
1

<210> SEQ ID NO 413
<211> LENGTH: 4
<212> TYPE: PRT
<213> ORGANISM: Artificial Sequence
<220> FEATURE:
<223> OTHER INFORMATION: Synthetic

<400> SEQUENCE: 413

Pro Asn Val Ser
1

<210> SEQ ID NO 414
<211> LENGTH: 4
<212> TYPE: PRT
<213> ORGANISM: Artificial Sequence
<220> FEATURE:
<223> OTHER INFORMATION: Synthetic

<400> SEQUENCE: 414

Pro Asn Tyr Thr
1

<210> SEQ ID NO 415
<211> LENGTH: 4
<212> TYPE: PRT
<213> ORGANISM: Artificial Sequence
<220> FEATURE:
<223> OTHER INFORMATION: Synthetic

<400> SEQUENCE: 415

Met Asn Ile Thr
1

<210> SEQ ID NO 416
<211> LENGTH: 4
<212> TYPE: PRT
<213> ORGANISM: Artificial Sequence
<220> FEATURE:
<223> OTHER INFORMATION: Synthetic

<400> SEQUENCE: 416

Pro Asn Arg Thr
1

<210> SEQ ID NO 417
<211> LENGTH: 4
<212> TYPE: PRT
<213> ORGANISM: Artificial Sequence
<220> FEATURE:
<223> OTHER INFORMATION: Synthetic

<400> SEQUENCE: 417

Ala Asn Arg Thr
1

<210> SEQ ID NO 418
<211> LENGTH: 4
<212> TYPE: PRT
<213> ORGANISM: Artificial Sequence
<220> FEATURE:
```

```
<223> OTHER INFORMATION: Synthetic

<400> SEQUENCE: 418

Pro Asn Ile Ser
1

<210> SEQ ID NO 419
<211> LENGTH: 4
<212> TYPE: PRT
<213> ORGANISM: Artificial Sequence
<220> FEATURE:
<223> OTHER INFORMATION: Synthetic

<400> SEQUENCE: 419

Ser Asn Val Thr
1

<210> SEQ ID NO 420
<211> LENGTH: 4
<212> TYPE: PRT
<213> ORGANISM: Artificial Sequence
<220> FEATURE:
<223> OTHER INFORMATION: Synthetic

<400> SEQUENCE: 420

Asn Asn Ala Thr
1

<210> SEQ ID NO 421
<211> LENGTH: 4
<212> TYPE: PRT
<213> ORGANISM: Artificial Sequence
<220> FEATURE:
<223> OTHER INFORMATION: Synthetic

<400> SEQUENCE: 421

Ala Asn Val Ser
1

<210> SEQ ID NO 422
<211> LENGTH: 4
<212> TYPE: PRT
<213> ORGANISM: Artificial Sequence
<220> FEATURE:
<223> OTHER INFORMATION: Synthetic

<400> SEQUENCE: 422

Val Asn Met Thr
1

<210> SEQ ID NO 423
<211> LENGTH: 4
<212> TYPE: PRT
<213> ORGANISM: Artificial Sequence
<220> FEATURE:
<223> OTHER INFORMATION: Synthetic

<400> SEQUENCE: 423

Ile Asn Val Thr
1

<210> SEQ ID NO 424
<211> LENGTH: 4
<212> TYPE: PRT
<213> ORGANISM: Artificial Sequence
<220> FEATURE:
<223> OTHER INFORMATION: Synthetic
```

```
<400> SEQUENCE: 424

Ala Asn His Thr
1

<210> SEQ ID NO 425
<211> LENGTH: 4
<212> TYPE: PRT
<213> ORGANISM: Artificial Sequence
<220> FEATURE:
<223> OTHER INFORMATION: Synthetic

<400> SEQUENCE: 425

Asn Asn Val Thr
1

<210> SEQ ID NO 426
<211> LENGTH: 4
<212> TYPE: PRT
<213> ORGANISM: Artificial Sequence
<220> FEATURE:
<223> OTHER INFORMATION: Synthetic

<400> SEQUENCE: 426

Pro Asn His Thr
1

<210> SEQ ID NO 427
<211> LENGTH: 4
<212> TYPE: PRT
<213> ORGANISM: Artificial Sequence
<220> FEATURE:
<223> OTHER INFORMATION: Synthetic

<400> SEQUENCE: 427

His Asn His Thr
1

<210> SEQ ID NO 428
<211> LENGTH: 4
<212> TYPE: PRT
<213> ORGANISM: Artificial Sequence
<220> FEATURE:
<223> OTHER INFORMATION: Synthetic

<400> SEQUENCE: 428

Trp Asn Val Thr
1

<210> SEQ ID NO 429
<211> LENGTH: 4
<212> TYPE: PRT
<213> ORGANISM: Artificial Sequence
<220> FEATURE:
<223> OTHER INFORMATION: Synthetic

<400> SEQUENCE: 429

Ala Asn Leu Thr
1

<210> SEQ ID NO 430
<211> LENGTH: 4
<212> TYPE: PRT
<213> ORGANISM: Artificial Sequence
<220> FEATURE:
<223> OTHER INFORMATION: Synthetic
```

```
<400> SEQUENCE: 430

Pro Asn Thr Thr
1

<210> SEQ ID NO 431
<211> LENGTH: 4
<212> TYPE: PRT
<213> ORGANISM: Artificial Sequence
<220> FEATURE:
<223> OTHER INFORMATION: Synthetic

<400> SEQUENCE: 431

Met Asn Val Thr
1

<210> SEQ ID NO 432
<211> LENGTH: 4
<212> TYPE: PRT
<213> ORGANISM: Artificial Sequence
<220> FEATURE:
<223> OTHER INFORMATION: Synthetic

<400> SEQUENCE: 432

Ala Asn Tyr Thr
1

<210> SEQ ID NO 433
<211> LENGTH: 4
<212> TYPE: PRT
<213> ORGANISM: Artificial Sequence
<220> FEATURE:
<223> OTHER INFORMATION: Synthetic

<400> SEQUENCE: 433

Met Asn Leu Thr
1

<210> SEQ ID NO 434
<211> LENGTH: 4
<212> TYPE: PRT
<213> ORGANISM: Artificial Sequence
<220> FEATURE:
<223> OTHER INFORMATION: Synthetic

<400> SEQUENCE: 434

Val Asn Ile Thr
1

<210> SEQ ID NO 435
<211> LENGTH: 4
<212> TYPE: PRT
<213> ORGANISM: Artificial Sequence
<220> FEATURE:
<223> OTHER INFORMATION: Synthetic

<400> SEQUENCE: 435

Pro Asn Ser Thr
1

<210> SEQ ID NO 436
<211> LENGTH: 4
<212> TYPE: PRT
<213> ORGANISM: Artificial Sequence
<220> FEATURE:
<223> OTHER INFORMATION: Synthetic

<400> SEQUENCE: 436
```

Trp Asn Ala Thr
1

<210> SEQ ID NO 437
<211> LENGTH: 4
<212> TYPE: PRT
<213> ORGANISM: Artificial Sequence
<220> FEATURE:
<223> OTHER INFORMATION: Synthetic

<400> SEQUENCE: 437

Phe Asn Ala Thr
1

<210> SEQ ID NO 438
<211> LENGTH: 4
<212> TYPE: PRT
<213> ORGANISM: Artificial Sequence
<220> FEATURE:
<223> OTHER INFORMATION: Synthetic

<400> SEQUENCE: 438

Ala Asn Ile Ser
1

<210> SEQ ID NO 439
<211> LENGTH: 4
<212> TYPE: PRT
<213> ORGANISM: Artificial Sequence
<220> FEATURE:
<223> OTHER INFORMATION: Synthetic

<400> SEQUENCE: 439

Thr Asn Val Thr
1

<210> SEQ ID NO 440
<211> LENGTH: 4
<212> TYPE: PRT
<213> ORGANISM: Artificial Sequence
<220> FEATURE:
<223> OTHER INFORMATION: Synthetic

<400> SEQUENCE: 440

Ile Asn Met Thr
1

<210> SEQ ID NO 441
<211> LENGTH: 4
<212> TYPE: PRT
<213> ORGANISM: Artificial Sequence
<220> FEATURE:
<223> OTHER INFORMATION: Synthetic

<400> SEQUENCE: 441

His Asn Val Ser
1

<210> SEQ ID NO 442
<211> LENGTH: 4
<212> TYPE: PRT
<213> ORGANISM: Artificial Sequence
<220> FEATURE:
<223> OTHER INFORMATION: Synthetic

<400> SEQUENCE: 442

His Asn Arg Thr
1

<210> SEQ ID NO 443
<211> LENGTH: 4
<212> TYPE: PRT
<213> ORGANISM: Artificial Sequence
<220> FEATURE:
<223> OTHER INFORMATION: Synthetic

<400> SEQUENCE: 443

Pro Asn Leu Ser
1

<210> SEQ ID NO 444
<211> LENGTH: 4
<212> TYPE: PRT
<213> ORGANISM: Artificial Sequence
<220> FEATURE:
<223> OTHER INFORMATION: Synthetic

<400> SEQUENCE: 444

Pro Asn Met Ser
1

<210> SEQ ID NO 445
<211> LENGTH: 4
<212> TYPE: PRT
<213> ORGANISM: Artificial Sequence
<220> FEATURE:
<223> OTHER INFORMATION: Synthetic

<400> SEQUENCE: 445

Val Asn Val Thr
1

<210> SEQ ID NO 446
<211> LENGTH: 4
<212> TYPE: PRT
<213> ORGANISM: Artificial Sequence
<220> FEATURE:
<223> OTHER INFORMATION: Synthetic

<400> SEQUENCE: 446

Ala Asn Ser Thr
1

<210> SEQ ID NO 447
<211> LENGTH: 4
<212> TYPE: PRT
<213> ORGANISM: Artificial Sequence
<220> FEATURE:
<223> OTHER INFORMATION: Synthetic

<400> SEQUENCE: 447

His Asn Ala Thr
1

<210> SEQ ID NO 448
<211> LENGTH: 4
<212> TYPE: PRT
<213> ORGANISM: Artificial Sequence
<220> FEATURE:
<223> OTHER INFORMATION: Synthetic

<400> SEQUENCE: 448

Ala Asn Thr Thr

```
<210> SEQ ID NO 449
<211> LENGTH: 4
<212> TYPE: PRT
<213> ORGANISM: Artificial Sequence
<220> FEATURE:
<223> OTHER INFORMATION: Synthetic

<400> SEQUENCE: 449

Trp Asn His Thr
1

<210> SEQ ID NO 450
<211> LENGTH: 4
<212> TYPE: PRT
<213> ORGANISM: Artificial Sequence
<220> FEATURE:
<223> OTHER INFORMATION: Synthetic

<400> SEQUENCE: 450

Asn Asn His Thr
1

<210> SEQ ID NO 451
<211> LENGTH: 4
<212> TYPE: PRT
<213> ORGANISM: Artificial Sequence
<220> FEATURE:
<223> OTHER INFORMATION: Synthetic

<400> SEQUENCE: 451

Pro Asn Tyr Ser
1

<210> SEQ ID NO 452
<211> LENGTH: 4
<212> TYPE: PRT
<213> ORGANISM: Artificial Sequence
<220> FEATURE:
<223> OTHER INFORMATION: Synthetic

<400> SEQUENCE: 452

His Asn Ile Thr
1

<210> SEQ ID NO 453
<211> LENGTH: 4
<212> TYPE: PRT
<213> ORGANISM: Artificial Sequence
<220> FEATURE:
<223> OTHER INFORMATION: Synthetic

<400> SEQUENCE: 453

Ser Asn His Thr
1

<210> SEQ ID NO 454
<211> LENGTH: 4
<212> TYPE: PRT
<213> ORGANISM: Artificial Sequence
<220> FEATURE:
<223> OTHER INFORMATION: Synthetic

<400> SEQUENCE: 454

Thr Asn His Thr
1
```

<210> SEQ ID NO 455
<211> LENGTH: 4
<212> TYPE: PRT
<213> ORGANISM: Artificial Sequence
<220> FEATURE:
<223> OTHER INFORMATION: Synthetic

<400> SEQUENCE: 455

Gly Asn Trp Thr
1

<210> SEQ ID NO 456
<211> LENGTH: 4
<212> TYPE: PRT
<213> ORGANISM: Artificial Sequence
<220> FEATURE:
<223> OTHER INFORMATION: Synthetic

<400> SEQUENCE: 456

Ser Asn Val Ser
1

<210> SEQ ID NO 457
<211> LENGTH: 4
<212> TYPE: PRT
<213> ORGANISM: Artificial Sequence
<220> FEATURE:
<223> OTHER INFORMATION: Synthetic

<400> SEQUENCE: 457

Phe Asn Val Thr
1

<210> SEQ ID NO 458
<211> LENGTH: 4
<212> TYPE: PRT
<213> ORGANISM: Artificial Sequence
<220> FEATURE:
<223> OTHER INFORMATION: Synthetic

<400> SEQUENCE: 458

Ser Asn Ala Thr
1

<210> SEQ ID NO 459
<211> LENGTH: 4
<212> TYPE: PRT
<213> ORGANISM: Artificial Sequence
<220> FEATURE:
<223> OTHER INFORMATION: Synthetic

<400> SEQUENCE: 459

Val Asn Ala Thr
1

<210> SEQ ID NO 460
<211> LENGTH: 4
<212> TYPE: PRT
<213> ORGANISM: Artificial Sequence
<220> FEATURE:
<223> OTHER INFORMATION: Synthetic

<400> SEQUENCE: 460

Pro Asn Lys Thr
1

<210> SEQ ID NO 461
<211> LENGTH: 4
<212> TYPE: PRT
<213> ORGANISM: Artificial Sequence
<220> FEATURE:
<223> OTHER INFORMATION: Synthetic

<400> SEQUENCE: 461

Asn Asn Arg Thr
1

<210> SEQ ID NO 462
<211> LENGTH: 4
<212> TYPE: PRT
<213> ORGANISM: Artificial Sequence
<220> FEATURE:
<223> OTHER INFORMATION: Synthetic

<400> SEQUENCE: 462

Trp Asn Met Thr
1

<210> SEQ ID NO 463
<211> LENGTH: 4
<212> TYPE: PRT
<213> ORGANISM: Artificial Sequence
<220> FEATURE:
<223> OTHER INFORMATION: Synthetic

<400> SEQUENCE: 463

Val Asn Arg Thr
1

<210> SEQ ID NO 464
<211> LENGTH: 4
<212> TYPE: PRT
<213> ORGANISM: Artificial Sequence
<220> FEATURE:
<223> OTHER INFORMATION: Synthetic

<400> SEQUENCE: 464

Leu Asn Leu Thr
1

<210> SEQ ID NO 465
<211> LENGTH: 4
<212> TYPE: PRT
<213> ORGANISM: Artificial Sequence
<220> FEATURE:
<223> OTHER INFORMATION: Synthetic

<400> SEQUENCE: 465

Pro Asn His Ser
1

<210> SEQ ID NO 466
<211> LENGTH: 4
<212> TYPE: PRT
<213> ORGANISM: Artificial Sequence
<220> FEATURE:
<223> OTHER INFORMATION: Synthetic

<400> SEQUENCE: 466

Leu Asn Met Thr
1

```
<210> SEQ ID NO 467
<211> LENGTH: 4
<212> TYPE: PRT
<213> ORGANISM: Artificial Sequence
<220> FEATURE:
<223> OTHER INFORMATION: Synthetic

<400> SEQUENCE: 467

His Asn Met Thr
1

<210> SEQ ID NO 468
<211> LENGTH: 4
<212> TYPE: PRT
<213> ORGANISM: Artificial Sequence
<220> FEATURE:
<223> OTHER INFORMATION: Synthetic

<400> SEQUENCE: 468

Ala Asn His Ser
1

<210> SEQ ID NO 469
<211> LENGTH: 4
<212> TYPE: PRT
<213> ORGANISM: Artificial Sequence
<220> FEATURE:
<223> OTHER INFORMATION: Synthetic

<400> SEQUENCE: 469

Ile Asn Ile Thr
1

<210> SEQ ID NO 470
<211> LENGTH: 4
<212> TYPE: PRT
<213> ORGANISM: Artificial Sequence
<220> FEATURE:
<223> OTHER INFORMATION: Synthetic

<400> SEQUENCE: 470

His Asn Thr Thr
1

<210> SEQ ID NO 471
<211> LENGTH: 4
<212> TYPE: PRT
<213> ORGANISM: Artificial Sequence
<220> FEATURE:
<223> OTHER INFORMATION: Synthetic

<400> SEQUENCE: 471

Ser Asn Ile Thr
1

<210> SEQ ID NO 472
<211> LENGTH: 4
<212> TYPE: PRT
<213> ORGANISM: Artificial Sequence
<220> FEATURE:
<223> OTHER INFORMATION: Synthetic

<400> SEQUENCE: 472

Tyr Asn Arg Thr
1

<210> SEQ ID NO 473
```

```
<211> LENGTH: 4
<212> TYPE: PRT
<213> ORGANISM: Artificial Sequence
<220> FEATURE:
<223> OTHER INFORMATION: Synthetic

<400> SEQUENCE: 473

Ile Asn Val Ser
1

<210> SEQ ID NO 474
<211> LENGTH: 4
<212> TYPE: PRT
<213> ORGANISM: Artificial Sequence
<220> FEATURE:
<223> OTHER INFORMATION: Synthetic

<400> SEQUENCE: 474

Tyr Asn Val Thr
1

<210> SEQ ID NO 475
<211> LENGTH: 4
<212> TYPE: PRT
<213> ORGANISM: Artificial Sequence
<220> FEATURE:
<223> OTHER INFORMATION: Synthetic

<400> SEQUENCE: 475

Ser Asn Tyr Thr
1

<210> SEQ ID NO 476
<211> LENGTH: 4
<212> TYPE: PRT
<213> ORGANISM: Artificial Sequence
<220> FEATURE:
<223> OTHER INFORMATION: Synthetic

<400> SEQUENCE: 476

Leu Asn Arg Thr
1

<210> SEQ ID NO 477
<211> LENGTH: 4
<212> TYPE: PRT
<213> ORGANISM: Artificial Sequence
<220> FEATURE:
<223> OTHER INFORMATION: Synthetic

<400> SEQUENCE: 477

Asn Asn Met Thr
1

<210> SEQ ID NO 478
<211> LENGTH: 4
<212> TYPE: PRT
<213> ORGANISM: Artificial Sequence
<220> FEATURE:
<223> OTHER INFORMATION: Synthetic

<400> SEQUENCE: 478

Leu Asn Val Thr
1

<210> SEQ ID NO 479
<211> LENGTH: 4
```

```
<212> TYPE: PRT
<213> ORGANISM: Artificial Sequence
<220> FEATURE:
<223> OTHER INFORMATION: Synthetic

<400> SEQUENCE: 479

His Asn His Ser
1

<210> SEQ ID NO 480
<211> LENGTH: 4
<212> TYPE: PRT
<213> ORGANISM: Artificial Sequence
<220> FEATURE:
<223> OTHER INFORMATION: Synthetic

<400> SEQUENCE: 480

Ala Asn Lys Thr
1

<210> SEQ ID NO 481
<211> LENGTH: 4
<212> TYPE: PRT
<213> ORGANISM: Artificial Sequence
<220> FEATURE:
<223> OTHER INFORMATION: Synthetic

<400> SEQUENCE: 481

Ala Asn Tyr Ser
1

<210> SEQ ID NO 482
<211> LENGTH: 4
<212> TYPE: PRT
<213> ORGANISM: Artificial Sequence
<220> FEATURE:
<223> OTHER INFORMATION: Synthetic

<400> SEQUENCE: 482

Val Asn Leu Thr
1

<210> SEQ ID NO 483
<211> LENGTH: 4
<212> TYPE: PRT
<213> ORGANISM: Artificial Sequence
<220> FEATURE:
<223> OTHER INFORMATION: Synthetic

<400> SEQUENCE: 483

Thr Asn Ala Thr
1

<210> SEQ ID NO 484
<211> LENGTH: 4
<212> TYPE: PRT
<213> ORGANISM: Artificial Sequence
<220> FEATURE:
<223> OTHER INFORMATION: Synthetic

<400> SEQUENCE: 484

Leu Asn Ile Thr
1

<210> SEQ ID NO 485
<211> LENGTH: 4
<212> TYPE: PRT
```

```
<213> ORGANISM: Artificial Sequence
<220> FEATURE:
<223> OTHER INFORMATION: Synthetic

<400> SEQUENCE: 485

Pro Asn Gln Thr
1

<210> SEQ ID NO 486
<211> LENGTH: 4
<212> TYPE: PRT
<213> ORGANISM: Artificial Sequence
<220> FEATURE:
<223> OTHER INFORMATION: Synthetic

<400> SEQUENCE: 486

Leu Asn Ala Thr
1

<210> SEQ ID NO 487
<211> LENGTH: 4
<212> TYPE: PRT
<213> ORGANISM: Artificial Sequence
<220> FEATURE:
<223> OTHER INFORMATION: Synthetic

<400> SEQUENCE: 487

Ala Asn Leu Ser
1

<210> SEQ ID NO 488
<211> LENGTH: 4
<212> TYPE: PRT
<213> ORGANISM: Artificial Sequence
<220> FEATURE:
<223> OTHER INFORMATION: Synthetic

<400> SEQUENCE: 488

Phe Asn His Thr
1

<210> SEQ ID NO 489
<211> LENGTH: 4
<212> TYPE: PRT
<213> ORGANISM: Artificial Sequence
<220> FEATURE:
<223> OTHER INFORMATION: Synthetic

<400> SEQUENCE: 489

Asn Asn Val Ser
1

<210> SEQ ID NO 490
<211> LENGTH: 4
<212> TYPE: PRT
<213> ORGANISM: Artificial Sequence
<220> FEATURE:
<223> OTHER INFORMATION: Synthetic

<400> SEQUENCE: 490

Pro Asn Phe Ser
1

<210> SEQ ID NO 491
<211> LENGTH: 4
<212> TYPE: PRT
<213> ORGANISM: Artificial Sequence
```

```
<220> FEATURE:
<223> OTHER INFORMATION: Synthetic

<400> SEQUENCE: 491

Gly Asn Val Thr
1

<210> SEQ ID NO 492
<211> LENGTH: 4
<212> TYPE: PRT
<213> ORGANISM: Artificial Sequence
<220> FEATURE:
<223> OTHER INFORMATION: Synthetic

<400> SEQUENCE: 492

Ala Asn Gln Thr
1

<210> SEQ ID NO 493
<211> LENGTH: 4
<212> TYPE: PRT
<213> ORGANISM: Artificial Sequence
<220> FEATURE:
<223> OTHER INFORMATION: Synthetic

<400> SEQUENCE: 493

Arg Asn His Thr
1

<210> SEQ ID NO 494
<211> LENGTH: 4
<212> TYPE: PRT
<213> ORGANISM: Artificial Sequence
<220> FEATURE:
<223> OTHER INFORMATION: Synthetic

<400> SEQUENCE: 494

Pro Asn Thr Ser
1

<210> SEQ ID NO 495
<211> LENGTH: 4
<212> TYPE: PRT
<213> ORGANISM: Artificial Sequence
<220> FEATURE:
<223> OTHER INFORMATION: Synthetic

<400> SEQUENCE: 495

Trp Asn Val Ser
1

<210> SEQ ID NO 496
<211> LENGTH: 4
<212> TYPE: PRT
<213> ORGANISM: Artificial Sequence
<220> FEATURE:
<223> OTHER INFORMATION: Synthetic

<400> SEQUENCE: 496

Ala Asn Ala Ser
1

<210> SEQ ID NO 497
<211> LENGTH: 4
<212> TYPE: PRT
<213> ORGANISM: Artificial Sequence
<220> FEATURE:
```

<223> OTHER INFORMATION: Synthetic

<400> SEQUENCE: 497

Met Asn Ala Thr
1

<210> SEQ ID NO 498
<211> LENGTH: 4
<212> TYPE: PRT
<213> ORGANISM: Artificial Sequence
<220> FEATURE:
<223> OTHER INFORMATION: Synthetic

<400> SEQUENCE: 498

His Asn Tyr Thr
1

<210> SEQ ID NO 499
<211> LENGTH: 4
<212> TYPE: PRT
<213> ORGANISM: Artificial Sequence
<220> FEATURE:
<223> OTHER INFORMATION: Synthetic

<400> SEQUENCE: 499

Ser Asn Leu Thr
1

<210> SEQ ID NO 500
<211> LENGTH: 4
<212> TYPE: PRT
<213> ORGANISM: Artificial Sequence
<220> FEATURE:
<223> OTHER INFORMATION: Synthetic

<400> SEQUENCE: 500

Thr Asn Ile Thr
1

<210> SEQ ID NO 501
<211> LENGTH: 8
<212> TYPE: PRT
<213> ORGANISM: Artificial Sequence
<220> FEATURE:
<223> OTHER INFORMATION: Synthetic

<400> SEQUENCE: 501

Gly Gly Asn Trp Thr Thr Arg Cys
1               5

<210> SEQ ID NO 502
<211> LENGTH: 8
<212> TYPE: PRT
<213> ORGANISM: Artificial Sequence
<220> FEATURE:
<223> OTHER INFORMATION: Synthetic

<400> SEQUENCE: 502

Phe Ala Asn Ala Thr Thr Arg Cys
1               5

<210> SEQ ID NO 503
<211> LENGTH: 8
<212> TYPE: PRT
<213> ORGANISM: Artificial Sequence
<220> FEATURE:
<223> OTHER INFORMATION: Synthetic

```
<400> SEQUENCE: 503

Tyr Ala Asn Ala Thr Ser Arg Cys
1               5

<210> SEQ ID NO 504
<211> LENGTH: 8
<212> TYPE: PRT
<213> ORGANISM: Artificial Sequence
<220> FEATURE:
<223> OTHER INFORMATION: Synthetic

<400> SEQUENCE: 504

Gly Ala Asn Ala Thr Ala Arg Cys
1               5

<210> SEQ ID NO 505
<211> LENGTH: 8
<212> TYPE: PRT
<213> ORGANISM: Artificial Sequence
<220> FEATURE:
<223> OTHER INFORMATION: Synthetic

<400> SEQUENCE: 505

Asp Gln Asn Ala Thr Phe Arg Cys
1               5

<210> SEQ ID NO 506
<211> LENGTH: 7
<212> TYPE: PRT
<213> ORGANISM: Artificial Sequence
<220> FEATURE:
<223> OTHER INFORMATION: Synthetic

<400> SEQUENCE: 506

Asn His Glu Thr Asp Arg Cys
1               5

<210> SEQ ID NO 507
<211> LENGTH: 8
<212> TYPE: PRT
<213> ORGANISM: Artificial Sequence
<220> FEATURE:
<223> OTHER INFORMATION: Synthetic

<400> SEQUENCE: 507

Gly Ser Asp Gln Asn Ala Thr Phe
1               5

<210> SEQ ID NO 508
<211> LENGTH: 4
<212> TYPE: PRT
<213> ORGANISM: Artificial Sequence
<220> FEATURE:
<223> OTHER INFORMATION: Synthetic

<400> SEQUENCE: 508

Cys Asn Ala Thr
1

<210> SEQ ID NO 509
<211> LENGTH: 4
<212> TYPE: PRT
<213> ORGANISM: Artificial Sequence
<220> FEATURE:
<223> OTHER INFORMATION: Synthetic
```

```
<400> SEQUENCE: 509

Asn Ala Thr Cys
1

<210> SEQ ID NO 510
<211> LENGTH: 6
<212> TYPE: PRT
<213> ORGANISM: Artificial Sequence
<220> FEATURE:
<223> OTHER INFORMATION: Synthetic

<400> SEQUENCE: 510

Gln Asn Ala Thr Phe Cys
1               5

<210> SEQ ID NO 511
<211> LENGTH: 8
<212> TYPE: PRT
<213> ORGANISM: Artificial Sequence
<220> FEATURE:
<223> OTHER INFORMATION: Synthetic

<400> SEQUENCE: 511

Tyr Ala Asn Ala Thr Thr Arg Cys
1               5

<210> SEQ ID NO 512
<211> LENGTH: 6
<212> TYPE: PRT
<213> ORGANISM: Haemophilus influenzae

<400> SEQUENCE: 512

Asn Ile Asn Ala Thr Ser
1               5

<210> SEQ ID NO 513
<211> LENGTH: 6
<212> TYPE: PRT
<213> ORGANISM: Homo sapiens

<400> SEQUENCE: 513

Gln Tyr Asn Ser Thr Tyr
1               5

<210> SEQ ID NO 514
<211> LENGTH: 6
<212> TYPE: PRT
<213> ORGANISM: Artificial Sequence
<220> FEATURE:
<223> OTHER INFORMATION: Synthetic

<400> SEQUENCE: 514

Gly Gly Asn Trp Thr Thr
1               5

<210> SEQ ID NO 515
<211> LENGTH: 6
<212> TYPE: PRT
<213> ORGANISM: Artificial Sequence
<220> FEATURE:
<223> OTHER INFORMATION: Synthetic

<400> SEQUENCE: 515

Gly Ala Asn Ala Thr Ala
1               5
```

```
<210> SEQ ID NO 516
<211> LENGTH: 4
<212> TYPE: PRT
<213> ORGANISM: Artificial Sequence
<220> FEATURE:
<223> OTHER INFORMATION: Synthetic

<400> SEQUENCE: 516

Arg Ala Thr Thr
1

<210> SEQ ID NO 517
<211> LENGTH: 4
<212> TYPE: PRT
<213> ORGANISM: Artificial Sequence
<220> FEATURE:
<223> OTHER INFORMATION: Synthetic

<400> SEQUENCE: 517

Ala Gly Gly Arg
1

<210> SEQ ID NO 518
<211> LENGTH: 6
<212> TYPE: PRT
<213> ORGANISM: Artificial Sequence
<220> FEATURE:
<223> OTHER INFORMATION: Synthetic

<400> SEQUENCE: 518

Tyr Ala Asn Ala Thr Thr
1               5

<210> SEQ ID NO 519
<211> LENGTH: 6
<212> TYPE: PRT
<213> ORGANISM: Artificial Sequence
<220> FEATURE:
<223> OTHER INFORMATION: Synthetic

<400> SEQUENCE: 519

Asp Gln Asn Ala Thr Phe
1               5

<210> SEQ ID NO 520
<211> LENGTH: 4
<212> TYPE: PRT
<213> ORGANISM: Artificial Sequence
<220> FEATURE:
<223> OTHER INFORMATION: Synthetic

<400> SEQUENCE: 520

Phe Asn Gln Thr
1

<210> SEQ ID NO 521
<211> LENGTH: 4
<212> TYPE: PRT
<213> ORGANISM: Artificial Sequence
<220> FEATURE:
<223> OTHER INFORMATION: Synthetic

<400> SEQUENCE: 521

Tyr Asn Leu Thr
1
```

```
<210> SEQ ID NO 522
<211> LENGTH: 4
<212> TYPE: PRT
<213> ORGANISM: Artificial Sequence
<220> FEATURE:
<223> OTHER INFORMATION: Synthetic

<400> SEQUENCE: 522

Ile Asn Trp Thr
1

<210> SEQ ID NO 523
<211> LENGTH: 4
<212> TYPE: PRT
<213> ORGANISM: Artificial Sequence
<220> FEATURE:
<223> OTHER INFORMATION: Synthetic

<400> SEQUENCE: 523

Trp Asn Trp Thr
1

<210> SEQ ID NO 524
<211> LENGTH: 4
<212> TYPE: PRT
<213> ORGANISM: Artificial Sequence
<220> FEATURE:
<223> OTHER INFORMATION: Synthetic

<400> SEQUENCE: 524

Ile Asn Gln Thr
1

<210> SEQ ID NO 525
<211> LENGTH: 5
<212> TYPE: PRT
<213> ORGANISM: Artificial Sequence
<220> FEATURE:
<223> OTHER INFORMATION: Synthetic

<400> SEQUENCE: 525

Ala Phe Asn Gln Thr
1               5

<210> SEQ ID NO 526
<211> LENGTH: 5
<212> TYPE: PRT
<213> ORGANISM: Artificial Sequence
<220> FEATURE:
<223> OTHER INFORMATION: Synthetic

<400> SEQUENCE: 526

Ser Tyr Asn Leu Thr
1               5

<210> SEQ ID NO 527
<211> LENGTH: 5
<212> TYPE: PRT
<213> ORGANISM: Artificial Sequence
<220> FEATURE:
<223> OTHER INFORMATION: Synthetic

<400> SEQUENCE: 527

Ala Tyr Asn Leu Thr
1               5

<210> SEQ ID NO 528
```

```
<211> LENGTH: 5
<212> TYPE: PRT
<213> ORGANISM: Artificial Sequence
<220> FEATURE:
<223> OTHER INFORMATION: Synthetic

<400> SEQUENCE: 528

Asp Phe Asn Gln Thr
1               5

<210> SEQ ID NO 529
<211> LENGTH: 5
<212> TYPE: PRT
<213> ORGANISM: Artificial Sequence
<220> FEATURE:
<223> OTHER INFORMATION: Synthetic

<400> SEQUENCE: 529

Ser Phe Asn Gln Thr
1               5

<210> SEQ ID NO 530
<211> LENGTH: 5
<212> TYPE: PRT
<213> ORGANISM: Artificial Sequence
<220> FEATURE:
<223> OTHER INFORMATION: Synthetic

<400> SEQUENCE: 530

Asp Tyr Asn Leu Thr
1               5

<210> SEQ ID NO 531
<211> LENGTH: 5
<212> TYPE: PRT
<213> ORGANISM: Artificial Sequence
<220> FEATURE:
<223> OTHER INFORMATION: Synthetic

<400> SEQUENCE: 531

Asn Glu Asn Val Thr
1               5

<210> SEQ ID NO 532
<211> LENGTH: 5
<212> TYPE: PRT
<213> ORGANISM: Artificial Sequence
<220> FEATURE:
<223> OTHER INFORMATION: Synthetic

<400> SEQUENCE: 532

Trp Gly Asn Trp Ser
1               5

<210> SEQ ID NO 533
<211> LENGTH: 5
<212> TYPE: PRT
<213> ORGANISM: Artificial Sequence
<220> FEATURE:
<223> OTHER INFORMATION: Synthetic

<400> SEQUENCE: 533

Phe Gly Asn Ile Ser
1               5

<210> SEQ ID NO 534
<211> LENGTH: 5
```

```
<212> TYPE: PRT
<213> ORGANISM: Artificial Sequence
<220> FEATURE:
<223> OTHER INFORMATION: Synthetic

<400> SEQUENCE: 534

Tyr Gly Asn Trp Ser
1               5

<210> SEQ ID NO 535
<211> LENGTH: 5
<212> TYPE: PRT
<213> ORGANISM: Artificial Sequence
<220> FEATURE:
<223> OTHER INFORMATION: Synthetic

<400> SEQUENCE: 535

Thr Gly Asn Ile Ser
1               5

<210> SEQ ID NO 536
<211> LENGTH: 5
<212> TYPE: PRT
<213> ORGANISM: Artificial Sequence
<220> FEATURE:
<223> OTHER INFORMATION: Synthetic

<400> SEQUENCE: 536

Leu Gly Asn Ile Ser
1               5

<210> SEQ ID NO 537
<211> LENGTH: 5
<212> TYPE: PRT
<213> ORGANISM: Artificial Sequence
<220> FEATURE:
<223> OTHER INFORMATION: Synthetic

<400> SEQUENCE: 537

Ala Gly Asn Ile Ser
1               5

<210> SEQ ID NO 538
<211> LENGTH: 5
<212> TYPE: PRT
<213> ORGANISM: Artificial Sequence
<220> FEATURE:
<223> OTHER INFORMATION: Synthetic

<400> SEQUENCE: 538

Val Gly Asn Ile Ser
1               5

<210> SEQ ID NO 539
<211> LENGTH: 5
<212> TYPE: PRT
<213> ORGANISM: Artificial Sequence
<220> FEATURE:
<223> OTHER INFORMATION: Synthetic

<400> SEQUENCE: 539

Met Gly Asn Ile Ser
1               5

<210> SEQ ID NO 540
<211> LENGTH: 5
<212> TYPE: PRT
```

```
<213> ORGANISM: Artificial Sequence
<220> FEATURE:
<223> OTHER INFORMATION: Synthetic

<400> SEQUENCE: 540

Ile Gly Asn Ile Ser
1               5

<210> SEQ ID NO 541
<211> LENGTH: 5
<212> TYPE: PRT
<213> ORGANISM: Artificial Sequence
<220> FEATURE:
<223> OTHER INFORMATION: Synthetic

<400> SEQUENCE: 541

Tyr Gly Asn Trp Thr
1               5

<210> SEQ ID NO 542
<211> LENGTH: 5
<212> TYPE: PRT
<213> ORGANISM: Artificial Sequence
<220> FEATURE:
<223> OTHER INFORMATION: Synthetic

<400> SEQUENCE: 542

Trp Pro Asn Leu Thr
1               5

<210> SEQ ID NO 543
<211> LENGTH: 5
<212> TYPE: PRT
<213> ORGANISM: Artificial Sequence
<220> FEATURE:
<223> OTHER INFORMATION: Synthetic

<400> SEQUENCE: 543

Trp Gly Asn Trp Thr
1               5

<210> SEQ ID NO 544
<211> LENGTH: 5
<212> TYPE: PRT
<213> ORGANISM: Artificial Sequence
<220> FEATURE:
<223> OTHER INFORMATION: Synthetic

<400> SEQUENCE: 544

Trp Pro Asn Ile Thr
1               5

<210> SEQ ID NO 545
<211> LENGTH: 5
<212> TYPE: PRT
<213> ORGANISM: Artificial Sequence
<220> FEATURE:
<223> OTHER INFORMATION: Synthetic

<400> SEQUENCE: 545

Trp Pro Asn Val Thr
1               5

<210> SEQ ID NO 546
<211> LENGTH: 6
<212> TYPE: PRT
<213> ORGANISM: Artificial Sequence
```

```
<220> FEATURE:
<223> OTHER INFORMATION: Synthetic

<400> SEQUENCE: 546

Trp Asp Tyr Asn Leu Thr
1               5

<210> SEQ ID NO 547
<211> LENGTH: 6
<212> TYPE: PRT
<213> ORGANISM: Artificial Sequence
<220> FEATURE:
<223> OTHER INFORMATION: Synthetic

<400> SEQUENCE: 547

Leu Asn Glu Asn Val Thr
1               5

<210> SEQ ID NO 548
<211> LENGTH: 6
<212> TYPE: PRT
<213> ORGANISM: Artificial Sequence
<220> FEATURE:
<223> OTHER INFORMATION: Synthetic

<400> SEQUENCE: 548

Tyr Met Gly Asn Ile Ser
1               5

<210> SEQ ID NO 549
<211> LENGTH: 6
<212> TYPE: PRT
<213> ORGANISM: Artificial Sequence
<220> FEATURE:
<223> OTHER INFORMATION: Synthetic

<400> SEQUENCE: 549

Trp Tyr Ala Asn Val Thr
1               5

<210> SEQ ID NO 550
<211> LENGTH: 669
<212> TYPE: PRT
<213> ORGANISM: Mannheimia haemolytica

<400> SEQUENCE: 550

Met Ser Ala Glu Asn Met Pro Ser Val Ile Arg Phe Glu Gln Ala Val
1               5                   10                  15

Ala Lys Lys Asp Tyr Glu Ser Ala Cys Thr Glu Leu Leu Ser Ile Leu
            20                  25                  30

Ser Lys Leu Asp Ser Asn Phe Gly Gly Ile Ser Asn Ile Glu Leu Asn
        35                  40                  45

Met Pro Glu Gln Ile Glu Asn Leu Glu Asn Asp Lys Ala Ile Tyr Phe
    50                  55                  60

Cys Thr Arg Met Ala Val Ala Ile Thr Arg Leu Phe Glu Asp Pro Ala
65                  70                  75                  80

Leu Glu Ile Ser Glu His Gly Ala Met Arg Phe Leu Thr Leu Gln Arg
                85                  90                  95

Trp Ile Ala Leu Ile Phe Ala Ser Ser Pro Tyr Val Asn Ala Asp His
            100                 105                 110

Ile Leu Arg Thr Tyr Asn Arg Asn Lys Glu Ser Ala Asn Pro Asn Thr
        115                 120                 125
```

```
Val Asp Leu Asp Ala Thr Leu Gln Ala Leu Ile Lys Phe Cys Ile Leu
130                 135                 140

Tyr Leu Pro Glu Ser Asn Ile Leu Leu Asn Leu Asp Ala Ala Trp Asn
145                 150                 155                 160

Ala Ser Ser Asp Leu Thr Ala Ser Leu Cys Phe Ala Leu Gln Ser Pro
                165                 170                 175

Arg Phe Ile Gly Thr Ser Ala Phe Ala Lys Arg Ala Ala Ile Leu
                180                 185                 190

Gln Trp Phe Pro Glu Lys Leu Ala Gln Ile Glu Asn Leu Asn Lys Leu
                195                 200                 205

Pro Ser Ala Ile Ser His Asp Val Tyr Met His Cys Ser Tyr Asp Ile
210                 215                 220

Glu Ala Asn Lys His Asn Val Lys Arg Ser Leu Asn Ala Val Ile Arg
225                 230                 235                 240

Arg His Leu Leu Ser Val Gly Trp Glu Asp Arg Lys Ile Glu Gln Leu
                245                 250                 255

Gly Thr Arg Asn Asn Lys Pro Val Met Val Val Leu Leu Glu His Phe
                260                 265                 270

His Ser Ser His Ser Ile Tyr Arg Thr His Ser Thr Ser Met Val Ala
    275                 280                 285

Ala Arg Glu His Phe His Leu Ile Gly Leu Gly Ser Asp Ala Val Asp
290                 295                 300

Glu Met Gly Gln Gln Val Phe Asp Glu Phe His Leu Leu Pro Gln Asp
305                 310                 315                 320

Gly Ser Leu Phe Asp Arg Leu Ser Phe Leu Lys Asp Ile Cys Asp Lys
                325                 330                 335

Asn Asn Pro Ala Val Phe Tyr Met Pro Ser Ile Gly Met Asp Leu Thr
                340                 345                 350

Thr Ile Phe Ala Ser Asn Thr Arg Leu Ala Pro Ile Gln Ala Val Ala
        355                 360                 365

Leu Gly His Pro Ala Thr Thr His Ser Asp Phe Ile Glu Tyr Val Ile
    370                 375                 380

Val Glu Asp Asp Tyr Val Gly Ser Glu Ser Cys Phe Ser Glu Gln Leu
385                 390                 395                 400

Leu Arg Leu Pro Lys Asp Ala Leu Pro Tyr Val Pro Ser Ala Leu Ala
                405                 410                 415

Pro Gln Asn Val Val Tyr Asn Leu Arg Glu Asn Pro Glu Val Ile His
                420                 425                 430

Ile Gly Ile Ala Ser Thr Thr Met Lys Leu Asn Pro Tyr Phe Leu Glu
            435                 440                 445

Ala Leu Lys Ala Ile Arg Asp Arg Ala Lys Val Lys Thr His Phe His
450                 455                 460

Phe Ala Leu Gly Gln Ser Ser Gly Ile Thr His Pro Tyr Val Glu Arg
465                 470                 475                 480

Phe Ile Lys Ser Tyr Leu Gly Asn Asp Ala Thr Ala His Pro His Ser
                485                 490                 495

Pro Tyr Asp Glu Tyr Leu Asn Ile Leu His Asn Cys Asp Met Met Leu
            500                 505                 510

Asn Pro Phe Pro Phe Gly Asn Thr Asn Gly Ile Ile Asp Met Val Thr
                515                 520                 525

Leu Gly Leu Val Gly Val Cys Lys Thr Gly Pro Glu Val His Glu His
    530                 535                 540

Ile Asp Glu Gly Leu Phe Lys Arg Leu Gly Leu Pro Asn Trp Leu Ile
```

```
545                 550                 555                 560
Thr Gln Thr Ala Glu Glu Tyr Val Thr Gln Ala Ile Arg Leu Ala Glu
                565                 570                 575

Asn His Glu Glu Arg Leu Ala Ile Arg Arg Asp Ile Ile Glu Asn Asn
                580                 585                 590

Lys Leu Gln Thr Leu Phe Ser Gly Asp Pro Arg Pro Met Gly Gln Ile
                595                 600                 605

Phe Leu Ala Lys Val Gln Ala Trp Leu Ala Asp Lys Asn Pro Lys Asn
610                 615                 620

Ala Glu Val Glu Val Lys Thr Lys Val Arg Lys Ala Ala Thr Ala
625                 630                 635                 640

Ser Gln Ser Ala Lys Lys Gln Thr Thr Ser Lys Thr Gln Thr Ala Lys
                645                 650                 655

Ala Glu Lys Asp Asn Ala Ala Lys Thr Glu Thr Lys Ser
                660                 665

<210> SEQ ID NO 551
<211> LENGTH: 654
<212> TYPE: PRT
<213> ORGANISM: Haemophilus ducreyi

<400> SEQUENCE: 551

Met Glu Leu His Ser Pro Ser Leu Glu Lys Phe Glu Ala Ala Val Ile
1                   5                   10                  15

Glu Lys Asp Tyr Glu Leu Ala Cys Thr Glu Leu Leu Ala Ile Leu Asp
                20                  25                  30

Lys Leu Asp Asn Asn Phe Gly Thr Leu Gln Asp Ile Glu Phe Ala Tyr
            35                  40                  45

Pro Pro Gln Leu Glu Asp Leu Glu Gln Asp Lys Val Val Tyr Phe Cys
        50                  55                  60

Thr Arg Met Ala Thr Val Ile Thr Thr Leu Phe Thr Asp Val Glu Phe
65                  70                  75                  80

Ala Ile Ser Ser Ala Gly Ala Gln Arg Phe Leu Val Phe Gln Arg Trp
                85                  90                  95

Leu Ser Phe Ile Phe Ala Ser Ser Pro Phe Ile Asn Ala Asp His Ile
                100                 105                 110

Leu Gln Ser Tyr Asn Cys Asn Pro Asp Arg Asp Ile Glu Asp Asp Ile
            115                 120                 125

His Leu Ala Ala Thr Lys Glu Ala Leu Ile Lys Phe Cys Val Met Tyr
130                 135                 140

Leu Pro Glu Ser Asn Leu Lys Leu Asn Leu Asp Ala Ala Trp Asn Val
145                 150                 155                 160

Asp Pro Glu Leu Cys Ala Ser Leu Cys Phe Ala Leu Gln Ser Pro Arg
                165                 170                 175

Phe Leu Gly Thr Val Ala Ala Tyr Ser Lys Arg Ser Ala Ile Leu Gln
            180                 185                 190

Trp Phe Pro Glu His Leu Ala Gln Leu Ala Asn Leu Asp Asn Ile Pro
        195                 200                 205

Ser Ala Ile Ser His Asp Val Tyr Met His Cys Ser Tyr Asp Ile Ala
        210                 215                 220

Glu Asn Lys His Ala Val Lys Lys Ala Leu Asn Gln Val Ile Arg Arg
225                 230                 235                 240

His Val Val Asn Glu Tyr Gly Trp Gln Asp Arg Asp Thr Thr Arg Ile
                245                 250                 255
```

```
Gly Tyr Arg Asn Asp Lys Pro Val Met Val Leu Leu Glu His Phe
            260                 265                 270

His Ser Ala His Ser Ile Tyr Arg Thr His Ser Thr Ser Met Ile Ala
        275                 280                 285

Ala Arg Glu His Phe Tyr Leu Ile Gly Leu Gly Ser Lys Ala Val Asp
290                 295                 300

Ala Asn Gly Gln Ala Val Phe Asp Glu Phe His Leu Leu Glu Asp Asp
305                 310                 315                 320

Asn Met Lys Asp Lys Leu Asp His Ile Arg Ser Ile Cys Glu Gln Asn
                325                 330                 335

Gly Ala Ala Ile Leu Tyr Met Pro Ser Val Gly Met Asp Leu Ser Thr
            340                 345                 350

Ile Phe Val Ser Asn Thr Arg Leu Ala Pro Ile Gln Val Ile Ala Leu
                355                 360                 365

Gly His Pro Ala Thr Thr Tyr Ser Glu Phe Ile Asp Tyr Val Ile Val
            370                 375                 380

Glu Glu Asp Tyr Ile Gly Ser Glu Ala Cys Phe Ser Glu Thr Leu Leu
385                 390                 395                 400

Pro Leu Pro Lys Asp Ala Leu Pro Tyr Val Pro Ser Ala Leu Ala Pro
                405                 410                 415

Glu Lys Val Glu Tyr Leu Leu Arg Glu Asn Pro Glu Val Val Asn Ile
            420                 425                 430

Gly Ile Ala Ala Thr Thr Met Lys Leu Asn Pro Tyr Phe Leu Asp Ala
                435                 440                 445

Leu Lys Val Ile Arg Asp Arg Ala Lys Val Lys Ile His Phe His Phe
            450                 455                 460

Ala Leu Gly Gln Ser Thr Gly Val Thr His Pro His Ile Ala Arg Phe
465                 470                 475                 480

Ile Lys Ser Tyr Leu Gly Asp Ser Ala Thr Ala Tyr Pro His Ala Pro
                485                 490                 495

Tyr His Gln Tyr Leu Thr Val Leu His Asn Cys Asp Met Met Leu Asn
            500                 505                 510

Pro Phe Pro Phe Gly Asn Thr Asn Gly Ile Ile Asp Met Val Thr Leu
                515                 520                 525

Gly Leu Val Gly Ile Cys Lys Thr Gly Asp Glu Val His Glu His Ile
            530                 535                 540

Asp Glu Gly Leu Phe Lys Arg Leu Gly Leu Pro Glu Trp Leu Ile Ala
545                 550                 555                 560

Asp Thr Val Asp Glu Tyr Ile Glu Cys Ala Leu Arg Leu Ala Glu Asn
                565                 570                 575

His Thr Glu Arg Leu Ala Leu Arg Arg His Ile Ile Glu Asn Asn Gly
            580                 585                 590

Leu Ala Thr Leu Phe Thr Gly Asp Pro Ser Pro Met Gly Ser Val Leu
            595                 600                 605

Leu Ala Lys Leu Asn Glu Trp Arg Glu Gln Gln Lys Thr Val Ala Pro
            610                 615                 620

Leu Lys Lys Thr Lys Lys Val Ala Lys Ala Thr Glu Thr Asn Lys
625                 630                 635                 640

Ser Val Thr Lys Lys Pro Val Ala Lys Lys Arg Ser Ser
                645                 650
```

<210> SEQ ID NO 552
<211> LENGTH: 620
<212> TYPE: PRT

<213> ORGANISM: Actinobacillus pleuropneumoniae

<400> SEQUENCE: 552

```
Met Glu Asn Glu Asn Lys Pro Asn Val Ala Asn Phe Glu Ala Ala Val
1               5                   10                  15

Ala Ala Lys Asp Tyr Glu Lys Ala Cys Ser Glu Leu Leu Ile Leu
            20                  25                  30

Ser Gln Leu Asp Ser Asn Phe Gly Gly Ile His Glu Ile Glu Phe Glu
            35                  40                  45

Tyr Pro Ala Gln Leu Gln Asp Leu Glu Gln Glu Lys Ile Val Tyr Phe
        50                  55                  60

Cys Thr Arg Met Ala Thr Ala Ile Thr Thr Leu Phe Ser Asp Pro Val
65                  70                  75                  80

Leu Glu Ile Ser Asp Leu Gly Val Gln Arg Phe Leu Val Tyr Gln Arg
                85                  90                  95

Trp Leu Ala Leu Ile Phe Ala Ser Ser Pro Phe Val Asn Ala Asp His
            100                 105                 110

Ile Leu Gln Thr Tyr Asn Arg Glu Pro Asn Arg Lys Asn Ser Leu Glu
        115                 120                 125

Ile His Leu Asp Ser Ser Lys Ser Ser Leu Ile Lys Phe Cys Ile Leu
130                 135                 140

Tyr Leu Pro Glu Ser Asn Val Asn Leu Asn Leu Asp Val Met Trp Asn
145                 150                 155                 160

Ile Ser Pro Glu Leu Cys Ala Ser Leu Cys Phe Ala Leu Gln Ser Pro
                165                 170                 175

Arg Phe Val Gly Thr Ser Thr Ala Phe Asn Lys Arg Ala Thr Ile Leu
            180                 185                 190

Gln Trp Phe Pro Arg His Leu Asp Gln Leu Lys Asn Leu Asn Asn Ile
        195                 200                 205

Pro Ser Ala Ile Ser His Asp Val Tyr Met His Cys Ser Tyr Asp Thr
210                 215                 220

Ser Val Asn Lys His Asp Val Lys Arg Ala Leu Asn His Val Ile Arg
225                 230                 235                 240

Arg His Ile Glu Ser Glu Tyr Gly Trp Lys Asp Arg Asp Val Ala His
                245                 250                 255

Ile Gly Tyr Arg Asn Asn Lys Pro Val Met Val Leu Leu Glu His
            260                 265                 270

Phe His Ser Ala His Ser Ile Tyr Arg Thr His Ser Thr Ser Met Ile
        275                 280                 285

Ala Ala Arg Glu His Phe Tyr Leu Ile Gly Leu Gly Ser Pro Ser Val
290                 295                 300

Asp Gln Ala Gly Gln Glu Val Phe Asp Glu Phe His Leu Val Ala Gly
305                 310                 315                 320

Asp Asn Met Lys Gln Lys Leu Glu Phe Ile Arg Ser Val Cys Glu Ser
                325                 330                 335

Asn Gly Ala Ala Ile Phe Tyr Met Pro Ser Ile Gly Met Asp Met Thr
            340                 345                 350

Thr Ile Phe Ala Ser Asn Thr Arg Leu Ala Pro Ile Gln Ala Ile Ala
        355                 360                 365

Leu Gly His Pro Ala Thr Thr His Ser Asp Phe Ile Glu Tyr Val Ile
370                 375                 380

Val Glu Asp Asp Tyr Val Gly Ser Glu Glu Cys Phe Ser Glu Thr Leu
385                 390                 395                 400
```

```
Leu Arg Leu Pro Lys Asp Ala Leu Pro Tyr Val Pro Ser Ala Leu Ala
                405             410                 415

Pro Glu Lys Val Asp Tyr Leu Leu Arg Glu Asn Pro Glu Val Val Asn
            420             425             430

Ile Gly Ile Ala Ser Thr Thr Met Lys Leu Asn Pro Tyr Phe Leu Glu
            435             440             445

Ala Leu Lys Ala Ile Arg Asp Arg Ala Lys Val Lys Val His Phe His
    450             455             460

Phe Ala Leu Gly Gln Ser Asn Gly Ile Thr His Pro Tyr Val Glu Arg
465             470             475                 480

Phe Ile Lys Ser Tyr Leu Gly Asp Ser Ala Thr Ala His Pro His Ser
                485             490             495

Pro Tyr His Gln Tyr Leu Arg Ile Leu His Asn Cys Asp Met Met Val
            500             505             510

Asn Pro Phe Pro Phe Gly Asn Thr Asn Gly Ile Ile Asp Met Val Thr
            515             520             525

Leu Gly Leu Val Gly Val Cys Lys Thr Gly Ala Glu Val His Glu His
    530             535             540

Ile Asp Glu Gly Leu Phe Lys Arg Leu Gly Leu Pro Glu Trp Leu Ile
545             550             555                 560

Ala Asn Thr Val Asp Glu Tyr Val Glu Arg Ala Val Arg Leu Ala Glu
            565             570             575

Asn His Gln Glu Arg Leu Glu Leu Arg Arg Tyr Ile Ile Glu Asn Asn
            580             585             590

Gly Leu Asn Thr Leu Phe Thr Gly Asp Pro Arg Pro Met Gly Gln Val
            595             600             605

Phe Leu Glu Lys Leu Asn Ala Phe Leu Lys Glu Asn
        610             615             620

<210> SEQ ID NO 553
<211> LENGTH: 5
<212> TYPE: PRT
<213> ORGANISM: Artificial Sequence
<220> FEATURE:
<223> OTHER INFORMATION: Synthetic

<400> SEQUENCE: 553

Phe Gly Asn Trp Ser
1               5
```